United States Patent
Han et al.

(10) Patent No.: US 9,725,715 B2
(45) Date of Patent: Aug. 8, 2017

(54) SIGNAL ACTIVATABLE CONSTRUCTS AND RELATED COMPONENTS COMPOSITIONS METHODS AND SYSTEMS

(71) Applicants: CALIFORNIA INSTITUTE OF TECHNOLOGY, Pasadena, CA (US); CITY OF HOPE, Duarte, CA (US)

(72) Inventors: Si-ping Han, Yorba Linda, CA (US); William A. Goddard, III, Pasadena, CA (US); Lisa Scherer, Monrovia, CA (US); John J. Rossi, Alta Loma, CA (US)

(73) Assignees: CALIFORNIA INSTITUTE OF TECHNOLOGY, Pasadena, CA (US); CITY OF HOPE, Duarte, CA (US)

( * ) Notice: Subject to any disclaimer, the term of this patent is extended or adjusted under 35 U.S.C. 154(b) by 0 days.

(21) Appl. No.: 14/641,261

(22) Filed: Mar. 6, 2015

(65) Prior Publication Data
US 2015/0315581 A1 Nov. 5, 2015

Related U.S. Application Data

(60) Provisional application No. 61/948,823, filed on Mar. 6, 2014.

(51) Int. Cl.
*C12N 15/113* (2010.01)
*C12N 15/11* (2006.01)

(52) U.S. Cl.
CPC .......... *C12N 15/111* (2013.01); *C12N 15/113* (2013.01); *C12N 2310/14* (2013.01); *C12N 2310/531* (2013.01); *C12N 2320/10* (2013.01); *C12N 2320/32* (2013.01); *C12N 2320/50* (2013.01)

(58) Field of Classification Search
USPC .... 435/6.1, 91.1, 91.31, 455, 458; 536/23.1, 536/24.5; 514/44
See application file for complete search history.

(56) References Cited

U.S. PATENT DOCUMENTS

| | | |
|---|---|---|
| 8,710,199 B2 | 4/2014 | Han et al. |
| 9,115,355 B2 | 8/2015 | Han et al. |
| 9,206,419 B2 | 12/2015 | Han et al. |
| 2006/0088864 A1 | 4/2006 | Smolke et al. |
| 2009/0004668 A1* | 1/2009 | Chen ...................... C12N 15/111 435/6.14 |
| 2009/0082217 A1 | 3/2009 | Smolke et al. |
| 2009/0234109 A1* | 9/2009 | Han et al. .................... 536/24.5 |
| 2010/0209487 A1 | 8/2010 | Quay et al. |
| 2015/0004615 A1 | 1/2015 | Pierce et al. |

FOREIGN PATENT DOCUMENTS

| | | |
|---|---|---|
| WO | 2007/107162 | 9/2007 |
| WO | 2010/145778 A1 | 12/2010 |
| WO | 2011/163526 | 12/2011 |
| WO | 2011/163526 A2 | 12/2011 |
| WO | WO 2011/163526 | * 12/2011 |

OTHER PUBLICATIONS

Doench et al, Genes & Development, vol. 18, No. 5, pp. 504-511 (2004).*
Opalinska et al, Nature Rev., vol. 1: pp. 503-514 (2002).*
Peracchi et al., Rev. Med. Virol., vol. 14, pp. 47-64 (2004).*
Holen et al, Nucleic Acids Res., vol. 30, No. 8, vol. 1757-1766 (2002).*
Wu, H., et al., "Properties of cloned and expressed human RNase H1," The Journal of Biological Chemistry, 1999, vol. 274, pp. 28270-28278.
Zamaratski, E., et al., "A critical survey of the structure-function of the antisense oligo/RNA heteroduplex as substrate for RNase H," Journal of Biochemical and Biophysical Methods, 2001, vol. 48, pp. 189-208.
Cazenave, C., et al., "Characterization and subcellular localization of ribonuclease Activities From Xenopus laevia oocytes," The Journal of Biological Chemistry, 1994, vol. 269, pp. 25185-25192.
Nowotny, M., et al. Crystal structures of RNase H bound to an RNA/DNA hybrid: substrate specificity and metal-dependent catalysis, Cell, 2005, vol. 121, pp. 1005-1016.
Song, J. J. et al., "The crystal structure of the Argonaute2 PAZ domain reveals an RNA binding motif in RNAi effector complexes", Nature Structural Biology, vol. 10, pp. 1026-1032 (2003).
Ma, J. B. et al., "Structural basis for overhang-specific small interfering RNA recognition by the PAZ domain", Nature, vol. 429, pp. 318-322 (2004).
Yan, K. S. et al., "Structure and conserved RNA binding of the PAZ domain", Nature, vol. 426, pp. 468-265 (2003).
Lingel, A. et al., "Structure and nucleic-acid binding of the Drosophila Argonaute 2 PAZ domain", Nature, vol. 426, pp. 465-469 (2003).
Behlke, M. A. et al., "Chemical modification of siRNAs for in vivo use", Oligonucleotides, vol. 18, pp. 305-320 (2008).
Rose, S. D. et al., "Functional polarity is introduced by Dicer processing of short substrate RNAs", Nucleic Acids Research, vol. 33, pp. 4140-4156 (2005).
Tomari, Y., et al., "A Protein Sensor for siRNA Asymmetry", Science, vol. 306, pp. 1377-1380, (2004).
Susan M. Freier and Karl-Heinz Altman, "The ups and downs of nucleic acid duplex stability: structure-stability studies on chemically-modified DNA:RNA duplexes," Nucleic Acids Research, 1997, vol. 25, No. 22 4429-4443.

(Continued)

Primary Examiner — Jane Zara
(74) Attorney, Agent, or Firm — Steinfl + Bruno LLP

(57) ABSTRACT

Provided herein are signal activatable molecular constructs for delivery of molecules and related components, compositions, methods, and systems, having a 17 to 30 bp targeting domain duplex RNA, at least one protection strand having a protection segment and linker segment and a sensor strand having a displacement segment and a toehold segment, in which in an inactive conformation the protection segment and the displacement segment form a sensor domain duplex polynucleotide covalently attached to the targeting domain and presenting the toehold segment for binding to a signal molecule. In an active conformation the sensor strand is bound to the signal molecule and is detached from the at least one protection strand and from the targeting domain; and the targeting domain attaches the at least one protection strand in a configuration allowing processing by Dicer and/or an Argonaute enzyme.

21 Claims, 31 Drawing Sheets

(56) References Cited

OTHER PUBLICATIONS

Majlessi, M. et al. "Advantages of 2'-O-methyl oligoribonucleotide probes for detecting RNA targets," *Nucleic Acids Research*, 1998, vol. 26, No. 9, pp. 2224-2229.

Kierzek, E. et al. "The influence of locked nucleic acid residues on the thermodynamic properties of 2'O-methyl RNA/RNA heteroduplexes," *Nucleic Acids Research*, 2005, vol. 33, No. 16, pp. 5082-5093.

Han, H. et al. "Sequence-specific recognition of double helical RNA and RNA.DNA by triple helix formation," *PNAS* May 1, 1993 vol. 90, pp. 3806-3810.

Burge S, Parkinson GN, Hazel P, Todd AK, Neidle S (2006). "Quadruplex DNA: sequence, topology and structure". *NAR* 34 (19): 5402-5415. doi:10.1093/nar/gkl655.

J.N. Zadeh, C.D. Steenberg, J.S. Bois, B.R. Wolfe, M.B. Pierce, A.R. Khan, R.M. Dirks, N.A. Pierce. "NUPACK: analysis and design of nucleic acid systems." *J Comput Chem*, 32, 170-173, 2011.

R.M. Dirks, J.S. Bois, J.M. Schaeffer, E. Winfree, and N.A. Pierce. (2007) "Thermodynamic analysis of interacting nucleic acid strands." *SIAM Rev*, 49, 65-88.

R.M. Dirks and N.A. Pierce. (2003) "A partition function algorithm for nucleic acid secondary structure including pseudoknots." *J Comput Chem*, 24, 1664-1677.

R.M. Dirks and N.A. Pierce. (2004) "An algorithm for computing nucleic acid base-pairing probabilities including pseudoknots." *J Comput Chem*, 25, 1295-1304.

J.N. Zadeh, B.R. Wolfe, N.A. Pierce. "Nucleic acid sequence design via efficient ensemble defect optimization." *J Comput Chem*, 32, 439-452, 2011.

M. Zuker. "Mfold web server for nucleic acid folding and hybridization prediction." *Nucleic Acids Res*. 31 (13), 3406-3415, 2003.

Waugh, P. Gendron, R. Altman, J. W. Brown, D. Case, D. Gautheret, S. C. Harvey, N. Leontis, J. Westbrook, E. Westhof, M. Zuker & F. Major. "RNAML: A standard syntax for exchanging RNA information." *RNA* 8 (6), 707-717, 2002.

M. Zuker & A. B. Jacobson. "Using Reliability Information to Annotate RNA Secondary Structures." *RNA* 4, 669-679, 1998. [Abstract][Preprint] Note: Explains color annotation of secondary structure.

N. R. Markham & M. Zuker. "UNAFold: Software for Nucleic Acid Folding and Hybridization. In Data, Sequence Analysis, and Evolution," J. Keith, ed., *Bioinformatics*: vol. 2, Chapter 1, pp. 1-33, Humana Press Inc., 2008.

M. Zuker, D. H. Mathews & D. H. Turner. "Algorithms and Thermodynamics for RNA Secondary Structure Prediction: A Practical Guide in RNA Biochemistry and Biotechnology," pp. 1-23, J. Barciszewski and B. F. C. Clark, eds. , NATO ASI Series, Kluwer Academic Publishers, Dordrecht, NL, 1999.

M. Zuker. "Prediction of RNA Secondary Structure by Energy Minimization. In Computer Analysis of Sequence Data" A. M. Griffin and H. G. Griffin eds. Methods in Molecular Biology, Humana Press Inc., 267-294, 1994.

J. A. Jaeger, D. H. Turner & M. Zuker. "Predicting Optimal and Suboptimal Secondary Structure for RNA." In Molecular Evolution: Computer Analysis of Protein and Nucleic Acid Sequences, R. F. Doolittle ed. Methods in Enzymology 183, 281-306, 1990.

M. Zuker. "On Finding All Suboptimal Foldings of an RNA Molecule." *Science* 244, 48-52, 1989.

D. H. Mathews, J. Sabina, M. Zuker & D. H. Turner. "Expanded Sequence Dependence of Thermodynamic Parameters Improves Prediction of RNA Secondary Structure," J. Mol. Biol. 288, 911-940, 1999.

E. Walter, D. H. Turner, J. Kim, M. H. Lyttle, P. Müller, D. H. Mathews & M. Zuker. "Coaxial stacking of helices enhances binding of oligoribonucleotides and improves predictions of RNA folding." *Proc. Natl. Acad. Sci. USA 91*, 9218-9222, 1994.

Mathews, D. H. et al. "RNA Secondary Structure Prediction." *In Current Protocols in Nucleic Acid Chemistry* S. Beaucage, D. E. Bergstrom, G. D. Glick, and R. A. Jones eds., John Wiley & Sons, New York, 11. 2. 1-11. 2. 10, (2007) DOI: 10.1002/0471142700. nc1102s28.

D. H. Mathews, S. J. Schroeder, D. H. Turner & M. Zuker. "Predicting RNA Secondary Structure." In the RNA World, R. F. Gesteland, T. R. Cech and J. F. Atkins eds., 3rd edition, Cold Spring Harbor Laboratory Press, Cold Spring Harbor, New York, Chapter 22, 631-657, 2006.

D. H. Mathews & M. Zuker. "Predictive Methods Using RNA Sequences." In Bioinformatics: A Practical Guide to the Analysis of Genes and Proteins, A. Baxevanis and F. Ouellette eds. ,3rd edition, John Wiley & Sons, New York, Chapter 6, 143-164, 2005.

D. H. Mathews, M. D. Disney, J. L. Childs, S. J. Schroeder, M. Zuker & D. H. Turner."Incorporating chemical modification constraints into a dynamic programming algorithm for prediction of RNA secondary structure." Proc. Natl. Acad. Sci. USA 101 (19), 7287-7292, 2004.

M. Zuker & D. Sankoff."RNA Secondary Structures and their Prediction." Bull. Mathematical Biology 46, 591-621, 1984.

M. Zuker & P. Stiegler. "Optimal computer folding of large RNA sequences using thermodynamics and auxiliary information." *Nucleic Acids Res*. 9, 133-148, 1981.

J. -M. Rouillard, M. Zuker & E. Gulari. "OligoArray 2. 0: design of oligonucleotide probes for DNA microarrays using a thermodynamic approach." *Nucleic Acids Res*. 31 (12), 3057-3062, 2003.

J. -M. Rouillard, C. J. Herbert & M. Zuker. "OligoArray: Genome-scale oligonucleotide design for microarrays." *Bioinformatics* 18 (3), 486-487, 2002.

Ding, Y. et al. "RNA secondary structure prediction by centroids in a Boltzmann weighted ensemble," *RNA* 2005. 11: pp. 1157-1166.

Braasch, D.A. et al. "RNA Interference in Mammalian Cells by Chemically-Modified RNA," *Biochemistry* 2003,42, pp. 7967-7975.

Ma, Jin-Biao, et al. "Structural basis for overhang specific small interfering RNA recognition by the PAZ domain," *Nature*, 429, 318-322 (2004).

Whitehead, K.A. et al. Nature Reviews Drug Discovery 8, 129-138 (Feb. 2009) | doi:10.1038/nrd2742, "Knocking down barriers: advances in siRNA delivery".

Simeoni, F. "Insight into the mechanism of the peptide.based gene delivery system MPG: implications for delivery of siRNA into mammalian cells." *Nucleic acids research* 31.11 (2003):2717-2724.

Liu, Z., Winters, M., Holodniy, M. and Dai, H. (2007), "siRNA Delivery into Human T Cells and Primary Cells with Carbon-Nanotube Transporters." *Angewandte Chemie*, 119: 2069-2073. doi: 10.1002/ange.200604295.

Chu, T.C. et al. "Aptamer mediated siRNA delivery," *Nucl. Acids Res*. 34(10): e73 doi:10.1093/nar/gkl388.

Rozema, D.B. et al. "Dynamic PolyConjugates for targeted in vivo delivery of siRNA to hepatocytes," *PNAS* 2007 104 (32) 12982-12987.

Derfus, A.M. et al. "Targeted Quantum Dot Conjugates for siRNA Delivery," *Bioconjugate Chem*., 2007, 18 (5), pp. 1391-1396, DOI: 10.1021/bc060367e.

Kumar, P. et al. "T Cell-Specific siRNA Delivery Suppresses HIV-1 Infection in Humanized Mice," *Cell*, vol. 134, Issue 4, Aug. 22, 2008, pp. 577-586.

Rinaudo, K. et al. "A universal RNAi-based logic evaluator that operates in mammalian cells," *Nature Biotechnology* 25, 795-801 (2007).

Ehsani, A. et al. "Rational Design of Micro-RNA-like Bifunctional siRNAs Targeting HIV and the HIV Coreceptor CCR5" *Molecular Therapy* (2010) 18:4, pp. 796-802. doi:10.1038/mt.2009.321.

Tiemann, K. et al."Dual-targeting siRNAs" *RNA* (2010), 16: pp. 1275-1284.

Judge, A.D. et al. "Design of Noninflammatory Synthetic siRNA Mediating Potent Gene Silencing in Vivo," *Molecular Therapy* (2006) 13, pp. 494-505.

Blight K.J. et al., "Secondary Structure Determination of the Conserved 98-Base Sequence at the 3' Terminus of Hepatitis C Virus Genome RNA" Journal of Virology, Oct. 1997, vol. 71, pp. 7345-7352.

(56) References Cited

OTHER PUBLICATIONS

Ehsani, A. et al. "Rational Design of Micro-RNA-like Bifunctional siRNAs Targeting HIV and the HIV Coreceptor CCR5," Molecular Therapy (2010) 18;3, pp. 796-802. doi;10.138/mt.2009.321.
PCT International Search Report mailed on Feb. 24, 2012 for PCT Application No. PCT/US2011/041703 filed Jun. 23, 2011 in the name of California Institute of Technology et al.
PCT Written Opinion completed on Feb. 22, 2012 for PCT Application No. PCT/US2011/041703 filed Jun. 23, 2011 in the name of California Institute of Technology et al.
Li, J. et al., "Enzymatic signal amplification of molecular beacons for sensitive DNA detection," Nucleic Acid Research 2008, 36: 1-17.
Weissleder, R., et al "In vivo imaging of tumors with proteaseactivated near-infrared fluorescent probes," Nature Biotechnology 1999, 17: 375-378.
PCT International Search Report mailed on Jul. 9, 2013 for PCT Application No. PCT/US2013/033380 filed Mar. 21, 2013 in the name of California Institute of Technology et al.
PCT Written Opinion mailed on Jul. 9, 2013 for PCT Application No. PCT/US2013/033380 filed Mar. 21, 2013 in the name of California Institute of Technology et al.
De Paula, D. et al. "Hydrophobization and bioconjugation for enhanced siRNA delivery and targeting." RNA, vol. 13, pp. 431-456, 2007.
Kim, J. et al. "Intracellular small interfering RNA delivery using genetically engineered double-stranded RNA binding protein domain." The Journal of Gene Medicine. vol. 11, pp. 804-812, 2009.
Wang, H.W. et al. "Structural Insights into RNA Processing by the Human RISC-Loading Complex." Nat Struct Mol Biol., vol. 16(1), pp. 1148-1153, 2009.
Mathews, D.H. et al. "Folding and Finding RNA Secondary Structure." Cold Spring Harbor Perspectives in Biology. 2010.
Restriction Requirement issued for U.S. Appl. No. 13/167,672, filed Jun. 23, 2011 filed in the name of Si-Ping Han mailed on Dec. 14, 2012.
Non-Final Office Action issued for U.S. Appl. No. 13/167,672, filed Jun. 23, 2011 filed in the name of Si-Ping Han mailed on Apr. 1, 2013.
Notice of Allowance issued for U.S. Appl. No. 13/167,672, filed Jun. 23, 2011 filed in the name of Si-Ping Han mailed on Dec. 12, 2013.
Matsukura, M. et al. "Phosphorothioate analogs of oligodeoxynucleotides: inhibitors of replication and cytopathic effects of human immunodeficiency virus." *Proceedings of the National Academy of Sciences* 84, 7706-7710 1987.
Collingwood, M., et al. "Chemical Modification Patterns Compatible with High Potency Dicer-Substrate Small Interfering RNAs." *Oligonucleotides* 18, 187-200 2008.
Lennox, K. A., et al. "Improved Performance of Anti-miRNA Oligonucleotides Using a Novel Non-Nucleotide Modifier." *Mol Ther Nucleic Acids* 2, e117, doi:10.1038/mtna.2013.46 2013.
Bramsen, J. B., et al. "A large-scale chemical modification screen identifies design rules to generate siRNAs with high activity, high stability and low toxicity." *Nucleic Acids Research* 37, 1-15, doi:10.1093/nar/gkp106 2009.
Mathy, N., et al. "5'-to-3' Exoribonuclease Activity in Bacteria: Role of RNase J1 in rRNA Maturation and 5' Stability of mRNA." *Cell* 129, 681-692 2007.
Yang X. et al. "Studies of the 5' Exonuclease and Endonuclease Activities of CPSF-73 in Histone Pre-mRNA Processing." *Molecular and Cellular Biology* 29, 31-42, doi:10.1128/mcb.00776-08 2009.
Efthymiou, T. C. et al "Evaluation of siRNAs that contain internal variable-length spacer linkages." *Bioorganic & Medicinal Chemistry Letters* 22, 5590-5594, doi:http://dx.doi.org/10.1016/j.bmcl.2012.07.006 2012.
Zhou, J., et al. Selection, characterization and application of new RNA HIV gp 120 aptamers for facile delivery of Dicer substrate siRNAs into HIV infected cells. *Nucleic Acids Research* 37, 3094-3109, doi:10.1093/nar/gkp185 2009.
Restriction Requirement issued for U.S. Appl. No. 13/848,687, filed Mar. 21, 2013 in the name of Si-ping Han et al. mailed on Nov. 7, 2014.
Restriction Requirement issued for U.S. Appl. No. 14/093,387, filed Nov. 29, 2013 in the name of Si-ping Han et al. mailed on Nov. 19, 2014.
Lee, H. et al. *Molecular Dynamics Studies of Polyethylene Oxide and Polyethylene Glycol: Hydrodynamic Radius and Shape Anisotropy*. Biophysical Journal, vol. 95, Aug. 2008, pp. 1590-1599.
Yurke, B. et al. *A DNA-fuelled molecular machine made of DNA*. Letters to Nature, vol. 406, Aug. 10, 2000, pp. 605-608.
IDT—Integrated DNA Technologies. OligoAnalyzer 3.1. Web. Retrieved from <http://www.idtdna.com/calc/analyzer> on Nov. 19, 2014.
NUPACK—Nucleic Acid Package. Web. Retrieved from <http://www.nupack.org> on Nov. 19, 2014.
GeneLink. *Gene Assays & SPCT*. Web. Retrieved from <http://genelink.com> on Nov. 19, 2014.
*Undecagold*. Nanoprobes. Revised 1.1. 2 pgs. Mar. 2000.
*Goldenhance*. Nanoprobes. Revised 1.5. 3 pgs. Oct. 2013.
Non-Final Office Action issued for U.S. Appl. No. 13/848,687, filed Mar. 21, 2013 in the name of Si-ping Han et al. mailed on Mar. 9, 2015.
Non-Final Office Action issued for U.S. Appl. No. 14/093,387, filed Nov. 29, 2013 in the name of Si-ping Han et al. mailed on Feb. 26, 2015.
Patterning Definition. Retrieved on Dec. 5, 2014 from the internet: <https://www.google.com/search?q=patterning+definition &spell=1>.
Song, J.H., et al. *Crystal Overgrowth on Gold Nanorods: Tuning the Shape, Facet, Aspect Ratio, and Composition of the Nanorods*. Chem. Eur. J. vol. 11, pp. 910-916. 2005.
Wang, J., et al. *Silver Enhanced Colloidal Gold Electrochemical Stripping Detection of DNA Hybridization*. Langmuir, vol. 17, pp. 5739-5741. 2001.
Gu, Q. et al. *DNA nanowire fabrication*. Nanotechnology, vol. 17, R14-R25. 2006.
Foultier, B., et al. *Comparison of DNA detection methods using nanoparticles and silver enhancement*. IEE Proc.-Nanobiotechnolo., vol. 152(1), pp. 3-12. 2005.
Barish, R.D. et al. *An information-bearing seed for nucleating algorithmic self-assembly*. PNAS, 106, pp. 6054-6059. 2009.
Fu, T.J., et al. *DNA Double-Crossover Molecules*. Biochemistry, 32, pp. 3211-3220. 1993.
Winfree, E., et al. *Design and self-assembly of two-dimensional DNA crystals*. Nature, vol. 394, pp. 539-544. 1998.
Zhang, Y., et al. *Construction of a DNA-Truncated Octahedron*. J. Am. Chem. Soc., vol. 116, pp. 1661-1669. 1994.
Chen, J., et al. *Synthesis from DNA of a molecule with the connectivity of a cube*. Nature, vol. 350, pp. 631-633. Apr. 1991.
Rothemund, P.W.K. *Folding DNA to create nanoscale shapes and patterns*. Nature, vol. 440, pp. 297-302. 2006.
Rothemund, P.W.K. et al. *Algorithmic Self-Assembly of DNA Sierpinski Triangles*. PLoS Biology 2(12), e424, pp. 2041-2053. 2004.
Barish, R.D., et al. *Two Computational Primitives for Algorithmic Self-Assembly: Copying and Counting*. Nano Letters, vol. 5(12), pp. 2586-2592. 2005.
Yan, H., et al. *Directed nucleation assembly of DNA tile complexes for barcode-patterned lattices*. Proc. Natl. Acad. Sci., vol. 100(14), pp. 8103-8108. 2003.
Schulman, R. et al. *Programmable Control of Nucleation for Algorithmic Self-assembly*. DNA Computing 10. Springer-Verlag: Berlin, Heidelberg, pp. 319-328. 2005.
Winfree-E. *Self-healing Tile Sets*, In Nanotechnology: Science and Computation, pp. 55-78. 2006.
Exiqon. *LNA™ Oligo Tools and Design Guidelines*. Web. Retrieved from <https://www.exiqon.com/oligo-tools> on Mar. 16, 2015.
"Worm-like Chain." Wikipedia: The Free Encyclopedia. Wikimedia Foundation, Inc. Web. Retrieved from < http://en.wikipedia.org/wiki/Worm-like_chain> on Mar. 26, 2015.

(56) References Cited

OTHER PUBLICATIONS

"Int Cy5™.".IDT—Integrated DNA Technologies. Web. Retrieved from <http://www.idtdna.com/site/Catalog/Modifications/Product/1476> on Mar. 26, 2015.
"The mfold Web Server." The RNA Institute College of Arts and Sciences. Web. Retrieved from <http://mfold.rna.albany.edu/?q=mfold> on Mar. 26, 2015.
"Sfold." Software for Statistical Folding of Nucleic Acids and Studies of Regulatory RNAs. Web. Retrieved from <http://sfold.wadsworth.org/cgi-bin/index.pl> on Mar. 26, 2015.
Diao, J.J. et al. "Self assembled nanoparticle wires by discontinuous vertical colloidal deposition." Applied Physics Letters, vol. 87, 103113, pp. 1-3 (2005).
"Divalent." Wikipedia: The Free Encyclopedia. Wikimedia Foundation, Inc. Web. Retrieved from <http://en.wikipedia.org/wiki/Divalent> on Mar. 16, 2015.
Northern, D.B.L. et al. "Atomic Force Microscopy of Mica Surface After Ion Replacement." Proceedings of the 49th Annual Meeting of the Electron Microscopy Society of America. San Francisco Press, Inc.: San Francisco. 1991.
Scheibel, T. et al. "Conducting nanowires built by controlled self-assembly of amyloid fibers and selective metal deposition." PNAS, vol. 100(8), pp. 4527-4532. 2003.
Seeman, N.C. "DNA in a material world." Nature, vol. 421, pp. 427-431. 2003.
Rothemund, P.W.K. "Folding DNA to create nanoscale shapes and patterns." Nature, vol. 440, pp. 297-302. 2006.
Castello, A. et al. "Insights into RNA Biology from an Atlas of Mammalian mRNA-Binding Proteins." Cell, vol. 149, pp. 1393-1406. 2012.
Chen, H. et al. "Ionic strength-dependent persistence lengths of single-stranded RNA and DNA." PNAS, vol. 109(3), pp. 799-804. 2012.
Delebecque, C.J. et al. "Organization of Intracellular Reactions with Rationally Designed RNA Assemblies." Science, vol. 333, pp. 470-474. 2011.
Delebecque, C.J. et al. "Supporting Online Material for Organization of Intracellular Reactions with Rationally Designed RNA Assemblies." Science, vol. 333, S1-S27. 2011.
Ding, Y. et al. "Sfold web server for statistical folding and rational design of nucleic acids." Nucleic Acids Research, vol. 32, W135-W141. 2004.
Geary, C. et al. "A single-stranded architecture for cotranscriptional folding of RNA nanostructures." Science, vol. 345, pp. 799-804. 2014.
Gohlke, C. et al. "Kinking of DNA and RNA helices by bulged nucleotides observed by fluorescence resonance energy transfer." Proc. Natl. Acad. Sci., vol. 91, pp. 11660-11664. 1994.
Hochrein, L.M. et al. Conditional Dicer Substrate Formation via Shape and Sequence Transduction with Small Conditional RNAs. Journal of the American Chemical Society, vol. 135, pp. 17322-17330. 2013.
Kahan, M. et al. "Towards molecular computers that operate in a biological environment." Physica D, vol. 237, pp. 1165-1172. 2008.
Kertesz, M. et al. "Genome-wide Measurement of RNA Secondary Structure in Yeast." Nature, vol. 467, pp. 103-107. 2010.
Lu, J. et al. "Iron-binding activity of human iron-sulfur cluster assembly protein hIscA1." Biochem. vol. 428, pp. 125-131. 2010.
Mizukoshi, T. et al. "Structural study of DNA duplexes containing the (6-4) photoproduct by fluorescence resonance of transfer." Nucleic Acids Research, vol. 29(24), pp. 4948-4954. 2001.
Pettersen, E.F. et al. "UCSF Chimera—A Visualization System for Exploratory Research and Analysis." J. Comput. Chem, vol. 25, pp. 1605-1612. 2004.
Rapaport, D.C. "The art of molecular dynamics simulation." Cambridge University Press. 2004. 13 pgs.
Scherer, L.J. "Optimization and characterization of tRNA-shRNA expression constructs." Nucleic Acids Research, vol. 35(8), pp. 2620-2628. 2007.
Srinivas, N. et al. "On the biophysics and kinetics of toehold-mediated DNA strand displacement." Nucleic Acids Research, vol. 41(22), pp. 10641-10658. 2013.
Tan, R. et al. "Structural variety of arginine-rich RNA-binding peptides." Proc. Natl. Acad. Sci. vol. 92, pp. 5282-5286. 1995.
Watts, J.M. et al. "Architecture and Secondary Structure of an Entire HIV-1 RNA Genome." Nature, vol. 460, pp. 711-716. 2009.
Zhang, D. Y. et al. "Dynamic DNA nanotechnology using strand-displacement reactions." Nature, vol. 3, pp. 103-113. 2011.
Zhang, F. et al. "Structureal DNA Nanotechnology: State of the Art and Future Perspective." Journal of the American Chemical Society, vol. 136, pp. 11198-11211. 2014.
Dreyfuss, G., et al. "Messenger-RNA-binding proteins and the messages they carry." Nat. Rev. Mol. Cell Biol., vol. 3, pp. 195-205. 2002.
Yusupov, M. M., et al. "Crystal structure of the ribosome at 5.5 A resolution." Science, vol. 292, pp. 883-896. 2001.
Douglas, S. M., et al. "A Logic-Gated Nanorobot for Targeted Transport of Molecular Payloads." Science, vol. 335, pp. 831-834. 2012.
Green, L. S., et al. "Inhibitory DNA Ligands to Platelet-Derived Growth Factor B-Chain." *Biochemistry* vol. 35, pp. 14413-14424, (1996).
Kienberger, F., et al. "Static and Dynamical Properties of Single Poly(Ethylene Glycol) Molecules Investigated by Force Spectrocopy." Single Molecules, vol. 1, pp. 123-128. 2000.
Lilley, D. M. et al. "Fluorescence resonance energy transfer as a structural tool for nucleic acids." Current Opinion in Chemical Biology, vol. 4, pp. 507-517. 2000.
Fürtig, B., et al. "Time-Resolved NMR Studies of RNA Folding." Biopolymers, vol. 86, pp. 360-383. 2007.
Varani, G., et al. NMR Investigation of RNA structure. Progress in Nuclear Magnetic Resonance Spectroscopy, vol. 29, pp. 51-127. 1996.
Russell, R. et al. "Small angle X-ray scattering reveals a compact intermediate in RNA folding." Nat Struct Mol Biol, vol. 7, pp. 367-370. 2000.
Lipfert, J. et al. "Small-Angle X-Ray Scattering from RNA, Proteins, and Protein Complexes." Annual Review of Biophysics and Biomolecular Structure. vol. 36, 307-327. 2007.
Takada, S. "Coarse-grained molecular simulations of large biomolecules." Current Opinion in Structural Biology, vol. 22, pp. 130-137. 2012.
Pascal, T. A., et al. "Role of Specific Cations and Water Entropy on the Stability of Branched DNA Motif Structures." The Journal of Physical Chemistry B, vol. 116, pp. 12159-12167. 2012.
Sim, A. Y. L., et al. "Modeling nucleic acids." Current Opinion in Structural Biology, vol. 22, pp. 273-278. 2012.
Dragan, A. I. Use of Fluorescence Resonance Energy Transfer (FRET) in Studying Protein-Induced DNA Bending. Methods in Enzymology. vol. 450 (Eds Brand Ludwig & L. Johnson Michael), Chapter 9, pp. 185-199. Academic Press. 2008.
Bassi, G.S. et al. "Ion-Induced folding of the hammerhead ribozyme: a fluorescence resonance energy transfer study." The EMBO Journal, vol. 16, pp. 7481-7489. 1997.
Houseley, J., et al. RNA-quality control by the exosome. Nat Rev Mol Cell Biol, vol. 7, pp. 529-539 2006.
Tinland, B. et al. "Persistence Length of Single-Stranded DNA." Macromolecules, vol. 30, pp. 5763-5765. 1997.
Restriction Requirement issued for U.S. Appl. No. 11/978,219, filed Oct. 26, 2007 filed in the name of Si-Ping Han et al. Mailed on Jun. 4, 2014.
Non-Final Office Action issued for U.S. Appl. No. 11/978,219, filed Oct. 26, 2007 filed in the name of Si-Ping Han et al. Mailed on Sep. 30, 2014.
Notice of Allowance issued for U.S. Appl. No. 13/848,687, filed Mar. 21, 2013 in the name of Si-ping Han. Mail date: Jul. 30, 2015.
Restriction Requirement issued for U.S. Appl. No. 14/882,346, filed Oct. 13, 2015 in the name of Si-ping Han. Mail date: Mar. 1, 2016.
Non-Final Office Action issued for U.S. Appl. No. 14/882,346, filed Oct. 13, 2015 in the name of Si-ping Han. Mail date: Jun. 22, 2016.
Notice of Allowance issued for U.S. Appl. No. 14/093,387, filed Nov. 29, 2013 in the name of Si-ping Han: Mail date: Jun. 5, 2015.

(56) References Cited

OTHER PUBLICATIONS

Notice of Allowability issued for U.S. Appl. No. 14/093,387, filed Nov. 29, 2013 in the name of Si-ping Han: Mail date: Jul. 2, 2015.
Final Office Action issued for U.S. Appl. No. 11/978,219, filed Oct. 26, 2007 in the name of Si-ping Han: Mail date: Jun. 1, 2015.
Ford et al. "Platinated DNA as Precursors to Templated Chains of Metal Nanoparticles" *Adv. Mater.* (Dec. 2001) 13(23): 1793-1797.
Cai et al. "Electrochemical detection of DNA hybridization based on silver-enhanced gold nanoparticle label" *Analytica Chimica Acta* (Jul. 2002) 469: 165-172.
Gu et al. "Cobalt metallization of DNA: toward magnetic nanowires" *Nanotechnology* (Jun. 2005) 16:1358-1363.
Non-Final Office Action issued for U.S. Appl. No. 11/978,219, filed Oct. 26, 2007 in the name of Si-ping Han: Mail date: Apr. 4, 2016.
Park et al. "Three-Helix Bundle DNA Tiles Self-Assemble into 2D Lattice or 1D Templates for Silver Nanowires." *Nano Letters.* (Feb. 2005). 5(4):693-696 and Supporting Information.
Braun et al. "DNA-templated assembly and electrode attachment of a conducting silver wire." *Nature.* (Feb. 1998) 391 :775-778.
Appasani "RNA Interference Technology From Basic Science to Drug Development" (2005) Cambridge University Press, p. 2.
Cheng, "Advanced Delivery and Therapeutic Applications of RNAi" (2013) Wiley. Preface.
Collingwood et al., "Chemical Modification Patterns Compatible with High Potency Dicer-Substrate Small Interfering RNAs." (Apr. 2008) *Oligonucleotides* 18:187-200.
Taxman "siRNA Design: Methods and Protocols." (Oct. 2012) *Humana Press.* Abstract.
Engels "Gene Silencing by Chemically Modified siRNAs" (Mar. 2013) *New Biotechnology* 30(3): 302-307.
Akinc et al. "Targeted Delivery of RNAi Therapeutics with Endogenous and Exogenous Ligand-Based Mechanisms" Molecular Therapy, vol. 18, No. 7, Jul. 2010, pp. 1357-1364.
Amarzguioui et al. "Principles of Dicer Substrate (D-siRNA) Design and Function" Methods in Molecular Biology, vol. 442, 2008, 8 pages.
Amarzguioui et al. "Rational design and in vitro and in vivo delivery of Dicer substrate siRNA" Nature Protocols, vol. 1, No. 2, 2006, pp. 508-517.
Birmingham et al. "A protocol for designing siRNAs with high functionality and specificity" Nature Protocols, vol. 2, No. 9, Aug. 23, 2007, pp. 2068-2078.
Boudreau et al. "Rational Design of Therapeutic siRNAs: Minimizing Off-targeting Potential to Improve the Safety of RNAi Therapy for Huntington's Disease" from Molecular Therapy, vol. 19, No. 12, Dec. 2011, 9 pages.
Coelho et al. "Safety and Efficacy of RNAi Therapy for Transthyretin Amyloidosis" New England Journal of Medicine, vol. 369, No. 9, Aug. 29, 2013, pp. 819-829.
Collingwood et al. "Chemical Modification Patterns Compatible with High Potency Dicer-Substrate Small Interfering RNAs" Oligonucleotides, vol. 18, 2008, pp. 187-200.
Fitzgerald et al. "Effect of an RNA interference drug on the synthesis of proprotein convertase subtilisin/kexin type 9 (PCSK9) and the concentration of serum LDL cholesterol in healthy volunteers: a randomized, single-blind, placebo-controlled, phase 1 trial" Lancet, vol. 383, Jan. 4, 2014, pp. 60-68.
Ford, W.E. et al. "Platinated DNA as Precursors to Templated Chains of Metal Nanoparticles." Advanced Materials. vol. 13 (23), 2001, pp. 1793-1797.
Gilleron et al. "Image-based analysis of lipid nanoparticle-mediated siRNA delivery, intracellular trafficking and endosomal escape" Nature Biotechnology, vol. 31, No. 7, Jul. 2013, pp. 638-649.
Jayaraman et al. "Maximizing the Potency of siRNA Lipid Nanoparticles for Hepatic Gene Silencing In Vivo" Angewandte Communications International Edition, vol. 51, Jul. 10, 2012, pp. 8529-8533.
Judge et al. "Design of Noninflammatory Synthetic siRNA Mediating Potent Gene Silencing in Vivo" Molecular Therapy, vol. 13, No. 3, Mar. 2006, pp. 494-505.
Kanasty et al. "Delivery materials for siRNA therapeutics" Nature Materials, vol. 12, Nov. 2013, pp. 967-977.
Maier et al. "Biodegradable Lipids Enabling Rapidly Eliminated Lipid Nanoparticles for Systemic Delivery of RNAi Therapeutics" Molecular Therapy, vol. 21, No. 8, Aug. 2013, pp. 1570-1578.
Nair et al. "Multivalent N-Acetylgalactosamine-Conjugated siRNA Localizes in Hepatocytes and Elecits Robust RNAi-Mediated Gene Silencing" Journal of the American Chemical Society, vol. 136, Dec. 1, 2014, pp. 16958-16961.
Naito et al. "Designing Functional siRNA with Reduced Off-Target Effects" Methods of Molecular Biology, vol. 942, 2013, pp. 57-68.
Nakayama et al. "Harnessing a Physiologic Mechanism for siRNA Delivery With Mimetic Lipoprotein Particles" Molecular Therapy, vol. 20, No. 8, Aug. 2012, pp. 1582-1589.
IDS Technologies (2011) "RNA Interference (RNAi) and DsiRNAs" 9 pages.
Reynolds et al. "Rational siRNA design for RNA interference" Nature Biotechnology, vol. 22, No. 3, Mar. 2004, pp. 326-330.
Sahay et al. "Efficiency of siRNA delivery by lipid nanoparticles is limited by endocytic recycling" Nature Biotechnology, vol. 31, No. 7, Jul. 2013, pp. 653-658 + 3 supplemental pages.
Sehgal et al. "Tissue-specific gene silencing monitored in circulating RNA" RNA, vol. 20, No. 2, Dec. 19, 2013, 7 pages.
Semple et al. "Rational design of cationic lipids for siRNA delivery" Nature Biotechnology, vol. 28, No. 2, Feb. 2010, pp. 172-176 + 2 supplemental pages.
Shukla et al. "Exploring Chemical Modifications for siRNA Therapeutics: A Structural and Functional Outlook" ChemMedChem, vol. 5, 2010, pp. 328-349.
Tafer et al. "The impact of target site accessibility on the design of effective siRNAs" Nature Biotechnology, vol. 26, No. 5, May 2008, pp. 578-583.
Wang et al. "Delivery of siRNA Therapeutics: Barriers and Carriers" AAPS Journal, vol. 12, No. 4, Dec. 2010, pp. 492-503.
Yakovchuk, P. et al. "Base-stacking and base-pairing contributions into thermal stability of the DNA double helix Nucleic Acids Research," 2006, vol. 34, No. 2, pp. 564-574.
Zhou et al. "Nanoparticle-Based Delivery of RNAi Therapeutics: Progress and Challenges" Pharmaceuticals, vol. 6, Jan. 16, 2013, pp. 85-107.
Final Office Action for U.S. Appl. No. 14/882,346, filed Oct. 13, 2015. Mail Date: Feb. 6, 2017. 15 pages.
Notice of Allowance for U.S. Appl. No. 14/093,387, filed Nov. 29, 2013. Mail Date: Jun. 5, 2015. 12 pages.
Final Office Action for U.S. Appl. No. 11/978,219, filed Oct. 26, 2007. Mail Date: Sep. 22, 2016. 14 pages.
Notice of Allowance for U.S. Appl. No. 11/978,219, filed Oct. 26, 2007 Mail Date: Jan. 26, 2017. 11 pages.

* cited by examiner

Distance measurements

Distance measurements

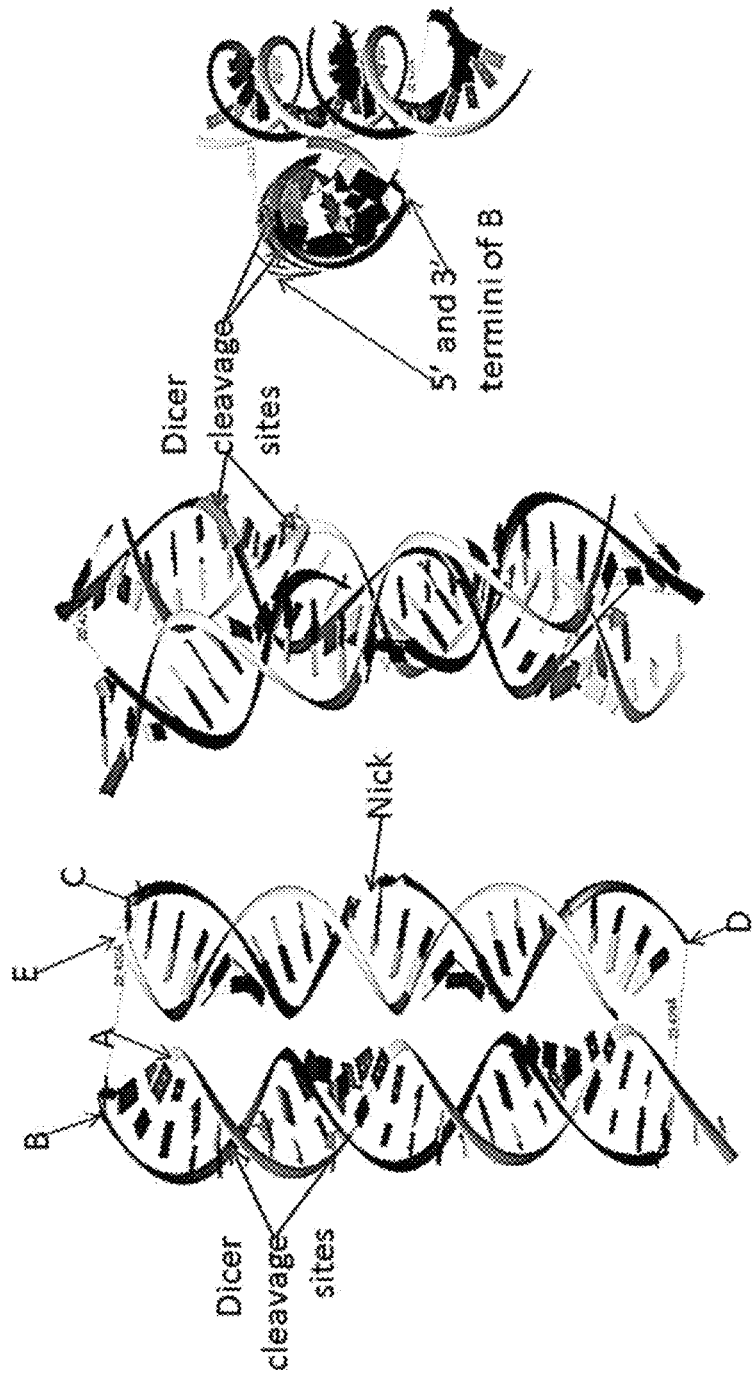

New

Old m: 2'-O-methyl RNA  NH2: Primary amine  PEG linker
+: LNA  ✻ Phosphorothioate  C3 linker
★ Inverted dT

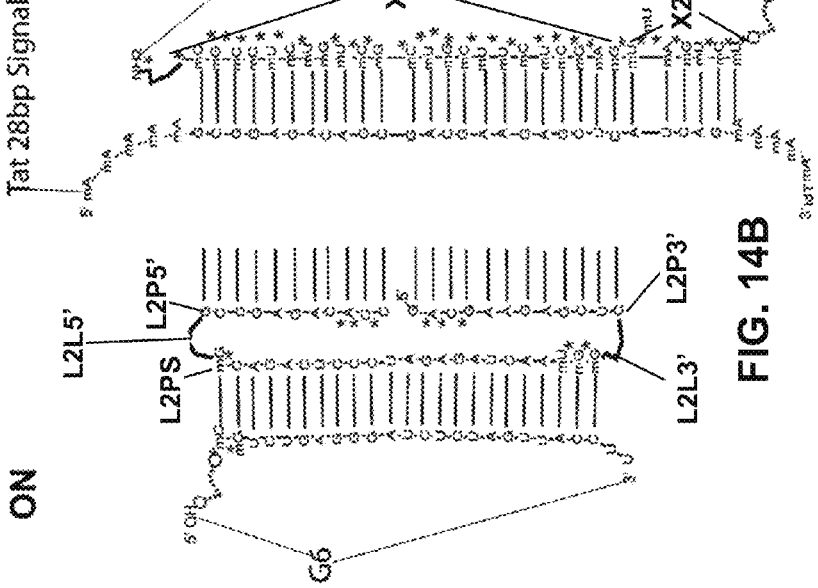
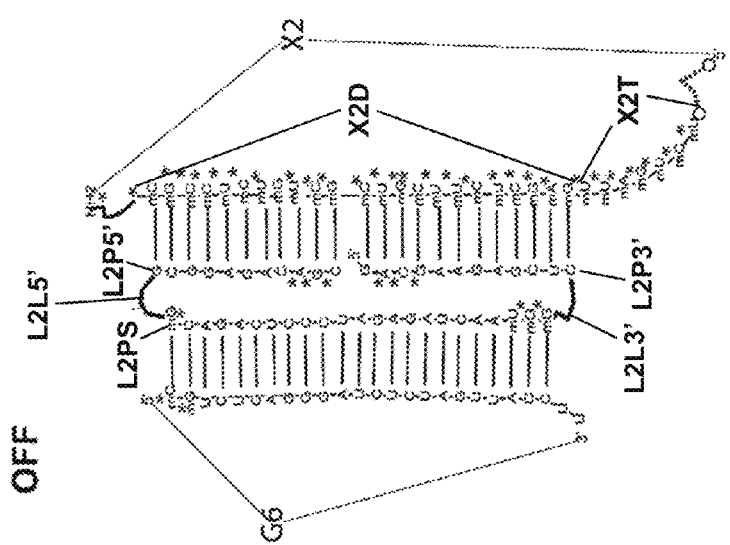
FIG. 14A
FIG. 14B

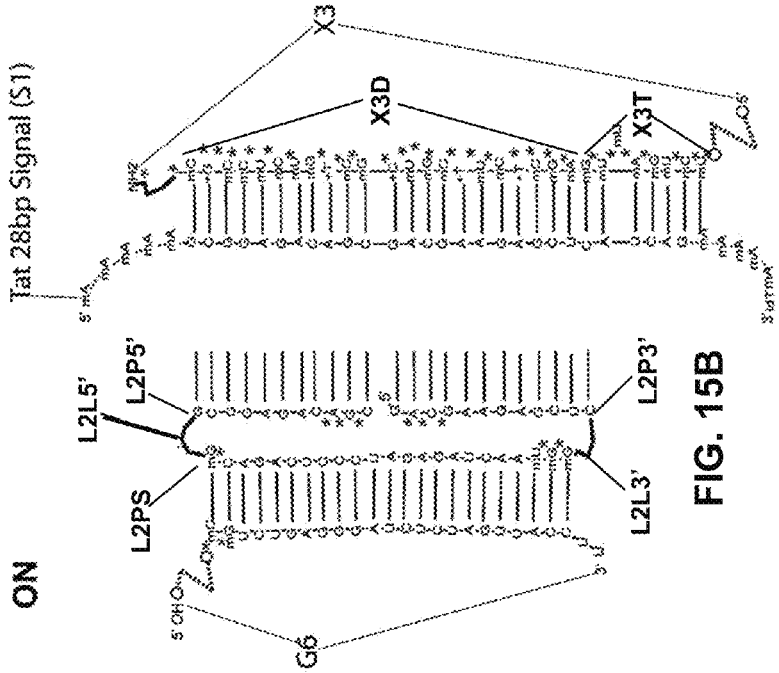
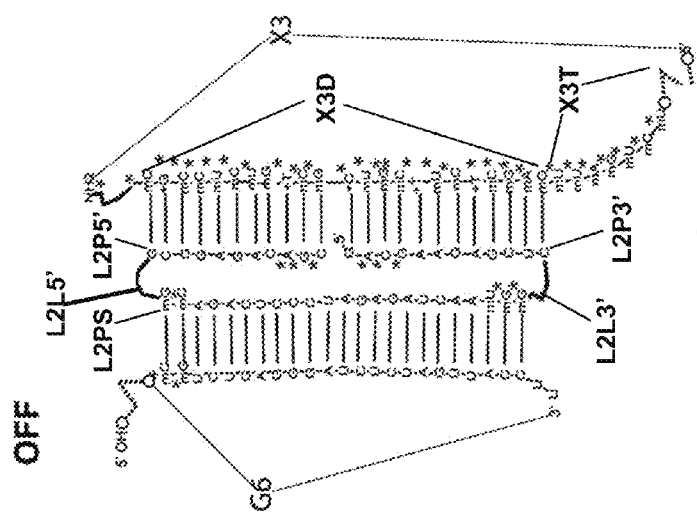
FIG. 15B
FIG. 15A

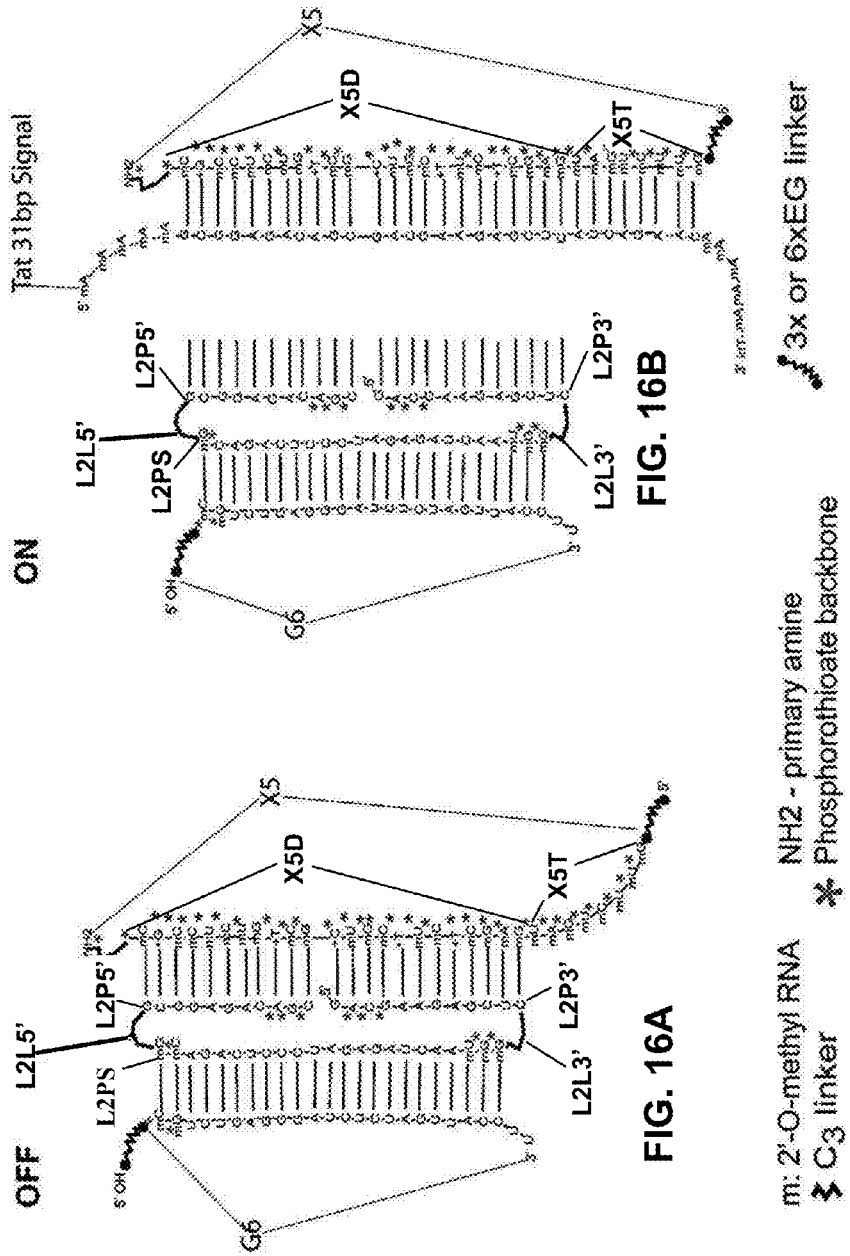

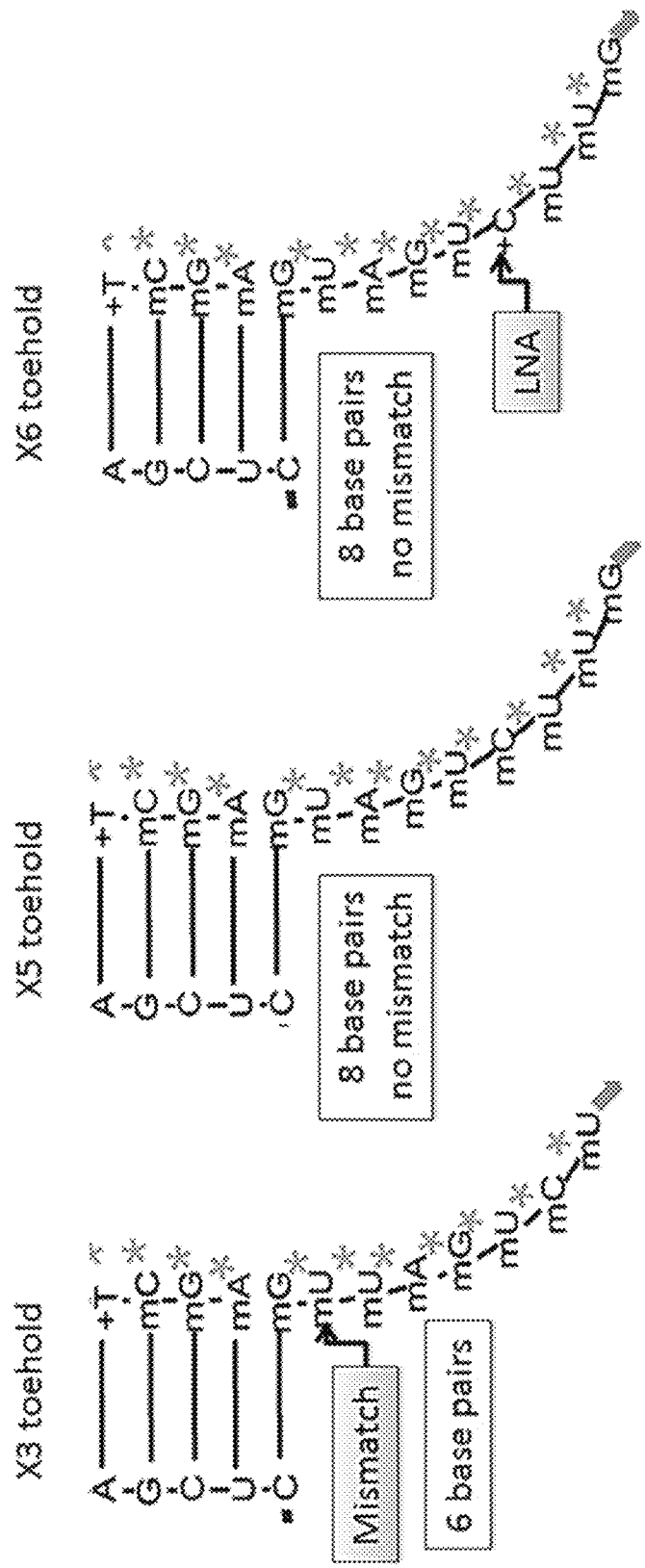

m: 2'-O-methyl RNA    NH2: Primary amine    ∕ PEG linker
+: LNA                ✱ Phosphorothioate    ≸ C3 linker

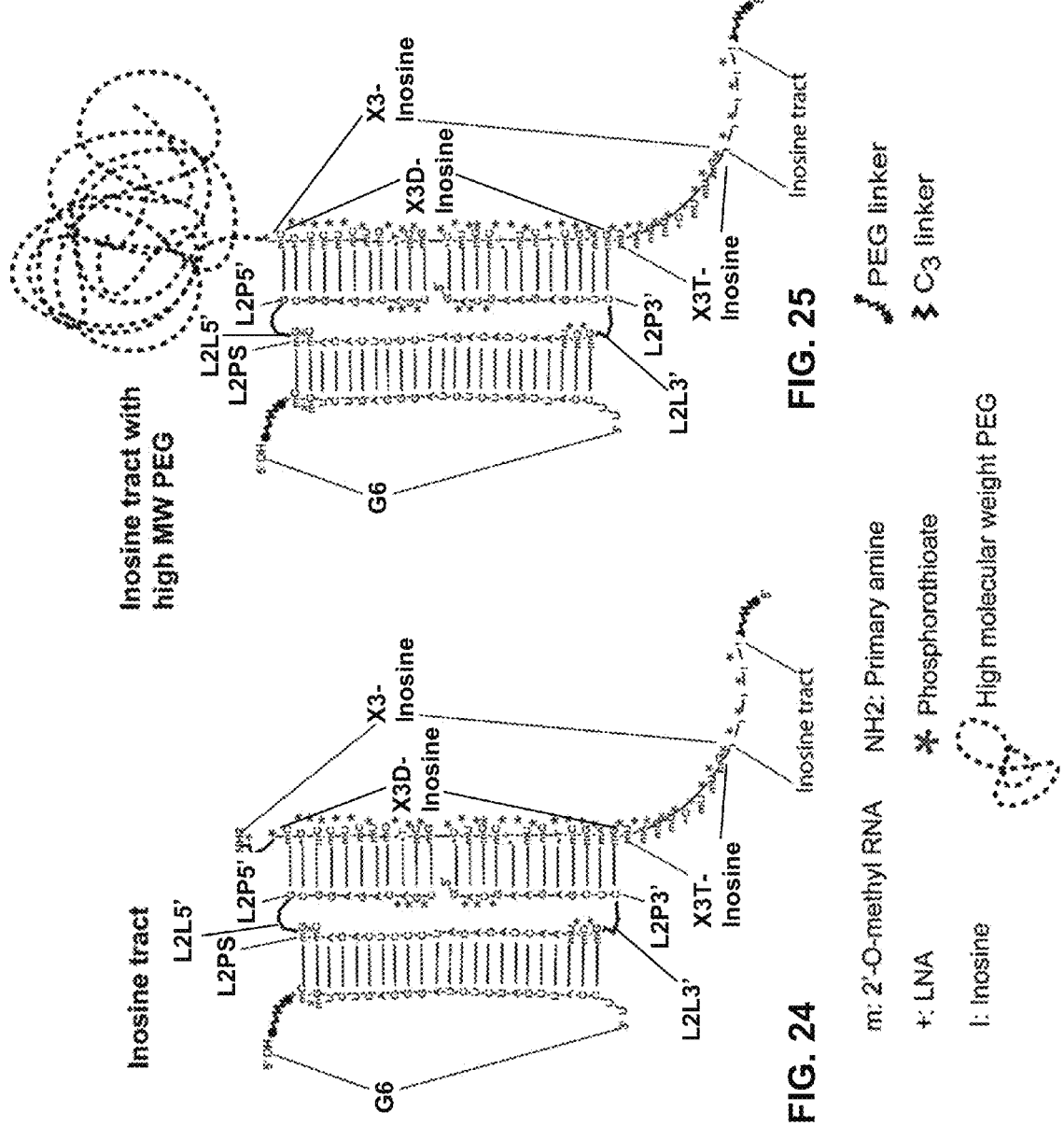

SEQUENCE LISTING

```
<160> NUMBER OF SEQ ID NOS: 118

<210> SEQ ID NO 1
<211> LENGTH: 25
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: modified_base
<222> LOCATION: (1)..(1)
<223> OTHER INFORMATION: cm
<220> FEATURE:
<221> NAME/KEY: misc_feature
<222> LOCATION: (1)..(2)
<223> OTHER INFORMATION: phosphorothioate backbone
<220> FEATURE:
<221> NAME/KEY: misc_feature
<222> LOCATION: (1)..(1)
<223> OTHER INFORMATION: (PEG) polyethylene glycol linker attached to 5'
      end of SEQ ID NO: 1
<220> FEATURE:
<221> NAME/KEY: modified_base
```

-continued

```
<222> LOCATION: (2)..(2)
<223> OTHER INFORMATION: gm

<400> SEQUENCE: 1
cgucugaggg aucucuaguu accuu                                              25

<210> SEQ ID NO 2
<211> LENGTH: 12
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(4)
<223> OTHER INFORMATION: phosphorothioate backbone
<220> FEATURE:
<221> NAME/KEY: misc_feature
<222> LOCATION: (12)..(12)
<223> OTHER INFORMATION: C3 linker attached to 5' end of SEQ ID NO: 3

<400> SEQUENCE: 2
gacgaagagc uc                                                            12

<210> SEQ ID NO 3
<211> LENGTH: 23
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: C3 linker attached to 3' end of SEQ ID NO: 2
<220> FEATURE:
<221> NAME/KEY: misc_feature
<222> LOCATION: (1)..(3)
<223> OTHER INFORMATION: phosphorothioate backbone
<220> FEATURE:
<221> NAME/KEY: modified_base
<222> LOCATION: (1)..(2)
<223> OTHER INFORMATION: gm
<220> FEATURE:
<221> NAME/KEY: modified_base
<222> LOCATION: (3)..(3)
<223> OTHER INFORMATION: um
<220> FEATURE:
<221> NAME/KEY: misc_feature
<222> LOCATION: (21)..(23)
<223> OTHER INFORMATION: phosphorothioate backbone
<220> FEATURE:
<221> NAME/KEY: modified_base
<222> LOCATION: (22)..(22)
<223> OTHER INFORMATION: cm
<220> FEATURE:
<221> NAME/KEY: misc_feature
<222> LOCATION: (23)..(23)
<223> OTHER INFORMATION: C3 linker attached to 5' end of SEQ ID NO: 4
<220> FEATURE:
<221> NAME/KEY: modified_base
<222> LOCATION: (23)..(23)
<223> OTHER INFORMATION: gm

<400> SEQUENCE: 3
gguaacuaga gaucccucag acg                                                23

<210> SEQ ID NO 4
<211> LENGTH: 11
<212> TYPE: DNA
<213> ORGANISM: Artificial Sequence
<220> FEATURE:
<223> OTHER INFORMATION: Synthetic Polynucleotide
<220> FEATURE:
```

```
<221> NAME/KEY: misc_feature
<222> LOCATION: (1)..(1)
<223> OTHER INFORMATION: C3 linker attached to 3' end of SEQ ID NO: 3
<220> FEATURE:
<221> NAME/KEY: misc_feature
<222> LOCATION: (8)..(11)
<223> OTHER INFORMATION: phosphorothioate backbone

<400> SEQUENCE: 4
gcggagacag c                                                          11

<210> SEQ ID NO 5
<211> LENGTH: 31
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: (PEG) polyethylene glycol linker attached to 5'
      end of SEQ ID NO: 5
<220> FEATURE:
<221> NAME/KEY: misc_feature
<222> LOCATION: (1)..(31)
<223> OTHER INFORMATION: phosphorothioate backbone
<220> FEATURE:
<221> NAME/KEY: modified_base
<222> LOCATION: (1)..(1)
<223> OTHER INFORMATION: gm
<220> FEATURE:
<221> NAME/KEY: modified_base
<222> LOCATION: (2)..(3)
<223> OTHER INFORMATION: um
<220> FEATURE:
<221> NAME/KEY: misc_feature
<222> LOCATION: (4)..(4)
<223> OTHER INFORMATION: locked nucleic acid (LNA) base
<220> FEATURE:
<221> NAME/KEY: modified_base
<222> LOCATION: (5)..(5)
<223> OTHER INFORMATION: um
<220> FEATURE:
<221> NAME/KEY: modified_base
<222> LOCATION: (6)..(6)
<223> OTHER INFORMATION: gm
<220> FEATURE:
<221> NAME/KEY: modified_base
<222> LOCATION: (7)..(7)
<223> OTHER INFORMATION: 2'-O-methyl adenosine
<220> FEATURE:
<221> NAME/KEY: modified_base
<222> LOCATION: (8)..(8)
<223> OTHER INFORMATION: um
<220> FEATURE:
<221> NAME/KEY: modified_base
<222> LOCATION: (9)..(9)
<223> OTHER INFORMATION: gm
<220> FEATURE:
<221> NAME/KEY: modified_base
<222> LOCATION: (10)..(10)
<223> OTHER INFORMATION: 2'-O-methyl adenosine
<220> FEATURE:
<221> NAME/KEY: modified_base
<222> LOCATION: (11)..(11)
<223> OTHER INFORMATION: gm
<220> FEATURE:
<221> NAME/KEY: modified_base
<222> LOCATION: (12)..(12)
<223> OTHER INFORMATION: cm
<220> FEATURE:
<221> NAME/KEY: misc_feature
<222> LOCATION: (13)..(13)
<223> OTHER INFORMATION: locked nucleic acid (LNA) base
<220> FEATURE:
<221> NAME/KEY: modified_base
<222> LOCATION: (14)..(14)
```

```
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: misc_feature
<222> LOCATION: (16)..(16)
<223> OTHER INFORMATION: locked nucleic acid (LNA) base
<220> FEATURE:
<221> NAME/KEY: modified_base
<222> LOCATION: (17)..(17)
<223> OTHER INFORMATION: cm
<220> FEATURE:
<221> NAME/KEY: modified_base
<222> LOCATION: (18)..(18)
<223> OTHER INFORMATION: gm
<220> FEATURE:
<221> NAME/KEY: modified_base
<222> LOCATION: (19)..(19)
<223> OTHER INFORMATION: um
<220> FEATURE:
<221> NAME/KEY: misc_feature
<222> LOCATION: (20)..(20)
<223> OTHER INFORMATION: locked nucleic acid (LNA) base
<220> FEATURE:
<221> NAME/KEY: modified_base
<222> LOCATION: (21)..(21)
<223> OTHER INFORMATION: gm
<220> FEATURE:
<221> NAME/KEY: modified_base
<222> LOCATION: (22)..(22)
<223> OTHER INFORMATION: cm
<220> FEATURE:
<221> NAME/KEY: misc_feature
<222> LOCATION: (23)..(23)
<223> OTHER INFORMATION: locked nucleic acid (LNA) base
<220> FEATURE:
<221> NAME/KEY: modified_base
<222> LOCATION: (24)..(24)
<223> OTHER INFORMATION: gm
<220> FEATURE:
<221> NAME/KEY: modified_base
<222> LOCATION: (25)..(25)
<223> OTHER INFORMATION: um
<220> FEATURE:
<221> NAME/KEY: modified_base
<222> LOCATION: (27)..(27)
<223> OTHER INFORMATION: um
<220> FEATURE:
<221> NAME/KEY: modified_base
<222> LOCATION: (28)..(29)
<223> OTHER INFORMATION: cm
<220> FEATURE:
<221> NAME/KEY: misc_feature
<222> LOCATION: (30)..(30)
<223> OTHER INFORMATION: locked nucleic acid (LNA) base
<220> FEATURE:
<221> NAME/KEY: misc_feature
<222> LOCATION: (31)..(31)
<223> OTHER INFORMATION: C3 linker attached to primary amine group
<220> FEATURE:
<221> NAME/KEY: modified_base
<222> LOCATION: (31)..(31)
<223> OTHER INFORMATION: cm

<400> SEQUENCE: 5
guucugauga gctcutcguc gctgucuccg c                               31

<210> SEQ ID NO 6
<211> LENGTH: 8
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
```

```
<222> LOCATION: (1)..(1)
<223> OTHER INFORMATION: (PEG) polyethylene glycol linker attached to 5'
      end of SEQ ID NO: 6
<220> FEATURE:
<221> NAME/KEY: modified_base
<222> LOCATION: (1)..(1)
<223> OTHER INFORMATION: gm
<220> FEATURE:
<221> NAME/KEY: misc_feature
<222> LOCATION: (1)..(8)
<223> OTHER INFORMATION: phosphorothioate backbone
<220> FEATURE:
<221> NAME/KEY: modified_base
<222> LOCATION: (2)..(3)
<223> OTHER INFORMATION: um
<220> FEATURE:
<221> NAME/KEY: misc_feature
<222> LOCATION: (4)..(4)
<223> OTHER INFORMATION: locked nucleic acid (LNA) base
<220> FEATURE:
<221> NAME/KEY: modified_base
<222> LOCATION: (5)..(5)
<223> OTHER INFORMATION: um
<220> FEATURE:
<221> NAME/KEY: modified_base
<222> LOCATION: (6)..(6)
<223> OTHER INFORMATION: gm
<220> FEATURE:
<221> NAME/KEY: misc_feature
<222> LOCATION: (7)..(7)
<223> OTHER INFORMATION: 2'-O-methyl adenosine
<220> FEATURE:
<221> NAME/KEY: modified_base
<222> LOCATION: (8)..(8)
<223> OTHER INFORMATION: um

<400> SEQUENCE: 6 guucugau                                                                 8

<210> SEQ ID NO 7
<211> LENGTH: 23
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: modified_base
<222> LOCATION: (1)..(1)
<223> OTHER INFORMATION: gm
<220> FEATURE:
<221> NAME/KEY: misc_feature
<222> LOCATION: (1)..(23)
<223> OTHER INFORMATION: phosphorothioate backbone
<220> FEATURE:
<221> NAME/KEY: misc_feature
<222> LOCATION: (2)..(2)
<223> OTHER INFORMATION: 2'-O-methyl adenosine
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (4)..(4)
<223> OTHER INFORMATION: cm
<220> FEATURE:
<221> NAME/KEY: misc_feature
<222> LOCATION: (5)..(5)
<223> OTHER INFORMATION: locked nucleic acid (LNA) base
<220> FEATURE:
<221> NAME/KEY: modified_base
<222> LOCATION: (6)..(6)
<223> OTHER INFORMATION: cm
<220> FEATURE:
<221> NAME/KEY: modified_base
<222> LOCATION: (7)..(7)
<223> OTHER INFORMATION: um
```

```
<220> FEATURE:
<221> NAME/KEY: misc_feature
<222> LOCATION: (8)..(8)
<223> OTHER INFORMATION: locked nucleic acid (LNA) base
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (10)..(10)
<223> OTHER INFORMATION: gm
<220> FEATURE:
<221> NAME/KEY: modified_base
<222> LOCATION: (11)..(11)
<223> OTHER INFORMATION: um
<220> FEATURE:
<221> NAME/KEY: misc_feature
<222> LOCATION: (12)..(12)
<223> OTHER INFORMATION: locked nucleic acid (LNA) base
<220> FEATURE:
<221> NAME/KEY: modified_base
<222> LOCATION: (13)..(13)
<223> OTHER INFORMATION: gm
<220> FEATURE:
<221> NAME/KEY: modified_base
<222> LOCATION: (14)..(14)
<223> OTHER INFORMATION: cm
<220> FEATURE:
<221> NAME/KEY: misc_feature
<222> LOCATION: (15)..(15)
<223> OTHER INFORMATION: locked nucleic acid (LNA) base
<220> FEATURE:
<221> NAME/KEY: modified_base
<222> LOCATION: (16)..(16)
<223> OTHER INFORMATION: gm
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(18)
<223> OTHER INFORMATION: cm
<220> FEATURE:
<221> NAME/KEY: modified_base
<222> LOCATION: (19)..(19)
<223> OTHER INFORMATION: um
<220> FEATURE:
<221> NAME/KEY: modified_base
<222> LOCATION: (20)..(21)
<223> OTHER INFORMATION: cm
<220> FEATURE:
<221> NAME/KEY: misc_feature
<222> LOCATION: (22)..(22)
<223> OTHER INFORMATION: locked nucleic acid (LNA) base
<220> FEATURE:
<221> NAME/KEY: misc_feature
<222> LOCATION: (23)..(23)
<223> OTHER INFORMATION: C3 linker attached to primary amine group
<220> FEATURE:
<221> NAME/KEY: modified_base
<222> LOCATION: (23)..(23)
<223> OTHER INFORMATION: cm

<400> SEQUENCE: 7
gagctcutcg ucgctgucuc cgc                                              23

<210> SEQ ID NO 8
<211> LENGTH: 25
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(2)
```

```
<223> OTHER INFORMATION: phosphorothioate backbone
<220> FEATURE:
<221> NAME/KEY: misc_feature
<222> LOCATION: (1)..(2)
<223> OTHER INFORMATION: 9s linker attached to 5' end of SEQ ID NO: 8
<220> FEATURE:
<221> NAME/KEY: modified_base
<222> LOCATION: (1)..(1)
<223> OTHER INFORMATION: cm
<220> FEATURE:
<221> NAME/KEY: modified_base
<222> LOCATION: (2)..(2)
<223> OTHER INFORMATION: gm

<400> SEQUENCE: 8
cgucugaggg aucucuaguu accuu                                         25

<210> SEQ ID NO 9
<211> LENGTH: 12
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(6)
<223> OTHER INFORMATION: phosphorothioate backbone
<220> FEATURE:
<221> NAME/KEY: misc_feature
<222> LOCATION: (1)..(6)
<223> OTHER INFORMATION: C3 linker attached to 5' end of SEQ ID NO: 10

<400> SEQUENCE: 9
gacgaagagc uc                                                       12

<210> SEQ ID NO 10
<211> LENGTH: 23
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: C3 linker attached to 3' end of SEQ ID NO: 9
<220> FEATURE:
<221> NAME/KEY: misc_feature
<222> LOCATION: (1)..(3)
<223> OTHER INFORMATION: phosphorothioate backbone
<220> FEATURE:
<221> NAME/KEY: modified_base
<222> LOCATION: (1)..(2)
<223> OTHER INFORMATION: gm
<220> FEATURE:
<221> NAME/KEY: modified_base
<222> LOCATION: (3)..(3)
<223> OTHER INFORMATION: um
<220> FEATURE:
<221> NAME/KEY: misc_feature
<222> LOCATION: (21)..(23)
<223> OTHER INFORMATION: phosphorothioate backbone
<220> FEATURE:
<221> NAME/KEY: modified_base
<222> LOCATION: (22)..(22)
<223> OTHER INFORMATION: cm
<220> FEATURE:
<221> NAME/KEY: misc_feature
<222> LOCATION: (23)..(23)
<223> OTHER INFORMATION: C3 linker attached to 5' end of SEQ ID NO: 11
<220> FEATURE:
<221> NAME/KEY: modified_base
<222> LOCATION: (23)..(23)
<223> OTHER INFORMATION: gm

<400> SEQUENCE: 10
```
gguaacuaga gaucccucag acg                                            23

<210> SEQ ID NO 11
<211> LENGTH: 11
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: C3 linker attached to 3' end of SEQ ID NO: 10
<220> FEATURE:
<221> NAME/KEY: misc_feature
<222> LOCATION: (6)..(11)
<223> OTHER INFORMATION: phosphorothioate backbone

<400> SEQUENCE: 11
gcggagacag c                                                          11

<210> SEQ ID NO 12
<211> LENGTH: 31
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: (PEG) polyethylene glycol linker attached to 5'
      end of SEQ ID NO: 12
<220> FEATURE:
<221> NAME/KEY: misc_feature
<222> LOCATION: (1)..(31)
<223> OTHER INFORMATION: phosphorothioate backbone
<220> FEATURE:
<221> NAME/KEY: modified_base
<222> LOCATION: (1)..(1)
<223> OTHER INFORMATION: gm
<220> FEATURE:
<221> NAME/KEY: modified_base
<222> LOCATION: (2)..(3)
<223> OTHER INFORMATION: um
<220> FEATURE:
<221> NAME/KEY: misc_feature
<222> LOCATION: (4)..(4)
<223> OTHER INFORMATION: locked nucleic acid (LNA) base
<220> FEATURE:
<221> NAME/KEY: modified_base
<222> LOCATION: (5)..(5)
<223> OTHER INFORMATION: um
<220> FEATURE:
<221> NAME/KEY: modified_base
<222> LOCATION: (6)..(6)
<223> OTHER INFORMATION: gm
<220> FEATURE:
<221> NAME/KEY: misc_feature
<222> LOCATION: (7)..(7)
<223> OTHER INFORMATION: 2'-O-methyl adenosine
<220> FEATURE:
<221> NAME/KEY: modified_base
<222> LOCATION: (8)..(8)
<223> OTHER INFORMATION: um
<220> FEATURE:
<221> NAME/KEY: modified_base
<222> LOCATION: (9)..(9)
<223> OTHER INFORMATION: gm
<220> FEATURE:
<221> NAME/KEY: misc_feature
<222> LOCATION: (10)..(10)
<223> OTHER INFORMATION: 2'-O-methyl adenosine
<220> FEATURE:
<221> NAME/KEY: modified_base
<222> LOCATION: (11)..(11)
<223> OTHER INFORMATION: gm -continued

```
<220> FEATURE:
<221> NAME/KEY: modified_base
<222> LOCATION: (12)..(12)
<223> OTHER INFORMATION: cm
<220> FEATURE:
<221> NAME/KEY: misc_feature
<222> LOCATION: (13)..(13)
<223> OTHER INFORMATION: locked nucleic acid (LNA) base
<220> FEATURE:
<221> NAME/KEY: modified_base
<222> LOCATION: (14)..(14)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: misc_feature
<222> LOCATION: (16)..(16)
<223> OTHER INFORMATION: locked nucleic acid (LNA) base
<220> FEATURE:
<221> NAME/KEY: modified_base
<222> LOCATION: (17)..(17)
<223> OTHER INFORMATION: cm
<220> FEATURE:
<221> NAME/KEY: modified_base
<222> LOCATION: (18)..(18)
<223> OTHER INFORMATION: gm
<220> FEATURE:
<221> NAME/KEY: modified_base
<222> LOCATION: (19)..(19)
<223> OTHER INFORMATION: um
<220> FEATURE:
<221> NAME/KEY: misc_feature
<222> LOCATION: (20)..(20)
<223> OTHER INFORMATION: locked nucleic acid (LNA) base
<220> FEATURE:
<221> NAME/KEY: modified_base
<222> LOCATION: (21)..(21)
<223> OTHER INFORMATION: gm
<220> FEATURE:
<221> NAME/KEY: modified_base
<222> LOCATION: (22)..(22)
<223> OTHER INFORMATION: cm
<220> FEATURE:
<221> NAME/KEY: misc_feature
<222> LOCATION: (23)..(23)
<223> OTHER INFORMATION: locked nucleic acid (LNA) base
<220> FEATURE:
<221> NAME/KEY: modified_base
<222> LOCATION: (24)..(24)
<223> OTHER INFORMATION: gm
<220> FEATURE:
<221> NAME/KEY: modified_base
<222> LOCATION: (25)..(25)
<223> OTHER INFORMATION: um
<220> FEATURE:
<221> NAME/KEY: modified_base
<222> LOCATION: (26)..(26)
<223> OTHER INFORMATION: cm
<220> FEATURE:
<221> NAME/KEY: modified_base
<222> LOCATION: (27)..(27)
<223> OTHER INFORMATION: um
<220> FEATURE:
<221> NAME/KEY: modified_base
<222> LOCATION: (28)..(29)
<223> OTHER INFORMATION: cm
<220> FEATURE:
<221> NAME/KEY: misc_feature
<222> LOCATION: (30)..(30)
<223> OTHER INFORMATION: locked nucleic acid (LNA) base
<220> FEATURE:
<221> NAME/KEY: modified_base
<222> LOCATION: (31)..(31)
<223> OTHER INFORMATION: cm
<220> FEATURE:
<221> NAME/KEY: misc_feature
<222> LOCATION: (31)..(31)
```

<223> OTHER INFORMATION: C3 linker attached to primary amine group

<400> SEQUENCE: 12
guucugauga gctcutcguc gctgucuccg c                                      31

<210> SEQ ID NO 13
<211> LENGTH: 30
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: 9s linker attached to 5' end of SEQ ID NO: 13
<220> FEATURE:
<221> NAME/KEY: modified_base
<222> LOCATION: (1)..(1)
<223> OTHER INFORMATION: um
<220> FEATURE:
<221> NAME/KEY: misc_feature
<222> LOCATION: (1)..(30)
<223> OTHER INFORMATION: phosphorothioate backbone
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (3)..(3)
<223> OTHER INFORMATION: um
<220> FEATURE:
<221> NAME/KEY: modified_base
<222> LOCATION: (4)..(4)
<223> OTHER INFORMATION: gm
<220> FEATURE:
<221> NAME/KEY: misc_feature
<222> LOCATION: (5)..(5)
<223> OTHER INFORMATION: 2'-O-methyl adenosine
<220> FEATURE:
<221> NAME/KEY: modified_base
<222> LOCATION: (6)..(7)
<223> OTHER INFORMATION: um
<220> FEATURE:
<221> NAME/KEY: modified_base
<222> LOCATION: (8)..(8)
<223> OTHER INFORMATION: gm
<220> FEATURE:
<221> NAME/KEY: misc_feature
<222> LOCATION: (9)..(9)
<223> OTHER INFORMATION: 2'-O-methyl adenosine
<220> FEATURE:
<221> NAME/KEY: modified_base
<222> LOCATION: (10)..(10)
<223> OTHER INFORMATION: gm
<220> FEATURE:
<221> NAME/KEY: modified_base
<222> LOCATION: (11)..(11)
<223> OTHER INFORMATION: cm
<220> FEATURE:
<221> NAME/KEY: modified_base
<222> LOCATION: (12)..(12)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (14)..(15)
<223> OTHER INFORMATION: um
<220> FEATURE:
<221> NAME/KEY: modified_base
<222> LOCATION: (16)..(16)
<223> OTHER INFORMATION: cm
<220> FEATURE:
<221> NAME/KEY: modified_base
<222> LOCATION: (17)..(17)
<223> OTHER INFORMATION: gm
<220> FEATURE:
<221> NAME/KEY: modified_base
<222> LOCATION: (18)..(18)
<223> OTHER INFORMATION: um
<220> FEATURE:
<221> NAME/KEY: modified_base
<222> LOCATION: (19)..(19)
<223> OTHER INFORMATION: cm
<220> FEATURE:
<221> NAME/KEY: modified_base
<222> LOCATION: (20)..(20)
<223> OTHER INFORMATION: gm
<220> FEATURE:
<221> NAME/KEY: modified_base
<222> LOCATION: (21)..(21)
<223> OTHER INFORMATION: cm
<220> FEATURE:
<221> NAME/KEY: modified_base
<222> LOCATION: (22)..(22)
<223> OTHER INFORMATION: um
<220> FEATURE:
<221> NAME/KEY: modified_base
<222> LOCATION: (23)..(23)
<223> OTHER INFORMATION: gm
<220> FEATURE:
<221> NAME/KEY: modified_base
<222> LOCATION: (24)..(24)
<223> OTHER INFORMATION: um
<220> FEATURE:
<221> NAME/KEY: modified_base
<222> LOCATION: (25)..(25)
<223> OTHER INFORMATION: cm
<220> FEATURE:
<221> NAME/KEY: modified_base
<222> LOCATION: (26)..(26)
<223> OTHER INFORMATION: um
<220> FEATURE:
<221> NAME/KEY: modified_base
<222> LOCATION: (27)..(28)
<223> OTHER INFORMATION: cm
<220> FEATURE:
<221> NAME/KEY: modified_base
<222> LOCATION: (29)..(29)
<223> OTHER INFORMATION: gm
<220> FEATURE:
<221> NAME/KEY: modified_base
<222> LOCATION: (30)..(30)
<223> OTHER INFORMATION: cm
<220> FEATURE:
<221> NAME/KEY: misc_feature
<222> LOCATION: (30)..(30)
<223> OTHER INFORMATION: C3 linker attached to inverted deoxynucleotide
    T

<400> SEQUENCE: 13
ucugauugag cucuucgucg cugucuccgc                                    30

<210> SEQ ID NO 14
<211> LENGTH: 7
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: 9s linker attached to 5' end of SEQ ID NO: 14
<220> FEATURE:
<221> NAME/KEY: misc_feature
<222> LOCATION: (1)..(7)
<223> OTHER INFORMATION: phosphorothioate backbone
<220> FEATURE:
<221> NAME/KEY: modified_base
<222> LOCATION: (1)..(1)
<223> OTHER INFORMATION: um

```
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (3)..(3)
<223> OTHER INFORMATION: um
<220> FEATURE:
<221> NAME/KEY: modified_base
<222> LOCATION: (4)..(4)
<223> OTHER INFORMATION: gm
<220> FEATURE:
<221> NAME/KEY: misc_feature
<222> LOCATION: (5)..(5)
<223> OTHER INFORMATION: 2'-O-methyl adenosine5
<220> FEATURE:
<221> NAME/KEY: modified_base
<222> LOCATION: (6)..(7)
<223> OTHER INFORMATION: um

<400> SEQUENCE: 14 ucugauu                                                                    7

<210> SEQ ID NO 15
<211> LENGTH: 23
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(23)
<223> OTHER INFORMATION: phosphorothioate backbone
<220> FEATURE:
<221> NAME/KEY: modified_base
<222> LOCATION: (1)..(1)
<223> OTHER INFORMATION: gm
<220> FEATURE:
<221> NAME/KEY: misc_feature
<222> LOCATION: (2)..(2)
<223> OTHER INFORMATION: 2'-O-methyl adenosine
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (4)..(4)
<223> OTHER INFORMATION: cm
<220> FEATURE:
<221> NAME/KEY: modified_base
<222> LOCATION: (5)..(5)
<223> OTHER INFORMATION: um
<220> FEATURE:
<221> NAME/KEY: modified_base
<222> LOCATION: (6)..(6)
<223> OTHER INFORMATION: cm
<220> FEATURE:
<221> NAME/KEY: modified_base
<222> LOCATION: (7)..(8)
<223> OTHER INFORMATION: um
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (10)..(10)
<223> OTHER INFORMATION: gm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (12)..(12)
```

```
<223> OTHER INFORMATION: cm
<220> FEATURE:
<221> NAME/KEY: modified_base
<222> LOCATION: (13)..(13)
<223> OTHER INFORMATION: gm
<220> FEATURE:
<221> NAME/KEY: modified_base
<222> LOCATION: (14)..(14)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (16)..(16)
<223> OTHER INFORMATION: gm
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(18)
<223> OTHER INFORMATION: cm
<220> FEATURE:
<221> NAME/KEY: modified_base
<222> LOCATION: (19)..(19)
<223> OTHER INFORMATION: um
<220> FEATURE:
<221> NAME/KEY: modified_base
<222> LOCATION: (20)..(21)
<223> OTHER INFORMATION: cm
<220> FEATURE:
<221> NAME/KEY: modified_base
<222> LOCATION: (22)..(22)
<223> OTHER INFORMATION: gm
<220> FEATURE:
<221> NAME/KEY: misc_feature
<222> LOCATION: (23)..(23)
<223> OTHER INFORMATION: C3 linker attached to inverted deoxynucleotide
      T
<220> FEATURE:
<221> NAME/KEY: modified_base
<222> LOCATION: (23)..(23)
<223> OTHER INFORMATION: cm

<400> SEQUENCE: 15
gagcucuucg ucgcugucuc cgc                                             23

<210> SEQ ID NO 16
<211> LENGTH: 12
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(4)
<223> OTHER INFORMATION: phosphorothioate backbone
<220> FEATURE:
<221> NAME/KEY: misc_feature
<222> LOCATION: (12)..(12)
<223> OTHER INFORMATION: C3 linker attached to 5' end of SEQ ID NO: 17

<400> SEQUENCE: 16
gacgaagagc uc                                                         12

<210> SEQ ID NO 17
<211> LENGTH: 23
<212> TYPE: RNA
<213> ORGANISM: Artificial Sequence
<220> FEATURE:
<223> OTHER INFORMATION: Synthetic Polynucleotide
<220> FEATURE:
```

```
<221> NAME/KEY: misc_feature
<222> LOCATION: (1)..(1)
<223> OTHER INFORMATION: C3 linker attached to 3' end of SEQ ID NO: 16
<220> FEATURE:
<221> NAME/KEY: misc_feature
<222> LOCATION: (1)..(3)
<223> OTHER INFORMATION: phosphorothioate backbone
<220> FEATURE:
<221> NAME/KEY: modified_base
<222> LOCATION: (1)..(2)
<223> OTHER INFORMATION: gm
<220> FEATURE:
<221> NAME/KEY: modified_base
<222> LOCATION: (3)..(3)
<223> OTHER INFORMATION: um
<220> FEATURE:
<221> NAME/KEY: misc_feature
<222> LOCATION: (22)..(23)
<223> OTHER INFORMATION: phosphorothioate backbone
<220> FEATURE:
<221> NAME/KEY: misc_feature
<222> LOCATION: (23)..(23)
<223> OTHER INFORMATION: C3 linker attached to 5' end of SEQ ID NO: 17
<220> FEATURE:
<221> NAME/KEY: modified_base
<222> LOCATION: (23)..(23)
<223> OTHER INFORMATION: gm

<400> SEQUENCE: 17
gguaacuaga gaucccucag acg                                         23

<210> SEQ ID NO 18
<211> LENGTH: 11
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: C3 linker attached to 3' end of SEQ ID NO: 17
<220> FEATURE:
<221> NAME/KEY: misc_feature
<222> LOCATION: (8)..(11)
<223> OTHER INFORMATION: phosphorothioate backbone

<400> SEQUENCE: 18
gcggagacag c                                                      11

<210> SEQ ID NO 19
<211> LENGTH: 30
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: 9s linker attached to 5' end of SEQ ID NO: 19
<220> FEATURE:
<221> NAME/KEY: misc_feature
<222> LOCATION: (1)..(30)
<223> OTHER INFORMATION: phosphorothioate backbone
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (3)..(3)
<223> OTHER INFORMATION: um
```

```
<220> FEATURE:
<221> NAME/KEY: modified_base
<222> LOCATION: (4)..(4)
<223> OTHER INFORMATION: gm
<220> FEATURE:
<221> NAME/KEY: misc_feature
<222> LOCATION: (5)..(5)
<223> OTHER INFORMATION: 2'-O-methyl adenosine
<220> FEATURE:
<221> NAME/KEY: modified_base
<222> LOCATION: (6)..(7)
<223> OTHER INFORMATION: um
<220> FEATURE:
<221> NAME/KEY: modified_base
<222> LOCATION: (8)..(8)
<223> OTHER INFORMATION: gm
<220> FEATURE:
<221> NAME/KEY: misc_feature
<222> LOCATION: (9)..(9)
<223> OTHER INFORMATION: 2'-O-methyl adenosine
<220> FEATURE:
<221> NAME/KEY: modified_base
<222> LOCATION: (10)..(10)
<223> OTHER INFORMATION: gm
<220> FEATURE:
<221> NAME/KEY: modified_base
<222> LOCATION: (11)..(11)
<223> OTHER INFORMATION: cm
<220> FEATURE:
<221> NAME/KEY: modified_base
<222> LOCATION: (12)..(12)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (14)..(15)
<223> OTHER INFORMATION: um
<220> FEATURE:
<221> NAME/KEY: modified_base
<222> LOCATION: (16)..(16)
<223> OTHER INFORMATION: cm
<220> FEATURE:
<221> NAME/KEY: modified_base
<222> LOCATION: (17)..(17)
<223> OTHER INFORMATION: gm
<220> FEATURE:
<221> NAME/KEY: modified_base
<222> LOCATION: (18)..(18)
<223> OTHER INFORMATION: um
<220> FEATURE:
<221> NAME/KEY: modified_base
<222> LOCATION: (19)..(19)
<223> OTHER INFORMATION: cm
<220> FEATURE:
<221> NAME/KEY: modified_base
<222> LOCATION: (20)..(20)
<223> OTHER INFORMATION: gm
<220> FEATURE:
<221> NAME/KEY: modified_base
<222> LOCATION: (21)..(21)
<223> OTHER INFORMATION: cm
<220> FEATURE:
<221> NAME/KEY: modified_base
<222> LOCATION: (22)..(22)
<223> OTHER INFORMATION: um
<220> FEATURE:
<221> NAME/KEY: modified_base
<222> LOCATION: (23)..(23)
<223> OTHER INFORMATION: gm
<220> FEATURE:
<221> NAME/KEY: modified_base
<222> LOCATION: (24)..(24)
<223> OTHER INFORMATION: um
<220> FEATURE:
<221> NAME/KEY: modified_base
<222> LOCATION: (25)..(25)
```

```
<223> OTHER INFORMATION: cm
<220> FEATURE:
<221> NAME/KEY: modified_base
<222> LOCATION: (26)..(26)
<223> OTHER INFORMATION: um
<220> FEATURE:
<221> NAME/KEY: modified_base
<222> LOCATION: (27)..(28)
<223> OTHER INFORMATION: cm
<220> FEATURE:
<221> NAME/KEY: modified_base
<222> LOCATION: (29)..(29)
<223> OTHER INFORMATION: gm
<220> FEATURE:
<221> NAME/KEY: modified_base
<222> LOCATION: (29)..(29)
<223> OTHER INFORMATION: um
<220> FEATURE:
<221> NAME/KEY: misc_feature
<222> LOCATION: (30)..(30)
<223> OTHER INFORMATION: C3 linker attached to 3' end of SEQ ID NO: 19
<220> FEATURE:
<221> NAME/KEY: modified_base
<222> LOCATION: (30)..(30)
<223> OTHER INFORMATION: cm

<400> SEQUENCE: 19
ucugauugag cucuucgucg cugucuccgc                                        30

<210> SEQ ID NO 20
<211> LENGTH: 7
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: 9s linker attached to 5' end of SEQ ID NO: 20
<220> FEATURE:
<221> NAME/KEY: misc_feature
<222> LOCATION: (1)..(7)
<223> OTHER INFORMATION: phosphorothioate backbone
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (3)..(3)
<223> OTHER INFORMATION: um
<220> FEATURE:
<221> NAME/KEY: modified_base
<222> LOCATION: (4)..(4)
<223> OTHER INFORMATION: gm
<220> FEATURE:
<221> NAME/KEY: misc_feature
<222> LOCATION: (5)..(5)
<223> OTHER INFORMATION: 2'-O-methyl adenosine
<220> FEATURE:
<221> NAME/KEY: modified_base
<222> LOCATION: (6)..(7)
<223> OTHER INFORMATION: um

<400> SEQUENCE: 20 ucugauu                                                                  7

<210> SEQ ID NO 21
<211> LENGTH: 23
<212> TYPE: RNA
<213> ORGANISM: Artificial Sequence
```

```
<220> FEATURE:
<223> OTHER INFORMATION: Synthetic Polynucleotide
<220> FEATURE:
<221> NAME/KEY: misc_feature
<222> LOCATION: (1)..(23)
<223> OTHER INFORMATION: phosphorothioate backbone
<220> FEATURE:
<221> NAME/KEY: modified_base
<222> LOCATION: (1)..(1)
<223> OTHER INFORMATION: gm
<220> FEATURE:
<221> NAME/KEY: misc_feature
<222> LOCATION: (2)..(2)
<223> OTHER INFORMATION: 2'-O-methyl adenosine
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (4)..(4)
<223> OTHER INFORMATION: cm
<220> FEATURE:
<221> NAME/KEY: modified_base
<222> LOCATION: (5)..(5)
<223> OTHER INFORMATION: um
<220> FEATURE:
<221> NAME/KEY: modified_base
<222> LOCATION: (6)..(6)
<223> OTHER INFORMATION: cm
<220> FEATURE:
<221> NAME/KEY: modified_base
<222> LOCATION: (7)..(8)
<223> OTHER INFORMATION: um
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (10)..(10)
<223> OTHER INFORMATION: gm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (12)..(12)
<223> OTHER INFORMATION: cm
<220> FEATURE:
<221> NAME/KEY: modified_base
<222> LOCATION: (13)..(13)
<223> OTHER INFORMATION: gm
<220> FEATURE:
<221> NAME/KEY: modified_base
<222> LOCATION: (14)..(14)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (16)..(16)
<223> OTHER INFORMATION: gm
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(18)
<223> OTHER INFORMATION: cm
<220> FEATURE:
<221> NAME/KEY: modified_base
<222> LOCATION: (19)..(19)
<223> OTHER INFORMATION: um
<220> FEATURE:
```

```
<221> NAME/KEY: modified_base
<222> LOCATION: (20)..(21)
<223> OTHER INFORMATION: cm
<220> FEATURE:
<221> NAME/KEY: modified_base
<222> LOCATION: (22)..(22)
<223> OTHER INFORMATION: gm
<220> FEATURE:
<221> NAME/KEY: misc_feature
<222> LOCATION: (23)..(23)
<223> OTHER INFORMATION: C3 linker attached to 3' end of SEQ ID NO: 21
<220> FEATURE:
<221> NAME/KEY: modified_base
<222> LOCATION: (23)..(23)
<223> OTHER INFORMATION: cm

<400> SEQUENCE: 21
gagcucuucg ucgcugucuc cgc                                            23

<210> SEQ ID NO 22
<211> LENGTH: 30
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Triethyleneglycol spacer attached to 5' end of
      SEQ ID NO: 22
<220> FEATURE:
<221> NAME/KEY: modified_base
<222> LOCATION: (1)..(1)
<223> OTHER INFORMATION: um
<220> FEATURE:
<221> NAME/KEY: misc_feature
<222> LOCATION: (1)..(30)
<223> OTHER INFORMATION: phosphorothioate backbone
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (3)..(3)
<223> OTHER INFORMATION: um
<220> FEATURE:
<221> NAME/KEY: modified_base
<222> LOCATION: (4)..(4)
<223> OTHER INFORMATION: gm
<220> FEATURE:
<221> NAME/KEY: misc_feature
<222> LOCATION: (5)..(5)
<223> OTHER INFORMATION: 2'-O-methyl adenosine
<220> FEATURE:
<221> NAME/KEY: modified_base
<222> LOCATION: (6)..(7)
<223> OTHER INFORMATION: um
<220> FEATURE:
<221> NAME/KEY: modified_base
<222> LOCATION: (8)..(8)
<223> OTHER INFORMATION: gm
<220> FEATURE:
<221> NAME/KEY: misc_feature
<222> LOCATION: (9)..(9)
<223> OTHER INFORMATION: 2'-O-methyl adenosine
<220> FEATURE:
<221> NAME/KEY: modified_base
<222> LOCATION: (10)..(10)
<223> OTHER INFORMATION: gm
<220> FEATURE:
<221> NAME/KEY: modified_base
<222> LOCATION: (11)..(11)
<223> OTHER INFORMATION: cm
<220> FEATURE:
<221> NAME/KEY: misc_feature
<222> LOCATION: (12)..(12)
```

```
<223> OTHER INFORMATION: locked nucleic acid (LNA) base
<220> FEATURE:
<221> NAME/KEY: modified_base
<222> LOCATION: (13)..(13)
<223> OTHER INFORMATION: cm
<220> FEATURE:
<221> NAME/KEY: modified_base
<222> LOCATION: (14)..(14)
<223> OTHER INFORMATION: um
<220> FEATURE:
<221> NAME/KEY: misc_feature
<222> LOCATION: (15)..(15)
<223> OTHER INFORMATION: locked nucleic acid (LNA) base
<220> FEATURE:
<221> NAME/KEY: modified_base
<222> LOCATION: (16)..(16)
<223> OTHER INFORMATION: cm
<220> FEATURE:
<221> NAME/KEY: modified_base
<222> LOCATION: (17)..(17)
<223> OTHER INFORMATION: gm
<220> FEATURE:
<221> NAME/KEY: modified_base
<222> LOCATION: (18)..(18)
<223> OTHER INFORMATION: um
<220> FEATURE:
<221> NAME/KEY: misc_feature
<222> LOCATION: (19)..(19)
<223> OTHER INFORMATION: locked nucleic acid (LNA) base
<220> FEATURE:
<221> NAME/KEY: modified_base
<222> LOCATION: (20)..(20)
<223> OTHER INFORMATION: gm
<220> FEATURE:
<221> NAME/KEY: modified_base
<222> LOCATION: (21)..(21)
<223> OTHER INFORMATION: cm
<220> FEATURE:
<221> NAME/KEY: misc_feature
<222> LOCATION: (22)..(22)
<223> OTHER INFORMATION: locked nucleic acid (LNA) base
<220> FEATURE:
<221> NAME/KEY: modified_base
<222> LOCATION: (23)..(23)
<223> OTHER INFORMATION: gm
<220> FEATURE:
<221> NAME/KEY: modified_base
<222> LOCATION: (24)..(24)
<223> OTHER INFORMATION: um
<220> FEATURE:
<221> NAME/KEY: modified_base
<222> LOCATION: (25)..(25)
<223> OTHER INFORMATION: cm
<220> FEATURE:
<221> NAME/KEY: modified_base
<222> LOCATION: (26)..(26)
<223> OTHER INFORMATION: um
<220> FEATURE:
<221> NAME/KEY: modified_base
<222> LOCATION: (27)..(28)
<223> OTHER INFORMATION: cm
<220> FEATURE:
<221> NAME/KEY: misc_feature
<222> LOCATION: (29)..(29)
<223> OTHER INFORMATION: locked nucleic acid (LNA) base
<220> FEATURE:
<221> NAME/KEY: misc_feature
<222> LOCATION: (30)..(30)
<223> OTHER INFORMATION: Amino modifier attached to 3' end of SEQ ID NO:
      22
<220> FEATURE:
<221> NAME/KEY: modified_base
<222> LOCATION: (30)..(30)
<223> OTHER INFORMATION: cm

<400> SEQUENCE: 22
ucugauugag ctcutcgucg ctgucuccgc                                      30
```

```
<210> SEQ ID NO 23
<211> LENGTH: 7
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Triethyleneglycol spacer attached to 5' end of
      SEQ ID NO: 23
<220> FEATURE:
<221> NAME/KEY: misc_feature
<222> LOCATION: (1)..(7)
<223> OTHER INFORMATION: phosphorothioate backbone
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (3)..(3)
<223> OTHER INFORMATION: um
<220> FEATURE:
<221> NAME/KEY: modified_base
<222> LOCATION: (4)..(4)
<223> OTHER INFORMATION: gm
<220> FEATURE:
<221> NAME/KEY: misc_feature
<222> LOCATION: (5)..(5)
<223> OTHER INFORMATION: 2'-O-methyl adenosine
<220> FEATURE:
<221> NAME/KEY: modified_base
<222> LOCATION: (6)..(7)
<223> OTHER INFORMATION: um

<400> SEQUENCE: 23 ucugauu                                                                  7

<210> SEQ ID NO 24
<211> LENGTH: 23
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(23)
<223> OTHER INFORMATION: phosphorothioate backbone
<220> FEATURE:
<221> NAME/KEY: modified_base
<222> LOCATION: (1)..(1)
<223> OTHER INFORMATION: gm
<220> FEATURE:
<221> NAME/KEY: misc_feature
<222> LOCATION: (2)..(2)
<223> OTHER INFORMATION: 2'-O-methyl adenosine
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (4)..(4)
<223> OTHER INFORMATION: cm
<220> FEATURE:
<221> NAME/KEY: misc_feature
<222> LOCATION: (5)..(5)
<223> OTHER INFORMATION: locked nucleic acid (LNA) base
<220> FEATURE:
<221> NAME/KEY: modified_base
<222> LOCATION: (6)..(6)
```

```
<223> OTHER INFORMATION: cm
<220> FEATURE:
<221> NAME/KEY: modified_base
<222> LOCATION: (7)..(7)
<223> OTHER INFORMATION: um
<220> FEATURE:
<221> NAME/KEY: misc_feature
<222> LOCATION: (8)..(8)
<223> OTHER INFORMATION: locked nucleic acid (LNA) base
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (10)..(10)
<223> OTHER INFORMATION: gm
<220> FEATURE:
<221> NAME/KEY: modified_base
<222> LOCATION: (11)..(11)
<223> OTHER INFORMATION: um
<220> FEATURE:
<221> NAME/KEY: misc_feature
<222> LOCATION: (12)..(12)
<223> OTHER INFORMATION: locked nucleic acid (LNA) base
<220> FEATURE:
<221> NAME/KEY: modified_base
<222> LOCATION: (13)..(13)
<223> OTHER INFORMATION: gm
<220> FEATURE:
<221> NAME/KEY: modified_base
<222> LOCATION: (14)..(14)
<223> OTHER INFORMATION: cm
<220> FEATURE:
<221> NAME/KEY: misc_feature
<222> LOCATION: (15)..(15)
<223> OTHER INFORMATION: locked nucleic acid (LNA) base
<220> FEATURE:
<221> NAME/KEY: modified_base
<222> LOCATION: (16)..(16)
<223> OTHER INFORMATION: gm
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(18)
<223> OTHER INFORMATION: cm
<220> FEATURE:
<221> NAME/KEY: modified_base
<222> LOCATION: (19)..(19)
<223> OTHER INFORMATION: um
<220> FEATURE:
<221> NAME/KEY: modified_base
<222> LOCATION: (20)..(21)
<223> OTHER INFORMATION: cm
<220> FEATURE:
<221> NAME/KEY: misc_feature
<222> LOCATION: (22)..(22)
<223> OTHER INFORMATION: locked nucleic acid (LNA) base
<220> FEATURE:
<221> NAME/KEY: misc_feature
<222> LOCATION: (23)..(23)
<223> OTHER INFORMATION: Amino modifier attached to 3' end of SEQ ID NO:
     24
<220> FEATURE:
<221> NAME/KEY: modified_base
<222> LOCATION: (23)..(23)
<223> OTHER INFORMATION: cm

<400> SEQUENCE: 24
gagctcutcg ucgctgucuc cgc                                            23

<210> SEQ ID NO 25
<211> LENGTH: 31
<212> TYPE: DNA
```

```
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Triethyleneglycol spacer attached to 5' end of
      SEQ ID NO: 25
<220> FEATURE:
<221> NAME/KEY: misc_feature
<222> LOCATION: (1)..(31)
<223> OTHER INFORMATION: phosphorothioate backbone
<220> FEATURE:
<221> NAME/KEY: modified_base
<222> LOCATION: (1)..(1)
<223> OTHER INFORMATION: gm
<220> FEATURE:
<221> NAME/KEY: modified_base
<222> LOCATION: (2)..(3)
<223> OTHER INFORMATION: um
<220> FEATURE:
<221> NAME/KEY: modified_base
<222> LOCATION: (4)..(4)
<223> OTHER INFORMATION: cm
<220> FEATURE:
<221> NAME/KEY: modified_base
<222> LOCATION: (5)..(5)
<223> OTHER INFORMATION: um
<220> FEATURE:
<221> NAME/KEY: modified_base
<222> LOCATION: (6)..(6)
<223> OTHER INFORMATION: gm
<220> FEATURE:
<221> NAME/KEY: misc_feature
<222> LOCATION: (7)..(7)
<223> OTHER INFORMATION: 2'-O-methyl adenosine
<220> FEATURE:
<221> NAME/KEY: modified_base
<222> LOCATION: (8)..(8)
<223> OTHER INFORMATION: um
<220> FEATURE:
<221> NAME/KEY: modified_base
<222> LOCATION: (9)..(9)
<223> OTHER INFORMATION: gm
<220> FEATURE:
<221> NAME/KEY: misc_feature
<222> LOCATION: (10)..(10)
<223> OTHER INFORMATION: 2'-O-methyl adenosine
<220> FEATURE:
<221> NAME/KEY: modified_base
<222> LOCATION: (11)..(11)
<223> OTHER INFORMATION: gm
<220> FEATURE:
<221> NAME/KEY: modified_base
<222> LOCATION: (12)..(12)
<223> OTHER INFORMATION: cm
<220> FEATURE:
<221> NAME/KEY: misc_feature
<222> LOCATION: (13)..(13)
<223> OTHER INFORMATION: locked nucleic acid (LNA) base
<220> FEATURE:
<221> NAME/KEY: modified_base
<222> LOCATION: (14)..(14)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: misc_feature
<222> LOCATION: (16)..(16)
<223> OTHER INFORMATION: locked nucleic acid (LNA) base
<220> FEATURE:
<221> NAME/KEY: modified_base
<222> LOCATION: (17)..(17)
<223> OTHER INFORMATION: cm
<220> FEATURE:
<221> NAME/KEY: modified_base
<222> LOCATION: (18)..(18)
```

```
<223> OTHER INFORMATION: gm
<220> FEATURE:
<221> NAME/KEY: modified_base
<222> LOCATION: (19)..(19)
<223> OTHER INFORMATION: um
<220> FEATURE:
<221> NAME/KEY: misc_feature
<222> LOCATION: (20)..(20)
<223> OTHER INFORMATION: locked nucleic acid (LNA) base
<220> FEATURE:
<221> NAME/KEY: modified_base
<222> LOCATION: (21)..(21)
<223> OTHER INFORMATION: gm
<220> FEATURE:
<221> NAME/KEY: modified_base
<222> LOCATION: (22)..(22)
<223> OTHER INFORMATION: cm
<220> FEATURE:
<221> NAME/KEY: misc_feature
<222> LOCATION: (23)..(23)
<223> OTHER INFORMATION: locked nucleic acid (LNA) base
<220> FEATURE:
<221> NAME/KEY: modified_base
<222> LOCATION: (24)..(24)
<223> OTHER INFORMATION: gm
<220> FEATURE:
<221> NAME/KEY: modified_base
<222> LOCATION: (25)..(25)
<223> OTHER INFORMATION: um
<220> FEATURE:
<221> NAME/KEY: modified_base
<222> LOCATION: (26)..(26)
<223> OTHER INFORMATION: cm
<220> FEATURE:
<221> NAME/KEY: modified_base
<222> LOCATION: (27)..(27)
<223> OTHER INFORMATION: um
<220> FEATURE:
<221> NAME/KEY: modified_base
<222> LOCATION: (28)..(29)
<223> OTHER INFORMATION: cm
<220> FEATURE:
<221> NAME/KEY: misc_feature
<222> LOCATION: (30)..(30)
<223> OTHER INFORMATION: locked nucleic acid (LNA) base
<220> FEATURE:
<221> NAME/KEY: misc_feature
<222> LOCATION: (31)..(31)
<223> OTHER INFORMATION: Amino modifier attached to 3' end of SEQ ID NO:
      22
<220> FEATURE:
<221> NAME/KEY: modified_base
<222> LOCATION: (31)..(31)
<223> OTHER INFORMATION: cm

<400> SEQUENCE: 25
guucugauga gctcutcguc gctgucuccg c                                        31

<210> SEQ ID NO 26
<211> LENGTH: 8
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(8)
<223> OTHER INFORMATION: phosphorothioate backbone
<220> FEATURE:
<221> NAME/KEY: misc_feature
<222> LOCATION: (1)..(1)
<223> OTHER INFORMATION: Triethyleneglycol spacer attached to 5' end of
      SEQ ID NO: 26
<220> FEATURE:
<221> NAME/KEY: modified_base
<222> LOCATION: (1)..(1)
<223> OTHER INFORMATION: gm
```

```
<220> FEATURE:
<221> NAME/KEY: modified_base
<222> LOCATION: (2)..(3)
<223> OTHER INFORMATION: um
<220> FEATURE:
<221> NAME/KEY: modified_base
<222> LOCATION: (4)..(4)
<223> OTHER INFORMATION: cm
<220> FEATURE:
<221> NAME/KEY: modified_base
<222> LOCATION: (5)..(5)
<223> OTHER INFORMATION: um
<220> FEATURE:
<221> NAME/KEY: modified_base
<222> LOCATION: (6)..(6)
<223> OTHER INFORMATION: gm
<220> FEATURE:
<221> NAME/KEY: misc_feature
<222> LOCATION: (7)..(7)
<223> OTHER INFORMATION: 2'-O-methyl adenosine
<220> FEATURE:
<221> NAME/KEY: modified_base
<222> LOCATION: (8)..(8)
<223> OTHER INFORMATION: um

<400> SEQUENCE: 26 guucugau                                                              8

<210> SEQ ID NO 27
<211> LENGTH: 23
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(23)
<223> OTHER INFORMATION: phosphorothioate backbone
<220> FEATURE:
<221> NAME/KEY: modified_base
<222> LOCATION: (1)..(1)
<223> OTHER INFORMATION: gm
<220> FEATURE:
<221> NAME/KEY: misc_feature
<222> LOCATION: (2)..(2)
<223> OTHER INFORMATION: 2'-O-methyl adenosine
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (4)..(4)
<223> OTHER INFORMATION: cm
<220> FEATURE:
<221> NAME/KEY: misc_feature
<222> LOCATION: (5)..(5)
<223> OTHER INFORMATION: locked nucleic acid (LNA) base
<220> FEATURE:
<221> NAME/KEY: modified_base
<222> LOCATION: (6)..(6)
<223> OTHER INFORMATION: cm
<220> FEATURE:
<221> NAME/KEY: modified_base
<222> LOCATION: (7)..(7)
<223> OTHER INFORMATION: um
<220> FEATURE:
<221> NAME/KEY: misc_feature
<222> LOCATION: (8)..(8)
<223> OTHER INFORMATION: locked nucleic acid (LNA) base
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (10)..(10)
```

```
<223> OTHER INFORMATION: gm
<220> FEATURE:
<221> NAME/KEY: modified_base
<222> LOCATION: (11)..(11)
<223> OTHER INFORMATION: um
<220> FEATURE:
<221> NAME/KEY: misc_feature
<222> LOCATION: (12)..(12)
<223> OTHER INFORMATION: locked nucleic acid (LNA) base
<220> FEATURE:
<221> NAME/KEY: modified_base
<222> LOCATION: (13)..(13)
<223> OTHER INFORMATION: gm
<220> FEATURE:
<221> NAME/KEY: modified_base
<222> LOCATION: (14)..(14)
<223> OTHER INFORMATION: cm
<220> FEATURE:
<221> NAME/KEY: misc_feature
<222> LOCATION: (15)..(15)
<223> OTHER INFORMATION: locked nucleic acid (LNA) base
<220> FEATURE:
<221> NAME/KEY: modified_base
<222> LOCATION: (16)..(16)
<223> OTHER INFORMATION: gm
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(18)
<223> OTHER INFORMATION: cm
<220> FEATURE:
<221> NAME/KEY: modified_base
<222> LOCATION: (19)..(19)
<223> OTHER INFORMATION: um
<220> FEATURE:
<221> NAME/KEY: modified_base
<222> LOCATION: (20)..(21)
<223> OTHER INFORMATION: cm
<220> FEATURE:
<221> NAME/KEY: misc_feature
<222> LOCATION: (22)..(22)
<223> OTHER INFORMATION: locked nucleic acid (LNA) base
<220> FEATURE:
<221> NAME/KEY: misc_feature
<222> LOCATION: (23)..(23)
<223> OTHER INFORMATION: Amino modifier attached to 3' end of SEQ ID NO:
     27
<220> FEATURE:
<221> NAME/KEY: modified_base
<222> LOCATION: (23)..(23)
<223> OTHER INFORMATION: cm

<400> SEQUENCE: 27
gagctcutcg ucgctgucuc cgc                                           23

<210> SEQ ID NO 28
<211> LENGTH: 31
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Triethyleneglycol spacer attached to 5' end of
     SEQ ID NO: 28
<220> FEATURE:
<221> NAME/KEY: misc_feature
<222> LOCATION: (1)..(31)
<223> OTHER INFORMATION: phosphorothioate backbone
<220> FEATURE:
<221> NAME/KEY: modified_base
<222> LOCATION: (1)..(1)
<223> OTHER INFORMATION: gm
```

```
<220> FEATURE:
<221> NAME/KEY: modified_base
<222> LOCATION: (2)..(3)
<223> OTHER INFORMATION: um
<220> FEATURE:
<221> NAME/KEY: modified_base
<222> LOCATION: (2)..(3)
<223> OTHER INFORMATION: um
<220> FEATURE:
<221> NAME/KEY: misc_feature
<222> LOCATION: (4)..(4)
<223> OTHER INFORMATION: locked nucleic acid (LNA) base
<220> FEATURE:
<221> NAME/KEY: modified_base
<222> LOCATION: (5)..(5)
<223> OTHER INFORMATION: um
<220> FEATURE:
<221> NAME/KEY: modified_base
<222> LOCATION: (6)..(6)
<223> OTHER INFORMATION: gm
<220> FEATURE:
<221> NAME/KEY: misc_feature
<222> LOCATION: (7)..(7)
<223> OTHER INFORMATION: 2'-O-methyl adenosine
<220> FEATURE:
<221> NAME/KEY: modified_base
<222> LOCATION: (8)..(8)
<223> OTHER INFORMATION: um
<220> FEATURE:
<221> NAME/KEY: modified_base
<222> LOCATION: (9)..(9)
<223> OTHER INFORMATION: gm
<220> FEATURE:
<221> NAME/KEY: misc_feature
<222> LOCATION: (10)..(10)
<223> OTHER INFORMATION: 2'-O-methyl adenosine
<220> FEATURE:
<221> NAME/KEY: modified_base
<222> LOCATION: (11)..(11)
<223> OTHER INFORMATION: gm
<220> FEATURE:
<221> NAME/KEY: modified_base
<222> LOCATION: (12)..(12)
<223> OTHER INFORMATION: cm
<220> FEATURE:
<221> NAME/KEY: misc_feature
<222> LOCATION: (13)..(13)
<223> OTHER INFORMATION: locked nucleic acid (LNA) base
<220> FEATURE:
<221> NAME/KEY: modified_base
<222> LOCATION: (14)..(14)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: misc_feature
<222> LOCATION: (16)..(16)
<223> OTHER INFORMATION: locked nucleic acid (LNA) base
<220> FEATURE:
<221> NAME/KEY: modified_base
<222> LOCATION: (17)..(17)
<223> OTHER INFORMATION: cm
<220> FEATURE:
<221> NAME/KEY: modified_base
<222> LOCATION: (18)..(18)
<223> OTHER INFORMATION: gm
<220> FEATURE:
<221> NAME/KEY: modified_base
<222> LOCATION: (19)..(19)
<223> OTHER INFORMATION: um
<220> FEATURE:
<221> NAME/KEY: misc_feature
<222> LOCATION: (20)..(20)
<223> OTHER INFORMATION: locked nucleic acid (LNA) base
<220> FEATURE:
<221> NAME/KEY: modified_base
<222> LOCATION: (21)..(21)
```

```
<223> OTHER INFORMATION: gm
<220> FEATURE:
<221> NAME/KEY: modified_base
<222> LOCATION: (22)..(22)
<223> OTHER INFORMATION: cm
<220> FEATURE:
<221> NAME/KEY: misc_feature
<222> LOCATION: (23)..(23)
<223> OTHER INFORMATION: locked nucleic acid (LNA) base
<220> FEATURE:
<221> NAME/KEY: modified_base
<222> LOCATION: (24)..(24)
<223> OTHER INFORMATION: gm
<220> FEATURE:
<221> NAME/KEY: modified_base
<222> LOCATION: (25)..(25)
<223> OTHER INFORMATION: um
<220> FEATURE:
<221> NAME/KEY: modified_base
<222> LOCATION: (26)..(26)
<223> OTHER INFORMATION: cm
<220> FEATURE:
<221> NAME/KEY: modified_base
<222> LOCATION: (27)..(27)
<223> OTHER INFORMATION: um
<220> FEATURE:
<221> NAME/KEY: modified_base
<222> LOCATION: (28)..(29)
<223> OTHER INFORMATION: cm
<220> FEATURE:
<221> NAME/KEY: misc_feature
<222> LOCATION: (30)..(30)
<223> OTHER INFORMATION: locked nucleic acid (LNA) base
<220> FEATURE:
<221> NAME/KEY: misc_feature
<222> LOCATION: (31)..(31)
<223> OTHER INFORMATION: Amino modifier attached to 3' end of SEQ ID NO:
      28
<220> FEATURE:
<221> NAME/KEY: modified_base
<222> LOCATION: (31)..(31)
<223> OTHER INFORMATION: cm

<400> SEQUENCE: 28
guucugauga gctcutcguc gctgucuccg c                                    31

<210> SEQ ID NO 29
<211> LENGTH: 8
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Triethyleneglycol spacer attached to 5' end of
      SEQ ID NO: 29
<220> FEATURE:
<221> NAME/KEY: misc_feature
<222> LOCATION: (1)..(8)
<223> OTHER INFORMATION: phosphorothioate backbone
<220> FEATURE:
<221> NAME/KEY: modified_base
<222> LOCATION: (1)..(1)
<223> OTHER INFORMATION: gm
<220> FEATURE:
<221> NAME/KEY: modified_base
<222> LOCATION: (2)..(3)
<223> OTHER INFORMATION: um
<220> FEATURE:
<221> NAME/KEY: misc_feature
<222> LOCATION: (4)..(4)
<223> OTHER INFORMATION: locked nucleic acid (LNA) base
<220> FEATURE:
<221> NAME/KEY: modified_base
<222> LOCATION: (5)..(5)
<223> OTHER INFORMATION: um
```

```
<220> FEATURE:
<221> NAME/KEY: modified_base
<222> LOCATION: (6)..(6)
<223> OTHER INFORMATION: gm
<220> FEATURE:
<221> NAME/KEY: misc_feature
<222> LOCATION: (7)..(7)
<223> OTHER INFORMATION: 2'-O-methyl adenosine
<220> FEATURE:
<221> NAME/KEY: modified_base
<222> LOCATION: (8)..(8)
<223> OTHER INFORMATION: um

<400> SEQUENCE: 29 guucugau                                                                    8

<210> SEQ ID NO 30
<211> LENGTH: 23
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(23)
<223> OTHER INFORMATION: phosphorothioate backbone
<220> FEATURE:
<221> NAME/KEY: modified_base
<222> LOCATION: (1)..(1)
<223> OTHER INFORMATION: gm
<220> FEATURE:
<221> NAME/KEY: misc_feature
<222> LOCATION: (2)..(2)
<223> OTHER INFORMATION: 2'-O-methyl adenosine
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (4)..(4)
<223> OTHER INFORMATION: cm
<220> FEATURE:
<221> NAME/KEY: misc_feature
<222> LOCATION: (5)..(5)
<223> OTHER INFORMATION: locked nucleic acid (LNA) base
<220> FEATURE:
<221> NAME/KEY: modified_base
<222> LOCATION: (6)..(6)
<223> OTHER INFORMATION: cm
<220> FEATURE:
<221> NAME/KEY: modified_base
<222> LOCATION: (7)..(7)
<223> OTHER INFORMATION: um
<220> FEATURE:
<221> NAME/KEY: misc_feature
<222> LOCATION: (8)..(8)
<223> OTHER INFORMATION: locked nucleic acid (LNA) base
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (10)..(10)
<223> OTHER INFORMATION: gm
<220> FEATURE:
<221> NAME/KEY: modified_base
<222> LOCATION: (11)..(11)
<223> OTHER INFORMATION: um
<220> FEATURE:
<221> NAME/KEY: misc_feature
<222> LOCATION: (12)..(12)
<223> OTHER INFORMATION: locked nucleic acid (LNA) base
<220> FEATURE:
<221> NAME/KEY: modified_base
<222> LOCATION: (13)..(13)
```

```
<223> OTHER INFORMATION: gm
<220> FEATURE:
<221> NAME/KEY: modified_base
<222> LOCATION: (14)..(14)
<223> OTHER INFORMATION: cm
<220> FEATURE:
<221> NAME/KEY: misc_feature
<222> LOCATION: (15)..(15)
<223> OTHER INFORMATION: locked nucleic acid (LNA) base
<220> FEATURE:
<221> NAME/KEY: modified_base
<222> LOCATION: (16)..(16)
<223> OTHER INFORMATION: gm
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(18)
<223> OTHER INFORMATION: cm
<220> FEATURE:
<221> NAME/KEY: modified_base
<222> LOCATION: (19)..(19)
<223> OTHER INFORMATION: um
<220> FEATURE:
<221> NAME/KEY: modified_base
<222> LOCATION: (20)..(21)
<223> OTHER INFORMATION: cm
<220> FEATURE:
<221> NAME/KEY: misc_feature
<222> LOCATION: (22)..(22)
<223> OTHER INFORMATION: locked nucleic acid (LNA) base
<220> FEATURE:
<221> NAME/KEY: misc_feature
<222> LOCATION: (23)..(23)
<223> OTHER INFORMATION: Amino modifier attached to 3' end of SEQ ID NO:
      30
<220> FEATURE:
<221> NAME/KEY: modified_base
<222> LOCATION: (23)..(23)
<223> OTHER INFORMATION: cm

<400> SEQUENCE: 30
gagctcutcg ucgctgucuc cgc                                              23

<210> SEQ ID NO 31
<211> LENGTH: 12
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(4)
<223> OTHER INFORMATION: phosphorothioate backbone
<220> FEATURE:
<221> NAME/KEY: misc_feature
<222> LOCATION: (12)..(12)
<223> OTHER INFORMATION: C3 linker attached to 5' end of SEQ ID NO: 32

<400> SEQUENCE: 31
gcggagacag cg                                                          12

<210> SEQ ID NO 32
<211> LENGTH: 23
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(3)
<223> OTHER INFORMATION: phosphorothioate backbone
<220> FEATURE:
```

```
<221> NAME/KEY: misc_feature
<222> LOCATION: (1)..(1)
<223> OTHER INFORMATION: C3 linker attached to 3' end of SEQ ID NO: 31
<220> FEATURE:
<221> NAME/KEY: modified_base
<222> LOCATION: (1)..(2)
<223> OTHER INFORMATION: gm
<220> FEATURE:
<221> NAME/KEY: modified_base
<222> LOCATION: (3)..(3)
<223> OTHER INFORMATION: um
<220> FEATURE:
<221> NAME/KEY: misc_feature
<222> LOCATION: (22)..(23)
<223> OTHER INFORMATION: phosphorothioate backbone
<220> FEATURE:
<221> NAME/KEY: misc_feature
<222> LOCATION: (23)..(23)
<223> OTHER INFORMATION: C3 linker attached to 35 end of SEQ ID NO: 33
<220> FEATURE:
<221> NAME/KEY: modified_base
<222> LOCATION: (23)..(23)
<223> OTHER INFORMATION: gm

<400> SEQUENCE: 32
gguaacuaga gaucccucag acg                                          23

<210> SEQ ID NO 33
<211> LENGTH: 11
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: C3 linker attached to 3' end of SEQ ID NO: 32
<220> FEATURE:
<221> NAME/KEY: misc_feature
<222> LOCATION: (8)..(11)
<223> OTHER INFORMATION: phosphorothioate backbone

<400> SEQUENCE: 33
ggcaggaaga a                                                       11

<210> SEQ ID NO 34
<211> LENGTH: 31
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Triethyleneglycol spacer attached to 5' end of
      SEQ ID NO: 34
<220> FEATURE:
<221> NAME/KEY: misc_feature
<222> LOCATION: (1)..(31)
<223> OTHER INFORMATION: phosphorothioate backbone
<220> FEATURE:
<221> NAME/KEY: modified_base
<222> LOCATION: (1)..(1)
<223> OTHER INFORMATION: cm
<220> FEATURE:
<221> NAME/KEY: modified_base
<222> LOCATION: (2)..(2)
<223> OTHER INFORMATION: um
<220> FEATURE:
<221> NAME/KEY: modified_base
<222> LOCATION: (3)..(3)
<223> OTHER INFORMATION: cm
<220> FEATURE:
<221> NAME/KEY: modified_base
<222> LOCATION: (4)..(5)
```

```
<223> OTHER INFORMATION: um
<220> FEATURE:
<221> NAME/KEY: modified_base
<222> LOCATION: (6)..(6)
<223> OTHER INFORMATION: cm
<220> FEATURE:
<221> NAME/KEY: modified_base
<222> LOCATION: (7)..(7)
<223> OTHER INFORMATION: gm
<220> FEATURE:
<221> NAME/KEY: modified_base
<222> LOCATION: (8)..(8)
<223> OTHER INFORMATION: um
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (10)..(10)
<223> OTHER INFORMATION: gm
<220> FEATURE:
<221> NAME/KEY: modified_base
<222> LOCATION: (11)..(11)
<223> OTHER INFORMATION: cm
<220> FEATURE:
<221> NAME/KEY: misc_feature
<222> LOCATION: (12)..(12)
<223> OTHER INFORMATION: locked nucleic acid (LNA) base
<220> FEATURE:
<221> NAME/KEY: modified_base
<222> LOCATION: (13)..(13)
<223> OTHER INFORMATION: gm
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (15)..(15)
<223> OTHER INFORMATION: cm
<220> FEATURE:
<221> NAME/KEY: misc_feature
<222> LOCATION: (16)..(16)
<223> OTHER INFORMATION: locked nucleic acid (LNA) base
<220> FEATURE:
<221> NAME/KEY: modified_base
<222> LOCATION: (17)..(18)
<223> OTHER INFORMATION: cm
<220> FEATURE:
<221> NAME/KEY: modified_base
<222> LOCATION: (19)..(19)
<223> OTHER INFORMATION: gm
<220> FEATURE:
<221> NAME/KEY: misc_feature
<222> LOCATION: (20)..(20)
<223> OTHER INFORMATION: locked nucleic acid (LNA) base
<220> FEATURE:
<221> NAME/KEY: modified_base
<222> LOCATION: (21)..(21)
<223> OTHER INFORMATION: um
<220> FEATURE:
<221> NAME/KEY: misc_feature
<222> LOCATION: (22)..(22)
<223> OTHER INFORMATION: locked nucleic acid (LNA) base
<220> FEATURE:
<221> NAME/KEY: modified_base
<222> LOCATION: (23)..(23)
<223> OTHER INFORMATION: cm
<220> FEATURE:
<221> NAME/KEY: modified_base
<222> LOCATION: (24)..(25)
<223> OTHER INFORMATION: um
<220> FEATURE:
<221> NAME/KEY: misc_feature
<222> LOCATION: (26)..(26)
<223> OTHER INFORMATION: locked nucleic acid (LNA) base
<220> FEATURE:
<221> NAME/KEY: modified_base
```

```
<222> LOCATION: (27)..(27)
<223> OTHER INFORMATION: cm
<220> FEATURE:
<221> NAME/KEY: modified_base
<222> LOCATION: (28)..(28)
<223> OTHER INFORMATION: um
<220> FEATURE:
<221> NAME/KEY: modified_base
<222> LOCATION: (29)..(29)
<223> OTHER INFORMATION: gm
<220> FEATURE:
<221> NAME/KEY: misc_feature
<222> LOCATION: (30)..(30)
<223> OTHER INFORMATION: locked nucleic acid (LNA) base
<220> FEATURE:
<221> NAME/KEY: misc_feature
<222> LOCATION: (31)..(31)
<223> OTHER INFORMATION: Amino modifier attached to 3' end of SEQ ID NO:
      22
<220> FEATURE:
<221> NAME/KEY: modified_base
<222> LOCATION: (31)..(31)
<223> OTHER INFORMATION: cm

<400> SEQUENCE: 34
cucuucgucg ctguctccgc utcuuccugc c                                        31

<210> SEQ ID NO 35
<211> LENGTH: 8
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Triethyleneglycol spacer attached to 5' end of
      SEQ ID NO: 35
<220> FEATURE:
<221> NAME/KEY: misc_feature
<222> LOCATION: (1)..(8)
<223> OTHER INFORMATION: phosphorothioate backbone
<220> FEATURE:
<221> NAME/KEY: modified_base
<222> LOCATION: (1)..(1)
<223> OTHER INFORMATION: cm
<220> FEATURE:
<221> NAME/KEY: modified_base
<222> LOCATION: (2)..(2)
<223> OTHER INFORMATION: um
<220> FEATURE:
<221> NAME/KEY: modified_base
<222> LOCATION: (3)..(3)
<223> OTHER INFORMATION: cm
<220> FEATURE:
<221> NAME/KEY: modified_base
<222> LOCATION: (4)..(5)
<223> OTHER INFORMATION: um
<220> FEATURE:
<221> NAME/KEY: modified_base
<222> LOCATION: (6)..(6)
<223> OTHER INFORMATION: cm
<220> FEATURE:
<221> NAME/KEY: modified_base
<222> LOCATION: (7)..(7)
<223> OTHER INFORMATION: gm
<220> FEATURE:
<221> NAME/KEY: modified_base
<222> LOCATION: (8)..(8)
<223> OTHER INFORMATION: um

<400> SEQUENCE: 35 cucuucgu                                                                   8

<210> SEQ ID NO 36
```

```
<211> LENGTH: 23
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(23)
<223> OTHER INFORMATION: phosphorothioate backbone
<220> FEATURE:
<221> NAME/KEY: modified_base
<222> LOCATION: (1)..(1)
<223> OTHER INFORMATION: cm
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (3)..(3)
<223> OTHER INFORMATION: cm
<220> FEATURE:
<221> NAME/KEY: misc_feature
<222> LOCATION: (4)..(4)
<223> OTHER INFORMATION: locked nucleic acid (LNA) base
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (6)..(6)
<223> OTHER INFORMATION: um
<220> FEATURE:
<221> NAME/KEY: modified_base
<222> LOCATION: (7)..(7)
<223> OTHER INFORMATION: cm
<220> FEATURE:
<221> NAME/KEY: misc_feature
<222> LOCATION: (8)..(8)
<223> OTHER INFORMATION: locked nucleic acid (LNA) base
<220> FEATURE:
<221> NAME/KEY: modified_base
<222> LOCATION: (9)..(10)
<223> OTHER INFORMATION: cm
<220> FEATURE:
<221> NAME/KEY: modified_base
<222> LOCATION: (11)..(11)
<223> OTHER INFORMATION: gm
<220> FEATURE:
<221> NAME/KEY: misc_feature
<222> LOCATION: (12)..(12)
<223> OTHER INFORMATION: locked nucleic acid (LNA) base
<220> FEATURE:
<221> NAME/KEY: modified_base
<222> LOCATION: (13)..(13)
<223> OTHER INFORMATION: um
<220> FEATURE:
<221> NAME/KEY: misc_feature
<222> LOCATION: (14)..(14)
<223> OTHER INFORMATION: locked nucleic acid (LNA) base
<220> FEATURE:
<221> NAME/KEY: modified_base
<222> LOCATION: (15)..(15)
<223> OTHER INFORMATION: cm
<220> FEATURE:
<221> NAME/KEY: modified_base
<222> LOCATION: (16)..(17)
<223> OTHER INFORMATION: um
<220> FEATURE:
<221> NAME/KEY: misc_feature
<222> LOCATION: (18)..(18)
<223> OTHER INFORMATION: locked nucleic acid (LNA) base
<220> FEATURE:
<221> NAME/KEY: modified_base
<222> LOCATION: (19)..(19)
<223> OTHER INFORMATION: cm
<220> FEATURE:
<221> NAME/KEY: modified_base
```

```
<222> LOCATION: (20)..(20)
<223> OTHER INFORMATION: um
<220> FEATURE:
<221> NAME/KEY: modified_base
<222> LOCATION: (21)..(21)
<223> OTHER INFORMATION: gm
<220> FEATURE:
<221> NAME/KEY: misc_feature
<222> LOCATION: (22)..(22)
<223> OTHER INFORMATION: locked nucleic acid (LNA) base
<220> FEATURE:
<221> NAME/KEY: misc_feature
<222> LOCATION: (23)..(23)
<223> OTHER INFORMATION: Amino modifier attached to 3' end of SEQ ID NO:
     36
<220> FEATURE:
<221> NAME/KEY: modified_base
<222> LOCATION: (23)..(23)
<223> OTHER INFORMATION: cm

<400> SEQUENCE: 36
cgctguctcc gcutcuuccu gcc                                              23

<210> SEQ ID NO 37
<211> LENGTH: 31
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Triethyleneglycol spacer attached to 5' end of
     SEQ ID NO: 37
<220> FEATURE:
<221> NAME/KEY: misc_feature
<222> LOCATION: (1)..(31)
<223> OTHER INFORMATION: phosphorothioate backbone
<220> FEATURE:
<221> NAME/KEY: modified_base
<222> LOCATION: (1)..(1)
<223> OTHER INFORMATION: cm
<220> FEATURE:
<221> NAME/KEY: modified_base
<222> LOCATION: (2)..(2)
<223> OTHER INFORMATION: um
<220> FEATURE:
<221> NAME/KEY: misc_feature
<222> LOCATION: (3)..(3)
<223> OTHER INFORMATION: locked nucleic acid (LNA) base
<220> FEATURE:
<221> NAME/KEY: modified_base
<222> LOCATION: (4)..(5)
<223> OTHER INFORMATION: um
<220> FEATURE:
<221> NAME/KEY: modified_base
<222> LOCATION: (6)..(6)
<223> OTHER INFORMATION: cm
<220> FEATURE:
<221> NAME/KEY: modified_base
<222> LOCATION: (7)..(7)
<223> OTHER INFORMATION: gm
<220> FEATURE:
<221> NAME/KEY: modified_base
<222> LOCATION: (8)..(8)
<223> OTHER INFORMATION: um
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (11)..(11)
<223> OTHER INFORMATION: cm
<220> FEATURE:
<221> NAME/KEY: misc_feature
<222> LOCATION: (12)..(12)
```

```
<223> OTHER INFORMATION: locked nucleic acid (LNA) base
<220> FEATURE:
<221> NAME/KEY: modified_base
<222> LOCATION: (13)..(13)
<223> OTHER INFORMATION: gm
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (15)..(15)
<223> OTHER INFORMATION: cm
<220> FEATURE:
<221> NAME/KEY: misc_feature
<222> LOCATION: (16)..(16)
<223> OTHER INFORMATION: locked nucleic acid (LNA) base
<220> FEATURE:
<221> NAME/KEY: modified_base
<222> LOCATION: (17)..(18)
<223> OTHER INFORMATION: cm
<220> FEATURE:
<221> NAME/KEY: modified_base
<222> LOCATION: (19)..(19)
<223> OTHER INFORMATION: gm
<220> FEATURE:
<221> NAME/KEY: misc_feature
<222> LOCATION: (20)..(20)
<223> OTHER INFORMATION: locked nucleic acid (LNA) base
<220> FEATURE:
<221> NAME/KEY: modified_base
<222> LOCATION: (21)..(21)
<223> OTHER INFORMATION: um
<220> FEATURE:
<221> NAME/KEY: misc_feature
<222> LOCATION: (22)..(22)
<223> OTHER INFORMATION: locked nucleic acid (LNA) base
<220> FEATURE:
<221> NAME/KEY: modified_base
<222> LOCATION: (23)..(23)
<223> OTHER INFORMATION: cm
<220> FEATURE:
<221> NAME/KEY: modified_base
<222> LOCATION: (24)..(25)
<223> OTHER INFORMATION: um
<220> FEATURE:
<221> NAME/KEY: misc_feature
<222> LOCATION: (26)..(26)
<223> OTHER INFORMATION: locked nucleic acid (LNA) base
<220> FEATURE:
<221> NAME/KEY: modified_base
<222> LOCATION: (27)..(27)
<223> OTHER INFORMATION: cm
<220> FEATURE:
<221> NAME/KEY: modified_base
<222> LOCATION: (29)..(29)
<223> OTHER INFORMATION: gm
<220> FEATURE:
<221> NAME/KEY: misc_feature
<222> LOCATION: (30)..(30)
<223> OTHER INFORMATION: locked nucleic acid (LNA) base
<220> FEATURE:
<221> NAME/KEY: misc_feature
<222> LOCATION: (31)..(31)
<223> OTHER INFORMATION: Amino modifier attached to 3' end of SEQ ID NO:
      37
<220> FEATURE:
<221> NAME/KEY: modified_base
<222> LOCATION: (31)..(31)
<223> OTHER INFORMATION: cm

<400> SEQUENCE: 37
cucuucgucg ctguctccgc utcuuccugc c                                    31

<210> SEQ ID NO 38
<211> LENGTH: 8
<212> TYPE: RNA
```

```
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Triethyleneglycol spacer attached to 5' end of
      SEQ ID NO: 38
<220> FEATURE:
<221> NAME/KEY: misc_feature
<222> LOCATION: (1)..(8)
<223> OTHER INFORMATION: phosphorothioate backbone
<220> FEATURE:
<221> NAME/KEY: modified_base
<222> LOCATION: (1)..(1)
<223> OTHER INFORMATION: cm
<220> FEATURE:
<221> NAME/KEY: modified_base
<222> LOCATION: (2)..(2)
<223> OTHER INFORMATION: um
<220> FEATURE:
<221> NAME/KEY: modified_base
<222> LOCATION: (4)..(5)
<223> OTHER INFORMATION: um
<220> FEATURE:
<221> NAME/KEY: modified_base
<222> LOCATION: (6)..(6)
<223> OTHER INFORMATION: cm
<220> FEATURE:
<221> NAME/KEY: modified_base
<222> LOCATION: (7)..(7)
<223> OTHER INFORMATION: gm
<220> FEATURE:
<221> NAME/KEY: modified_base
<222> LOCATION: (8)..(8)
<223> OTHER INFORMATION: um
<220> FEATURE:
<221> NAME/KEY: misc_feature
<222> LOCATION: (13)..(3)
<223> OTHER INFORMATION: locked nucleic acid (LNA) base

<400> SEQUENCE: 38 cucuucgu                                                                 8

<210> SEQ ID NO 39
<211> LENGTH: 23
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(23)
<223> OTHER INFORMATION: phosphorothioate backbone
<220> FEATURE:
<221> NAME/KEY: modified_base
<222> LOCATION: (1)..(1)
<223> OTHER INFORMATION: cm
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (3)..(3)
<223> OTHER INFORMATION: cm
<220> FEATURE:
<221> NAME/KEY: misc_feature
<222> LOCATION: (4)..(4)
<223> OTHER INFORMATION: locked nucleic acid (LNA) base
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (6)..(6)
```

```
<223> OTHER INFORMATION: um
<220> FEATURE:
<221> NAME/KEY: modified_base
<222> LOCATION: (7)..(7)
<223> OTHER INFORMATION: cm
<220> FEATURE:
<221> NAME/KEY: misc_feature
<222> LOCATION: (8)..(8)
<223> OTHER INFORMATION: locked nucleic acid (LNA) base
<220> FEATURE:
<221> NAME/KEY: modified_base
<222> LOCATION: (9)..(10)
<223> OTHER INFORMATION: cm
<220> FEATURE:
<221> NAME/KEY: modified_base
<222> LOCATION: (11)..(11)
<223> OTHER INFORMATION: gm
<220> FEATURE:
<221> NAME/KEY: misc_feature
<222> LOCATION: (12)..(12)
<223> OTHER INFORMATION: locked nucleic acid (LNA) base
<220> FEATURE:
<221> NAME/KEY: modified_base
<222> LOCATION: (13)..(13)
<223> OTHER INFORMATION: um
<220> FEATURE:
<221> NAME/KEY: misc_feature
<222> LOCATION: (14)..(14)
<223> OTHER INFORMATION: locked nucleic acid (LNA) base
<220> FEATURE:
<221> NAME/KEY: modified_base
<222> LOCATION: (15)..(15)
<223> OTHER INFORMATION: cm
<220> FEATURE:
<221> NAME/KEY: modified_base
<222> LOCATION: (16)..(17)
<223> OTHER INFORMATION: um
<220> FEATURE:
<221> NAME/KEY: misc_feature
<222> LOCATION: (18)..(18)
<223> OTHER INFORMATION: locked nucleic acid (LNA) base
<220> FEATURE:
<221> NAME/KEY: modified_base
<222> LOCATION: (19)..(19)
<223> OTHER INFORMATION: cm
<220> FEATURE:
<221> NAME/KEY: modified_base
<222> LOCATION: (20)..(20)
<223> OTHER INFORMATION: um
<220> FEATURE:
<221> NAME/KEY: modified_base
<222> LOCATION: (21)..(21)
<223> OTHER INFORMATION: gm
<220> FEATURE:
<221> NAME/KEY: misc_feature
<222> LOCATION: (22)..(22)
<223> OTHER INFORMATION: locked nucleic acid (LNA) base
<220> FEATURE:
<221> NAME/KEY: misc_feature
<222> LOCATION: (23)..(23)
<223> OTHER INFORMATION: Amino modifier attached to 3' end of SEQ ID NO:
     39
<220> FEATURE:
<221> NAME/KEY: modified_base
<222> LOCATION: (23)..(23)
<223> OTHER INFORMATION: cm

<400> SEQUENCE: 39
cgctguctcc gcutcuuccu gcc                                             23

<210> SEQ ID NO 40
<211> LENGTH: 28
<212> TYPE: RNA
<213> ORGANISM: Artificial Sequence
<220> FEATURE:
<223> OTHER INFORMATION: Synthetic Polynucleotide
```

```
<400> SEQUENCE: 40
gcggagacag cgacgaagag cucaucag                                            28

<210> SEQ ID NO 41
<211> LENGTH: 38
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(5)
<223> OTHER INFORMATION: 2'-O-methyl adenosine
<220> FEATURE:
<221> NAME/KEY: misc_feature
<222> LOCATION: (34)..(38)
<223> OTHER INFORMATION: 2'-O-methyl adenosine
<220> FEATURE:
<221> NAME/KEY: misc_feature
<222> LOCATION: (38)..(38)
<223> OTHER INFORMATION: Inverted deoxynucleotide T attached to 3' end
      of SEQ ID NO: 41

<400> SEQUENCE: 41
aaaaagcgga gacagcgacg aagagcucau cagaaaaa                                 38

<210> SEQ ID NO 42
<211> LENGTH: 41
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(5)
<223> OTHER INFORMATION: 2'-O-methyl adenosine
<220> FEATURE:
<221> NAME/KEY: misc_feature
<222> LOCATION: (37)..(41)
<223> OTHER INFORMATION: 2'-O-methyl adenosine
<220> FEATURE:
<221> NAME/KEY: misc_feature
<222> LOCATION: (41)..(41)
<223> OTHER INFORMATION: Inverted deoxynucleotide T attached to 3' end
      of SEQ ID NO: 42

<400> SEQUENCE: 42
aaaaagcgga gacagcgacg aagagcucau cagaacaaaa a                             41

<210> SEQ ID NO 43
<211> LENGTH: 53
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(5)
<223> OTHER INFORMATION: 2'-O-methyl adenosine
<220> FEATURE:
<221> NAME/KEY: misc_feature
<222> LOCATION: (49)..(53)
<223> OTHER INFORMATION: 2'-O-methyl adenosine
<220> FEATURE:
<221> NAME/KEY: misc_feature
<222> LOCATION: (53)..(53)
<223> OTHER INFORMATION: Inverted deoxynucleotide T attached to 3' end
      of SEQ ID NO: 43

<400> SEQUENCE: 43
aaaaaggcag gaagaagcgg agacagcgac gaagagcuca ucagaacaaa aaa                53
```

<210> SEQ ID NO 44
<211> LENGTH: 12
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(4)
<223> OTHER INFORMATION: phosphorothioate backbone
<220> FEATURE:
<221> NAME/KEY: misc_feature
<222> LOCATION: (12)..(12)
<223> OTHER INFORMATION: C3 linker attached to 5' end of SEQ ID NO: 45

<400> SEQUENCE: 44
gacgaagagc uc                                                          12

<210> SEQ ID NO 45
<211> LENGTH: 23
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: C3 linker attached to 3' end of SEQ ID NO: 44
<220> FEATURE:
<221> NAME/KEY: misc_feature
<222> LOCATION: (1)..(3)
<223> OTHER INFORMATION: phosphorothioate backbone
<220> FEATURE:
<221> NAME/KEY: modified_base
<222> LOCATION: (1)..(2)
<223> OTHER INFORMATION: gm
<220> FEATURE:
<221> NAME/KEY: modified_base
<222> LOCATION: (3)..(3)
<223> OTHER INFORMATION: um
<220> FEATURE:
<221> NAME/KEY: misc_feature
<222> LOCATION: (22)..(23)
<223> OTHER INFORMATION: phosphorothioate backbone
<220> FEATURE:
<221> NAME/KEY: modified_base
<222> LOCATION: (22)..(22)
<223> OTHER INFORMATION: cm
<220> FEATURE:
<221> NAME/KEY: misc_feature
<222> LOCATION: (23)..(23)
<223> OTHER INFORMATION: C3 linker attached to 5' end of SEQ ID NO: 46
<220> FEATURE:
<221> NAME/KEY: modified_base
<222> LOCATION: (23)..(23)
<223> OTHER INFORMATION: gm

<400> SEQUENCE: 45
gguaacuaga gaucccucag acg                                              23

<210> SEQ ID NO 46
<211> LENGTH: 12
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: C3 linker attached to 3' end of SEQ ID NO: 45
<220> FEATURE:
<221> NAME/KEY: misc_feature
<222> LOCATION: (8)..(11)
<223> OTHER INFORMATION: phosphorothioate backbone

<400> SEQUENCE: 46
gcggagacag cc                                                                  12

<210> SEQ ID NO 47
<211> LENGTH: 39
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Triethyleneglycol spacer attached to 5' end of
      SEQ ID NO: 47
<220> FEATURE:
<221> NAME/KEY: misc_feature
<222> LOCATION: (1)..(39)
<223> OTHER INFORMATION: phosphorothioate backbone
<220> FEATURE:
<221> NAME/KEY: modified_base
<222> LOCATION: (1)..(1)
<223> OTHER INFORMATION: gm
<220> FEATURE:
<221> NAME/KEY: modified_base
<222> LOCATION: (2)..(3)
<223> OTHER INFORMATION: um
<220> FEATURE:
<221> NAME/KEY: misc_feature
<222> LOCATION: (4)..(4)
<223> OTHER INFORMATION: locked nucleic acid (LNA) base
<220> FEATURE:
<221> NAME/KEY: modified_base
<222> LOCATION: (5)..(5)
<223> OTHER INFORMATION: um
<220> FEATURE:
<221> NAME/KEY: modified_base
<222> LOCATION: (6)..(6)
<223> OTHER INFORMATION: gm
<220> FEATURE:
<221> NAME/KEY: misc_feature
<222> LOCATION: (7)..(7)
<223> OTHER INFORMATION: 2'-O-methyl adenosine
<220> FEATURE:
<221> NAME/KEY: modified_base
<222> LOCATION: (8)..(9)
<223> OTHER INFORMATION: um
<220> FEATURE:
<221> NAME/KEY: modified_base
<222> LOCATION: (10)..(10)
<223> OTHER INFORMATION: cm
<220> FEATURE:
<221> NAME/KEY: misc_feature
<222> LOCATION: (11)..(11)
<223> OTHER INFORMATION: 2'-O-methyl adenosine
<220> FEATURE:
<221> NAME/KEY: modified_base
<222> LOCATION: (12)..(12)
<223> OTHER INFORMATION: gm
<220> FEATURE:
<221> NAME/KEY: modified_base
<222> LOCATION: (13)..(13)
<223> OTHER INFORMATION: cm
<220> FEATURE:
<221> NAME/KEY: misc_feature
<222> LOCATION: (14)..(14)
<223> OTHER INFORMATION: locked nucleic acid (LNA) base
<220> FEATURE:
<221> NAME/KEY: modified_base
<222> LOCATION: (15)..(15)
<223> OTHER INFORMATION: cm
<220> FEATURE:
<221> NAME/KEY: modified_base
<222> LOCATION: (16)..(16)
<223> OTHER INFORMATION: um
<220> FEATURE:
<221> NAME/KEY: misc_feature -continued

```
<222> LOCATION: (17)..(17)
<223> OTHER INFORMATION: locked nucleic acid (LNA) base
<220> FEATURE:
<221> NAME/KEY: modified_base
<222> LOCATION: (18)..(18)
<223> OTHER INFORMATION: cm
<220> FEATURE:
<221> NAME/KEY: modified_base
<222> LOCATION: (19)..(19)
<223> OTHER INFORMATION: gm
<220> FEATURE:
<221> NAME/KEY: modified_base
<222> LOCATION: (20)..(20)
<223> OTHER INFORMATION: um
<220> FEATURE:
<221> NAME/KEY: misc_feature
<222> LOCATION: (21)..(21)
<223> OTHER INFORMATION: locked nucleic acid (LNA) base
<220> FEATURE:
<221> NAME/KEY: modified_base
<222> LOCATION: (22)..(22)
<223> OTHER INFORMATION: gm
<220> FEATURE:
<221> NAME/KEY: modified_base
<222> LOCATION: (23)..(23)
<223> OTHER INFORMATION: cm
<220> FEATURE:
<221> NAME/KEY: misc_feature
<222> LOCATION: (24)..(24)
<223> OTHER INFORMATION: locked nucleic acid (LNA) base
<220> FEATURE:
<221> NAME/KEY: modified_base
<222> LOCATION: (25)..(25)
<223> OTHER INFORMATION: gm
<220> FEATURE:
<221> NAME/KEY: modified_base
<222> LOCATION: (27)..(27)
<223> OTHER INFORMATION: cm
<220> FEATURE:
<221> NAME/KEY: modified_base
<222> LOCATION: (28)..(28)
<223> OTHER INFORMATION: um
<220> FEATURE:
<221> NAME/KEY: modified_base
<222> LOCATION: (29)..(30)
<223> OTHER INFORMATION: cm
<220> FEATURE:
<221> NAME/KEY: misc_feature
<222> LOCATION: (31)..(31)
<223> OTHER INFORMATION: locked nucleic acid (LNA) base
<220> FEATURE:
<221> NAME/KEY: modified_base
<222> LOCATION: (32)..(32)
<223> OTHER INFORMATION: cm
<220> FEATURE:
<221> NAME/KEY: modified_base
<222> LOCATION: (33)..(34)
<223> OTHER INFORMATION: um
<220> FEATURE:
<221> NAME/KEY: modified_base
<222> LOCATION: (35)..(35)
<223> OTHER INFORMATION: cm
<220> FEATURE:
<221> NAME/KEY: modified_base
<222> LOCATION: (36)..(37)
<223> OTHER INFORMATION: um
<220> FEATURE:
<221> NAME/KEY: modified_base
<222> LOCATION: (38)..(38)
<223> OTHER INFORMATION: cm
<220> FEATURE:
<221> NAME/KEY: misc_feature
<222> LOCATION: (39)..(39)
<223> OTHER INFORMATION: Amino modifier attached to 3' end of SEQ ID NO:
      47
<220> FEATURE:
<221> NAME/KEY: modified_base
<222> LOCATION: (39)..(39)
<223> OTHER INFORMATION: gm
```

<400> SEQUENCE: 47
guucugauug agctcutcgu cgctgucucc gcuucuucg                                    39

<210> SEQ ID NO 48
<211> LENGTH: 9
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Triethyleneglycol spacer attached to 5' end of
      SEQ ID NO: 48
<220> FEATURE:
<221> NAME/KEY: misc_feature
<222> LOCATION: (1)..(9)
<223> OTHER INFORMATION: phosphorothioate backbone
<220> FEATURE:
<221> NAME/KEY: modified_base
<222> LOCATION: (1)..(1)
<223> OTHER INFORMATION: gm
<220> FEATURE:
<221> NAME/KEY: modified_base
<222> LOCATION: (2)..(3)
<223> OTHER INFORMATION: um
<220> FEATURE:
<221> NAME/KEY: misc_feature
<222> LOCATION: (4)..(4)
<223> OTHER INFORMATION: locked nucleic acid (LNA) base
<220> FEATURE:
<221> NAME/KEY: modified_base
<222> LOCATION: (5)..(5)
<223> OTHER INFORMATION: um
<220> FEATURE:
<221> NAME/KEY: modified_base
<222> LOCATION: (6)..(6)
<223> OTHER INFORMATION: gm
<220> FEATURE:
<221> NAME/KEY: misc_feature
<222> LOCATION: (7)..(7)
<223> OTHER INFORMATION: 2'-O-methyl adenosine
<220> FEATURE:
<221> NAME/KEY: modified_base
<222> LOCATION: (8)..(9)
<223> OTHER INFORMATION: um

<400> SEQUENCE: 48 guucugauu                                                                     9

<210> SEQ ID NO 49
<211> LENGTH: 23
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(23)
<223> OTHER INFORMATION: phosphorothioate backbone
<220> FEATURE:
<221> NAME/KEY: modified_base
<222> LOCATION: (1)..(1)
<223> OTHER INFORMATION: gm
<220> FEATURE:
<221> NAME/KEY: misc_feature
<222> LOCATION: (2)..(2)
<223> OTHER INFORMATION: 2'-O-methyl adenosine
<220> FEATURE:
<221> NAME/KEY: modified_base
<222> LOCATION: (3)..(3)
<223> OTHER INFORMATION: gm
<220> FEATURE:
<221> NAME/KEY: modified_base

```
<222> LOCATION: (4)..(4)
<223> OTHER INFORMATION: cm
<220> FEATURE:
<221> NAME/KEY: misc_feature
<222> LOCATION: (5)..(5)
<223> OTHER INFORMATION: locked nucleic acid (LNA) base
<220> FEATURE:
<221> NAME/KEY: modified_base
<222> LOCATION: (6)..(6)
<223> OTHER INFORMATION: cm
<220> FEATURE:
<221> NAME/KEY: modified_base
<222> LOCATION: (7)..(7)
<223> OTHER INFORMATION: um
<220> FEATURE:
<221> NAME/KEY: misc_feature
<222> LOCATION: (8)..(8)
<223> OTHER INFORMATION: locked nucleic acid (LNA) base
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (10)..(10)
<223> OTHER INFORMATION: gm
<220> FEATURE:
<221> NAME/KEY: modified_base
<222> LOCATION: (11)..(11)
<223> OTHER INFORMATION: um
<220> FEATURE:
<221> NAME/KEY: misc_feature
<222> LOCATION: (12)..(12)
<223> OTHER INFORMATION: locked nucleic acid (LNA) base
<220> FEATURE:
<221> NAME/KEY: modified_base
<222> LOCATION: (13)..(13)
<223> OTHER INFORMATION: gm
<220> FEATURE:
<221> NAME/KEY: modified_base
<222> LOCATION: (14)..(14)
<223> OTHER INFORMATION: cm
<220> FEATURE:
<221> NAME/KEY: misc_feature
<222> LOCATION: (15)..(15)
<223> OTHER INFORMATION: locked nucleic acid (LNA) base
<220> FEATURE:
<221> NAME/KEY: modified_base
<222> LOCATION: (16)..(16)
<223> OTHER INFORMATION: gm
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(18)
<223> OTHER INFORMATION: cm
<220> FEATURE:
<221> NAME/KEY: modified_base
<222> LOCATION: (19)..(19)
<223> OTHER INFORMATION: um
<220> FEATURE:
<221> NAME/KEY: modified_base
<222> LOCATION: (20)..(21)
<223> OTHER INFORMATION: cm
<220> FEATURE:
<221> NAME/KEY: misc_feature
<222> LOCATION: (22)..(22)
<223> OTHER INFORMATION: locked nucleic acid (LNA) base
<220> FEATURE:
<221> NAME/KEY: modified_base
<222> LOCATION: (23)..(23)
<223> OTHER INFORMATION: cm

<400> SEQUENCE: 49
gagctcutcg ucgctgucuc cgc                                           23
```

```
<210> SEQ ID NO 50
<211> LENGTH: 7
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(7)
<223> OTHER INFORMATION: phosphorothioate backbone
<220> FEATURE:
<221> NAME/KEY: modified_base
<222> LOCATION: (1)..(2)
<223> OTHER INFORMATION: um
<220> FEATURE:
<221> NAME/KEY: modified_base
<222> LOCATION: (3)..(3)
<223> OTHER INFORMATION: cm
<220> FEATURE:
<221> NAME/KEY: modified_base
<222> LOCATION: (4)..(5)
<223> OTHER INFORMATION: um
<220> FEATURE:
<221> NAME/KEY: modified_base
<222> LOCATION: (6)..(7)
<223> OTHER INFORMATION: cm
<220> FEATURE:
<221> NAME/KEY: misc_feature
<222> LOCATION: (7)..(7)
<223> OTHER INFORMATION: Amino modifier attached to 3' end of SEQ ID NO:
      50

<400> SEQUENCE: 50 uucuucc                                                                     7

<210> SEQ ID NO 51
<211> LENGTH: 36
<212> TYPE: RNA
<213> ORGANISM: Artificial Sequence
<220> FEATURE:
<223> OTHER INFORMATION: Synthetic Polynucleotide

<400> SEQUENCE: 51
ggagaagcgg agacagcgac gaagagcuca aucaga                                    36

<210> SEQ ID NO 52
<211> LENGTH: 12
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(4)
<223> OTHER INFORMATION: phosphorothioate backbone
<220> FEATURE:
<221> NAME/KEY: misc_feature
<222> LOCATION: (12)..(12)
<223> OTHER INFORMATION: C3 linker attached to 5' end of SEQ ID NO: 53

<400> SEQUENCE: 52
gaagagcuca uc                                                              12

<210> SEQ ID NO 53
<211> LENGTH: 23
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
```

```
<223> OTHER INFORMATION: C3 linker attached to 3' end of SEQ ID NO: 52
<220> FEATURE:
<221> NAME/KEY: misc_feature
<222> LOCATION: (1)..(3)
<223> OTHER INFORMATION: phosphorothioate backbone
<220> FEATURE:
<221> NAME/KEY: modified_base
<222> LOCATION: (1)..(2)
<223> OTHER INFORMATION: gm
<220> FEATURE:
<221> NAME/KEY: modified_base
<222> LOCATION: (3)..(3)
<223> OTHER INFORMATION: um
<220> FEATURE:
<221> NAME/KEY: misc_feature
<222> LOCATION: (22)..(23)
<223> OTHER INFORMATION: phosphorothioate backbone
<220> FEATURE:
<221> NAME/KEY: modified_base
<222> LOCATION: (22)..(22)
<223> OTHER INFORMATION: cm
<220> FEATURE:
<221> NAME/KEY: misc_feature
<222> LOCATION: (23)..(23)
<223> OTHER INFORMATION: C3 linker attached to 5' end of SEQ ID NO: 54
<220> FEATURE:
<221> NAME/KEY: modified_base
<222> LOCATION: (23)..(23)
<223> OTHER INFORMATION: gm

<400> SEQUENCE: 53
gguaacuaga gaucccucag acg                                              23

<210> SEQ ID NO 54
<211> LENGTH: 11
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: C3 linker attached to 3' end of SEQ ID NO: 53
<220> FEATURE:
<221> NAME/KEY: misc_feature
<222> LOCATION: (8)..(11)
<223> OTHER INFORMATION: phosphorothioate backbone

<400> SEQUENCE: 54
agagcggaga c                                                           11

<210> SEQ ID NO 55
<211> LENGTH: 29
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Triethyleneglycol spacer attached to 5' end of
      SEQ ID NO: 55
<220> FEATURE:
<221> NAME/KEY: misc_feature
<222> LOCATION: (1)..(29)
<223> OTHER INFORMATION: phosphorothioate backbone
<220> FEATURE:
<221> NAME/KEY: modified_base
<222> LOCATION: (1)..(1)
<223> OTHER INFORMATION: gm
<220> FEATURE:
<221> NAME/KEY: misc_feature
<222> LOCATION: (2)..(2)
<223> OTHER INFORMATION: 2'-O-methyl adenosine
<220> FEATURE:
```

-continued

```
<221> NAME/KEY: misc_feature
<222> LOCATION: (3)..(3)
<223> OTHER INFORMATION: locked nucleic acid (LNA) base
<220> FEATURE:
<221> NAME/KEY: modified_base
<222> LOCATION: (4)..(4)
<223> OTHER INFORMATION: gm
<220> FEATURE:
<221> NAME/KEY: misc_feature
<222> LOCATION: (5)..(5)
<223> OTHER INFORMATION: 2'-O-methyl adenosine
<220> FEATURE:
<221> NAME/KEY: modified_base
<222> LOCATION: (6)..(6)
<223> OTHER INFORMATION: gm
<220> FEATURE:
<221> NAME/KEY: modified_base
<222> LOCATION: (7)..(7)
<223> OTHER INFORMATION: cm
<220> FEATURE:
<221> NAME/KEY: misc_feature
<222> LOCATION: (8)..(8)
<223> OTHER INFORMATION: locked nucleic acid (LNA) base
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (10)..(10)
<223> OTHER INFORMATION: um
<220> FEATURE:
<221> NAME/KEY: misc_feature
<222> LOCATION: (11)..(11)
<223> OTHER INFORMATION: locked nucleic acid (LNA) base
<220> FEATURE:
<221> NAME/KEY: modified_base
<222> LOCATION: (12)..(12)
<223> OTHER INFORMATION: cm
<220> FEATURE:
<221> NAME/KEY: modified_base
<222> LOCATION: (13)..(13)
<223> OTHER INFORMATION: gm
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (15)..(15)
<223> OTHER INFORMATION: cm
<220> FEATURE:
<221> NAME/KEY: modified_base
<222> LOCATION: (16)..(16)
<223> OTHER INFORMATION: gm
<220> FEATURE:
<221> NAME/KEY: modified_base
<222> LOCATION: (17)..(17)
<223> OTHER INFORMATION: cm
<220> FEATURE:
<221> NAME/KEY: modified_base
<222> LOCATION: (18)..(18)
<223> OTHER INFORMATION: um
<220> FEATURE:
<221> NAME/KEY: modified_base
<222> LOCATION: (19)..(19)
<223> OTHER INFORMATION: gm
<220> FEATURE:
<221> NAME/KEY: modified_base
<222> LOCATION: (20)..(20)
<223> OTHER INFORMATION: um
<220> FEATURE:
<221> NAME/KEY: modified_base
<222> LOCATION: (21)..(21)
<223> OTHER INFORMATION: cm
<220> FEATURE:
<221> NAME/KEY: misc_feature
<222> LOCATION: (22)..(22)
<223> OTHER INFORMATION: locked nucleic acid (LNA) base
```

```
<220> FEATURE:
<221> NAME/KEY: modified_base
<222> LOCATION: (23)..(24)
<223> OTHER INFORMATION: cm
<220> FEATURE:
<221> NAME/KEY: misc_feature
<222> LOCATION: (25)..(25)
<223> OTHER INFORMATION: locked nucleic acid (LNA) base
<220> FEATURE:
<221> NAME/KEY: modified_base
<222> LOCATION: (26)..(26)
<223> OTHER INFORMATION: cm
<220> FEATURE:
<221> NAME/KEY: modified_base
<222> LOCATION: (27)..(27)
<223> OTHER INFORMATION: um
<220> FEATURE:
<221> NAME/KEY: misc_feature
<222> LOCATION: (28)..(28)
<223> OTHER INFORMATION: locked nucleic acid (LNA) base
<220> FEATURE:
<221> NAME/KEY: misc_feature
<222> LOCATION: (29)..(29)
<223> OTHER INFORMATION: C3 linker attached to Amino modifier at 3' end
      of SEQ ID NO: 55
<220> FEATURE:
<221> NAME/KEY: modified_base
<222> LOCATION: (29)..(29)
<223> OTHER INFORMATION: um

<400> SEQUENCE: 55
gatgagctcu tcgucgcugu ctccgcucu                                           29

<210> SEQ ID NO 56
<211> LENGTH: 8
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(8)
<223> OTHER INFORMATION: phosphorothioate backbone
<220> FEATURE:
<221> NAME/KEY: modified_base
<222> LOCATION: (1)..(1)
<223> OTHER INFORMATION: cm
<220> FEATURE:
<221> NAME/KEY: modified_base
<222> LOCATION: (2)..(2)
<223> OTHER INFORMATION: gm
<220> FEATURE:
<221> NAME/KEY: modified_base
<222> LOCATION: (3)..(3)
<223> OTHER INFORMATION: um
<220> FEATURE:
<221> NAME/KEY: modified_base
<222> LOCATION: (4)..(4)
<223> OTHER INFORMATION: cm
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (6)..(6)
<223> OTHER INFORMATION: cm
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (8)..(8)
<223> OTHER INFORMATION: gm

<400> SEQUENCE: 56
``` cgucgcug                                                          8

<210> SEQ ID NO 57
<211> LENGTH: 11
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Triethyleneglycol spacer attached to 5' end of
      SEQ ID NO: 57
<220> FEATURE:
<221> NAME/KEY: modified_base
<222> LOCATION: (1)..(1)
<223> OTHER INFORMATION: gm
<220> FEATURE:
<221> NAME/KEY: misc_feature
<222> LOCATION: (1)..(11)
<223> OTHER INFORMATION: phosphorothioate backbone
<220> FEATURE:
<221> NAME/KEY: misc_feature
<222> LOCATION: (2)..(2)
<223> OTHER INFORMATION: 2'-O-methyl adenosine
<220> FEATURE:
<221> NAME/KEY: misc_feature
<222> LOCATION: (3)..(3)
<223> OTHER INFORMATION: locked nucleic acid (LNA) base
<220> FEATURE:
<221> NAME/KEY: modified_base
<222> LOCATION: (4)..(4)
<223> OTHER INFORMATION: gm
<220> FEATURE:
<221> NAME/KEY: misc_feature
<222> LOCATION: (5)..(5)
<223> OTHER INFORMATION: 2'-O-methyl adenosine
<220> FEATURE:
<221> NAME/KEY: modified_base
<222> LOCATION: (6)..(6)
<223> OTHER INFORMATION: gm
<220> FEATURE:
<221> NAME/KEY: modified_base
<222> LOCATION: (7)..(7)
<223> OTHER INFORMATION: cm
<220> FEATURE:
<221> NAME/KEY: misc_feature
<222> LOCATION: (8)..(8)
<223> OTHER INFORMATION: locked nucleic acid (LNA) base
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (10)..(10)
<223> OTHER INFORMATION: um
<220> FEATURE:
<221> NAME/KEY: misc_feature
<222> LOCATION: (11)..(11)
<223> OTHER INFORMATION: locked nucleic acid (LNA) base

<400> SEQUENCE: 57
gatgagctcu t                                                      11

<210> SEQ ID NO 58
<211> LENGTH: 10
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(10)
<223> OTHER INFORMATION: phosphorothioate backbone

```
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (2)..(2)
<223> OTHER INFORMATION: cm
<220> FEATURE:
<221> NAME/KEY: misc_feature
<222> LOCATION: (3)..(3)
<223> OTHER INFORMATION: locked nucleic acid (LNA) base
<220> FEATURE:
<221> NAME/KEY: modified_base
<222> LOCATION: (4)..(5)
<223> OTHER INFORMATION: cm
<220> FEATURE:
<221> NAME/KEY: misc_feature
<222> LOCATION: (6)..(6)
<223> OTHER INFORMATION: locked nucleic acid (LNA) base
<220> FEATURE:
<221> NAME/KEY: modified_base
<222> LOCATION: (7)..(7)
<223> OTHER INFORMATION: cm
<220> FEATURE:
<221> NAME/KEY: modified_base
<222> LOCATION: (8)..(8)
<223> OTHER INFORMATION: um
<220> FEATURE:
<221> NAME/KEY: misc_feature
<222> LOCATION: (9)..(9)
<223> OTHER INFORMATION: locked nucleic acid (LNA) base
<220> FEATURE:
<221> NAME/KEY: misc_feature
<222> LOCATION: (10)..(10)
<223> OTHER INFORMATION: C3 linker attached to Amino modifier at 3' end
      of SEQ ID NO: 58
<220> FEATURE:
<221> NAME/KEY: modified_base
<222> LOCATION: (10)..(10)
<223> OTHER INFORMATION: um

<400> SEQUENCE: 58
uctccgcucu                                                              10

<210> SEQ ID NO 59
<211> LENGTH: 29
<212> TYPE: RNA
<213> ORGANISM: Artificial Sequence
<220> FEATURE:
<223> OTHER INFORMATION: Synthetic Polynucleotide

<400> SEQUENCE: 59
agagcggaga cagcgacgaa gagcucauc                                         29

<210> SEQ ID NO 60
<211> LENGTH: 12
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(4)
<223> OTHER INFORMATION: phosphorothioate backbone
<220> FEATURE:
<221> NAME/KEY: misc_feature
<222> LOCATION: (12)..(12)
<223> OTHER INFORMATION: C3 linker attached to 5' end of SEQ ID NO: 61

<400> SEQUENCE: 60
gaagagcuca uc                                                           12
```

```
<210> SEQ ID NO 61
<211> LENGTH: 23
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: C3 linker attached to 3' end of SEQ ID NO: 60
<220> FEATURE:
<221> NAME/KEY: misc_feature
<222> LOCATION: (1)..(3)
<223> OTHER INFORMATION: phosphorothioate backbone
<220> FEATURE:
<221> NAME/KEY: modified_base
<222> LOCATION: (1)..(2)
<223> OTHER INFORMATION: gm
<220> FEATURE:
<221> NAME/KEY: modified_base
<222> LOCATION: (3)..(3)
<223> OTHER INFORMATION: um
<220> FEATURE:
<221> NAME/KEY: misc_feature
<222> LOCATION: (21)..(21)
<223> OTHER INFORMATION: 2'-O-methyl adenosine
<220> FEATURE:
<221> NAME/KEY: misc_feature
<222> LOCATION: (22)..(23)
<223> OTHER INFORMATION: phosphorothioate backbone
<220> FEATURE:
<221> NAME/KEY: modified_base
<222> LOCATION: (22)..(22)
<223> OTHER INFORMATION: cm
<220> FEATURE:
<221> NAME/KEY: misc_feature
<222> LOCATION: (23)..(23)
<223> OTHER INFORMATION: C3 linker attached to 5' end of SEQ ID NO: 62
<220> FEATURE:
<221> NAME/KEY: modified_base
<222> LOCATION: (23)..(23)
<223> OTHER INFORMATION: gm

<400> SEQUENCE: 61
gguaacuaga gaucccucag acg                                             23

<210> SEQ ID NO 62
<211> LENGTH: 11
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: C3 linker attached to 3' end of SEQ ID NO: 61
<220> FEATURE:
<221> NAME/KEY: misc_feature
<222> LOCATION: (8)..(11)
<223> OTHER INFORMATION: phosphorothioate backbone

<400> SEQUENCE: 62
agagcggaga c                                                          11

<210> SEQ ID NO 63
<211> LENGTH: 36
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Triethyleneglycol spacer attached to 5' end of
      SEQ ID NO: 63
```

-continued

```
<220> FEATURE:
<221> NAME/KEY: modified_base
<222> LOCATION: (1)..(1)
<223> OTHER INFORMATION: gm
<220> FEATURE:
<221> NAME/KEY: misc_feature
<222> LOCATION: (1)..(36)
<223> OTHER INFORMATION: phosphorothioate backbone
<220> FEATURE:
<221> NAME/KEY: misc_feature
<222> LOCATION: (2)..(2)
<223> OTHER INFORMATION: 2'-O-methyl adenosine
<220> FEATURE:
<221> NAME/KEY: misc_feature
<222> LOCATION: (3)..(3)
<223> OTHER INFORMATION: locked nucleic acid (LNA) base
<220> FEATURE:
<221> NAME/KEY: modified_base
<222> LOCATION: (4)..(4)
<223> OTHER INFORMATION: gm
<220> FEATURE:
<221> NAME/KEY: misc_feature
<222> LOCATION: (5)..(5)
<223> OTHER INFORMATION: 2'-O-methyl adenosine
<220> FEATURE:
<221> NAME/KEY: modified_base
<222> LOCATION: (6)..(6)
<223> OTHER INFORMATION: gm
<220> FEATURE:
<221> NAME/KEY: modified_base
<222> LOCATION: (7)..(7)
<223> OTHER INFORMATION: cm
<220> FEATURE:
<221> NAME/KEY: misc_feature
<222> LOCATION: (8)..(8)
<223> OTHER INFORMATION: locked nucleic acid (LNA) base
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (10)..(10)
<223> OTHER INFORMATION: um
<220> FEATURE:
<221> NAME/KEY: misc_feature
<222> LOCATION: (11)..(11)
<223> OTHER INFORMATION: locked nucleic acid (LNA) base
<220> FEATURE:
<221> NAME/KEY: modified_base
<222> LOCATION: (12)..(12)
<223> OTHER INFORMATION: cm
<220> FEATURE:
<221> NAME/KEY: modified_base
<222> LOCATION: (13)..(13)
<223> OTHER INFORMATION: gm
<220> FEATURE:
<221> NAME/KEY: modified_base
<222> LOCATION: (15)..(15)
<223> OTHER INFORMATION: cm
<220> FEATURE:
<221> NAME/KEY: modified_base
<222> LOCATION: (16)..(16)
<223> OTHER INFORMATION: gm
<220> FEATURE:
<221> NAME/KEY: modified_base
<222> LOCATION: (17)..(17)
<223> OTHER INFORMATION: cm
<220> FEATURE:
<221> NAME/KEY: modified_base
<222> LOCATION: (18)..(18)
<223> OTHER INFORMATION: um
<220> FEATURE:
<221> NAME/KEY: modified_base
<222> LOCATION: (19)..(19)
<223> OTHER INFORMATION: gm
<220> FEATURE:
<221> NAME/KEY: modified_base
<222> LOCATION: (20)..(20)
```

```
<223> OTHER INFORMATION: um
<220> FEATURE:
<221> NAME/KEY: modified_base
<222> LOCATION: (21)..(21)
<223> OTHER INFORMATION: cm
<220> FEATURE:
<221> NAME/KEY: misc_feature
<222> LOCATION: (22)..(22)
<223> OTHER INFORMATION: locked nucleic acid (LNA) base
<220> FEATURE:
<221> NAME/KEY: modified_base
<222> LOCATION: (23)..(24)
<223> OTHER INFORMATION: cm
<220> FEATURE:
<221> NAME/KEY: misc_feature
<222> LOCATION: (25)..(25)
<223> OTHER INFORMATION: locked nucleic acid (LNA) base
<220> FEATURE:
<221> NAME/KEY: modified_base
<222> LOCATION: (26)..(26)
<223> OTHER INFORMATION: cm
<220> FEATURE:
<221> NAME/KEY: modified_base
<222> LOCATION: (27)..(27)
<223> OTHER INFORMATION: um
<220> FEATURE:
<221> NAME/KEY: misc_feature
<222> LOCATION: (28)..(28)
<223> OTHER INFORMATION: locked nucleic acid (LNA) base
<220> FEATURE:
<221> NAME/KEY: modified_base
<222> LOCATION: (29)..(29)
<223> OTHER INFORMATION: um
<220> FEATURE:
<221> NAME/KEY: modified_base
<222> LOCATION: (30)..(30)
<223> OTHER INFORMATION: gm
<220> FEATURE:
<221> NAME/KEY: modified_base
<222> LOCATION: (31)..(32)
<223> OTHER INFORMATION: um
<220> FEATURE:
<221> NAME/KEY: misc_feature
<222> LOCATION: (33)..(33)
<223> OTHER INFORMATION: locked nucleic acid (LNA) base
<220> FEATURE:
<221> NAME/KEY: modified_base
<222> LOCATION: (34)..(34)
<223> OTHER INFORMATION: um
<220> FEATURE:
<221> NAME/KEY: modified_base
<222> LOCATION: (35)..(35)
<223> OTHER INFORMATION: gm
<220> FEATURE:
<221> NAME/KEY: misc_feature
<222> LOCATION: (36)..(36)
<223> OTHER INFORMATION: C3 linker attached to Amino modifier at 3' end
     of SEQ ID NO: 63
<220> FEATURE:
<221> NAME/KEY: misc_feature
<222> LOCATION: (36)..(36)
<223> OTHER INFORMATION: 2'-O-methyl adenosine

<400> SEQUENCE: 63
gatgagctcu tcgucgcugu ctccgcucug uucuga                              36

<210> SEQ ID NO 64
<211> LENGTH: 7
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: modified_base
<222> LOCATION: (1)..(1)
<223> OTHER INFORMATION: gm
<220> FEATURE:
```

```
<221> NAME/KEY: modified_base
<222> LOCATION: (2)..(3)
<223> OTHER INFORMATION: um
<220> FEATURE:
<221> NAME/KEY: misc_feature
<222> LOCATION: (4)..(4)
<223> OTHER INFORMATION: locked nucleic acid (LNA) base
<220> FEATURE:
<221> NAME/KEY: modified_base
<222> LOCATION: (5)..(5)
<223> OTHER INFORMATION: um
<220> FEATURE:
<221> NAME/KEY: modified_base
<222> LOCATION: (6)..(6)
<223> OTHER INFORMATION: gm
<220> FEATURE:
<221> NAME/KEY: misc_feature
<222> LOCATION: (7)..(7)
<223> OTHER INFORMATION: C3 linker attached to Amino modifier at 3' end
     of SEQ ID NO: 64
<220> FEATURE:
<221> NAME/KEY: misc_feature
<222> LOCATION: (7)..(7)
<223> OTHER INFORMATION: 2'-O-methyl adenosine

<400> SEQUENCE: 64 guucuga                                                                       7

<210> SEQ ID NO 65
<211> LENGTH: 11
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(11)
<223> OTHER INFORMATION: phosphorothioate backbone
<220> FEATURE:
<221> NAME/KEY: modified_base
<222> LOCATION: (1)..(1)
<223> OTHER INFORMATION: gm
<220> FEATURE:
<221> NAME/KEY: modified_base
<222> LOCATION: (2)..(2)
<223> OTHER INFORMATION: um
<220> FEATURE:
<221> NAME/KEY: modified_base
<222> LOCATION: (3)..(3)
<223> OTHER INFORMATION: cm
<220> FEATURE:
<221> NAME/KEY: misc_feature
<222> LOCATION: (4)..(4)
<223> OTHER INFORMATION: locked nucleic acid (LNA) base
<220> FEATURE:
<221> NAME/KEY: modified_base
<222> LOCATION: (5)..(6)
<223> OTHER INFORMATION: cm
<220> FEATURE:
<221> NAME/KEY: misc_feature
<222> LOCATION: (7)..(7)
<223> OTHER INFORMATION: locked nucleic acid (LNA) base
<220> FEATURE:
<221> NAME/KEY: modified_base
<222> LOCATION: (8)..(8)
<223> OTHER INFORMATION: cm
<220> FEATURE:
<221> NAME/KEY: modified_base
<222> LOCATION: (9)..(9)
<223> OTHER INFORMATION: um
<220> FEATURE:
<221> NAME/KEY: misc_feature
<222> LOCATION: (10)..(10)
<223> OTHER INFORMATION: locked nucleic acid (LNA) base
<220> FEATURE:
<221> NAME/KEY: modified_base
<222> LOCATION: (11)..(11)
```

<223> OTHER INFORMATION: um

<400> SEQUENCE: 65
guctccgcuc u                                                                11

<210> SEQ ID NO 66
<211> LENGTH: 12
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Triethyleneglycol spacer attached to 5' end of
      SEQ ID NO: 66
<220> FEATURE:
<221> NAME/KEY: misc_feature
<222> LOCATION: (1)..(12)
<223> OTHER INFORMATION: phosphorothioate backbone
<220> FEATURE:
<221> NAME/KEY: modified_base
<222> LOCATION: (1)..(1)
<223> OTHER INFORMATION: gm
<220> FEATURE:
<221> NAME/KEY: misc_feature
<222> LOCATION: (2)..(2)
<223> OTHER INFORMATION: 2'-O-methyl adenosine
<220> FEATURE:
<221> NAME/KEY: misc_feature
<222> LOCATION: (3)..(3)
<223> OTHER INFORMATION: locked nucleic acid (LNA) base
<220> FEATURE:
<221> NAME/KEY: modified_base
<222> LOCATION: (4)..(4)
<223> OTHER INFORMATION: gm
<220> FEATURE:
<221> NAME/KEY: misc_feature
<222> LOCATION: (5)..(5)
<223> OTHER INFORMATION: 2'-O-methyl adenosine
<220> FEATURE:
<221> NAME/KEY: modified_base
<222> LOCATION: (6)..(6)
<223> OTHER INFORMATION: gm
<220> FEATURE:
<221> NAME/KEY: modified_base
<222> LOCATION: (7)..(7)
<223> OTHER INFORMATION: cm
<220> FEATURE:
<221> NAME/KEY: misc_feature
<222> LOCATION: (8)..(8)
<223> OTHER INFORMATION: locked nucleic acid (LNA) base
<220> FEATURE:
<221> NAME/KEY: modified_base
<222> LOCATION: (9)..(9)
<223> OTHER INFORMATION: cm
<220> FEATURE:
<221> NAME/KEY: misc_feature
<222> LOCATION: (11)..(11)
<223> OTHER INFORMATION: locked nucleic acid (LNA) base
<220> FEATURE:
<221> NAME/KEY: modified_base
<222> LOCATION: (12)..(12)
<223> OTHER INFORMATION: cm

<400> SEQUENCE: 66
gatgagctcu tc                                                               12

<210> SEQ ID NO 67
<211> LENGTH: 6
<212> TYPE: RNA
<213> ORGANISM: Artificial Sequence
<220> FEATURE:
<223> OTHER INFORMATION: Synthetic Polynucleotide
<220> FEATURE:

```
<221> NAME/KEY: misc_feature
<222> LOCATION: (1)..(6)
<223> OTHER INFORMATION: phosphorothioate backbone
<220> FEATURE:
<221> NAME/KEY: modified_base
<222> LOCATION: (1)..(1)
<223> OTHER INFORMATION: gm
<220> FEATURE:
<221> NAME/KEY: modified_base
<222> LOCATION: (2)..(6)
<223> OTHER INFORMATION: um
<220> FEATURE:
<221> NAME/KEY: modified_base
<222> LOCATION: (3)..(3)
<223> OTHER INFORMATION: cm
<220> FEATURE:
<221> NAME/KEY: modified_base
<222> LOCATION: (4)..(4)
<223> OTHER INFORMATION: gm
<220> FEATURE:
<221> NAME/KEY: modified_base
<222> LOCATION: (5)..(5)
<223> OTHER INFORMATION: cm

<400> SEQUENCE: 67 gucgcu                                                                  6

<210> SEQ ID NO 68
<211> LENGTH: 18
<212> TYPE: RNA
<213> ORGANISM: Artificial Sequence
<220> FEATURE:
<223> OTHER INFORMATION: Synthetic Polynucleotide

<400> SEQUENCE: 68
ucagaacaga gcggagac                                                    18

<210> SEQ ID NO 69
<211> LENGTH: 18
<212> TYPE: RNA
<213> ORGANISM: Artificial Sequence
<220> FEATURE:
<223> OTHER INFORMATION: Synthetic Polynucleotide

<400> SEQUENCE: 69
agcgacgaag agcucauc                                                    18

<210> SEQ ID NO 70
<211> LENGTH: 12
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (12)..(12)
<223> OTHER INFORMATION: C3 linker attached to 5' end of SEQ ID NO: 71

<400> SEQUENCE: 70
gacgaagagc uc                                                          12

<210> SEQ ID NO 71
<211> LENGTH: 23
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: C3 linker attached to 3' end of SEQ ID NO: 70
```

```
<220> FEATURE:
<221> NAME/KEY: misc_feature
<222> LOCATION: (1)..(3)
<223> OTHER INFORMATION: phosphorothioate backbone
<220> FEATURE:
<221> NAME/KEY: modified_base
<222> LOCATION: (1)..(2)
<223> OTHER INFORMATION: gm
<220> FEATURE:
<221> NAME/KEY: modified_base
<222> LOCATION: (3)..(3)
<223> OTHER INFORMATION: um
<220> FEATURE:
<221> NAME/KEY: misc_feature
<222> LOCATION: (22)..(23)
<223> OTHER INFORMATION: phosphorothioate backbone
<220> FEATURE:
<221> NAME/KEY: modified_base
<222> LOCATION: (22)..(22)
<223> OTHER INFORMATION: cm
<220> FEATURE:
<221> NAME/KEY: misc_feature
<222> LOCATION: (23)..(23)
<223> OTHER INFORMATION: C3 linker attached to 5' end of SEQ ID NO: 72
<220> FEATURE:
<221> NAME/KEY: modified_base
<222> LOCATION: (23)..(23)
<223> OTHER INFORMATION: gm

<400> SEQUENCE: 71
gguaacuaga gaucccucag acg                                              23

<210> SEQ ID NO 72
<211> LENGTH: 11
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: C3 linker attached to 3' end of SEQ ID NO: 71

<400> SEQUENCE: 72
gcggagacag c                                                           11

<210> SEQ ID NO 73
<211> LENGTH: 31
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Triethyleneglycol spacer attached to 5' end of
      SEQ ID NO: 73
<220> FEATURE:
<221> NAME/KEY: misc_feature
<222> LOCATION: (1)..(31)
<223> OTHER INFORMATION: phosphorothioate backbone
<220> FEATURE:
<221> NAME/KEY: modified_base
<222> LOCATION: (1)..(1)
<223> OTHER INFORMATION: gm
<220> FEATURE:
<221> NAME/KEY: modified_base
<222> LOCATION: (2)..(3)
<223> OTHER INFORMATION: um
<220> FEATURE:
<221> NAME/KEY: misc_feature
<222> LOCATION: (4)..(4)
<223> OTHER INFORMATION: locked nucleic acid (LNA) base
<220> FEATURE:
<221> NAME/KEY: modified_base
```

```
<222> LOCATION: (5)..(5)
<223> OTHER INFORMATION: um
<220> FEATURE:
<221> NAME/KEY: modified_base
<222> LOCATION: (6)..(6)
<223> OTHER INFORMATION: gm
<220> FEATURE:
<221> NAME/KEY: misc_feature
<222> LOCATION: (7)..(7)
<223> OTHER INFORMATION: 2'-O-methyl adenosine
<220> FEATURE:
<221> NAME/KEY: modified_base
<222> LOCATION: (8)..(8)
<223> OTHER INFORMATION: um
<220> FEATURE:
<221> NAME/KEY: modified_base
<222> LOCATION: (9)..(9)
<223> OTHER INFORMATION: gm
<220> FEATURE:
<221> NAME/KEY: misc_feature
<222> LOCATION: (10)..(10)
<223> OTHER INFORMATION: 2'-O-methyl adenosine
<220> FEATURE:
<221> NAME/KEY: modified_base
<222> LOCATION: (11)..(11)
<223> OTHER INFORMATION: gm
<220> FEATURE:
<221> NAME/KEY: modified_base
<222> LOCATION: (12)..(12)
<223> OTHER INFORMATION: cm
<220> FEATURE:
<221> NAME/KEY: misc_feature
<222> LOCATION: (13)..(13)
<223> OTHER INFORMATION: locked nucleic acid (LNA) base
<220> FEATURE:
<221> NAME/KEY: modified_base
<222> LOCATION: (14)..(14)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: misc_feature
<222> LOCATION: (16)..(16)
<223> OTHER INFORMATION: locked nucleic acid (LNA) base
<220> FEATURE:
<221> NAME/KEY: modified_base
<222> LOCATION: (17)..(17)
<223> OTHER INFORMATION: cm
<220> FEATURE:
<221> NAME/KEY: modified_base
<222> LOCATION: (18)..(18)
<223> OTHER INFORMATION: gm
<220> FEATURE:
<221> NAME/KEY: modified_base
<222> LOCATION: (19)..(19)
<223> OTHER INFORMATION: um
<220> FEATURE:
<221> NAME/KEY: misc_feature
<222> LOCATION: (20)..(20)
<223> OTHER INFORMATION: locked nucleic acid (LNA) base
<220> FEATURE:
<221> NAME/KEY: modified_base
<222> LOCATION: (21)..(21)
<223> OTHER INFORMATION: gm
<220> FEATURE:
<221> NAME/KEY: modified_base
<222> LOCATION: (22)..(22)
<223> OTHER INFORMATION: cm
<220> FEATURE:
<221> NAME/KEY: misc_feature
<222> LOCATION: (23)..(23)
<223> OTHER INFORMATION: locked nucleic acid (LNA) base
<220> FEATURE:
<221> NAME/KEY: modified_base
<222> LOCATION: (24)..(24)
<223> OTHER INFORMATION: gm
<220> FEATURE:
```

```
<221> NAME/KEY: modified_base
<222> LOCATION: (25)..(25)
<223> OTHER INFORMATION: um
<220> FEATURE:
<221> NAME/KEY: modified_base
<222> LOCATION: (26)..(26)
<223> OTHER INFORMATION: cm
<220> FEATURE:
<221> NAME/KEY: modified_base
<222> LOCATION: (27)..(27)
<223> OTHER INFORMATION: um
<220> FEATURE:
<221> NAME/KEY: modified_base
<222> LOCATION: (28)..(28)
<223> OTHER INFORMATION: cm
<220> FEATURE:
<221> NAME/KEY: modified_base
<222> LOCATION: (29)..(29)
<223> OTHER INFORMATION: cm
<220> FEATURE:
<221> NAME/KEY: misc_feature
<222> LOCATION: (30)..(30)
<223> OTHER INFORMATION: locked nucleic acid (LNA) base
<220> FEATURE:
<221> NAME/KEY: misc_feature
<222> LOCATION: (31)..(31)
<223> OTHER INFORMATION: Amino modifier attached to 3' end of SEQ ID NO:
      73
<220> FEATURE:
<221> NAME/KEY: modified_base
<222> LOCATION: (31)..(31)
<223> OTHER INFORMATION: cm

<400> SEQUENCE: 73
guucugauga gctcutcguc gctgucuccg c                                      31

<210> SEQ ID NO 74
<211> LENGTH: 8
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Triethyleneglycol spacer attached to 5' end of
      SEQ ID NO: 74
<220> FEATURE:
<221> NAME/KEY: misc_feature
<222> LOCATION: (1)..(8)
<223> OTHER INFORMATION: phosphorothioate backbone
<220> FEATURE:
<221> NAME/KEY: modified_base
<222> LOCATION: (1)..(1)
<223> OTHER INFORMATION: gm
<220> FEATURE:
<221> NAME/KEY: modified_base
<222> LOCATION: (2)..(3)
<223> OTHER INFORMATION: um
<220> FEATURE:
<221> NAME/KEY: misc_feature
<222> LOCATION: (4)..(4)
<223> OTHER INFORMATION: locked nucleic acid (LNA) base
<220> FEATURE:
<221> NAME/KEY: modified_base
<222> LOCATION: (5)..(5)
<223> OTHER INFORMATION: um
<220> FEATURE:
<221> NAME/KEY: modified_base
<222> LOCATION: (6)..(6)
<223> OTHER INFORMATION: gm
<220> FEATURE:
<221> NAME/KEY: misc_feature
<222> LOCATION: (7)..(7)
<223> OTHER INFORMATION: 2'-O-methyl adenosine
<220> FEATURE:
<221> NAME/KEY: modified_base
```

```
<222> LOCATION: (8)..(8)
<223> OTHER INFORMATION: um

<400> SEQUENCE: 74 guucugau                                                                8

<210> SEQ ID NO 75
<211> LENGTH: 23
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(23)
<223> OTHER INFORMATION: phosphorothioate backbone
<220> FEATURE:
<221> NAME/KEY: modified_base
<222> LOCATION: (1)..(1)
<223> OTHER INFORMATION: gm
<220> FEATURE:
<221> NAME/KEY: misc_feature
<222> LOCATION: (2)..(2)
<223> OTHER INFORMATION: 2'-O-methyl adenosine
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (4)..(4)
<223> OTHER INFORMATION: cm
<220> FEATURE:
<221> NAME/KEY: misc_feature
<222> LOCATION: (5)..(5)
<223> OTHER INFORMATION: locked nucleic acid (LNA) base
<220> FEATURE:
<221> NAME/KEY: modified_base
<222> LOCATION: (6)..(6)
<223> OTHER INFORMATION: cm
<220> FEATURE:
<221> NAME/KEY: modified_base
<222> LOCATION: (7)..(7)
<223> OTHER INFORMATION: um
<220> FEATURE:
<221> NAME/KEY: misc_feature
<222> LOCATION: (8)..(8)
<223> OTHER INFORMATION: locked nucleic acid (LNA) base
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (10)..(10)
<223> OTHER INFORMATION: gm
<220> FEATURE:
<221> NAME/KEY: modified_base
<222> LOCATION: (11)..(11)
<223> OTHER INFORMATION: um
<220> FEATURE:
<221> NAME/KEY: misc_feature
<222> LOCATION: (12)..(12)
<223> OTHER INFORMATION: locked nucleic acid (LNA) base
<220> FEATURE:
<221> NAME/KEY: modified_base
<222> LOCATION: (13)..(13)
<223> OTHER INFORMATION: gm
<220> FEATURE:
<221> NAME/KEY: modified_base
<222> LOCATION: (14)..(14)
<223> OTHER INFORMATION: cm
<220> FEATURE:
<221> NAME/KEY: misc_feature
<222> LOCATION: (15)..(15)
<223> OTHER INFORMATION: locked nucleic acid (LNA) base
<220> FEATURE:
```

```
<221> NAME/KEY: modified_base
<222> LOCATION: (16)..(16)
<223> OTHER INFORMATION: gm
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(18)
<223> OTHER INFORMATION: cm
<220> FEATURE:
<221> NAME/KEY: modified_base
<222> LOCATION: (19)..(19)
<223> OTHER INFORMATION: um
<220> FEATURE:
<221> NAME/KEY: modified_base
<222> LOCATION: (20)..(21)
<223> OTHER INFORMATION: cm
<220> FEATURE:
<221> NAME/KEY: misc_feature
<222> LOCATION: (22)..(22)
<223> OTHER INFORMATION: locked nucleic acid (LNA) base
<220> FEATURE:
<221> NAME/KEY: misc_feature
<222> LOCATION: (23)..(23)
<223> OTHER INFORMATION: Amino modifier attached to 3' end of SEQ ID NO:
     75
<220> FEATURE:
<221> NAME/KEY: modified_base
<222> LOCATION: (23)..(23)
<223> OTHER INFORMATION: cm

<400> SEQUENCE: 75
gagctcutcg ucgctgucuc cgc                                              23

<210> SEQ ID NO 76
<211> LENGTH: 31
<212> TYPE: RNA
<213> ORGANISM: Artificial Sequence
<220> FEATURE:
<223> OTHER INFORMATION: Synthetic Polynucleotide

<400> SEQUENCE: 76
gcggagacag cgacgaagag cucaucagaa c                                     31

<210> SEQ ID NO 77
<211> LENGTH: 11
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (10)..(11)
<223> OTHER INFORMATION: phosphorothioate backbone
<220> FEATURE:
<221> NAME/KEY: misc_feature
<222> LOCATION: (11)..(11)
<223> OTHER INFORMATION: C3 linker attached to 5' end of SEQ ID NO: 78
<220> FEATURE:
<221> NAME/KEY: modified_base
<222> LOCATION: (11)..(11)
<223> OTHER INFORMATION: gm

<400> SEQUENCE: 77
ucccucagac g                                                           11

<210> SEQ ID NO 78
<211> LENGTH: 23
<212> TYPE: RNA
<213> ORGANISM: Artificial Sequence
<220> FEATURE:
```

```
<223> OTHER INFORMATION: Synthetic Polynucleotide
<220> FEATURE:
<221> NAME/KEY: misc_feature
<222> LOCATION: (1)..(1)
<223> OTHER INFORMATION: C3 linker attached to 3' end of SEQ ID NO: 77
<220> FEATURE:
<221> NAME/KEY: misc_feature
<222> LOCATION: (23)..(23)
<223> OTHER INFORMATION: C3 linker attached to 5' end of SEQ ID NO: 79

<400> SEQUENCE: 78
gcggagacag cgacgaagag cuc                                            23

<210> SEQ ID NO 79
<211> LENGTH: 12
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: C3 linker attached to 3' end of SEQ ID NO: 78
<220> FEATURE:
<221> NAME/KEY: misc_feature
<222> LOCATION: (1)..(3)
<223> OTHER INFORMATION: phosphorothioate backbone
<220> FEATURE:
<221> NAME/KEY: modified_base
<222> LOCATION: (1)..(2)
<223> OTHER INFORMATION: gm
<220> FEATURE:
<221> NAME/KEY: modified_base
<222> LOCATION: (3)..(3)
<223> OTHER INFORMATION: um

<400> SEQUENCE: 79
gguaacuaga ga                                                        12

<210> SEQ ID NO 80
<211> LENGTH: 31
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Triethyleneglycol spacer attached to 5' end of
      SEQ ID NO: 80
<220> FEATURE:
<221> NAME/KEY: modified_base
<222> LOCATION: (1)..(1)
<223> OTHER INFORMATION: gm
<220> FEATURE:
<221> NAME/KEY: modified_base
<222> LOCATION: (2)..(3)
<223> OTHER INFORMATION: um
<220> FEATURE:
<221> NAME/KEY: misc_feature
<222> LOCATION: (4)..(4)
<223> OTHER INFORMATION: locked nucleic acid (LNA) base
<220> FEATURE:
<221> NAME/KEY: modified_base
<222> LOCATION: (5)..(5)
<223> OTHER INFORMATION: um
<220> FEATURE:
<221> NAME/KEY: modified_base
<222> LOCATION: (6)..(6)
<223> OTHER INFORMATION: gm
<220> FEATURE:
<221> NAME/KEY: misc_feature
<222> LOCATION: (7)..(7)
<223> OTHER INFORMATION: 2'-O-methyl adenosine
<220> FEATURE:
```

-continued

```
<221> NAME/KEY: modified_base
<222> LOCATION: (8)..(8)
<223> OTHER INFORMATION: um
<220> FEATURE:
<221> NAME/KEY: modified_base
<222> LOCATION: (9)..(9)
<223> OTHER INFORMATION: gm
<220> FEATURE:
<221> NAME/KEY: misc_feature
<222> LOCATION: (10)..(10)
<223> OTHER INFORMATION: 2'-O-methyl adenosine
<220> FEATURE:
<221> NAME/KEY: modified_base
<222> LOCATION: (11)..(11)
<223> OTHER INFORMATION: gm
<220> FEATURE:
<221> NAME/KEY: modified_base
<222> LOCATION: (12)..(12)
<223> OTHER INFORMATION: cm
<220> FEATURE:
<221> NAME/KEY: misc_feature
<222> LOCATION: (13)..(13)
<223> OTHER INFORMATION: locked nucleic acid (LNA) base
<220> FEATURE:
<221> NAME/KEY: modified_base
<222> LOCATION: (14)..(14)
<223> OTHER INFORMATION: cm
<220> FEATURE:
<221> NAME/KEY: misc_feature
<222> LOCATION: (16)..(16)
<223> OTHER INFORMATION: locked nucleic acid (LNA) base
<220> FEATURE:
<221> NAME/KEY: modified_base
<222> LOCATION: (17)..(17)
<223> OTHER INFORMATION: cm
<220> FEATURE:
<221> NAME/KEY: modified_base
<222> LOCATION: (18)..(18)
<223> OTHER INFORMATION: gm
<220> FEATURE:
<221> NAME/KEY: modified_base
<222> LOCATION: (19)..(19)
<223> OTHER INFORMATION: um
<220> FEATURE:
<221> NAME/KEY: misc_feature
<222> LOCATION: (20)..(20)
<223> OTHER INFORMATION: locked nucleic acid (LNA) base
<220> FEATURE:
<221> NAME/KEY: modified_base
<222> LOCATION: (21)..(21)
<223> OTHER INFORMATION: gm
<220> FEATURE:
<221> NAME/KEY: modified_base
<222> LOCATION: (22)..(22)
<223> OTHER INFORMATION: cm
<220> FEATURE:
<221> NAME/KEY: misc_feature
<222> LOCATION: (23)..(23)
<223> OTHER INFORMATION: locked nucleic acid (LNA) base
<220> FEATURE:
<221> NAME/KEY: modified_base
<222> LOCATION: (24)..(24)
<223> OTHER INFORMATION: gm
<220> FEATURE:
<221> NAME/KEY: modified_base
<222> LOCATION: (25)..(25)
<223> OTHER INFORMATION: um
<220> FEATURE:
<221> NAME/KEY: modified_base
<222> LOCATION: (26)..(26)
<223> OTHER INFORMATION: cm
<220> FEATURE:
<221> NAME/KEY: modified_base
<222> LOCATION: (27)..(27)
<223> OTHER INFORMATION: um
<220> FEATURE:
<221> NAME/KEY: modified_base
<222> LOCATION: (28)..(29)
<223> OTHER INFORMATION: cm
```

-continued

```
<220> FEATURE:
<221> NAME/KEY: misc_feature
<222> LOCATION: (30)..(30)
<223> OTHER INFORMATION: locked nucleic acid (LNA) base
<220> FEATURE:
<221> NAME/KEY: misc_feature
<222> LOCATION: (31)..(31)
<223> OTHER INFORMATION: Amino modifier attached to 3' end of SEQ ID NO:
      80
<220> FEATURE:
<221> NAME/KEY: modified_base
<222> LOCATION: (31)..(31)
<223> OTHER INFORMATION: cm

<400> SEQUENCE: 80
guucugauga gctcutcguc gctgucuccg c                                       31

<210> SEQ ID NO 81
<211> LENGTH: 8
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Triethyleneglycol spacer attached to 5' end of
      SEQ ID NO: 81
<220> FEATURE:
<221> NAME/KEY: misc_feature
<222> LOCATION: (1)..(8)
<223> OTHER INFORMATION: phosphorothioate backbone
<220> FEATURE:
<221> NAME/KEY: modified_base
<222> LOCATION: (1)..(1)
<223> OTHER INFORMATION: gm
<220> FEATURE:
<221> NAME/KEY: modified_base
<222> LOCATION: (2)..(3)
<223> OTHER INFORMATION: um
<220> FEATURE:
<221> NAME/KEY: misc_feature
<222> LOCATION: (4)..(4)
<223> OTHER INFORMATION: locked nucleic acid (LNA) base
<220> FEATURE:
<221> NAME/KEY: modified_base
<222> LOCATION: (5)..(5)
<223> OTHER INFORMATION: um
<220> FEATURE:
<221> NAME/KEY: modified_base
<222> LOCATION: (6)..(6)
<223> OTHER INFORMATION: gm
<220> FEATURE:
<221> NAME/KEY: misc_feature
<222> LOCATION: (7)..(7)
<223> OTHER INFORMATION: 2'-O-methyl adenosine
<220> FEATURE:
<221> NAME/KEY: modified_base
<222> LOCATION: (8)..(8)
<223> OTHER INFORMATION: um

<400> SEQUENCE: 81 guucugau                                                                  8

<210> SEQ ID NO 82
<211> LENGTH: 23
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(23)
<223> OTHER INFORMATION: 2'-O-methyl adenosine
<220> FEATURE:
```

-continued

```
<221> NAME/KEY: modified_base
<222> LOCATION: (1)..(1)
<223> OTHER INFORMATION: gm
<220> FEATURE:
<221> NAME/KEY: misc_feature
<222> LOCATION: (2)..(2)
<223> OTHER INFORMATION: 2'-O-methyl adenosine
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (4)..(4)
<223> OTHER INFORMATION: cm
<220> FEATURE:
<221> NAME/KEY: misc_feature
<222> LOCATION: (5)..(5)
<223> OTHER INFORMATION: locked nucleic acid (LNA) base
<220> FEATURE:
<221> NAME/KEY: modified_base
<222> LOCATION: (6)..(6)
<223> OTHER INFORMATION: cm
<220> FEATURE:
<221> NAME/KEY: modified_base
<222> LOCATION: (7)..(7)
<223> OTHER INFORMATION: um
<220> FEATURE:
<221> NAME/KEY: misc_feature
<222> LOCATION: (8)..(8)
<223> OTHER INFORMATION: locked nucleic acid (LNA) base
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (10)..(10)
<223> OTHER INFORMATION: gm
<220> FEATURE:
<221> NAME/KEY: misc_feature
<222> LOCATION: (12)..(12)
<223> OTHER INFORMATION: locked nucleic acid (LNA) base
<220> FEATURE:
<221> NAME/KEY: modified_base
<222> LOCATION: (13)..(13)
<223> OTHER INFORMATION: gm
<220> FEATURE:
<221> NAME/KEY: modified_base
<222> LOCATION: (14)..(14)
<223> OTHER INFORMATION: cm
<220> FEATURE:
<221> NAME/KEY: misc_feature
<222> LOCATION: (15)..(15)
<223> OTHER INFORMATION: locked nucleic acid (LNA) base
<220> FEATURE:
<221> NAME/KEY: modified_base
<222> LOCATION: (16)..(16)
<223> OTHER INFORMATION: gm
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(18)
<223> OTHER INFORMATION: cm
<220> FEATURE:
<221> NAME/KEY: modified_base
<222> LOCATION: (19)..(19)
<223> OTHER INFORMATION: um
<220> FEATURE:
<221> NAME/KEY: modified_base
<222> LOCATION: (20)..(21)
<223> OTHER INFORMATION: cm
<220> FEATURE:
<221> NAME/KEY: misc_feature
<222> LOCATION: (22)..(22)
<223> OTHER INFORMATION: locked nucleic acid (LNA) base
```

```
<220> FEATURE:
<221> NAME/KEY: misc_feature
<222> LOCATION: (23)..(23)
<223> OTHER INFORMATION: Amino modifier attached to 3' end of SEQ ID NO:
      82
<220> FEATURE:
<221> NAME/KEY: modified_base
<222> LOCATION: (23)..(23)
<223> OTHER INFORMATION: cm

<400> SEQUENCE: 82
gagctcutcg ucgctgucuc cgc                                              23

<210> SEQ ID NO 83
<211> LENGTH: 31
<212> TYPE: RNA
<213> ORGANISM: Artificial Sequence
<220> FEATURE:
<223> OTHER INFORMATION: Synthetic Polynucleotide

<400> SEQUENCE: 83
gcggagacag cgacgaagag cucaucagaa c                                     31

<210> SEQ ID NO 84
<211> LENGTH: 31
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Triethyleneglycol spacer attached to 5' end of
      SEQ ID NO: 84
<220> FEATURE:
<221> NAME/KEY: modified_base
<222> LOCATION: (1)..(1)
<223> OTHER INFORMATION: gm
<220> FEATURE:
<221> NAME/KEY: modified_base
<222> LOCATION: (2)..(3)
<223> OTHER INFORMATION: um
<220> FEATURE:
<221> NAME/KEY: misc_feature
<222> LOCATION: (4)..(4)
<223> OTHER INFORMATION: locked nucleic acid (LNA) base
<220> FEATURE:
<221> NAME/KEY: modified_base
<222> LOCATION: (5)..(5)
<223> OTHER INFORMATION: um
<220> FEATURE:
<221> NAME/KEY: modified_base
<222> LOCATION: (6)..(6)
<223> OTHER INFORMATION: gm
<220> FEATURE:
<221> NAME/KEY: misc_feature
<222> LOCATION: (7)..(7)
<223> OTHER INFORMATION: 2'-O-methyl adenosine
<220> FEATURE:
<221> NAME/KEY: modified_base
<222> LOCATION: (8)..(8)
<223> OTHER INFORMATION: um
<220> FEATURE:
<221> NAME/KEY: modified_base
<222> LOCATION: (9)..(9)
<223> OTHER INFORMATION: gm
<220> FEATURE:
<221> NAME/KEY: misc_feature
<222> LOCATION: (10)..(10)
<223> OTHER INFORMATION: 2'-O-methyl adenosine
<220> FEATURE:
<221> NAME/KEY: modified_base
<222> LOCATION: (11)..(11)
<223> OTHER INFORMATION: gm
<220> FEATURE:
```

-continued

```
<221> NAME/KEY: modified_base
<222> LOCATION: (12)..(12)
<223> OTHER INFORMATION: cm
<220> FEATURE:
<221> NAME/KEY: misc_feature
<222> LOCATION: (13)..(13)
<223> OTHER INFORMATION: locked nucleic acid (LNA) base
<220> FEATURE:
<221> NAME/KEY: modified_base
<222> LOCATION: (14)..(14)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: misc_feature
<222> LOCATION: (16)..(16)
<223> OTHER INFORMATION: locked nucleic acid (LNA) base
<220> FEATURE:
<221> NAME/KEY: modified_base
<222> LOCATION: (17)..(17)
<223> OTHER INFORMATION: cm
<220> FEATURE:
<221> NAME/KEY: modified_base
<222> LOCATION: (18)..(18)
<223> OTHER INFORMATION: gm
<220> FEATURE:
<221> NAME/KEY: modified_base
<222> LOCATION: (19)..(19)
<223> OTHER INFORMATION: um
<220> FEATURE:
<221> NAME/KEY: modified_base
<222> LOCATION: (21)..(21)
<223> OTHER INFORMATION: gm
<220> FEATURE:
<221> NAME/KEY: modified_base
<222> LOCATION: (22)..(22)
<223> OTHER INFORMATION: cm
<220> FEATURE:
<221> NAME/KEY: misc_feature
<222> LOCATION: (23)..(23)
<223> OTHER INFORMATION: locked nucleic acid (LNA) base
<220> FEATURE:
<221> NAME/KEY: modified_base
<222> LOCATION: (24)..(24)
<223> OTHER INFORMATION: gm
<220> FEATURE:
<221> NAME/KEY: modified_base
<222> LOCATION: (25)..(25)
<223> OTHER INFORMATION: um
<220> FEATURE:
<221> NAME/KEY: modified_base
<222> LOCATION: (26)..(26)
<223> OTHER INFORMATION: cm
<220> FEATURE:
<221> NAME/KEY: modified_base
<222> LOCATION: (27)..(27)
<223> OTHER INFORMATION: um
<220> FEATURE:
<221> NAME/KEY: modified_base
<222> LOCATION: (28)..(29)
<223> OTHER INFORMATION: cm
<220> FEATURE:
<221> NAME/KEY: misc_feature
<222> LOCATION: (30)..(30)
<223> OTHER INFORMATION: locked nucleic acid (LNA) base
<220> FEATURE:
<221> NAME/KEY: misc_feature
<222> LOCATION: (31)..(31)
<223> OTHER INFORMATION: Amino modifier attached to 3' end of SEQ ID NO:
      84
<220> FEATURE:
<221> NAME/KEY: modified_base
<222> LOCATION: (31)..(31)
<223> OTHER INFORMATION: cm

<400> SEQUENCE: 84
```
guucugauga gctcutcguc gctgucuccg c                                             31

```
<210> SEQ ID NO 85
<211> LENGTH: 8
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Triethyleneglycol spacer attached to 5' end of
      SEQ ID NO: 85
<220> FEATURE:
<221> NAME/KEY: misc_feature
<222> LOCATION: (1)..(8)
<223> OTHER INFORMATION: phosphorothioate backbone
<220> FEATURE:
<221> NAME/KEY: modified_base
<222> LOCATION: (1)..(1)
<223> OTHER INFORMATION: gm
<220> FEATURE:
<221> NAME/KEY: modified_base
<222> LOCATION: (2)..(3)
<223> OTHER INFORMATION: um
<220> FEATURE:
<221> NAME/KEY: misc_feature
<222> LOCATION: (4)..(4)
<223> OTHER INFORMATION: locked nucleic acid (LNA) base
<220> FEATURE:
<221> NAME/KEY: modified_base
<222> LOCATION: (5)..(5)
<223> OTHER INFORMATION: um
<220> FEATURE:
<221> NAME/KEY: modified_base
<222> LOCATION: (6)..(6)
<223> OTHER INFORMATION: gm
<220> FEATURE:
<221> NAME/KEY: misc_feature
<222> LOCATION: (7)..(7)
<223> OTHER INFORMATION: 2'-O-methyl adenosine
<220> FEATURE:
<221> NAME/KEY: modified_base
<222> LOCATION: (8)..(8)
<223> OTHER INFORMATION: um

<400> SEQUENCE: 85
``` guucugau                                                                        8

```
<210> SEQ ID NO 86
<211> LENGTH: 23
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(23)
<223> OTHER INFORMATION: phosphorothioate backbone
<220> FEATURE:
<221> NAME/KEY: modified_base
<222> LOCATION: (1)..(1)
<223> OTHER INFORMATION: gm
<220> FEATURE:
<221> NAME/KEY: misc_feature
<222> LOCATION: (2)..(2)
<223> OTHER INFORMATION: 2'-O-methyl adenosine
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (4)..(4)
<223> OTHER INFORMATION: cm
<220> FEATURE:
```

```
<221> NAME/KEY: misc_feature
<222> LOCATION: (5)..(5)
<223> OTHER INFORMATION: locked nucleic acid (LNA) base
<220> FEATURE:
<221> NAME/KEY: modified_base
<222> LOCATION: (6)..(6)
<223> OTHER INFORMATION: cm
<220> FEATURE:
<221> NAME/KEY: modified_base
<222> LOCATION: (7)..(7)
<223> OTHER INFORMATION: um
<220> FEATURE:
<221> NAME/KEY: misc_feature
<222> LOCATION: (8)..(8)
<223> OTHER INFORMATION: locked nucleic acid (LNA) base
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (10)..(10)
<223> OTHER INFORMATION: gm
<220> FEATURE:
<221> NAME/KEY: modified_base
<222> LOCATION: (11)..(11)
<223> OTHER INFORMATION: um
<220> FEATURE:
<221> NAME/KEY: misc_feature
<222> LOCATION: (12)..(12)
<223> OTHER INFORMATION: locked nucleic acid (LNA) base
<220> FEATURE:
<221> NAME/KEY: modified_base
<222> LOCATION: (13)..(13)
<223> OTHER INFORMATION: gm
<220> FEATURE:
<221> NAME/KEY: modified_base
<222> LOCATION: (14)..(14)
<223> OTHER INFORMATION: cm
<220> FEATURE:
<221> NAME/KEY: misc_feature
<222> LOCATION: (15)..(15)
<223> OTHER INFORMATION: locked nucleic acid (LNA) base
<220> FEATURE:
<221> NAME/KEY: modified_base
<222> LOCATION: (16)..(16)
<223> OTHER INFORMATION: gm
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(18)
<223> OTHER INFORMATION: cm
<220> FEATURE:
<221> NAME/KEY: modified_base
<222> LOCATION: (19)..(19)
<223> OTHER INFORMATION: um
<220> FEATURE:
<221> NAME/KEY: modified_base
<222> LOCATION: (20)..(21)
<223> OTHER INFORMATION: cm
<220> FEATURE:
<221> NAME/KEY: misc_feature
<222> LOCATION: (22)..(22)
<223> OTHER INFORMATION: locked nucleic acid (LNA) base
<220> FEATURE:
<221> NAME/KEY: modified_base
<222> LOCATION: (23)..(23)
<223> OTHER INFORMATION: cm

<400> SEQUENCE: 86
gagctcutcg ucgctgucuc cgc                                           23

<210> SEQ ID NO 87
<211> LENGTH: 31
```

```
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Triethyleneglycol spacer attached to 5' end of
      SEQ ID NO: 87
<220> FEATURE:
<221> NAME/KEY: misc_feature
<222> LOCATION: (1)..(31)
<223> OTHER INFORMATION: phosphorothioate backbone
<220> FEATURE:
<221> NAME/KEY: modified_base
<222> LOCATION: (1)..(1)
<223> OTHER INFORMATION: gm
<220> FEATURE:
<221> NAME/KEY: modified_base
<222> LOCATION: (2)..(3)
<223> OTHER INFORMATION: um
<220> FEATURE:
<221> NAME/KEY: misc_feature
<222> LOCATION: (4)..(4)
<223> OTHER INFORMATION: locked nucleic acid (LNA) base
<220> FEATURE:
<221> NAME/KEY: modified_base
<222> LOCATION: (5)..(5)
<223> OTHER INFORMATION: um
<220> FEATURE:
<221> NAME/KEY: modified_base
<222> LOCATION: (6)..(6)
<223> OTHER INFORMATION: gm
<220> FEATURE:
<221> NAME/KEY: misc_feature
<222> LOCATION: (7)..(7)
<223> OTHER INFORMATION: 2'-O-methyl adenosine
<220> FEATURE:
<221> NAME/KEY: modified_base
<222> LOCATION: (8)..(8)
<223> OTHER INFORMATION: um
<220> FEATURE:
<221> NAME/KEY: modified_base
<222> LOCATION: (9)..(9)
<223> OTHER INFORMATION: gm
<220> FEATURE:
<221> NAME/KEY: misc_feature
<222> LOCATION: (10)..(10)
<223> OTHER INFORMATION: 2'-O-methyl adenosine
<220> FEATURE:
<221> NAME/KEY: modified_base
<222> LOCATION: (11)..(11)
<223> OTHER INFORMATION: gm
<220> FEATURE:
<221> NAME/KEY: modified_base
<222> LOCATION: (12)..(12)
<223> OTHER INFORMATION: cm
<220> FEATURE:
<221> NAME/KEY: misc_feature
<222> LOCATION: (13)..(13)
<223> OTHER INFORMATION: locked nucleic acid (LNA) base
<220> FEATURE:
<221> NAME/KEY: modified_base
<222> LOCATION: (14)..(14)
<223> OTHER INFORMATION: cm
<220> FEATURE:
<221> NAME/KEY: modified_base
<222> LOCATION: (15)..(15)
<223> OTHER INFORMATION: um
<220> FEATURE:
<221> NAME/KEY: misc_feature
<222> LOCATION: (16)..(16)
<223> OTHER INFORMATION: locked nucleic acid (LNA) base
<220> FEATURE:
<221> NAME/KEY: modified_base
<222> LOCATION: (17)..(17)
<223> OTHER INFORMATION: cm
<220> FEATURE:
<221> NAME/KEY: modified_base
```

<222> LOCATION: (18)..(18)
<223> OTHER INFORMATION: gm
<220> FEATURE:
<221> NAME/KEY: modified_base
<222> LOCATION: (19)..(19)
<223> OTHER INFORMATION: um
<220> FEATURE:
<221> NAME/KEY: misc_feature
<222> LOCATION: (20)..(20)
<223> OTHER INFORMATION: locked nucleic acid (LNA) base
<220> FEATURE:
<221> NAME/KEY: modified_base
<222> LOCATION: (21)..(21)
<223> OTHER INFORMATION: gm
<220> FEATURE:
<221> NAME/KEY: modified_base
<222> LOCATION: (22)..(22)
<223> OTHER INFORMATION: cm
<220> FEATURE:
<221> NAME/KEY: misc_feature
<222> LOCATION: (23)..(23)
<223> OTHER INFORMATION: locked nucleic acid (LNA) base
<220> FEATURE:
<221> NAME/KEY: modified_base
<222> LOCATION: (24)..(24)
<223> OTHER INFORMATION: gm
<220> FEATURE:
<221> NAME/KEY: modified_base
<222> LOCATION: (25)..(25)
<223> OTHER INFORMATION: um
<220> FEATURE:
<221> NAME/KEY: modified_base
<222> LOCATION: (26)..(26)
<223> OTHER INFORMATION: cm
<220> FEATURE:
<221> NAME/KEY: modified_base
<222> LOCATION: (27)..(27)
<223> OTHER INFORMATION: um
<220> FEATURE:
<221> NAME/KEY: modified_base
<222> LOCATION: (28)..(28)
<223> OTHER INFORMATION: cm
<220> FEATURE:
<221> NAME/KEY: modified_base
<222> LOCATION: (29)..(29)
<223> OTHER INFORMATION: cm
<220> FEATURE:
<221> NAME/KEY: misc_feature
<222> LOCATION: (30)..(30)
<223> OTHER INFORMATION: locked nucleic acid (LNA) base
<220> FEATURE:
<221> NAME/KEY: modified_base
<222> LOCATION: (31)..(31)
<223> OTHER INFORMATION: cm

<400> SEQUENCE: 87
guucugauga gctcutcguc gctgucuccg c                                  31

<210> SEQ ID NO 88
<211> LENGTH: 8
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Triethyleneglycol spacer attached to 5' end of
      SEQ ID NO: 88
<220> FEATURE:
<221> NAME/KEY: misc_feature
<222> LOCATION: (1)..(8)
<223> OTHER INFORMATION: phosphorothioate backbone
<220> FEATURE:
<221> NAME/KEY: modified_base
<222> LOCATION: (1)..(1)
<223> OTHER INFORMATION: gm

```
<220> FEATURE:
<221> NAME/KEY: modified_base
<222> LOCATION: (2)..(3)
<223> OTHER INFORMATION: um
<220> FEATURE:
<221> NAME/KEY: misc_feature
<222> LOCATION: (4)..(4)
<223> OTHER INFORMATION: locked nucleic acid (LNA) base
<220> FEATURE:
<221> NAME/KEY: modified_base
<222> LOCATION: (5)..(5)
<223> OTHER INFORMATION: um
<220> FEATURE:
<221> NAME/KEY: modified_base
<222> LOCATION: (6)..(6)
<223> OTHER INFORMATION: gm
<220> FEATURE:
<221> NAME/KEY: misc_feature
<222> LOCATION: (7)..(7)
<223> OTHER INFORMATION: 2'-O-methyl adenosine
<220> FEATURE:
<221> NAME/KEY: modified_base
<222> LOCATION: (8)..(8)
<223> OTHER INFORMATION: um

<400> SEQUENCE: 88 guucugau                                                                     8

<210> SEQ ID NO 89
<211> LENGTH: 23
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(23)
<223> OTHER INFORMATION: phosphorothioate backbone
<220> FEATURE:
<221> NAME/KEY: modified_base
<222> LOCATION: (1)..(1)
<223> OTHER INFORMATION: gm
<220> FEATURE:
<221> NAME/KEY: misc_feature
<222> LOCATION: (2)..(2)
<223> OTHER INFORMATION: 2'-O-methyl adenosine
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (4)..(4)
<223> OTHER INFORMATION: cm
<220> FEATURE:
<221> NAME/KEY: misc_feature
<222> LOCATION: (5)..(5)
<223> OTHER INFORMATION: locked nucleic acid (LNA) base
<220> FEATURE:
<221> NAME/KEY: modified_base
<222> LOCATION: (6)..(6)
<223> OTHER INFORMATION: cm
<220> FEATURE:
<221> NAME/KEY: modified_base
<222> LOCATION: (7)..(7)
<223> OTHER INFORMATION: um
<220> FEATURE:
<221> NAME/KEY: misc_feature
<222> LOCATION: (8)..(8)
<223> OTHER INFORMATION: locked nucleic acid (LNA) base
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (10)..(10)
```

<223> OTHER INFORMATION: gm
<220> FEATURE:
<221> NAME/KEY: modified_base
<222> LOCATION: (11)..(11)
<223> OTHER INFORMATION: um
<220> FEATURE:
<221> NAME/KEY: misc_feature
<222> LOCATION: (12)..(12)
<223> OTHER INFORMATION: locked nucleic acid (LNA) base
<220> FEATURE:
<221> NAME/KEY: modified_base
<222> LOCATION: (13)..(13)
<223> OTHER INFORMATION: gm
<220> FEATURE:
<221> NAME/KEY: modified_base
<222> LOCATION: (14)..(14)
<223> OTHER INFORMATION: cm
<220> FEATURE:
<221> NAME/KEY: misc_feature
<222> LOCATION: (15)..(15)
<223> OTHER INFORMATION: locked nucleic acid (LNA) base
<220> FEATURE:
<221> NAME/KEY: modified_base
<222> LOCATION: (16)..(16)
<223> OTHER INFORMATION: gm
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (18)..(18)
<223> OTHER INFORMATION: cm
<220> FEATURE:
<221> NAME/KEY: modified_base
<222> LOCATION: (19)..(19)
<223> OTHER INFORMATION: um
<220> FEATURE:
<221> NAME/KEY: modified_base
<222> LOCATION: (20)..(21)
<223> OTHER INFORMATION: cm
<220> FEATURE:
<221> NAME/KEY: misc_feature
<222> LOCATION: (22)..(22)
<223> OTHER INFORMATION: locked nucleic acid (LNA) base
<220> FEATURE:
<221> NAME/KEY: modified_base
<222> LOCATION: (23)..(23)
<223> OTHER INFORMATION: cm

<400> SEQUENCE: 89
gagctcutcg ucgctgucuc cgc                                    23

<210> SEQ ID NO 90
<211> LENGTH: 10
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: locked nucleic acid (LNA) base
<220> FEATURE:
<221> NAME/KEY: misc_feature
<222> LOCATION: (1)..(4)
<223> OTHER INFORMATION: phosphorothioate backbone
<220> FEATURE:
<221> NAME/KEY: misc_feature
<222> LOCATION: (7)..(7)
<223> OTHER INFORMATION: locked nucleic acid (LNA) base
<220> FEATURE:
<221> NAME/KEY: misc_feature
<222> LOCATION: (10)..(10)
<223> OTHER INFORMATION: (PEG) polyethylene glycol linker attached to 5'
      end of SEQ ID NO: 91

```
<400> SEQUENCE: 90
ttgggaccac                                                              10

<210> SEQ ID NO 91
<211> LENGTH: 23
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: (PEG) polyethylene glycol linker attached to 3'
      end of SEQ ID NO: 90
<220> FEATURE:
<221> NAME/KEY: misc_feature
<222> LOCATION: (1)..(3)
<223> OTHER INFORMATION: phosphorothioate backbone
<220> FEATURE:
<221> NAME/KEY: modified_base
<222> LOCATION: (1)..(2)
<223> OTHER INFORMATION: gm
<220> FEATURE:
<221> NAME/KEY: modified_base
<222> LOCATION: (3)..(3)
<223> OTHER INFORMATION: um
<220> FEATURE:
<221> NAME/KEY: misc_feature
<222> LOCATION: (22)..(23)
<223> OTHER INFORMATION: phosphorothioate backbone
<220> FEATURE:
<221> NAME/KEY: modified_base
<222> LOCATION: (22)..(22)
<223> OTHER INFORMATION: cm
<220> FEATURE:
<221> NAME/KEY: misc_feature
<222> LOCATION: (23)..(23)
<223> OTHER INFORMATION: (PEG) polyethylene glycol linker attached to 5'
      end of SEQ ID NO: 92
<220> FEATURE:
<221> NAME/KEY: modified_base
<222> LOCATION: (23)..(23)
<223> OTHER INFORMATION: gm

<400> SEQUENCE: 91
gguaacuaga gaucccucag acg                                               23

<210> SEQ ID NO 92
<211> LENGTH: 11
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: (PEG) polyethylene glycol linker attached to 3'
      end of SEQ ID NO: 91
<220> FEATURE:
<221> NAME/KEY: misc_feature
<222> LOCATION: (3)..(3)
<223> OTHER INFORMATION: locked nucleic acid (LNA) base
<220> FEATURE:
<221> NAME/KEY: misc_feature
<222> LOCATION: (5)..(5)
<223> OTHER INFORMATION: locked nucleic acid (LNA) base
<220> FEATURE:
<221> NAME/KEY: misc_feature
<222> LOCATION: (8)..(11)
<223> OTHER INFORMATION: phosphorothioate backbone

<400> SEQUENCE: 92
tactcagccc a                                                            11
```

```
<210> SEQ ID NO 93
<211> LENGTH: 44
<212> TYPE: DNA
<213> ORGANISM: Artificial Sequence
<220> FEATURE:
<223> OTHER INFORMATION: Synthetic Polynucleotide

<400> SEQUENCE: 93
cactcagggc actgcaagca attgtggtcc caatgggctg agta                44

<210> SEQ ID NO 94
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 94
cactcagggc actgcaagca att                                       23

<210> SEQ ID NO 95
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 95
gtggtcccaa tgggctgagt a                                         21

<210> SEQ ID NO 96
<211> LENGTH: 37
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Triethyleneglycol spacer attached to 5' end of
      SEQ ID NO: 96
<220> FEATURE:
<221> NAME/KEY: misc_feature
<222> LOCATION: (1)..(37)
<223> OTHER INFORMATION: phosphorothioate backbone
<220> FEATURE:
<221> NAME/KEY: misc_feature
<222> LOCATION: (1)..(1)
<223> OTHER INFORMATION: 2'-O-methyl adenosine
<220> FEATURE:
<221> NAME/KEY: modified_base
<222> LOCATION: (2)..(2)
<223> OTHER INFORMATION: um
<220> FEATURE:
<221> NAME/KEY: misc_feature
<222> LOCATION: (3)..(3)
<223> OTHER INFORMATION: locked nucleic acid (LNA) base
<220> FEATURE:
<221> NAME/KEY: misc_feature
<222> LOCATION: (4)..(6)
<223> OTHER INFORMATION: 2'-O-methyl adenosine
<220> FEATURE:
<221> NAME/KEY: modified_base
<222> LOCATION: (7)..(7)
<223> OTHER INFORMATION: gm
<220> FEATURE:
<221> NAME/KEY: modified_base
<222> LOCATION: (8)..(9)
<223> OTHER INFORMATION: um
<220> FEATURE:
<221> NAME/KEY: modified_base
<222> LOCATION: (10)..(10)
```

```
<223> OTHER INFORMATION: cm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (12)..(12)
<223> OTHER INFORMATION: gm
<220> FEATURE:
<221> NAME/KEY: misc_feature
<222> LOCATION: (13)..(13)
<223> OTHER INFORMATION: 2'-O-methyl adenosine
<220> FEATURE:
<221> NAME/KEY: modified_base
<222> LOCATION: (14)..(14)
<223> OTHER INFORMATION: um
<220> FEATURE:
<221> NAME/KEY: modified_base
<222> LOCATION: (15)..(15)
<223> OTHER INFORMATION: gm
<220> FEATURE:
<221> NAME/KEY: misc_feature
<222> LOCATION: (16)..(16)
<223> OTHER INFORMATION: 2'-O-methyl adenosine
<220> FEATURE:
<221> NAME/KEY: modified_base
<222> LOCATION: (17)..(17)
<223> OTHER INFORMATION: gm
<220> FEATURE:
<221> NAME/KEY: modified_base
<222> LOCATION: (18)..(18)
<223> OTHER INFORMATION: cm
<220> FEATURE:
<221> NAME/KEY: misc_feature
<222> LOCATION: (19)..(19)
<223> OTHER INFORMATION: locked nucleic acid (LNA) base
<220> FEATURE:
<221> NAME/KEY: modified_base
<222> LOCATION: (20)..(20)
<223> OTHER INFORMATION: cm
<220> FEATURE:
<221> NAME/KEY: modified_base
<222> LOCATION: (21)..(21)
<223> OTHER INFORMATION: um
<220> FEATURE:
<221> NAME/KEY: misc_feature
<222> LOCATION: (22)..(22)
<223> OTHER INFORMATION: locked nucleic acid (LNA) base
<220> FEATURE:
<221> NAME/KEY: modified_base
<222> LOCATION: (23)..(23)
<223> OTHER INFORMATION: cm
<220> FEATURE:
<221> NAME/KEY: modified_base
<222> LOCATION: (24)..(24)
<223> OTHER INFORMATION: gm
<220> FEATURE:
<221> NAME/KEY: modified_base
<222> LOCATION: (25)..(25)
<223> OTHER INFORMATION: um
<220> FEATURE:
<221> NAME/KEY: misc_feature
<222> LOCATION: (26)..(26)
<223> OTHER INFORMATION: locked nucleic acid (LNA) base
<220> FEATURE:
<221> NAME/KEY: modified_base
<222> LOCATION: (27)..(27)
<223> OTHER INFORMATION: gm
<220> FEATURE:
<221> NAME/KEY: modified_base
<222> LOCATION: (28)..(28)
<223> OTHER INFORMATION: cm
<220> FEATURE:
<221> NAME/KEY: misc_feature
<222> LOCATION: (29)..(29)
<223> OTHER INFORMATION: locked nucleic acid (LNA) base
<220> FEATURE:
<221> NAME/KEY: modified_base
```

```
<222> LOCATION: (30)..(30)
<223> OTHER INFORMATION: gm
<220> FEATURE:
<221> NAME/KEY: modified_base
<222> LOCATION: (31)..(31)
<223> OTHER INFORMATION: um
<220> FEATURE:
<221> NAME/KEY: modified_base
<222> LOCATION: (32)..(32)
<223> OTHER INFORMATION: cm
<220> FEATURE:
<221> NAME/KEY: modified_base
<222> LOCATION: (33)..(33)
<223> OTHER INFORMATION: um
<220> FEATURE:
<221> NAME/KEY: modified_base
<222> LOCATION: (34)..(35)
<223> OTHER INFORMATION: cm
<220> FEATURE:
<221> NAME/KEY: misc_feature
<222> LOCATION: (36)..(36)
<223> OTHER INFORMATION: locked nucleic acid (LNA) base
<220> FEATURE:
<221> NAME/KEY: misc_feature
<222> LOCATION: (37)..(37)
<223> OTHER INFORMATION: Amino modifier attached to 3' end of SEQ ID NO:
      96
<220> FEATURE:
<221> NAME/KEY: modified_base
<222> LOCATION: (37)..(37)
<223> OTHER INFORMATION: cm

<400> SEQUENCE: 96
aucaaaguuc ugaugagcuc ucgucgcug ucuccgc                             37

<210> SEQ ID NO 97
<211> LENGTH: 8
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(8)
<223> OTHER INFORMATION: phosphorothioate backbone
<220> FEATURE:
<221> NAME/KEY: modified_base
<222> LOCATION: (1)..(1)
<223> OTHER INFORMATION: gm
<220> FEATURE:
<221> NAME/KEY: modified_base
<222> LOCATION: (2)..(3)
<223> OTHER INFORMATION: um
<220> FEATURE:
<221> NAME/KEY: modified_base
<222> LOCATION: (4)..(4)
<223> OTHER INFORMATION: cm
<220> FEATURE:
<221> NAME/KEY: modified_base
<222> LOCATION: (5)..(5)
<223> OTHER INFORMATION: um
<220> FEATURE:
<221> NAME/KEY: modified_base
<222> LOCATION: (6)..(6)
<223> OTHER INFORMATION: gm
<220> FEATURE:
<221> NAME/KEY: misc_feature
<222> LOCATION: (7)..(7)
<223> OTHER INFORMATION: 2'-O-methyl adenosine
<220> FEATURE:
<221> NAME/KEY: modified_base
<222> LOCATION: (8)..(8)
<223> OTHER INFORMATION: um

<400> SEQUENCE: 97 guucugau                                                            8
```

```
<210> SEQ ID NO 98
<211> LENGTH: 23
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(23)
<223> OTHER INFORMATION: phosphorothioate backbone
<220> FEATURE:
<221> NAME/KEY: modified_base
<222> LOCATION: (1)..(1)
<223> OTHER INFORMATION: gm
<220> FEATURE:
<221> NAME/KEY: misc_feature
<222> LOCATION: (2)..(2)
<223> OTHER INFORMATION: 2'-O-methyl adenosine
<220> FEATURE:
<221> NAME/KEY: modified_base
<222> LOCATION: (3)..(3)
<223> OTHER INFORMATION: gm
<220> FEATURE:
<221> NAME/KEY: modified_base
<222> LOCATION: (4)..(4)
<223> OTHER INFORMATION: cm
<220> FEATURE:
<221> NAME/KEY: misc_feature
<222> LOCATION: (5)..(5)
<223> OTHER INFORMATION: locked nucleic acid (LNA) base
<220> FEATURE:
<221> NAME/KEY: modified_base
<222> LOCATION: (6)..(6)
<223> OTHER INFORMATION: cm
<220> FEATURE:
<221> NAME/KEY: modified_base
<222> LOCATION: (7)..(7)
<223> OTHER INFORMATION: um
<220> FEATURE:
<221> NAME/KEY: misc_feature
<222> LOCATION: (8)..(8)
<223> OTHER INFORMATION: locked nucleic acid (LNA) base
<220> FEATURE:
<221> NAME/KEY: modified_base
<222> LOCATION: (9)..(9)
<223> OTHER INFORMATION: cm
<220> FEATURE:
<221> NAME/KEY: modified_base
<222> LOCATION: (10)..(10)
<223> OTHER INFORMATION: gm
<220> FEATURE:
<221> NAME/KEY: modified_base
<222> LOCATION: (11)..(11)
<223> OTHER INFORMATION: um
<220> FEATURE:
<221> NAME/KEY: misc_feature
<222> LOCATION: (12)..(12)
<223> OTHER INFORMATION: locked nucleic acid (LNA) base
<220> FEATURE:
<221> NAME/KEY: modified_base
<222> LOCATION: (13)..(13)
<223> OTHER INFORMATION: gm
<220> FEATURE:
<221> NAME/KEY: modified_base
<222> LOCATION: (14)..(14)
<223> OTHER INFORMATION: cm
<220> FEATURE:
<221> NAME/KEY: misc_feature
<222> LOCATION: (15)..(15)
<223> OTHER INFORMATION: locked nucleic acid (LNA) base
<220> FEATURE:
<221> NAME/KEY: modified_base
<222> LOCATION: (16)..(16)
<223> OTHER INFORMATION: gm
<220> FEATURE:
<221> NAME/KEY: modified_base
<222> LOCATION: (17)..(17)
```

```
<223> OTHER INFORMATION: um
<220> FEATURE:
<221> NAME/KEY: modified_base
<222> LOCATION: (18)..(18)
<223> OTHER INFORMATION: cm
<220> FEATURE:
<221> NAME/KEY: modified_base
<222> LOCATION: (19)..(19)
<223> OTHER INFORMATION: um
<220> FEATURE:
<221> NAME/KEY: modified_base
<222> LOCATION: (20)..(21)
<223> OTHER INFORMATION: cm
<220> FEATURE:
<221> NAME/KEY: misc_feature
<222> LOCATION: (22)..(22)
<223> OTHER INFORMATION: locked nucleic acid (LNA) base
<220> FEATURE:
<221> NAME/KEY: misc_feature
<222> LOCATION: (23)..(23)
<223> OTHER INFORMATION: Amino modifier attached to 3' end of SEQ ID NO:
      98
<220> FEATURE:
<221> NAME/KEY: modified_base
<222> LOCATION: (23)..(23)
<223> OTHER INFORMATION: cm

<400> SEQUENCE: 98
gagctcutcg ucgctgucuc cgc                                            23

<210> SEQ ID NO 99
<211> LENGTH: 31
<212> TYPE: RNA
<213> ORGANISM: Artificial Sequence
<220> FEATURE:
<223> OTHER INFORMATION: Synthetic Polynucleotide

<400> SEQUENCE: 99
gcggagacag cgacgaagag cucaucagaa c                                   31

<210> SEQ ID NO 100
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 100
ugagggaucu cuaguuacc                                                 19

<210> SEQ ID NO 101
<211> LENGTH: 18
<212> TYPE: RNA
<213> ORGANISM: Artificial Sequence
<220> FEATURE:
<223> OTHER INFORMATION: Synthetic Polynucleotide

<400> SEQUENCE: 101
gguaacuaga gaucccuc                                                  18

<210> SEQ ID NO 102
<211> LENGTH: 26
<212> TYPE: RNA
<213> ORGANISM: Artificial Sequence
<220> FEATURE:
<223> OTHER INFORMATION: Synthetic Polynucleotide

<400> SEQUENCE: 102
gcggagacag cgaagagcuc aucaga                                         26
```

<210> SEQ ID NO 103
<211> LENGTH: 11
<212> TYPE: DNA
<213> ORGANISM: Artificial Sequence
<220> FEATURE:
<223> OTHER INFORMATION: Synthetic Polynucleotide

<400> SEQUENCE: 103
gcggagacag c                                                                 11

<210> SEQ ID NO 104
<211> LENGTH: 12
<212> TYPE: RNA
<213> ORGANISM: Artificial Sequence
<220> FEATURE:
<223> OTHER INFORMATION: Synthetic Polynucleotide

<400> SEQUENCE: 104
gacgaagagc uc                                                                12

<210> SEQ ID NO 105
<211> LENGTH: 5
<212> TYPE: RNA
<213> ORGANISM: Artificial Sequence
<220> FEATURE:
<223> OTHER INFORMATION: Synthetic Polynucleotide

<400> SEQUENCE: 105 ucaga                                                                         5

<210> SEQ ID NO 106
<211> LENGTH: 6
<212> TYPE: RNA
<213> ORGANISM: Artificial Sequence
<220> FEATURE:
<223> OTHER INFORMATION: Synthetic Polynucleotide

<400> SEQUENCE: 106 ucugau                                                                        6

<210> SEQ ID NO 107
<211> LENGTH: 12
<212> TYPE: RNA
<213> ORGANISM: Artificial Sequence
<220> FEATURE:
<223> OTHER INFORMATION: Synthetic Polynucleotide

<400> SEQUENCE: 107
ugagcucuug uc                                                                12

<210> SEQ ID NO 108
<211> LENGTH: 11
<212> TYPE: RNA
<213> ORGANISM: Artificial Sequence
<220> FEATURE:
<223> OTHER INFORMATION: Synthetic Polynucleotide

<400> SEQUENCE: 108
gcugucuccg c                                                                 11

<210> SEQ ID NO 109
<211> LENGTH: 29
<212> TYPE: RNA
<213> ORGANISM: Artificial Sequence
<220> FEATURE:
<223> OTHER INFORMATION: Synthetic Polynucleotide

```
<400> SEQUENCE: 109
ucugauugag cucuugucgc ugucuccgc                                              29

<210> SEQ ID NO 110
<211> LENGTH: 7
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(7)
<223> OTHER INFORMATION: phosphorothioate backbone
<220> FEATURE:
<221> NAME/KEY: modified_base
<222> LOCATION: (1)..(1)
<223> OTHER INFORMATION: um
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (3)..(3)
<223> OTHER INFORMATION: um
<220> FEATURE:
<221> NAME/KEY: modified_base
<222> LOCATION: (4)..(4)
<223> OTHER INFORMATION: gm
<220> FEATURE:
<221> NAME/KEY: misc_feature
<222> LOCATION: (5)..(5)
<223> OTHER INFORMATION: 2'-O-methyl adenosine
<220> FEATURE:
<221> NAME/KEY: modified_base
<222> LOCATION: (6)..(7)
<223> OTHER INFORMATION: um

<400> SEQUENCE: 110 ucugauu                                                                       7

<210> SEQ ID NO 111
<211> LENGTH: 8
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(8)
<223> OTHER INFORMATION: phosphorothioate backbone
<220> FEATURE:
<221> NAME/KEY: modified_base
<222> LOCATION: (1)..(1)
<223> OTHER INFORMATION: gm
<220> FEATURE:
<221> NAME/KEY: modified_base
<222> LOCATION: (2)..(3)
<223> OTHER INFORMATION: um
<220> FEATURE:
<221> NAME/KEY: modified_base
<222> LOCATION: (4)..(4)
<223> OTHER INFORMATION: cm
<220> FEATURE:
<221> NAME/KEY: modified_base
<222> LOCATION: (5)..(5)
<223> OTHER INFORMATION: um
<220> FEATURE:
<221> NAME/KEY: modified_base
<222> LOCATION: (6)..(6)
<223> OTHER INFORMATION: gm
<220> FEATURE:
<221> NAME/KEY: misc_feature
<222> LOCATION: (7)..(7)
```

<223> OTHER INFORMATION: 2'-O-methyl adenosine
<220> FEATURE:
<221> NAME/KEY: modified_base
<222> LOCATION: (8)..(8)
<223> OTHER INFORMATION: um

<400> SEQUENCE: 111 guucugau                                                                   8

<210> SEQ ID NO 112
<211> LENGTH: 8
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(8)
<223> OTHER INFORMATION: phosphorothioate backbone
<220> FEATURE:
<221> NAME/KEY: modified_base
<222> LOCATION: (1)..(1)
<223> OTHER INFORMATION: gm
<220> FEATURE:
<221> NAME/KEY: modified_base
<222> LOCATION: (2)..(3)
<223> OTHER INFORMATION: um
<220> FEATURE:
<221> NAME/KEY: misc_feature
<222> LOCATION: (4)..(4)
<223> OTHER INFORMATION: locked nucleic acid (LNA) base
<220> FEATURE:
<221> NAME/KEY: modified_base
<222> LOCATION: (5)..(5)
<223> OTHER INFORMATION: um
<220> FEATURE:
<221> NAME/KEY: modified_base
<222> LOCATION: (6)..(6)
<223> OTHER INFORMATION: gm
<220> FEATURE:
<221> NAME/KEY: misc_feature
<222> LOCATION: (7)..(7)
<223> OTHER INFORMATION: 2'-O-methyl adenosine
<220> FEATURE:
<221> NAME/KEY: modified_base
<222> LOCATION: (8)..(8)
<223> OTHER INFORMATION: um

<400> SEQUENCE: 112 guucugau                                                                   8

<210> SEQ ID NO 113
<211> LENGTH: 26
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: modified_base
<222> LOCATION: (1)..(1)
<223> OTHER INFORMATION: cm
<220> FEATURE:
<221> NAME/KEY: modified_base
<222> LOCATION: (2)..(2)
<223> OTHER INFORMATION: gm
<220> FEATURE:
<221> NAME/KEY: misc_feature
<222> LOCATION: (3)..(3)
<223> OTHER INFORMATION: locked nucleic acid (LNA) base
<220> FEATURE:
<221> NAME/KEY: misc_feature
<222> LOCATION: (22)..(22)
<223> OTHER INFORMATION: locked nucleic acid (LNA) base

<400> SEQUENCE: 113
cgcgucugag ggaucucuag uaccuu                                            26

<210> SEQ ID NO 114
<211> LENGTH: 12
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (10)..(12)
<223> OTHER INFORMATION: phosphorothioate backbone
<220> FEATURE:
<221> NAME/KEY: modified_base
<222> LOCATION: (11)..(12)
<223> OTHER INFORMATION: cm
<220> FEATURE:
<221> NAME/KEY: misc_feature
<222> LOCATION: (12)..(12)
<223> OTHER INFORMATION: 9s linker attached to 5' end of SEQ ID NO: 115

<400> SEQUENCE: 114
cccucagacg cc                                                          12

<210> SEQ ID NO 115
<211> LENGTH: 14
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: 9s linker attached to 3' end of SEQ ID NO: 114
<220> FEATURE:
<221> NAME/KEY: misc_feature
<222> LOCATION: (1)..(14)
<223> OTHER INFORMATION: phosphorothioate backbone
<220> FEATURE:
<221> NAME/KEY: modified_base
<222> LOCATION: (1)..(1)
<223> OTHER INFORMATION: gm
<220> FEATURE:
<221> NAME/KEY: misc_feature
<222> LOCATION: (2)..(2)
<223> OTHER INFORMATION: 2'-O-methyl adenosine
<220> FEATURE:
<221> NAME/KEY: modified_base
<222> LOCATION: (3)..(3)
<223> OTHER INFORMATION: um
<220> FEATURE:
<221> NAME/KEY: modified_base
<222> LOCATION: (4)..(4)
<223> OTHER INFORMATION: gm
<220> FEATURE:
<221> NAME/KEY: misc_feature
<222> LOCATION: (5)..(5)
<223> OTHER INFORMATION: 2'-O-methyl adenosine
<220> FEATURE:
<221> NAME/KEY: modified_base
<222> LOCATION: (6)..(6)
<223> OTHER INFORMATION: gm
<220> FEATURE:
<221> NAME/KEY: modified_base
<222> LOCATION: (7)..(7)
<223> OTHER INFORMATION: cm
<220> FEATURE:
<221> NAME/KEY: modified_base
<222> LOCATION: (8)..(9)
<223> OTHER INFORMATION: um
<220> FEATURE:
<221> NAME/KEY: modified_base
<222> LOCATION: (10)..(10)
<223> OTHER INFORMATION: cm
<220> FEATURE:

```
<221> NAME/KEY: modified_base
<222> LOCATION: (11)..(11)
<223> OTHER INFORMATION: gm
<220> FEATURE:
<221> NAME/KEY: modified_base
<222> LOCATION: (12)..(12)
<223> OTHER INFORMATION: um
<220> FEATURE:
<221> NAME/KEY: modified_base
<222> LOCATION: (13)..(13)
<223> OTHER INFORMATION: cm
<220> FEATURE:
<221> NAME/KEY: misc_feature
<222> LOCATION: (14)..(14)
<223> OTHER INFORMATION: 9s linker attached to 5' end of SEQ ID NO: 116
<220> FEATURE:
<221> NAME/KEY: modified_base
<222> LOCATION: (14)..(14)
<223> OTHER INFORMATION: gm

<400> SEQUENCE: 115
gaugagcuuc gucg                                                         14

<210> SEQ ID NO 116
<211> LENGTH: 8
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(8)
<223> OTHER INFORMATION: 9s linker attached to 3' end of SEQ ID NO: 115
<220> FEATURE:
<221> NAME/KEY: misc_feature
<222> LOCATION: (1)..(8)
<223> OTHER INFORMATION: phosphorothioate backbone
<220> FEATURE:
<221> NAME/KEY: modified_base
<222> LOCATION: (1)..(1)
<223> OTHER INFORMATION: gm
<220> FEATURE:
<221> NAME/KEY: modified_base
<222> LOCATION: (2)..(2)
<223> OTHER INFORMATION: um
<220> FEATURE:
<221> NAME/KEY: modified_base
<222> LOCATION: (3)..(3)
<223> OTHER INFORMATION: cm
<220> FEATURE:
<221> NAME/KEY: modified_base
<222> LOCATION: (4)..(4)
<223> OTHER INFORMATION: um
<220> FEATURE:
<221> NAME/KEY: modified_base
<222> LOCATION: (5)..(6)
<223> OTHER INFORMATION: cm
<220> FEATURE:
<221> NAME/KEY: modified_base
<222> LOCATION: (7)..(7)
<223> OTHER INFORMATION: gm
<220> FEATURE:
<221> NAME/KEY: misc_feature
<222> LOCATION: (8)..(8)
<223> OTHER INFORMATION: 18s linker attached to inverted deoxynucleotide
      T
<220> FEATURE:
<221> NAME/KEY: modified_base
<222> LOCATION: (8)..(8)
<223> OTHER INFORMATION: cm

<400> SEQUENCE: 116 gucuccgc                                                                 8

<210> SEQ ID NO 117
```

```
<211> LENGTH: 14
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: 18s linker attached to 5' end of SEQ ID NO: 117
<220> FEATURE:
<221> NAME/KEY: misc_feature
<222> LOCATION: (1)..(4)
<223> OTHER INFORMATION: phosphorothioate backbone
<220> FEATURE:
<221> NAME/KEY: misc_feature
<222> LOCATION: (118)..(118)
<223> OTHER INFORMATION: C3 linker attached to 5' end of SEQ ID NO: 118

<400> SEQUENCE: 117
cgacgaagcu cauc                                                      14

<210> SEQ ID NO 118
<211> LENGTH: 13
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(3)
<223> OTHER INFORMATION: phosphorothioate backbone
<220> FEATURE:
<221> NAME/KEY: misc_feature
<222> LOCATION: (1)..(1)
<223> OTHER INFORMATION: C3 linker attached to 3' end of SEQ ID NO: 117
<220> FEATURE:
<221> NAME/KEY: modified_base
<222> LOCATION: (1)..(2)
<223> OTHER INFORMATION: gm
<220> FEATURE:
<221> NAME/KEY: modified_base
<222> LOCATION: (3)..(3)
<223> OTHER INFORMATION: um
<220> FEATURE:
<221> NAME/KEY: misc_feature
<222> LOCATION: (8)..(8)
<223> OTHER INFORMATION: 2'-O-methyl adenosine
<220> FEATURE:
<221> NAME/KEY: modified_base
<222> LOCATION: (11)..(11)
<223> OTHER INFORMATION: gm
<220> FEATURE:
<221> NAME/KEY: modified_base
<222> LOCATION: (13)..(13)
<223> OTHER INFORMATION: um

<400> SEQUENCE: 118
gguaacuaga gau                                                       13
```

SIGNAL ACTIVATABLE CONSTRUCTS AND RELATED COMPONENTS COMPOSITIONS METHODS AND SYSTEMS

CROSS REFERENCE TO RELATED APPLICATIONS

The present application claims priority to U.S. Provisional Application No. 61/948,823, filed on Mar. 6, 2014, which is incorporated herein by reference in its entirety. This application is also related to U.S. application Ser. No. 13/848,687 entitled "Targeting Domain and Related Signal Activated Molecular Delivery" filed on Mar. 21, 2013, which claims priority to U.S. Provisional Application entitled "Pseudoknot construct for signal activated RNA interference" Ser. No. 61/613,617, filed on Mar. 21, 2012, the disclosure of which is incorporated herein by reference in its entirety. The Application is also related to U.S. Provisional Application entitled "Controlled Release of Therapeutic Cargo by Exonucleases" Ser. No. 61/731,420, filed on Nov. 29, 2012, the disclosure of which is incorporated herein by reference in its entirety. This application is also related to U.S. application Ser. No. 14/093,387 entitled "Exonuclease Resistant Polynucleotide and Related Duplex Polynucleotides, Constructs, Compositions, Methods and Systems" filed on Nov. 29, 2013, which claims priority to U.S. Provisional No. 61/613,617, and U.S. Provisional Application No. 61/731,420, filed on Nov. 29, 2012, the disclosure of which is incorporated herein by reference in its entirety. The present application might also be related to U.S. application entitled "Signal Activated Molecular Delivery" Ser. No. 13/167,672 filed on Jun. 23, 2011, and to International Application "Signal Activated Molecular Delivery" Serial No. PCT/US 11/41703 filed on Jun. 23, 2011, the disclosure of each of which is also incorporated by reference in its entirety.

STATEMENT OF GOVERNMENT GRANT

This invention was made with government support under Grant No. 1332411 awarded by the National Science Foundation. The government has certain rights in the invention.

FIELD

The present disclosure relates to signal activated molecular delivery and in particular to signal activatable constructs, and related components, compositions, methods and systems.

BACKGROUND

Molecular delivery has been a challenge in the field of biological molecule analysis, in particular when aimed at obtaining controlled delivery of analytes of interest to specific environments. Whether for medical applications or for fundamental biology studies, several methods are commonly used for the delivery of various classes of biomaterials and biomolecules.

Controlled delivery of targets to specific environments, e.g., specific cell types and/or tissues of individuals in vitro and/or in vivo, is currently still challenging, especially when directed at providing controlled release of the target in a controllable conformation, typically associated to a biological activity.

SUMMARY

Provided herein, are signal activatable constructs for molecular delivery, and related components, compositions, methods and systems and in particular tile-like pseudoknot structures for signal activated molecular delivery and related components compositions methods and systems. In several embodiments, signal activatable constructs herein described comprise activatable molecular complexes and activated complexes suitable for controlled release of a targeting domain, which can comprise molecules of various chemical natures.

According to a first aspect described herein are signal activatable constructs for signal-activated molecular delivery, comprising a 17 to 30 bp targeting domain duplex RNA having a guide strand complementarily bound to a passenger strand, the targeting domain duplex RNA also having opposite ends and being in a configuration where the opposite ends, each presenting a 5'-3' terminal base pair and being in a configuration in which a distance between centers of the 5'-3' terminal base pairs at the opposite ends is equal to the length of the targeting domain ±25%. In a first inactive conformation of the activatable construct, a 5' end of the passenger strand is covalently attached to a 3' end of at least one protection strand and a 3' end of the passenger strand is covalently attached to a 5' end of the at least one protection strand, the covalent attachment independently performed by a linker segment of the at least one protection strand having a relaxed average end-to-end distance of up to approximately 12 nm. In the first inactive conformation of the activatable construct, a protection segment of the at least one protection strand is complementarily bound to at least one displacement segment of a sensor strand to form a 12 to 30 bp sensor domain duplex polynucleotide in which the sensor strand further comprises at least one toehold segment presented for binding to a signal molecule. In the first inactive conformation of the activatable construct herein described, the targeting domain is in a configuration minimizing processing by Dicer and/or an Argonaute enzyme of the targeting domain. In a second activated conformation of the activatable construct the sensor strand is bound to the signal molecule and is detached from the at least one protection strand and from the targeting domain and the targeting domain is in a configuration allowing processing by Dicer and/or an Argonaute enzyme in which a 5' end of the passenger strand is covalently attached to a 3' end of at least one protection strand and a 3' end of the passenger strand is covalently attached to a 5' end of the at least one protection strand.

According to a second aspect, a molecular complex for signal-activated molecular delivery, and related compositions, methods, and systems, are described. The molecular complex comprises a targeting domain and a sensor domain. In the molecular complex, the targeting domain comprises a targeting domain duplex RNA having a length of about 17 to about 30 bp and comprising a guide strand complementarily bound to a passenger strand, each of the guide strand and the passenger strand having a 5' end and a 3' end. In the molecular complex, the sensor domain comprises a sensor domain duplex polynucleotide having a length of about 12 to about 30 bp and comprising a sensor strand complementarily bound to a first, 5' terminal protection strand, and to a second 3' terminal protection strand. In the sensor domain, the sensor strand comprises a displacement segment and a toehold segment each having a 5' end and a 3' end. In the sensor domain, the first 5' terminal protection strand comprise a 5' terminal protection segment 5' terminal linker segment each having a 5'end and a 3' end the 5' terminal linker segment covalently attached at the 5' end of the first 5' terminal protection segment. In the sensor domain, the second 3' terminal protection strand comprise a 3' terminal protection segment and a 3' terminal linker segment each having a 5'end and a 3' end, the second 3' terminal linker segment covalently attached at the 3' end of the second 3' terminal protection segment. In the first 5' terminal protection strand and the second 3' terminal protection strand, each of the 5' terminal linker segment and 3' terminal linker segment having independently a relaxed average end-to-end distance of up to approximately 12 nm.

In the sensor strand, the displacement segment is bound to a same toehold segment through covalent attachment of the 5' end of the displacement segment to the 3' end of the same toehold segment, or through covalent attachment of the 5' end of the displacement segment to the 3' end of the same toehold segment, with the toehold segment presented for binding to a signal molecule. In the first 5' terminal protection strand the first, 5' terminal protection segment is covalently attached to the 3' end of the passenger strand through covalent direct attachment of the 5' linker segment, and the 3' terminal protection strand is covalently attached to the 5' end of the passenger strand through covalent direct attachment of the 3' linker segment. In the sensor domain, each of the first 5' terminal protection segment and the second 3' terminal protection segment is complementary bound to the displacement segment of the sensor strand, with a gap between the 3' end of the first 5' terminal protection segment and the 5' end of the second 3' terminal protection segment.

In the molecular complex, the targeting domain, the first 5' terminal protection segment, the second 3' terminal protection segment, the displacement segment, and the toehold segment are in a configuration minimizing processing by Dicer and/or an Argonaute enzyme of the targeting domain. In the molecular complex, the targeting domain, the first 5' terminal protection segment, the second 3' terminal protection segment, the displacement segment, and the toehold segment are configured so that upon binding of the signal molecule to the toehold segment, the displacement segment is displaced from the protection segment, the sensor strand forms a sensor strand-signal molecule complex detached from the targeting domain, and the targeting domain is in a configuration allowing processing by Dicer and/or an Argonaute enzyme of the targeting domain presents in which the first 5' terminal protection strand as an overhang of the 3' end of the passenger strand and the second 3' terminal protection strand as an overhang of the 5' end of the passenger strand.

The composition comprises one or more molecular complexes herein described together with a suitable vehicle. The method comprises: contacting the molecular complex with the signal molecule for a time and under condition to allow release of the targeting domain from the molecular complex. The system comprises: at least two of a molecular complex and a signal molecule complementary to the toehold segment of the molecular complex, for simultaneous combined or sequential use to control release of the targeting domain from the molecular complex according to the methods herein described.

According to a third aspect, an activatable molecular complex and related, activated complexes, compositions, methods, and systems are described. The activatable molecular complex comprises a targeting domain, a first 5' terminal protection strand, a second 3' terminal protection strand and a sensor strand. In the activatable molecular complex, the targeting domain comprises a targeting domain duplex RNA having a length of about 17 to about 30 bp and comprising a guide strand complementarily bound to a passenger strand, each of the guide strand and passenger strand having a 5' end and a 3' end. In the activatable molecular complex, the first 5' terminal protection strand comprise a 5' terminal protection segment 5' terminal linker segment each having a 5'end and a 3' end the 5' terminal linker segment covalently attached at the 5' end of the first 5' terminal protection segment. In the activatable construct, the second 3' terminal protection strand comprise a 3' terminal protection segment and a 3' terminal linker segment each having a 5'end and a 3' end, the second 3' terminal linker segment covalently attached at the 3' end of the second 3' terminal protection segment. In the first 5' terminal protection strand and the second 3' terminal protection strand, each of the 5' terminal linker segment and 3' terminal linker segment having independently a relaxed average end-to-end distance of up to approximately 12 nm.

In the first 5' terminal protection strand the first, 5' terminal protection segment is covalently attached to the 3' end of the passenger strand through covalent direct attachment of the 5' linker segment, and the 3' terminal protection strand is covalently attached to the 5' end of the passenger strand through covalent direct attachment of the 3' linker segment.

In the activatable molecule complex the sensor strand comprises a displacement segment having a 5' end and a 3' end; and at least one toehold segment having a 5' end and a 3' end. In the sensor strand, the displacement segment is bound to a same toehold segment through covalent attachment of the 5' end of the displacement segment to the 3' end of the toehold segment, or through covalent attachment of the 5' end of the displacement segment to the 3' end of the toehold segment.

The activatable molecular complex is configured to exhibit a first conformation and a second, activated, conformation, wherein, in the first conformation, each of the first 5' terminal protection segment and the second 3' terminal protection segment is complementarily bound to the displacement segment, thus forming a sensor domain duplex polynucleotide having a length of about 12 to about 30 bp and with a gap between the 3' end of the first 5' terminal protection segment and the 5' end of the second 3' terminal protection segment, and the at least toehold segment is presented for binding to the signal molecule. In the first conformation of the activatable complex, the sensor domain is bound to the targeting domain through covalent attachment of the 5' end of the first 5' terminal linker segment to the 3' end of passenger strand, and through covalent attachment of the 3' end of the second 3' terminal linker segment to the 5' end of passenger strand. In the first conformation of the activatable complex the targeting domain is in a conformation configured to minimize processing by Dicer and/or an Argonaute enzyme.

In the activatable molecular complex, in the second, activated conformation the sensor strand complementarily binds the signal molecule, forming a sensor strand-signal molecule complex detached from the targeting domain, and the targeting domain presents the first 5' terminal protection strand as an overhang of the 3' end of the passenger strand and the second 3' terminal protection strand as an overhang of the 5' end of the passenger strand. In the activatable molecular complex, in the second activated conformation, the targeting domain is in a conformation configured to allow processing by Dicer and/or an Argonaute enzyme.

The composition comprises one or more activatable complexes and a suitable vehicle. The method comprises contacting an activatable molecular complex with a signal molecule capable of binding to the toehold segment of the activatable molecular complex for a time and under condition to allow release of the targeting domain from the molecular complex. The system comprises at least two of one or more activatable molecular complexes and a signal molecule capable of binding to the toehold segment of the molecular complexes, for simultaneous combined or sequential use to control release of the targeting domain from the molecular complex.

According to fourth aspect, an activated molecular complex and related compositions, methods, and systems are described. The activated molecular complex comprises a targeting domain presenting a first 5' terminal overhang and a second 3' terminal overhang. In the activated molecular complex, the targeting domain comprises a targeting domain duplex RNA having a length of about 17 to about 30 bp and comprising a guide strand complementarily bound to a passenger strand, each of the guide strand and passenger strand having a 5' end and a 3' end. In the activated molecular complex, the first 5' terminal overhang is attached to the 3' end of the passenger strand through covalent attachment of a 5' linker segment, the second 3' terminal overhang is attached to the 5' end of the passenger strand through covalent attachment of a 3' linker segment. In the activated molecular complex, the targeting domain is in a conformation configured to allow processing by Dicer and/or an Argonaute enzyme.

The related composition comprises one or more activated molecular complexes and a suitable vehicle. The related method to provide the activated molecular complex comprises contacting the activatable molecular complex herein described in the first condition, with a signal molecule capable of binding the toehold segment to allow switching of the molecular complex from the first condition to the second activated condition of the molecular complex. The related method for controlled release of a targeting domain from an activated complex comprises: contacting the activated molecular complex with a signal molecule capable of binding to the toehold segment for a time and under condition to allow release of the targeting domain from the activated molecular complex.

According to a fifth aspect, an exonuclease-resistant molecular complex for enzyme-assisted molecular delivery, and related compositions, methods, and systems, are described. The exonuclease resistant molecular complex comprises a targeting domain and a sensor domain. In the exonuclease-resistant molecular complex, the targeting domain comprises a targeting domain duplex RNA having a length of about 17 to about 30 bp and comprising a guide strand complementarily bound to a passenger strand, each of the guide strand and passenger strand having a 5' end and a 3' end, the guide strand and/or passenger strand possibly comprising a modified polynucleotide portion, a non-nucleic acid portion, and/or a phosphorothioate portion. In the exonuclease-resistant molecular complex, the sensor domain comprises a sensor domain duplex polynucleotide having a length of about 14 to about 30 bp and comprising a sensor strand complementarily bound to a first 5' terminal protection segment and a second 3' terminal protection segment each having a 5' end and a 3' end, each of the first 5' terminal protection segment and the second 3' terminal protection segments comprising a modified polynucleotide portion, a non-nucleic acid portion, and/or a phosphorothioate portion. In the sensor domain, each of the first 5' terminal protection segment and the second 3' terminal protection segment is complementary bound to a displacement segment of the sensor strand, with a gap between the 3' end of the first 5' terminal protection segment and the 5' end of the second 3' terminal protection segment.

In the sensor domain, the sensor strand comprises the displacement segment and a toehold segment each having a 5' end and a 3' end, the displacement segment comprising a modified polynucleotide portion, and/or a phosphorothioate portion and/or the toehold segment comprising a modified polynucleotide portion, a non-nucleic acid portion, and/or a phosphorothioate portion. In the sensor strand, the displacement segment is bound to a same toehold segment through covalent attachment of the 5' end of the displacement segment to the 3' end of the toehold segment, or through covalent attachment of the 5' end of the displacement segment to the 3' end of the toehold segment, with the toehold segment presented for binding to a signal molecule. In the sensor domain, each of the first 5' terminal protection segment and the 3' terminal second protection segment is complementary bound to the displacement segment of the sensor strand, with a gap between the 3' end of the protection segment and the 5' end of the second protection segment. In the exonuclease-resistant molecular complex, the sensor domain is bound to the targeting domain through covalent attachment of the 5' end of the first 5' terminal protection segment to the 3' end of passenger strand via a 5' terminal linker segment having a relaxed average end-to-end distance of up to approximately 12 nm, the sensor domain further bound to the targeting domain, and through covalent attachment of the 3' end of the second 3' terminal protection segment to the 5' end of passenger strand via a 5' terminal linker segment having a relaxed average end-to-end distance of up to approximately 12 nm.

In the exonuclease-resistant molecular complex, the targeting domain, the first 5' terminal protection segment, the second 3' terminal protection segment, the displacement segment, and the toehold segment are configured so that upon binding of the signal molecule to the toehold segment, the displacement segment is displaced from the first 5' terminal protection segment and the second 3' terminal protection segment, the sensor strand forms a sensor strand-signal molecule complex detached from the targeting domain, and the targeting domain presents the first 5' terminal protection segment as an overhang of the 3' end of the passenger strand and the second 3' terminal protection segment as an overhang of the 5' end of the passenger strand The composition comprises one or more exonuclease-resistant molecular complexes herein described together with a suitable vehicle. The method comprises: contacting the molecular complex with the signal molecule for a time and under condition to allow release of the targeting domain from the molecular complex. The system comprises: at least two of a molecular complex and a signal molecule capable of binding to the toehold segment of the molecular complex, for simultaneous combined or sequential use to control release of the targeting domain from the molecular complex according to the methods herein described.

According to sixth aspect, a method for treating a disease in an individual through signal activated molecular delivery in cells, and related compositions and systems, are described. The method comprises administering to the individual an effective amount of one or more of the signal activatable constructs herein described and in particular one or more of the molecular complexes, activatable molecular complex, activated complexes and/or exonuclease resistant complexes herein described. The related pharmaceutical composition comprises one or more signal activatable constructs herein described, and in particular one or more of the molecular complexes, activatable molecular complex, activated complexes and/or exonuclease resistant complexes herein described, with a pharmaceutical acceptable vehicle.

According to a seventh aspect, complexes herein described can be provided by a method comprising providing a first polynucleotide strand, a second polynucleotide strand and a third polynucleotide strand. The first polynucleotide strand comprises the guide strand of the complexes herein described. The second polynucleotide strand comprises from the 5' end to 3' end the first 5' terminal protection segment, the passenger strand, and the second 3' terminal protection segment. The third polynucleotide strand comprises a displacement segment and a toehold segment in any one of the configuration of the complexes herein described. The method further comprises contacting the first polynucleotide strand, the second polynucleotide strand, and the third polynucleotide strand for a time and under condition to allow annealing of the strands to form the signal-activatable molecular complex of herein disclosed.

The constructs, systems, compositions, and methods herein described allow in several embodiments to perform cell type specific molecular delivery.

The constructs, systems, compositions, and methods herein described also allow in several embodiments integration of signal detection, signal transduction, and targeting in a single compact molecular construct with easier delivery and/or administration as well as enhanced efficiency of signal transduction with respect to some approaches of the art.

The constructs, systems, compositions, and methods herein described also allow in several embodiments intracellular information processing and controlling, in which the presence of one set of biomolecules (e.g., protein or nucleic acid) is coupled with inhibition or activation of another set of biomolecules in the cells.

The methods and systems herein described can be used in connection with applications wherein cell-type specific modulation of cells is desired, including but not limited to medical application, biological analysis, research and diagnostics including but not limited to clinical, therapeutic, and pharmaceutical applications, such as cell type specific drug delivery, cell type specific modeling or therapy, including but not limited to gene therapy and RNAi.

The details of one or more embodiments of the disclosure are set forth in the accompanying drawings and the description below. Other features, objects, and advantages will be apparent from the description and drawings, and from the claims.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

FIG. 1A illustrates the front view of the three-dimensional model. FIG. 1B shows a zoom in of the 5'-3' base pair of Atom 1 of FIG. 1A, and FIG. 1C shows a zoom in of the 5'-3' base pair of Atom 2 of FIG. 1A.

FIG. 2A shows measurement of distances between several pairs of atoms to estimate a true center to center distance, FIG. 2B shows a bottom up view of both base-pairs used for the measurement.

FIG. 5A illustrates the front view of the three-dimensional model, showing that the two duplexes are configured so that the Dicer cleavage sites of the targeting duplex and the sensor duplex are oriented towards the interior of the two duplexes. FIG. 5B illustrates the top view of the three-dimensional model.

FIG. 6A illustrates the front view of the three-dimensional model. FIG. 6B shows the right side view of the same three-dimensional model, and FIG. 6C illustrates the top view of the three dimensional model shown in FIG. 6B and FIG. 6C.

FIG. 7A illustrates the front view of the three-dimensional model. FIG. 7B shows the right side view of the same three-dimensional model, and FIG. 7C illustrates the top view of the three dimensional model shown in FIG. 7B and FIG. 7C.

FIGS. 8A-C illustrate a three-dimensional model of an exemplary signal-activated tile saRNA comprising a targeting and sensor duplexes as in FIGS. 6A-C, wherein the targeting and sensor duplexes are each 27 base pairs long. FIG. 8A illustrates the front view of the three-dimensional model. FIG. 8B shows the right side view of the same three-dimensional model, and FIG. 8C illustrates the top view of the three dimensional model shown in FIG. 8B and FIG. 8C.

In FIG. 10B, element C indicates an activation segment (SEQ ID NO: 117).

FIG. 11A illustrates the chemical structure of the C6 amino chemical group modification from GE Dharmacon. FIG. 11B illustrates the chemical structure of the 3AmMO 3' amino chemical group modification from IDT.

FIGS. 14A-B show a schematic illustration of an exemplary signal-activated molecular complex, G6L2X2, comprising a guide strand G6 (SEQ ID NO. 8), a passenger strand L2PS (SEQ ID NO. 17) a 5' protection segment L2P5' (SEQ ID NO: 18) and a 3' protection segment L2P3' (SEQ ID NO: 16) attached to the passenger strand L2PS (SEQ ID NO. 17) by C3 linkers L2L5' and L2L3' (indicated by black lines), and a sensor strand X2 (SEQ ID NO. 19) comprising a toehold segment X2T (SEQ ID NO:20) and a displacement segment X2D (SEQ ID NO: 21). In particular, FIG. 14A shows the inactive OFF conformation of the molecular construct and FIG. 14B shows the active ON conformation of the molecular construct after binding of signal strand S1 (SEQ ID NO. 41).

FIGS. 15A-B show a schematic illustration of an exemplary signal-activated molecular complex, G6L2X3, comprising a guide strand G6 (SEQ ID NO. 8), a passenger strand L2PS (SEQ ID NO. 17) which further comprises a 5' protection segment L2P5' (SEQ ID NO: 18) and a 3' protection segment L2P3' (SEQ ID NO: 16) connected to the passenger strand L2PS (SEQ ID NO. 17) by C3 linkers L2L5' and L2L3' (indicated by black lines), and a sensor strand X3 (SEQ ID NO. 22) comprising a toehold segment X3T (SEQ ID NO:23) and a displacement segment X2D (SEQ ID NO: 24). In particular, FIG. 15A shows the inactive OFF conformation and FIG. 15B shows the active ON conformation of the molecular construct after binding of signal strand S1 (SEQ ID NO. 41).

FIGS. 16A-B show a schematic illustration of an exemplary signal-activated molecular complex, G6L2X5, comprising a guide strand G6 (SEQ ID NO. 8), a passenger strand L2Ps (SEQ ID NO. 17) which attaches 5' protection segment L2P5' (SEQ ID NO: 18) and a 3' protection segment L2P3' (SEQ ID NO: 16) modified to include phosphorothioate linkages as indicated in the figure and connected to the passenger strand L2PS (SEQ ID NO: 17) by C3 linkers L2L5' and L2L3' (indicated by black lines), and a sensor strand X5 (SEQ ID NO. 25) comprising a toehold segment X5T (SEQ ID NO:26) and a displacement segment X5D (SEQ ID NO: 27) also modified to include phosphorothioate linkages as indicated in the figure. In particular, FIG. 16A shows the inactive OFF conformation and FIG. 16B shows the active ON conformation of the molecular construct after binding of signal strand S2 (SEQ ID NO. 42).

FIG. 17A shows the inactive OFF conformation and FIG. 17B shows the active ON conformation of the molecular construct after binding of signal strand S2 (SEQ ID NO. 42).

FIGS. 18A-C show a schematic illustration of exemplary 5' sensor strand toeholds of an exemplary signal-activated molecular construct according to embodiments herein described. FIG. 18A shows the 5' toehold X3T (SEQ ID NO: 23) of construct G6L2X3 (FIG. 15A and FIG. 15B), which comprises six base pairs complementary to a signal strand and a mismatch to said strand at position 7 of the toehold.

FIG. 18B illustrates the 5' toehold X5T (SEQ ID NO: 26) of construct G6L2X5 (FIG. 16A and FIG. 16B), which comprises eight base pairs complementary to a signal strand and has no mismatches. FIG. 18C illustrates the 5' toehold X6T (SEQ ID NO: 29) of construct G6L2X6 (FIG. 17A and FIG. 17B), which comprises eight base pairs complementary to a signal strand, has no mismatches, and further comprises an LNA modified base.

FIG. 21A shows a schematic of the interaction of a first activation sequence with 3' terminal toehold E3T2 (SEQ ID NO:67). FIG. 21B shows a schematic of the interaction of a first activation sequence with 3' terminal toehold E3T1 (SEQ ID NO:64).

FIG. 22A shows a schematic of the construct A-B4C4D4-E4 in an OFF position (in absence of a signal molecule). FIG. 22B of the construct A-B4C4D4-E4 in an ON position (in presence of activation sequence (SEQ ID NO:76).

FIG. 23A shows a schematic of the construct A B5$_1$C5D5 B5$_2$-E5in an OFF position (in absence of a signal molecule). FIG. 23B of the construct A B5$_1$C5D5 B5$_2$-E5 in an ON position (in presence of activation sequence (SEQ ID NO:83).

FIG. 24 shows the exemplary molecular construct G6-L2-X3-Inosine having a guide strand G6 (SEQ ID NO. 8), a segment L2 comprising a passenger strand L2PSs (SEQ ID NO.17) attaching at the 5' terminus a second, 5' protection segment L2P5' (SEQ ID NO: 18) and attaching at the 3' terminus a 3' terminal protection segment L2P3' (SEQ ID NO: 16) both connected to the passenger strand B2 (SEQ ID NO: 17) by C3 linkers L2-5' and L2-3' (indicated by black lines), and a sensor strand X3-inosine (SEQ ID NO. 84). Sensor X3-inosine comprises a displacement segment X3D (SEQ ID NO:86) and an inosine toehold segment X3T-Inosine (SEQ ID NO:85).

FIG. 25 shows the exemplary molecular construct G6-L2-X3-Inosine-HMW-PEG having a guide strand G6 (SEQ ID NO. 8), and a segment L2 comprising a passenger strand L2PSs (SEQ ID NO: 17) attaching a 5' terminal protection segment L2P5' (SEQ ID NO: 18) and a 3' terminal protection segment L2P3' (SEQ ID NO: 16) both connected to the passenger strand L2Ps (SEQ ID NO: 17) by C3 linkers L2-5' and L2-3'(indicated by black lines), and a sensor strand X3-inosine-HMW-PEG (SEQ ID NO. 87). Sensor X3-inosine-HMW-PEG comprises a displacement segment X3D (SEQ ID NO:89) directly attaching at the related 5' terminus, the 3' terminus of an inosine toehold segment X3T-Inosine-HMW-PEG (SEQ ID NO:88).

Sensor X5-Loop comprises a displacement segment X5D (SEQ ID NO: 98) directly attaching at its 5' terminus the 3' terminus of a 5' terminal toehold X5T-Loop (SEQ ID NO: 97). FIG. 27A shows a schematic of the construct G6 L2 X5-Loop in an OFF position (in absence of a signal molecule). FIG. 27B of the construct G6 L2 X5-Loop in an ON position (in presence of activation sequence (SEQ ID NO:99).

FIG. 29 shows the result for targeting domain polynucleotides G6L1 and G6L2 and for double duplex polynucleotides G6L2X1, G6L2X2, and G6L2X3 in the OFF state.

FIG. 30 illustrates the level of luciferase protein remaining on the y axis versus the final nanomolar concentration of two of the polynucleotide constructs used in the assay (G6L2 and G6L2X3) on the x axis.

FIG. 31 shows the result for the targeting domain polynucleotide G6L2, for double duplex polynucleotide G6L2X3 in the OFF and in the ON state (together with signal strand S1), for individual strands G6, L2, S1, X3, and for duplex polynucleotides G6X3, L2X3, and X3S1.

FIG. 32 illustrates the normalized relative luciferase unit ratio on the y axis versus the final nanomolar concentration of two of the polynucleotide constructs used in the assay (G6L2X3 in the OFF state and G6L2X3 in the ON state) on the x axis.

FIG. 33 shows the result for double duplex polynucleotide constructs G6L2X3, G6L2X5, and G6L2X6 in the OFF and in the ON state (together with signal strand S1).

DETAILED DESCRIPTION

Figure 1A:
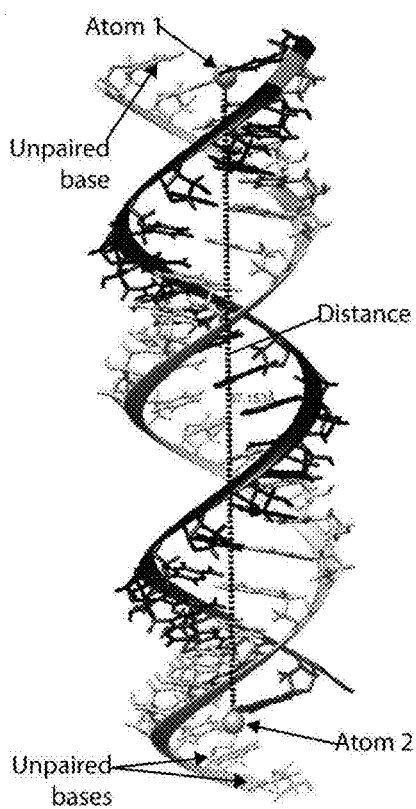
FIGS. 1A-1C illustrate a three-dimensional model of an exemplary model 22 base-pair targeting domain

Herein described are signal activatable constructs for molecular delivery and related components, compositions, methods and systems.

The term "signal activatable construct" as used herein indicates a molecular complex that can have more than one conformation, and at least one of the conformations results from the binding of a signal molecule to the molecular complex. Typically, the conformation associated with the binding of a signal molecule to the molecular complex is also associated with a chemical and/or biological activity that characterizes the conformation as active with respect to the identified activity. Accordingly, signal activatable constructs herein described can have at least one active conformation and at least one inactive conformation with respect to the enzymatic activity of the enzyme assisted molecular delivery. Switching between an inactive conformation to an active conformation is triggered by binding of the signal molecule to the construct.

Signal activatable constructs and related components herein described comprise one or more polynucleotides. The term "polynucleotide" as used herein indicates an organic polymer composed of two or more monomers including nucleotides, nucleosides or analogs thereof. The term "nucleotide" refers to any of several compounds that consist of a ribose or deoxyribose sugar joined to a purine or pyrimidine base and to a phosphate group and that is the basic structural unit of nucleic acids. The term "nucleoside" refers to a compound (such as guanosine or adenosine) that consists of a purine or pyrimidine base combined with deoxyribose or ribose and is found especially in nucleic acids. The term "nucleotide analog" or "nucleoside analog" refers respectively to a nucleotide or nucleoside in which one or more individual atoms have been replaced with a different atom or a with a different functional group. Exemplary functional groups that can be comprised in an analog include methyl groups and hydroxyl groups and additional groups identifiable by a skilled person.

Exemplary monomers of a polynucleotide comprise deoxyribonucleotide, ribonucleotides, LNA nucleotides and PNA nucleotides. The term "deoxyribonucleotide" refers to the monomer, or single unit, of DNA, or deoxyribonucleic acid. Each deoxyribonucleotide comprises three parts: a nitrogenous base, a deoxyribose sugar, and one or more phosphate groups. The nitrogenous base is typically bonded to the 1' carbon of the deoxyribose, which is distinguished from ribose by the presence of a proton on the 2' carbon rather than an —OH group. The phosphate group is typically bound to the 5' carbon of the sugar.

The term "ribonucleotide" refers to the monomer, or single unit, of RNA, or ribonucleic acid. Ribonucleotides have one, two, or three phosphate groups attached to the ribose sugar.

The term "locked nucleic acids" (LNA) as used herein indicates a modified RNA nucleotide. The ribose moiety of an LNA nucleotide is modified with an extra bridge connecting the 2' and 4' carbons. The bridge "locks" the ribose in the 3'-endo structural conformation, which is often found in the A-form of DNA or RNA. LNA nucleotides can be mixed with DNA or RNA bases in the oligonucleotide whenever desired. The locked ribose conformation enhances base stacking and backbone pre-organization. This significantly increases the thermal stability (melting temperature) of oligonucleotides. LNA oligonucleotides display unprecedented hybridization affinity toward complementary single-stranded RNA and complementary single- or double-stranded DNA. Structural studies have shown that LNA oligonucleotides induce A-type (RNA-like) duplex conformations as will be understood by a skilled person.

The term "polyamide polynucleotide", "peptide nucleic acid" or "PNA" as used herein indicates a type of artificially synthesized polymer composed of monomers linked to form a backbone composed of repeating N-(2-aminoethyl)-glycine units linked by peptide bonds. The various purine and pyrimidine bases are linked to the backbone by methylene carbonyl bonds. Since the backbone of PNA contains no charged phosphate groups, the binding between PNA/DNA strands is stronger than between DNA/DNA strands due to the lack of electrostatic repulsion. PNA oligomers also show greater specificity in binding to complementary DNAs, with a PNA/DNA base mismatch being more destabilizing than a similar mismatch in a DNA/DNA duplex. This binding strength and specificity also applies to PNA/RNA duplexes. PNAs are not easily recognized by either nucleases or proteases, making them resistant to enzyme degradation. PNAs are also stable over a wide pH range. In some embodiments, polynucleotides can comprise one or more non-nucleotidic or non nucleosidic monomers identifiable by a skilled person.

Accordingly, the term "polynucleotide" includes nucleic acids of any length, and in particular DNA, RNA, analogs thereof, such as LNA and PNA, and fragments thereof, possibly including non-nucleotidic or non-nucleosidic monomers, each of which can be isolated from natural sources, recombinantly produced, or artificially synthesized. Polynucleotides can typically be provided in single-stranded form or double-stranded form (herein also duplex form, or duplex).

A "single-stranded polynucleotide" refers to an individual string of monomers linked together through an alternating sugar phosphate backbone. In particular, the sugar of one nucleotide is bond to the phosphate of the next adjacent nucleotide by a phosphodiester bond. Depending on the sequence of the nucleotides, a single-stranded polynucleotide can have various secondary structures, such as the stem-loop or hairpin structure, through intramolecular self-base-paring. A hairpin loop or stem loop structure occurs when two regions of the same strand, usually complementary in nucleotide sequence when read in opposite directions, base-pairs to form a double helix that ends in an unpaired loop. The resulting lollipop-shaped structure is a key building block of many RNA secondary structures as will be understood by a skilled person. The term "small hairpin RNA" or "short hairpin RNA" or "shRNA" as used herein indicate a sequence of RNA that makes a tight hairpin turn and can be used to silence gene expression via RNAi. A single strand polynucleotide has a 5' end and a 3' end The terms "5' end" and "3' end" of a single stranded polynucleotide indicate the terminal residues of the single strand polynucleotide and are distinguished based on the nature of the free group on each extremity. The 5'-end of a single strand polynucleotide designates the terminal residue of the single strand polynucleotide that has the fifth carbon in the sugar-ring of the deoxyribose or ribose at its terminus (5' terminus). The 3'-end of a single strand polynucleotide designates the residue terminating at the hydroxyl group of the third carbon in the sugar-ring of the nucleotide or nucleoside at its terminus (3' terminus). The 5' end and 3' end terminus in various cases can be modified chemically or biologically e.g. by the addition of functional groups or other compounds as will be understood by the skilled person.

A "double-stranded polynucleotide" or "duplex polynucleotide" refers to two single-stranded polynucleotides bound to each other through complementarily binding. The duplex typically has a helical structure, such as a double-stranded DNA (dsDNA) molecule or a double stranded RNA, which is maintained largely by non-covalent bonding of base pairs between the strands and by base stacking interactions. The term "5'-3' terminal base pair" with reference to a duplex polynucleotide refers to the base pair positioned at an end of the duplex polynucleotide that is formed by the '5 end of one single strand of the two single strand forming the duplex polynucleotide base-paired with the 3' end of the single strand forming the duplex polynucleotide complementary to the one single strand. Accordingly a duplex polynucleotide formed by a first single strand complementarily bound to a second single strand, has two opposite ends: a first end of the duplex polynucleotide having a "5'-3' terminal base pair" formed by the 5' end of the first single strand and the 3' end of the second single strand, and a second end of the duplex polynucleotide opposite to the first formed by the 5' end of the first single strand and the 3' end of the second single strand.

The constructs and components herein described are suitable in some embodiments for enzyme assisted molecular delivery. The term "molecular delivery" as used herein indicates any process by which controlled activation of molecular complexes regulates the release of a chemical compound for various purposes.

The term "enzyme-assisted" as used herein is defined to mean any chemical process where a protein or other chemical entity is used to catalyze or increase the rate of a chemical reaction. The protein used for this purpose can include, but is not limited to, chains of amino acids (natural or unnatural), that may or may not contain other chemical variations and can have a defined secondary structure. The chemical reaction can include, but is not limited to, reactions of RNA or portions of RNA, DNA or portions of DNA, and/or any nucleotide or derivative thereof. Typically, enzymes catalyze reactions through binding to specific or non-specific target molecular portions usually indicated as binding sites.

In several embodiments, the enzyme-assisted molecular delivery herein described is an XRN1 assisted molecular delivery. The term "XRN1" as used herein refers to an exoribonuclease enzyme that is capable of degrading ribopolynucleotides by removing terminal nucleotides from the 5' terminus of the ribopolynucleotide. As used herein, the term "XRN1" comprises any enzyme, whether naturally occurring or synthetically modified and including any enzyme modified in one or more residues, which substantially retain an exoribonuclease activity such as the one herein described. Naturally occurring XRN1 enzymes which are members of the XRN1 family can be found in many organisms including yeast, nematode, fruit fly, and human. XRN1 is also referred as Pacman, KEM1, SEP1, DST2, RAR5, SKI1, and DST2 to one skilled in the art.

In several embodiments, the enzyme-assisted molecular delivery herein described is an exosome complex assisted molecular delivery. The term "exosome complex" as used herein refers to a multi-protein enzyme complex that is capable of degrading ribopolynucleotides by removing terminal nucleotides from the 3' terminus of the ribopolynucleotide, as, for example, described in H Houseley, J., LaCava, J. & Tollervey, D. RNA-quality control by the exosome. *Nat Rev Mol Cell Biol* 7, 529-539 (2006) (herein incorporated by reference in its entirety). As used herein, the term "exosome complex" comprises any enzyme complex, whether naturally occurring or synthetically modified and including any enzyme modified in one or more residues, which substantially retain a ribopolynucleotide-degrading activity such as the one herein described. Naturally occurring exosome complexes can be found in many organisms including yeast, nematode, fruit fly, and human. The exosome complex is also referred as the PM/Scl complex or the exosome to one skilled in the art.

In particular in some embodiments, the enzyme assisted molecular delivery is directed to release a targeting domain within a desired environment, such as a biological environment and in particular within a cell, and the release of the targeting domain can be catalyzed by XRN1 and/or the exosome complex in combination with Dicer and/or an Argonaute enzyme.

A "domain" in the sense of the present disclosure indicates a part of a given polynucleotide having a structure specifically associated with a function and that exist independently of the rest of the polynucleotide. The structure/function association in a domain is typically conserved during the chemical and/or biological reaction associated with the polynucleotide.

A "targeting domain" as used herein indicates a domain of a polynucleotide associated with the function of binding or reacting with a predetermined target within a biological environment and in particular within a cell.

The term "target" as used herein indicates an analyte of interest. The term "analyte" refers to a substance, compound, moiety, or component whose presence or absence in a sample is to be detected. Analytes include but are not limited to biomolecules and in particular biomarkers. The term "biomolecule" as used herein indicates a substance, compound or component associated with a biological environment including but not limited to sugars, amino acids, peptides, proteins, oligonucleotides, polynucleotides, polypeptides, organic molecules, haptens, epitopes, biological cells, parts of biological cells, vitamins, hormones and the like. The term "biomarker" indicates a biomolecule that is associated with a specific state of a biological environment including but not limited to a phase of cellular cycle, health and disease state. The presence, absence, reduction, upregulation of the biomarker is associated with and is indicative of a particular state. The "biological environment" refers to any biological setting, including, for example, ecosystems, orders, families, genera, species, subspecies, organisms, tissues, cells, viruses, organelles, cellular substructures, prions, and samples of biological origin.

Exemplary targeting domains in the sense of the present disclosure comprise siRNA, saRNA, microRNA, and additional polynucleotides identifiable by a skilled person.

In some embodiments herein described, the targeting domain of the disclosure is a duplex RNA of about 17 to about 30 bp in length and having a first end and a second end, the duplex RNA comprising a guide strand complementary bound to a passenger strand, each of the guide and passenger strands having a 5' end and a 3' end. In some embodiments, the duplex RNA is 19 to 27 base pairs in length. In some embodiments, the duplex RNA is 23 to 27 base pairs in length. In some embodiments, the duplex RNA is 23 to 25 base pairs in length. In some embodiments, the duplex RNA is approximately 23 base pairs or 25 base pairs in length.

In embodiments herein described, the two opposite ends of the targeting domain each present a 5'-3' terminal base pair. In particular in the targeting domain a first 5'-3' terminal base pair is formed by the 5' end of the guide strand based paired with the 3' end of the passenger strand and a second 5'-3' terminal base pair is formed by the 5' end of the passenger strand based paired with the 3' end of the guide strand. In the targeting domain the first and second terminal base pair define opposite ends of the targeting domain.

In some embodiments herein described, the two opposite ends of the targeting domain are in a configuration in which a distance between centers of the 5'-3' terminal base pairs at the opposite ends is equal to the length of the targeting domain ±25%, where the "length" of the targeting domain RNA duplex is the distance defined by the number of nucleotides of the guide strand involved in the base pairs forming the duplex polynucleotide. Calculation of the length of a duplex polynucleotide can be performed with techniques identifiable by a skilled person. For example estimating the end to end length of a duplex segment formed by RNA base pairs can be performed considering such length to be approximately 0.25 nm per base-pair, wherein approximately with reference to by distances indicates a variation of ±0.05 nm. In a solution, targeting domains herein described are expected to change in accordance with temperature, length of linkage between the opposite ends presence of a nicks in a strand, of the duplex and additional parameters identifiable by a skilled person. Therefore the in activatable construct herein described, the length of the targeting domain and a distance between centers of the 5'-3' terminal base pairs at the opposite ends of the targeting domain can differ of a ±25%.

In some embodiments the distance between centers of the 5'-3' terminal base pairs at the opposite ends of the targeting domain is preferably equal to the length of the targeting domain preferably ±10%, more preferably ±5%. In some more preferred embodiments the targeting domain duplex RNA is substantially straight with a distance between centers of the 5'-3' terminal base pairs at the opposite ends is equal to the length of the targeting domain.

The distance between centers of the 5'-3' terminal base pairs at the opposite ends of the targeting domain can be measured with various techniques such as Fluorescence resonance energy transfer (FRET) nuclear magnetic resonance (NMR) small angle X-ray scattering (SAXS) and additional techniques identifiable by a skilled person.

Fluorescence resonance energy transfer (also called Förster resonance energy transfer) is a well-established experimental technique used by those skilled in the art to determine the structure and conformation of both DNA (see e.g. Mizukoshi, T., et al. *Nucleic Acids Research* 29, 4948-4954 (2001). Dragan, A. I. & Privalov, P. L. in *Methods in Enzymology* Vol. Volume 450 (eds Brand Ludwig & L. Johnson Michael) 185-199 (Academic Press, 2008) and RNA structures (see e.g. Lilley, D. M. J. & Wilson, T. J. in. *Current Opinion in Chemical Biology* 4, 507-517, (2000) and Gohlke, C and atl in. *Proceedings of the National Academy of Sciences* 91, 11660-11664 (1994), especially duplexes. In an exemplary method to measure the end-to-end distance of a duplex polynucleotide, a pair of fluorophores known to have FRET activity is attached to the two ends of the duplex polynucleotide via 3', 5', or internal covalent linkers attached to the constituent strands of the duplex. Parameters such as the steady state FRET efficiency and the fluorescence lifetime can be measured. These measurements allow calculation of the exact distance between the donor and acceptor fluorophores using mathematical formulas known to those skilled in the art (see e.g. Mizukoshi, T., et al in *Nucleic Acids Research* 29, 4948-4954 (2001).; Lilley, D. M. J. & Wilson, T. J. in *Current Opinion in Chemical Biology* 4, 507-517, (2000), G. S., Murchie, et al. *The EMBO Journal* 16, 7481-7489, (1997)). For example, it is known that the efficiency of the FRET varies as the sixth power of the distance. To improve the accuracy of the distance extrapolation, geometric standards, for example, perfectly base-paired duplexes of a known length can be prepared for FRET measurements under identical experimental conditions to help obtain accurate parameters for the extrapolation equations. The extrapolated distance between the donor and acceptor fluorophores can then be used to determine a geometrically accurate model of the RNA or DNA structure (see e.g Lilley, D. M. J. & Wilson, T. J. in *Current Opinion in Chemical Biology* 4, 507-517, (2000). If necessary, the attachment positions of the donor or acceptor fluorophores can be varied to acquire additional geometric constraints for the modeling processing.

In addition to FRET technique, nuclear magnetic resonance (NMR) is a well-established technique for providing detailed atomic structure of smaller RNA domains (see e.g. Fürtig, B., et al in. *Biopolymers* 86, 360-383, (2007). Varani, G., et al in. *Progress in Nuclear Magnetic Resonance Spectroscopy* 29, 51-127, (1996) Lu, K., et al in *J Biomol NMR* 46, 113-125, (2010)), while small angle X-ray scattering (SAXS) can provide size estimates for the overall physical dimensions of the construct (see e.g. Russell, R., in *Nat Struct Mol Biol* 7, 367-370 (2000) Lipfert, J. & Doniach, S. in. *Annual Review of Biophysics and Biomolecular Structure* 36, 307-327, (2007)) NMR and SAXS techniques are well known to those skilled in the art. The combination of FRET, NMR and SAXS with well-established computational techniques to model nucleic acids in solution (see e.g. Takada, S. in *Current Opinion in Structural Biology* 22, 130-137, (2012) Pascal, T. A., et als in *The Journal of Physical Chemistry B* 116, 12159-12167, (2012), Sim, A. Y. L., et al in *Current Opinion in Structural Biology* 22, 273-278, (2012)), can give accurate models of the end to end distance of the targeting domain and the overall structure of the construct.

In an exemplary application of these techniques to the signal activated targeting domain, the donor and acceptor fluorophore pairs can be attached to the 3' and 5' termini of the guide strand or at various internal positions on the guide strand and the passenger strand. Steady state measurements of the FRET efficiency and fluorescence life time can be used to determine the distance between the pairs. To increase the accuracy of the measurement, multiple end labeled RNA duplexes of known number of base-pairs and known structure can be measured to improve the parameters for extrapolation of the distance. The extrapolated distances can then used to provide geometric constraints to build an accurate model of the structure of the targeting domain. The end to end distance is then measured using this model.

To simplify the construction of the model an internal Cy3 (see webpage dtdna.com/site/catalog/modifications/product/1476) and Cy5 (see webpage idtdna.com/site/catalog/modifications/product/1476) donor/acceptor pair can be attached on the guide strand at positions directly flanking the two base-paired ends of the targeting duplex. The distance between the two fluorophores provide a close approximation of the center to center distance between the end base-pairs. Similarly, in a second measurement, a C3 and C5 donor acceptor pair can be attached to flanking positions on the passenger strand and provide a second measurement for the distance. The average of the two measurements provides a measurement of the end to end distance after subtracting ~0.5 nm for the extra length introduced by the attachment of the fluorophores. Further refinement of the measured distance can be obtained after a molecular model is constructed. FRET measurements are preferably used to determine distances between 2.0 nm to 8.0 nm. NMR and SAXS measurement can be used to augment distance measurements outside this range as will be understood by a skilled person.

Figure 1B:
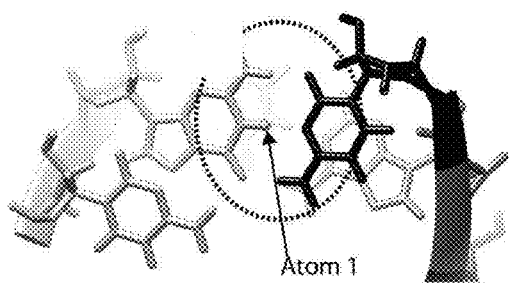
Figure 1C:
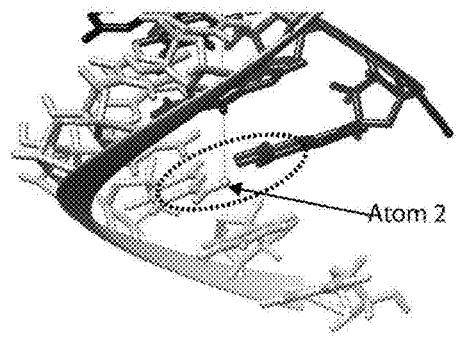

An exemplary illustration of the end to end distance and related measurement is provided in FIGS. 1A to 1C which illustrate the measurement of the end to end distance for a model 22 base-pair targeting domain using the molecular modeling program UCSF Chimera (Pettersen, E. F., Goddard, T. D., Huang, C. C., Couch, G. S., Greenblatt, D. M., Meng, E. C., and Ferrin, T. E. "UCSF Chimera—A Visualization System for Exploratory Research and Analysis." *J. Comput. Chem.* 25:1605-1612 (2004)). As shown in FIG. 1A, the end to end distance is the distance between the centers for the terminal base-pairs on the two ends of the duplex RNA domain. Unpaired bases on the two ends are ignored. In many molecular modeling programs, it is more convenient to measure the distance between two particular atoms. In this case, several distance measurements can be made between different pairs of atoms in the two pertinent pairs of bases to obtain a good estimate of the "true" end to end distance. FIG. 1B shows a top down view of the upper base-pair measured in FIG. 1A. The dashed ellipse shows the area around the center of the base-pair. For this particular pair of bases, Atom 1 is near the center and chosen as one of the atoms. FIG. 1C shows the bottom base-pair. Here, Atom 2 is close to the center and used as the second atom for the distance measurement. For a model 22 base-pair RNA:RNA duplex, this measurement gives a distance of 5.7 nm.

Figure 2A:
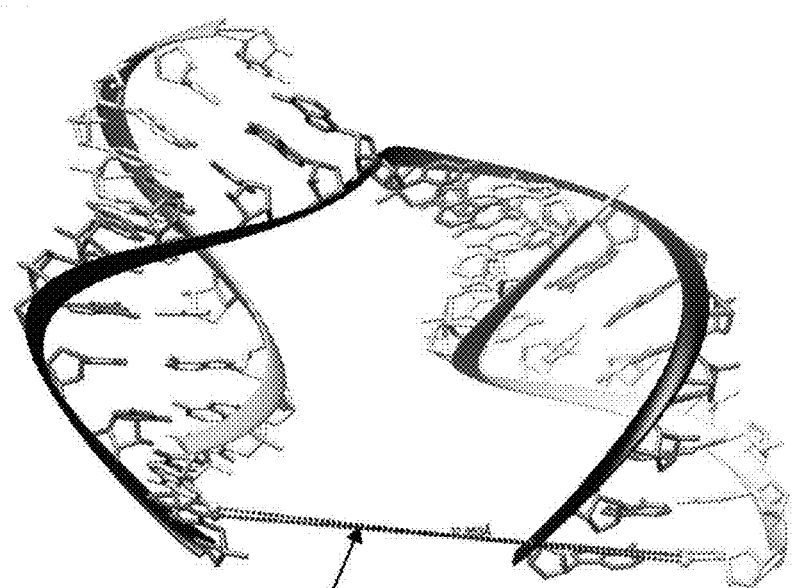
FIGS. 2A-2B illustrate a three-dimensional model of an exemplary 22 base-pair targeting domain that is bent in the middle into two 11 base-pair segments.
Figure 2B:
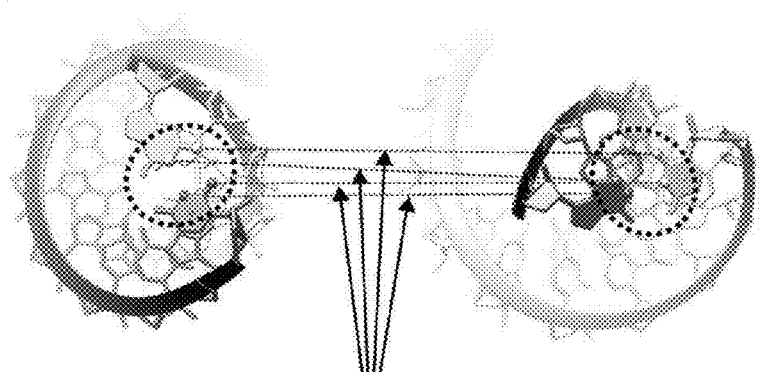

In comparison FIGS. 2A and 2B illustrate the measurement of the end to end distance for a model 22 base-pair targeting domain that is bent in the middle into two 11 base-pair segments. The measurement is performed using the molecular modeling program UCSF Chimera (Pettersen, E. F., Goddard, T. D., Huang, C. C., Couch, G. S., Greenblatt, D. M., Meng, E. C., and Ferrin, T. E. "UCSF Chimera—A Visualization System for Exploratory Research and Analysis." *J. Comput. Chem.* 25:1605-1612 (2004)). Once again, the distances between several pairs of atoms are measured to estimate a true center to center distance, as shown in FIG. 2A. FIG. 2B shows a bottom up view of both base-pairs used for the measurement. Several atoms around the center of each base-pair are used in different distance measurements to give an estimate of the center to center distance. In this case, the measured distances are between 3.15 nm and 3.30 nm.

In some embodiments, complexes herein described are signal activatable complexes that comprise a sensor domain duplex polynucleotide and targeting domain duplex RNA configured for providing different conformations upon binding of a signal molecule. The wording "signal molecule" as used herein indicates a molecule capable of binding a segment of a signal activatable construct herein described in a configuration triggering a switch between an inactive conformation and an active conformation of the signal activated molecular construct upon said binding.

In some embodiments herein described, the signal molecule is a signal polynucleotide. The term "signal polynucleotide" as used herein indicates a polynucleotide that is capable of acting as a signal molecule for the signal activated constructs and related components herein described. Accordingly, a signal polynucleotide herein described is capable of triggering a switch between an inactive conformation and an active conformation of the signal activated molecular construct upon binding to a segment of the signal activated construct.

The term "segment" as used herein indicates a portion of a polynucleotide or construct having chemical and/or biological properties that are functional to the chemical and/or biological properties of the entire polynucleotide or construct as a whole. The term "segment" as used herein in connection with a signal activated construct indicates a portion of a signal activated construct having chemical and/or biological properties that are functional to changes in conformation of the signal activated construct or components thereof, and/or to a related ability to perform the enzyme assisted release herein described.

In some embodiments, the sensor domain duplex polynucleotide comprises a first 5' terminal and a second 3' terminal protection segment, each of the first and second segments comprising a 5' end and a 3' end. The sensor domain duplex polynucleotide further comprises a sensor strand having a 5' end and a 3' end and comprising a displacement segment and a toehold segment presented for binding to a signal molecule.

In embodiments herein described the sensor domain duplex polynucleotide has a length which is the distance defined by the number of nucleotides of the sensor strand involved in the base pairs forming the sensor domain duplex polynucleotide. Calculation of the length of the sensor domain duplex polynucleotide can be performed with similar techniques indicated with reference to the targeting domain duplex RNA as will be understood by a skilled person. Also a distance between centers of the 5'-3' terminal base pairs at the opposite ends of the sensor domain duplex polynucleotide can be determined with similar techniques indicated with reference to the targeting domain as will be understood by a skilled person.

In a sensor domain duplex polynucleotide the protection segments, displacement segment and toehold segment comprise at least one polynucleotide portion and are configured so that: i) the toehold segment is presented for binding to a signal molecule; ii) the 5' end of the first 5' terminal protection segment is covalently attached to the 3' end of the passenger strand of the targeting duplex in, and the 3' end of second 3' terminal protection segment is covalently attached to the 5' end of the passenger strand of the targeting duplex RNA; and iii) the first 5' terminal and second 3' terminal protection segments are complementary to the displacement segment, with a gap between the 3' end of the first 5' terminal protection segment and the 5' end of the second 3' terminal protection segment. In some embodiments each protection segment in the sensor duplex polynucleotide has a minimum length of 4 consecutive base pairs with a gap between the 3' end of the first 5' terminal protection segment and the 5' end of the second 3' terminal protection segment.

The term "gap" as used herein indicates a separation in space between two molecules, or a break in continuity between two molecules. As used herein, a gap between the 3' end of the first 5' terminal protection segment and the 5' end of the second 3' terminal protection segment indicates a separation between the indicated ends of the two polynucleotide segments, or an intervening space between the segment. In some embodiments herein described, a gap between the 3' end of the first 5' terminal protection segment and the 5' end of the second 3' terminal protection segment indicates a lack of covalent attachment, complementary binding, or other direct attachment between the 3' end of the first 5' terminal protection segment and the 5' end of the second 3' terminal protection segment. In some embodiments the gap can be absent and the 3' terminus of 5' terminal protection segment can be covalently linked to the 5' terminus of the 3' terminal protection segment.

The term "covalent binding" or "covalently linked" as used herein indicates connection between two segments through formation of a chemical bonding that is characterized by sharing of pairs of electrons between atoms, known as the covalent bond. Examples of covalent binding can include, but are not limited to, covalent bonds formed between any two of the following: RNA or portions RNA, DNA or portions of DNA, any nucleotide or derivative thereof, and/or enzyme.

In embodiments herein described attachment of the first 5' terminal protection segment to the 3' end of the passenger strand of the targeting duplex is performed through a 5' linker segment having a relaxed average length up to approximately 12 nm and attachment of the second 3' terminal protection segment to the 5' end of the passenger strand of the targeting duplex is performed through a 3' linker segment having a relaxed average length up to approximately 12 nm.

Measurement of the relaxed end to end average length of a polymer can be performed with methods identifiable by a skilled person. In particular the end to end distance of a polymer in solvent can be estimated by well known models for the statistical behavior of polymers in solvent.

For example, more rigid polymers such as single stranded RNA or certain poly peptides are sometimes described using the Worm Like Chain model (see webpage en.wikipedia.org/wiki/Worm-like_chain). This model envisions the polymer as an isotropic rod that is continuously flexible. The square of the relaxed end to end distance of polymers in this regime is:

$$\langle R^2 \rangle = 2Pl\left[1 - \frac{P}{l}\left(1 - e^{-\frac{l}{P}}\right)\right]$$

where R is the mean end to end distance, P is the persistence length, and l is the fully extended length of the polymer.

In other examples more flexible polymers such as poly ethylene glycol are typically described by the Freely Jointed Chain model (Boyd, R. H. & Phillips, P. j. *The Science of Polymer Molecules*. (Cambridge University Press, 1993). In this case the end to end distance scales as $\sim N^{(3/5)}$ where N is the number of freely jointed segments. $N\sim1/(2\ P)$ where l is the overall maximum length of the polymer and P is the persistence length.

The persistence length of many polymers such as single stranded RNA (see e.g. Chen, H., et al in. *Proceedings of the National Academy of Sciences* 109, 799-804, (2012),), DNA (see e.g Tinland, B., et al in. *Macromolecules* 30, 5763-5765, (1997 and polyethylene glycol (see e.g. Kienberger, F et al in *Single Molecules* 1, 123-128, (2000)) are known to those skilled in the art. To experimentally measure the average end to end distance of the polymer linkers for the signal activated construct, donor and acceptor fluorophore pairs can be attached covalently to the two ends of the linker attachment points. A steady state FRET efficiency and the fluorescence lifetimes can be measured under normal experimental conditions (e.g., 1× PBS buffer, room temperature, pH ~7.0). This data can then be used to directly extrapolate the average end to end distance of the linker. FRET works well for distances in solution in the range of 2 nm to 8 nm Lilley, D. M. J. & Wilson, T. J. Fluorescence resonance energy transfer as a structural tool for nucleic acids. *Current Opinion in Chemical Biology* 4, 507-517, (2000). For shorter distances, the average end to end distance of the polymer can be estimated by molecular dynamics simulations (Rapaport, D. C. *The art of molecular dynamics simulation*. (Cambridge university press, 2004)).

In several embodiments of the signal activatable constructs herein described, in absence of a signal polynucleotide, the first and second protection segments and the at least one displacement segment form a sensor duplex through complementarily binding, and the toehold segment is presented for binding of a complementary signal polynucleotide. In the presence of the signal polynucleotide, the toehold and displacement segments are complementarily bound to the signal polynucleotide.

The term "complementary" as used herein indicates a property of single stranded polynucleotides in which the sequence of the constituent monomers on one strand chemically matches the sequence on another other strand to form a double stranded polynucleotide. Chemical matching indicates that the base pairs between the monomers of the single strand can be non-covalently connected via two or three hydrogen bonds with corresponding monomers in the another strand. In particular, in this application, when two polynucleotide strands, sequences or segments are noted to be complementary, this indicates that they have a sufficient number of complementary bases to form a thermodynamically stable double-stranded duplex. Double stranded of complementary single stranded polynucleotides include dsDNA, dsRNA, DNA: RNA duplexes as well as intramolecular base paring duplexes formed by complementary sequences of a single polynucleotide strand (e.g., hairpin loop).

The terms "complementary bind", "base pair", and "complementary base pair" as used herein with respect to nucleic acids indicates the two nucleotides on opposite polynucleotide strands or sequences that are connected via hydrogen bonds. For example, in the canonical Watson-Crick DNA base pairing, adenine (A) forms a base pair with thymine (T) and guanine (G) forms a base pair with cytosine (C). In RNA base paring, adenine (A) forms a base pair with uracil (U) and guanine (G) forms a base pair with cytosine (C). Accordingly, the term "base pairing" as used herein indicates formation of hydrogen bonds between base pairs on opposite complementary polynucleotide strands or sequences following the Watson-Crick base pairing rule as will be applied by a skilled person to provide duplex polynucleotides. Accordingly, when two polynucleotide strands, sequences or segments are noted to be binding to each other through complementarily binding or complementarily bind to each other, this indicate that a sufficient number of bases pairs forms between the two strands, sequences or segments to form a thermodynamically stable double-stranded duplex, although the duplex can contain mismatches, bulges and/or wobble base pairs as will be understood by a skilled person.

The term "attach" or "attached" as used herein, refers to connecting or uniting by a bond, link, force, or tie in order to keep two or more components together, which encompasses either direct or indirect attachment. For example, "direct attachment" refers to a first molecule directly bound to a second molecule or material, while "indirect attachment" in refers to one or more intermediate molecules being disposed between the first molecule and the second molecule or material.

In an inactive conformation signal activatable constructs herein described the targeting domain is covalently attached to the sensor domain duplex polynucleotide in a configuration minimizing processing by Dicer and/or Argonaute enzyme.

In some embodiments, the inactive conformation of the signal-activated molecular complexes herein disclosed is converted into the active conformation following binding of signal molecule to the toehold segment and the displacement segment to displace the first and second protection segments, which in the active conformation are presented as overhangs of the 3' and 5' ends of the passenger strand, respectively.

The term "overhang" as described herein, refers to a stretch of unpaired nucleotides at one of the ends of a double stranded polynucleotide. In particular, in an overhang the unpaired nucleotides can be on either strand of the polynucleotide, and can be included at either the 3' end of the strand (3' overhangs) or at the 5' end of the strand (5' overhangs).

In several embodiments, the inactivated conformation of the sensor domain is more thermodynamically stable than the conformation of the targeting duplex. In some embodiments, the meting temperature of double-stranded duplex portion formed by the first 5' terminal protection segment and the displacement segment is at least about 37° C. and the meting temperature of the double-stranded duplex portion formed by the second 3' terminal protection segment and the displacement segment is also at least about 37° C., so that the entire double-stranded duplex formed by the first and second protection segments and the displacement segment has a predicted melting temperature of approximately 50° C. or greater to maximize the constructs that in the absence of the signal polynucleotide adopt the inactive conformation, with the first and second protection segments complementarily binding to the displacement segment. The strand melting temperature (Tm) of the double-stranded duplex formed by the first and second protection segments and the displacement segment can be experimentally tested or measured.

The term "thermodynamic stability" as used herein indicates a lowest energy state of a chemical system. Thermodynamic stability can be used in connection with description of two chemical entities (e.g., two molecules or portions thereof) to compare the relative energies of the chemical entities. For example, when a chemical entity is a polynucleotide, thermodynamic stability can be used in absolute terms to indicate a conformation that is at a lowest energy state, or in relative terms to describe conformations of the polynucleotide or portions thereof to identify the prevailing conformation as a result of the prevailing conformation being in a lower energy state. Thermodynamic stability can be detected using methods and techniques identifiable by a skilled person. For example, for polynucleotides thermodynamic stability can be determined based on measurement of melting temperature $T_m$, among other methods, wherein a higher $T_m$ can be associated with a more thermodynamically stable chemical entity as will be understood by a skilled person. Contributors to thermodynamic stability can include, but are not limited to, chemical compositions, base compositions, neighboring chemical compositions, and geometry of the chemical entity.

The configurations of the first 5' terminal and second 3' terminal protection segments, the toehold segment, and the displacement segment in an inactive conformation suitable to transform to an activated conformation in presence of signal polynucleotide are such that the binding of the signal polynucleotide to the toehold segment has a melting temperature (Tm) of at least about 15° C.

In some embodiments, the preferred melting temperature is approximately 37° C. In some embodiments, the minimum length of the toehold segment is two polynucleotides. In some of those embodiments, sequence length and composition of the toehold segment and displacement segment is such that binding of the signal polynucleotide to the toehold segment and displacement segment is at least as stable as the binding between the first and second protection segments and the displacement segment to minimize partial displacement of the protection segments from the displacement segment upon binding of the signal polynucleotide. For example, in some embodiments the toehold segment and the signal polynucleotide can have at least 3 consecutive base pairs to initiate binding to the signal polynucleotide and the strand displacement process, and the toehold typically comprises at least 4 consecutive base pairs to allow functioning at the human body temperature of 37° C.

Additionally, in some embodiments, sequences of the displacement segment and the first 5' terminal and second 3' terminal protection segments can be configured with respect to the complementarity of the displacement segment and signal polynucleotide so that up to every base-pair exchange is at least equal-energy, to minimize incomplete displacement process. For example, according to some embodiments, if at certain position of the sensor duplex, the displacement segment and the first or second protection segments have a GC base-pair, then the signal polynucleotide can also have a GC base pair with the displacement segment at the corresponding position; if the displacement segment and the first or second protection segments have a 2'-O-methyl G base pairs with a C at certain position, also the signal polynucleotide can base pair to the displacement segment with a 2'-O-methyl G base pairs with a C.

In some embodiments, the complementary binding between the displacement segment with the signal polynucleotide can be at least as stable, and possible more stable, than the complementarily binding between the displacement segment and the first and second protection segment. Accordingly, mismatches between the displacement segment and the protection segment at certain position, can correspond to mismatches between the signal polynucleotide and the displacement segment. In some embodiments stabilizing modifications such as 2'-O-methyls can be localized in the displacement segment, since that displacement segment of the construct base pairs with both the signal polynucleotide and the first and second protection segments. In determining the configuration, length, and sequence, the delivery conditions can also be considered (e.g., temperature and salts concentrations).

Figures 3A, 3B:
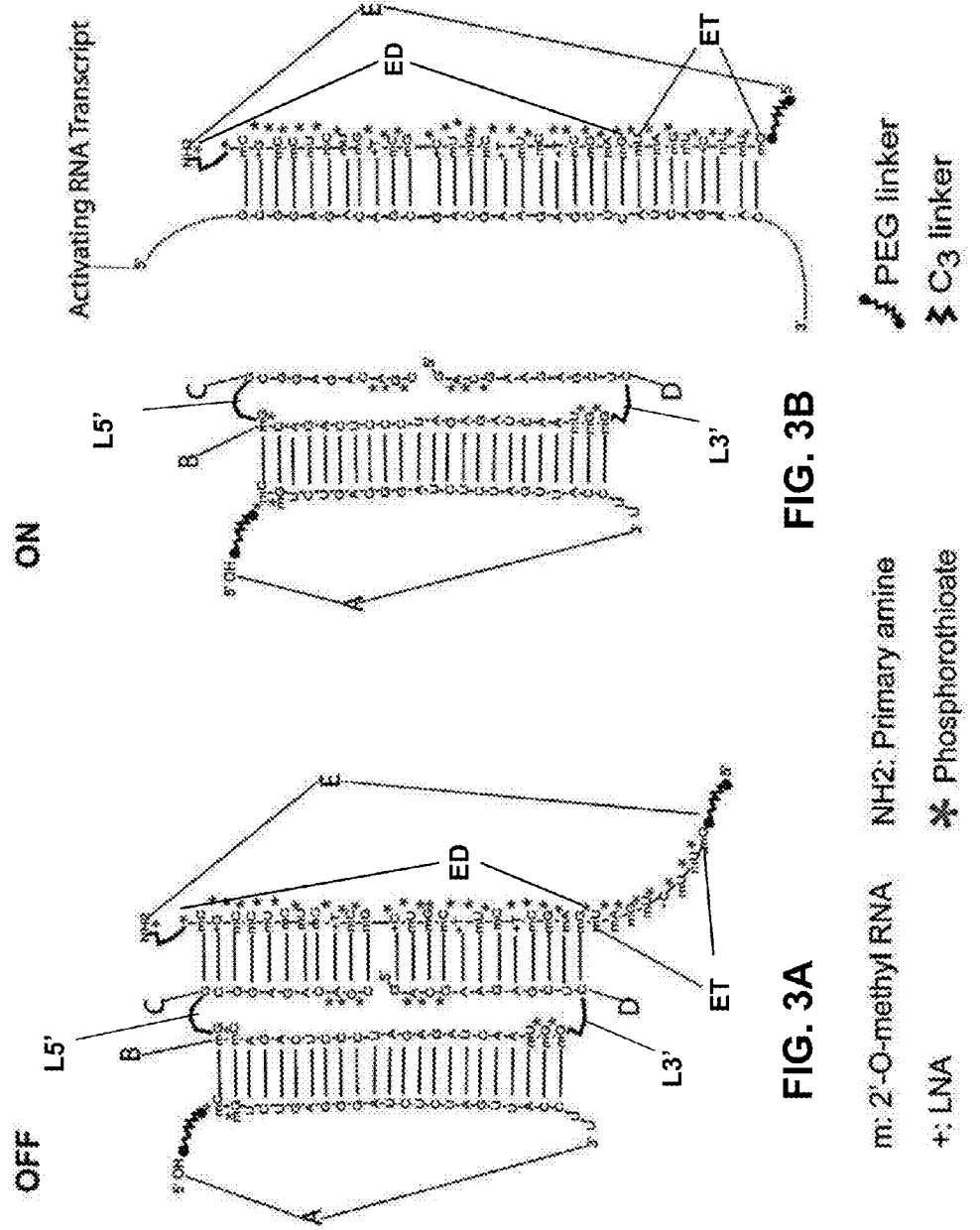
FIGS. 3A-B show a schematic illustration of signal-activated molecular constructs according to embodiments herein described showing the OFF inactive conformation (FIG. 3A) and the ON active conformation (FIG. 3B). The exemplary construct illustrated in FIGS. 3A and 3B (AB-CDE) comprises a guide strand A (SEQ ID NO. 1), a passenger strand B (SEQ ID NO. 3) which further comprises a first, 5' protection segment C (SEQ ID NO: 4) and a second, 3' protection segment D (SEQ ID NO: 2) connected to the passenger strand B (SEQ ID NO: 3) by C3 linkers L5' and L3' (indicated by black lines), and a sensor strand E (SEQ ID NO. 5) that comprises the displacement segment ED (SEQ ID NO: 7) and a 5' toehold segment ET (SEQ ID NO: 6). The 5' ends of the guide strand and the toehold further comprise PEG linkers, indicated by black lines with black circles on the ends.

Reference is made to the schematic illustration of FIGS. 3A-B, which show exemplary signal activatable constructs according to an embodiment herein described, in a depiction schematically illustrating the inactive conformation of the exemplary signal activatable constructs in FIG. 3A, and the active conformation of the exemplary signal activatable constructs in FIG. 3B.

In the illustration of FIGS. 3A-B, the exemplary molecular complexes AB-CDE and G6L1M1 in inactive form comprise a targeting domain and a sensor domain. The targeting domain of construct AB-CDE shown in FIGS. 3A-3B comprises a guide strand (A) and a passenger strand (B), each comprising a 5' end and a 3' end, with the guide strand (A) complementary and complementarily binding to passenger strand (B) to form an RNA duplex targeting domain. The passenger strand of the targeting domain RNA duplex is covalently attached to a first 5' terminal and second 3' terminal RNA protection segments C and D, each having a 5' end and a 3' end, with a gap between the 3' end of the first 5' terminal protection segment C and the 5' end of the second 3' terminal protection segment D. In particular, the 5' end of the passenger strand B is covalently linked to the 3' end of the 3' terminal protection segment D, through the linker segment L3' and the 3' end of the passenger strand B is covalently linked to the 5' end of the 5' terminal protection segment C through the linker segment L5'. In the illustrations of FIGS. 3A-B, the protection segment C and D and the linker segments L5' and L3' form a protection strand and in particular the protection segment C the linker segments L5' form a first 5' terminal protection strand the protection D and the linker segments L3' form a second 3' terminal protection strand. In the illustrations of FIGS. 3A-B, the protection segments C and D are not directly attached to each other and a gap is defined between the 3' terminus of D and the 5' terminus of C. In particular, the 5' end of protection segment D is not attached to the 3' end of protection segment C. In other embodiments herein described the gap can be removed and the 3' terminus of the 5' terminal protection segment is covalently linked to the 5' terminus of the 3' terminal protection segment (see FIGS. 22A and 22B).

The sensor domain of construct AB-CDE shown in FIGS. 3A-3B comprises a sensor strand (E) that comprises a displacement segment (ED) and a toehold segment (ET). In the illustration of FIGS. 3A-3B the displacement segment (ED) of sensor strand E is complementary to the protection segments C and D, and the toehold segment (ET) is complementary to the signal molecule. In the inactive conformation of the exemplary molecular complex illustrated in FIG. 3A, the displacement segment is complementarily bound to the protection segments C and D to form a polynucleotide duplex, a with a gap between the 3' end of first the protection segment C and the 5' end of the second protection segment D, and the toehold is presented for binding to a signal molecule. In the illustration of FIGS. 3A-3B the gap is positioned approximately in the middle of the sensor domain and is a 1 bp gap. In other embodiments the gap can be more than 1 bp and/or can be positioned at different distances from the opposite ends of the sensor domain according to thermodynamically stable configurations which are identifiable by a skilled person upon reading of the present disclosure.

In the active conformation illustrated in FIG. 3B, the sensor strand is complementarily bound to the signal strand (in the illustrated case, an activating RNA transcript) to form and is detached from the targeting domain. The protection segments remain covalently attached to the 5' and 3' ends of the passenger strand through their respective linker segment L5' and L3' as shown, and form single-stranded overhangs on said 5' and 3' ends. In particular the first 5' terminal protection strand forms an overhang at the 3' end of the passenger strand and the second 3' terminal protection strand forms an n overhang at the 3' end of the passenger strand as shown in FIG. 3B.

In particular the exemplary illustrations of FIGS. 3A-B, the guide strand A is the guide strand of an RNAi trigger, which in the illustration of FIGS. 3A-B is a siRNA, but can be other RNAai triggers such as a Dicer substrate siRNA, a miRNA, or another Dicer substrates as will be understood by a skilled person.

The configuration of the guide strand passenger strand, protection segment displacement segment and toehold segments in activatable constructs herein described is also affected by the angle of helical twist in RNA helices which varies in different construct in view of various factors as will be understood by a skilled person.

Figure 4:
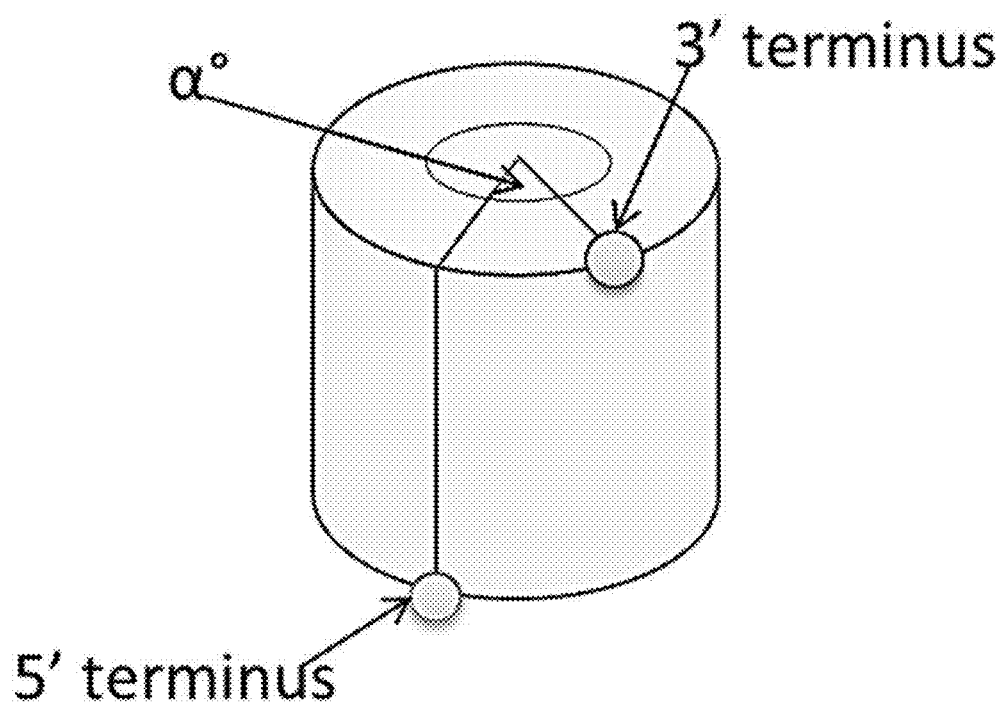
FIG. 4 shows a diagram schematically illustrating the angle between termini on RNA helices in RNA duplexes, which have helical twists of ~11 base pairs per 360 degrees.

FIG. 4 shows a diagram illustrating the angle between termini on RNA helices in exemplary RNA duplexes according to some embodiments of the present disclosure. RNA:RNA duplexes have helical twists of approximately 11 base pairs per 360° wherein approximately with reference to angles indicates a variation of ±2°. According to some embodiments herein described, the angle, α, between termini on the RNA helices of an exemplary targeting domain RNA duplex is determined by factors such as duplex length, and is not greater than 100°. Preferably, the angle is close to zero, which occurs when the duplex is approximately 22 base pairs long. Dimensions shorter or longer than 22 base pairs result in an angular difference of ~32.7° per base pair, which leads to strain. Maximum strain occurs at a duplex length of ~16 base pairs and ~28 base pairs—this leads to a ~180° between the two ends of the passenger strand. To minimize strain and maintain an α of not greater than 100°, the RNA targeting duplex is preferably a 19 to 25 base pairs in length.

The exemplary sensor domain illustrated in FIG. 3A is an RNA:RNA duplex that is 23 base pairs in length. In other embodiments, the sensor domain can be an RNA:RNA duplex, an RNA:DNA duplex, or a DNA:DNA duplex, with varying inclusions of chemical modifications such as LNA bases, and can range from 14 or 16 to 30 base pairs in length. In some embodiments, the sensor duplex can be 19 to 25 base pairs in length; preferably, the sensor duplex can be 21 to 23 base pairs in length. In the exemplary sensor domain of FIG. 3A, protection segment D is 12 base pairs in length, and protection segment C is 11 base pairs in length; in other embodiments, protection segments D and C can each be 8 base pairs in length or longer.

In the exemplary embodiment shown in FIG. 3A, the portion of the sensor duplex formed by complementary binding of protection segment D and the complementary portion of the displacement segment, and the portion of the sensor duplex formed by complementary binding of protection segment C and the complementary portion of the displacement segment displacement, are bound with 100% complementarity and contain no mismatches or bulges. In other embodiments, each of the two portions of the sensor duplex can comprise up to three mismatches, as long as the melting temperature Tm of each portion of the duplex is 37° C. or greater. Advantageously, the melting temperature Tm of each portion of the sensor duplex is 50° C. or greater. In a preferred embodiment, the angle between the ends of protection segments C and D that connect the protection segments to the passenger strand of the targeting duplex, β, is 40° or less. However, in alternate embodiments, the angle is 100° or less.

Figure 5A:
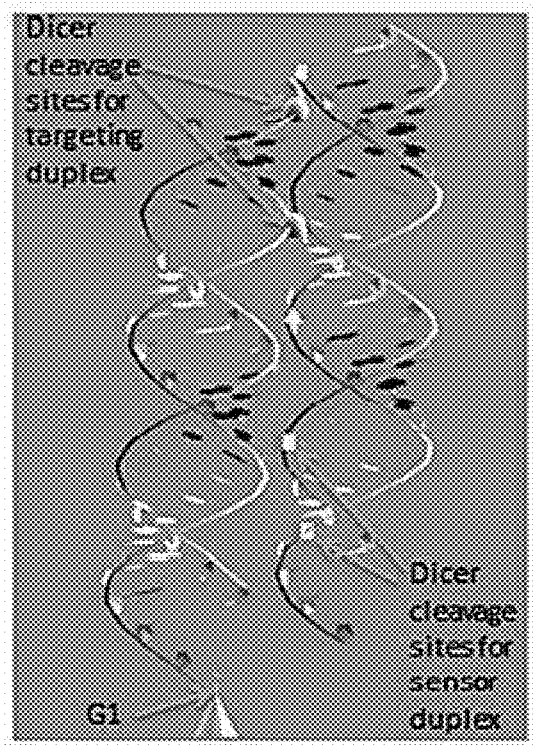
FIGS. 5A-B show a three-dimensional model of a targeting duplex and a sensor duplex of an exemplary signal-activated molecular construct comprising a tile saRNA.
Figure 5B:
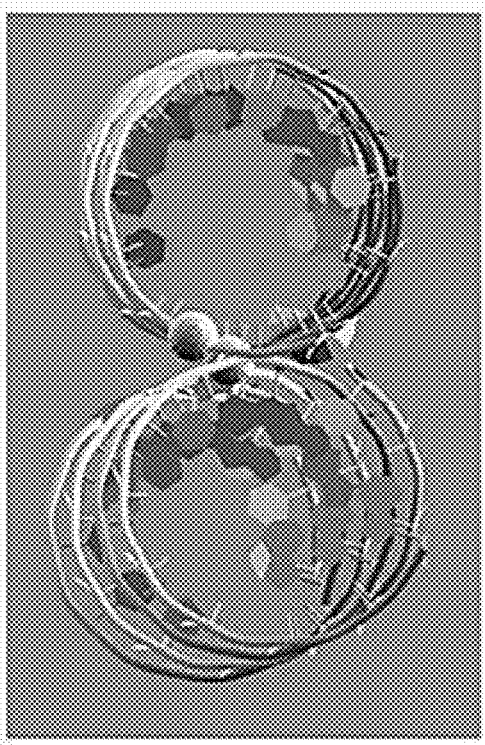

As illustrated in FIGS. 3A-B, in the exemplary molecular complexes according to some embodiments of the present disclosure, in an inactive conformation the targeting and sensor domains are positioned adjacently to each other and are substantially straight In accordance with the illustration of FIGS. 3A-B the length of the linker segments L5' and L3' is approximately 0.5 Additional positioning of the targeting domain and sensor domain one with respect to the other are expected to result in functional activatable constructs as long as the length of the linker L5' and L3' is up to 12 nm preferably less than approximately 5 nm preferably between approximately 0.3 nm and 2 nm. In some embodiments herein described in the inactive conformation the relative position of the targeting duplex and the sensor duplex is such that the Dicer cleavage sites of the targeting duplex and the sensor duplex are oriented towards the interior of the two duplexes. In embodiments herein described, this positioning hinders the binding of Dicer to the targeting duplex and processing of the targeting duplex by Dicer to produce an activated targeting duplex by preventing Dicer from accessing canonical binding sites of Dicer's RNA binding domain and Dicer's RNAse cleavage domain. The ability of Dicer to bind and process the targeting domain is further hindered by the presence of displacement segment D attached to the 5' of the passenger strand B, which prevents binding of the PAZ domain of Dicer to the 5' terminal phosphate of the passenger strand, and by the complementary binding of the protection segments C and D to the displacement segment of strand E, which further hinders Dicer's ability to bind and cleave the targeting domain. An exemplary illustration of such positioning is provided in FIGS. 5A-B, where the targeting domain and the sensor domain are shown in a substantially parallel configuration one with respect to the other.

Additional configurations are encompassed by the present disclosure some of which are illustrated in the exemplary embodiments of FIGS. 3A to 5B.

Figures 6A, 6B, 6C:
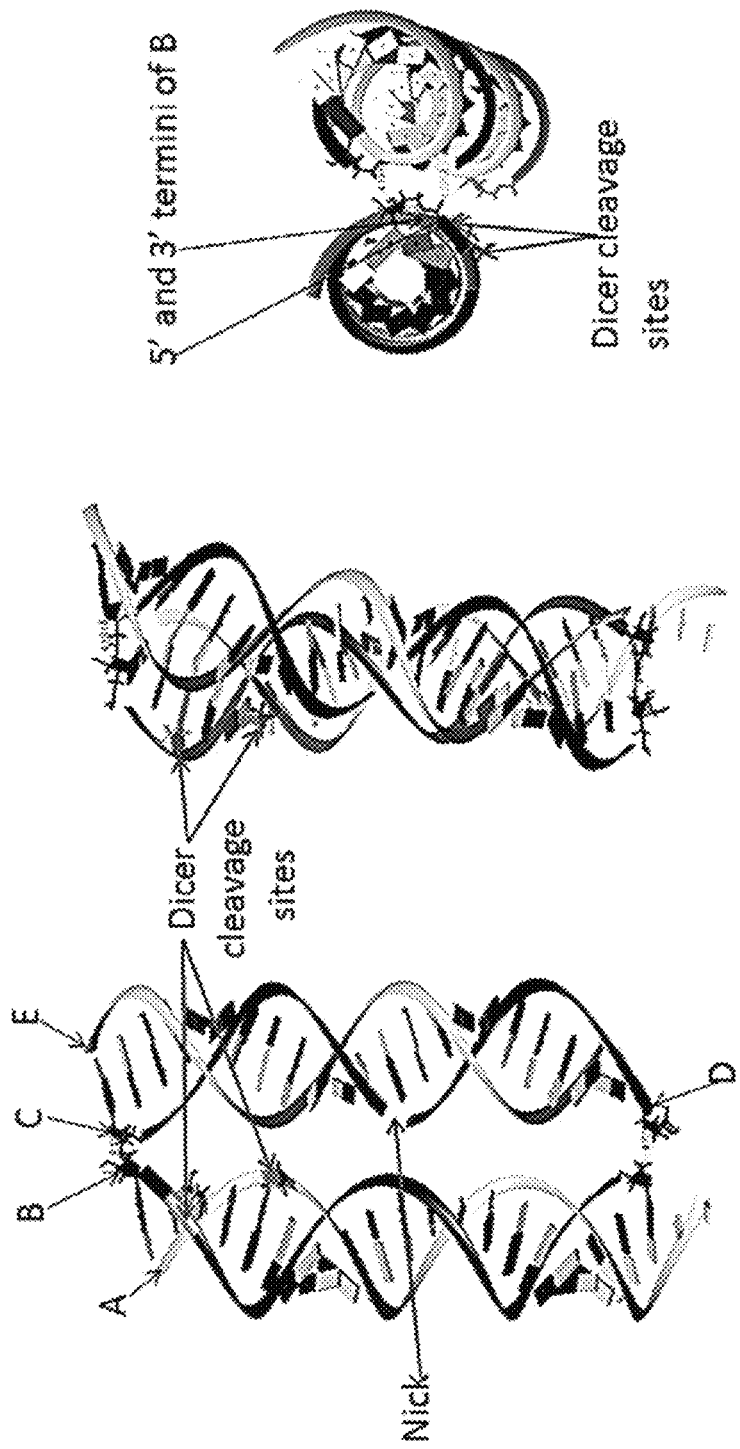
FIGS. 6A-C show a three-dimensional model of a 23 base pair targeting duplex and a 23 base pair sensor duplex of an exemplary signal-activated molecular construct comprising a tile saRNA as shown in FIGS. 3A and 3B.

FIGS. 6A, 6B and 6C provide a three dimensional illustration of an exemplary tile saRNA with 23 bp targeting duplex and 23 bp sensor duplex. As shown in the illustration of FIGS. 6A, 6B and 6C, the duplex lengths lead to a very small distance of ~0.5 nm between the two duplexes at the B-C and B-D termini, allowing a small linker such as a C3. In the illustration of FIGS. 6A, 6B and 6C, the Dicer cleavage sites of both duplexes are oriented towards the center of the two duplexes, thereby making those cleavage sites more protected from Dicer processing. In the preferred design shown in FIGS. 6A, 6B and 6C, the nick between the D-E and C-E duplexes is also oriented towards the center, making the structure geometrically more rigid and protecting the C and D overhangs from processing in an inactive conformation in absence of the signal molecule.

Figures 7A, 7B, 7C:
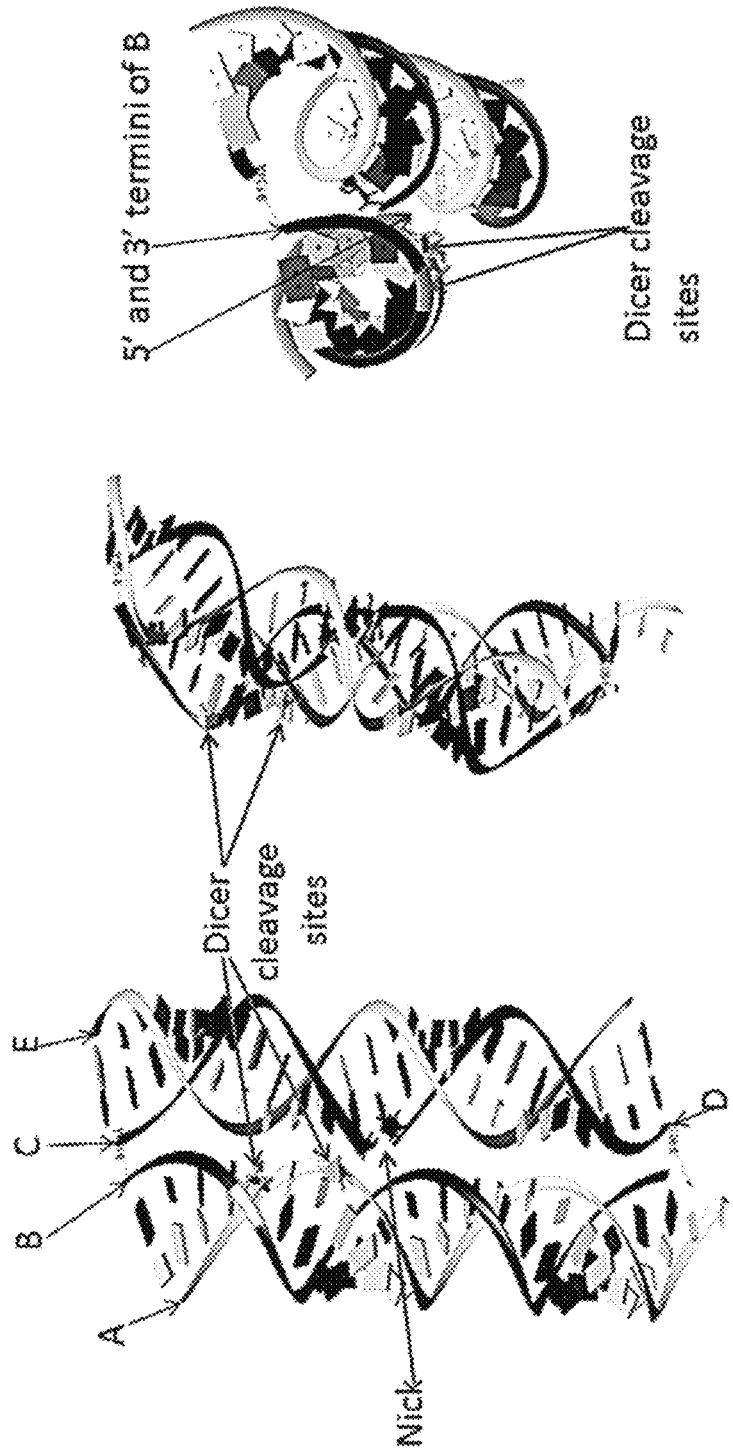
FIGS. 7A-C illustrate a three-dimensional model of an exemplary signal-activated tile saRNA comprising a targeting and sensor duplexes as in FIGS. 6A-C, wherein the targeting and sensor duplexes are each 25 base pairs long.

FIGS. 7A, 7B and 7C provide a three dimensional illustration of the structure of an exemplary tile saRNA with 25 bp targeting domain and a 25 bp sensor domain. In this structure the gap distance between B-C and B-D is near 1 nm and can be bridged by a longer linker, such as a tri- or hex-ethylene glycol.

FIGS. 8A, 8B and 8C illustrate the three dimensional structure of an exemplary tile saRNA composed of a 27 bp targeting domain and a 27 bp RNA sensor domain. In this embodiment, the 5' and the 3' of strand B are arrayed on the opposing sides of the targeting duplex (see top view of FIG. 8C), as the termini of the corresponding D and C domains. The configuration of the targeting domain and sensor domain illustrated in FIGS. 8A, 8B and 8C leads to a structure with ~2.3 nm of separation between the termini of the sensor and targeting duplexes. Thus, in this case, the linker is set usually to be approximately 2.5 nm long or longer. An exemplary linker within this length range can be provided by two segments of hex-ethylene glycol connected by a phosphate backbone group (commercially available spacer chemistry for incorporation into oligonucleotides, see, for example, IDT Inc. product page). In the configuration of the targeting domain and sensor domain illustrated in FIGS. 8A, 8B and 8C, the Dicer cleavage sites at distant from the center of the two duplexes and the nick is also on the side of the sensor duplex at a distance from the center of the targeting domain and sensor duplexes.

Additional length combinations of the targeting duplex RNA and sensor duplex polynucleotide can be identified by a skilled person upon reading of the present disclosure.

In the exemplary embodiments of FIGS. 3A-B the signal activatable constructs adopts thermodynamically stable inactive and active conformations depending on binding presence of a signal polynucleotide. In particular, the signal activatable construct adopts an inactive conformation in absence of the signal molecule (FIG. 3A), and switch to an active conformation upon binding of the signal molecule (FIG. 3B).

Figure 9:
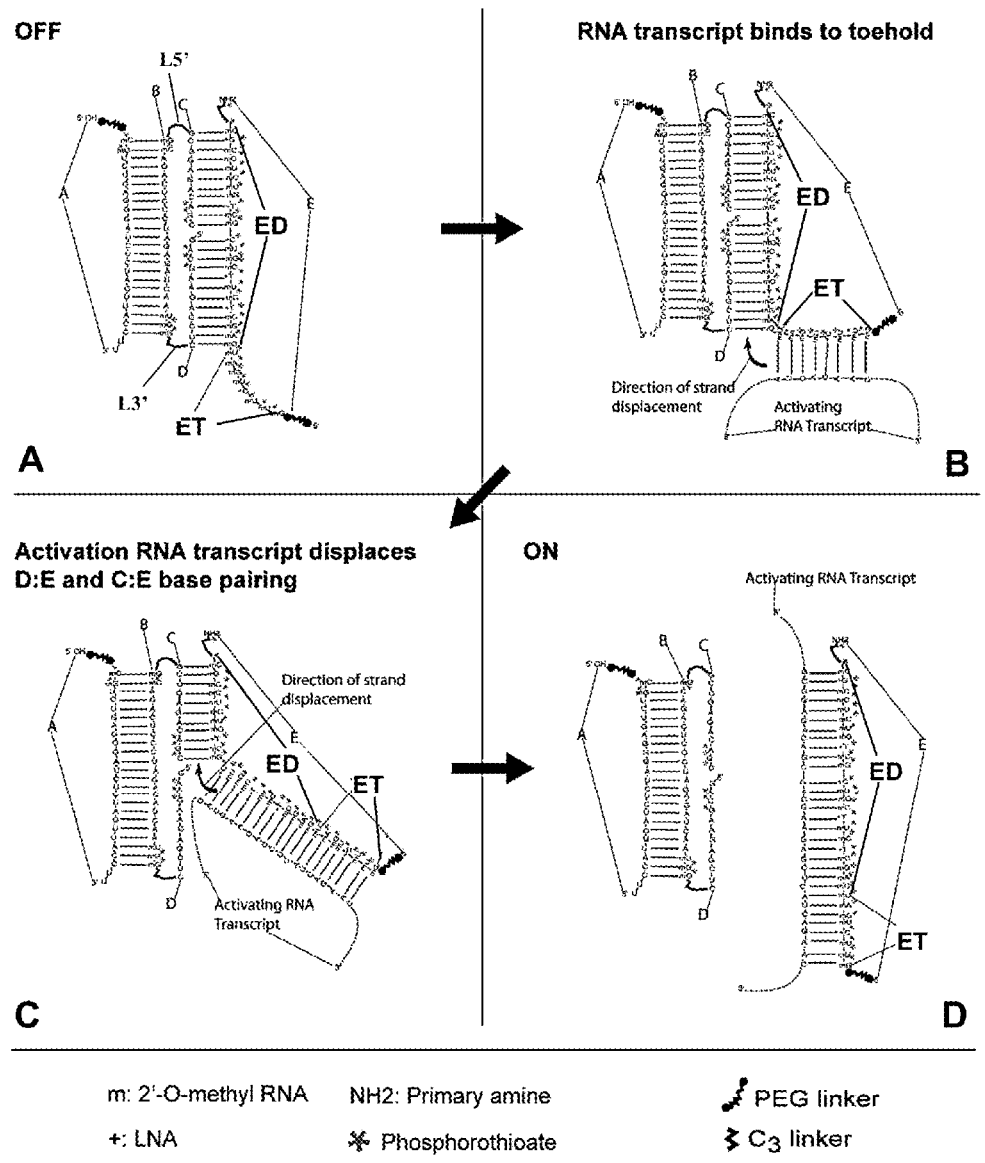
FIG. 9 (panels A-D) shows a schematic representation of an exemplary method to release a targeting domain from the exemplary molecular construct AB-CDE of FIGS. 3A and 3B having a guide strand A (SEQ ID NO. 1), a passenger strand B (SEQ ID NO. 3) attaching at the 5' terminus a first, 5' protection segment C (SEQ ID NO: 4) and attaching at the 3' terminus a second, 3' protection segment D (SEQ ID NO: 2) connected to the passenger strand B (SEQ ID NO: 3) by C3 linkers L5' and L3' (indicated by black lines), and a sensor strand E (SEQ ID NO. 5) (FIG. 9, panel A). Following binding of an activating RNA transcript to the toehold of the sensor strand E (FIG. 9, panel B), the activation RNA transcript displaces the base pairing between the 5' protection segment D and the 3' protection segment C and the sensor strand E (FIG. 9, panel C), leading to dissociation of the targeting duplex from the sensor duplex in an active state (FIG. 9, panel D).

FIG. 9 (panels A-D) illustrates the process of activation for an exemplary molecular complex AB-CDE of FIG. 3A according to embodiments herein described. In particular, FIG. 9 (panel A) illustrates construct AB-CDE in the inactive configuration, wherein the guide strand A is complementarily bound to the passenger strand B to form a targeting duplex, the displacement segment of sensor strand E is complementarily bound to the protection segments C and D to form a sensor duplex, and the toehold of sensor strand E is presented for binding to a signal molecule. As illustrated in FIG. 9 (panel B), the complementary binding of an activating RNA transcript signal molecule to the toehold on strand E initiates the strand displacement process further binding of the RNA transcript signal molecule to the sensor E from toehold segment ET into at least part of the displacement segment ED, displaces base pairing of ED:C and ED:D duplexes and release the protection segments C and D from the complementary binding to the displacement segment ED (FIG. 9, panel C). This process is commonly known as a strand displacement or branch migration reaction. Due to partial or complete displacement of the protection segment, the protection segments disassociate with the displacement segment. In particular To activate the construct, a signal molecule can displace all or part of the base pairs in the sensor strand E to the extent that the displacement is sufficient to alter the thermodynamic stability of the double strand resulting in a decouplement of the strand from the rest of the structure in the environment where the reaction is performed.

Following the strand displacement, the exemplary molecular complex of FIG. 9 (panels A-D) assumes an active configuration as illustrated in FIG. 9 (panel D), wherein the displacement segment and toehold segment of sensor strand E are complementarily bound to the signal strand to form a sensor strand-signal strand complex and are detached from the targeting duplex, the protection segments C and D are single-stranded overhangs of the passenger strand and are not complementarily bound to the displacement segment, and the targeting duplex is associable for processing by Dicer and/or Argonaut enzyme. As shown in the exemplary illustration of FIG. 9 (panel D), completion of the activation leaves E bound to the activation strand. E is completely decoupled from A, B, C and D. The targeting domain A:B with C and D overhangs of FIG. 9 (panel D) can efficiently induce RNAi targeting. In some cases in the construct of FIG. 9 (panels A-D), overhang D is first removed by cellular exonucleases before Dicer processes A:B. In the illustration of FIG. 9, panels A to D, the toehold is at the 5' terminus of the sensor strand E. In additional variations of FIG. 9, panels A to D, according to configuration herein described, a toehold can be placed on either the 5' or the 3' side of E, or both. In those variations, the signal molecule can be an activating RNA transcript of one strand or two strands displacing sensor strand E from both sides.

The term "displacement", "strand displacement reaction", or "branch migration reaction" as used herein generally indicates the process in which two polynucleotide strands with partially or full complementarity hybridize, displacing in the process one or more pre-hybridized strand or sequence. The strand displacement process can be experimentally tested or measured according to techniques that are identifiable by a skilled person.

Figure 10A:
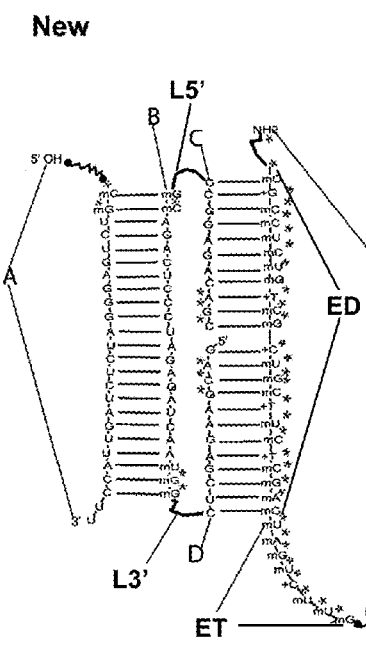
FIGS. 10A-B illustrate a schematic representation of an exemplary signal activated molecular construct ABCDE comprising A(SEQ ID NO: 1) B(SEQ ID NO: 3) -C(SEQ ID NO: 4) D(SEQ ID NO: X2) E(SEQ ID NO: 5) L5' and L3' of FIGS. 3A and 3B (FIG. 10A) compared to exemplary signal-activated molecular construct G3A8B12 of related application No. 61/613,617 (FIG. 10B) in which A indicates the guide strand (SEQ ID NO: 113) B1 (SEQ ID NO:114) and B2 (SEQ ID NO:118) indicate the two portion of a nicked passenger strand, D indicates an element comprising a toehold (SEQ ID NO: 116) and a displacement segment Ds (SEQ ID NO: 115) attached by a C3 linker.
Figure 10B:
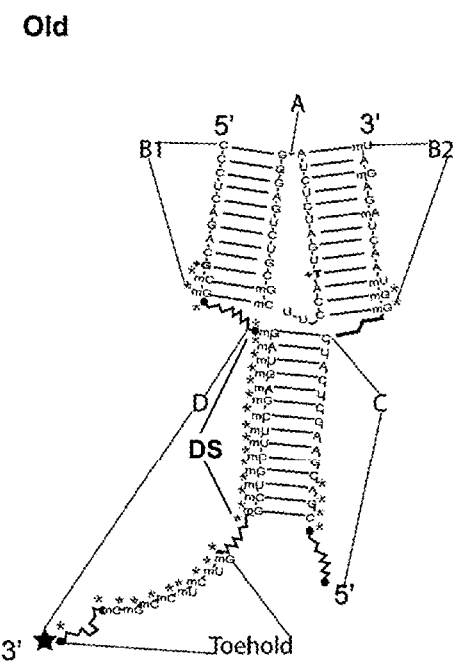

A comparison between the activatable constructs of the disclosure and other constructs also activated through displacement is provided in FIGS. 10A-B, where an exemplary signal activated molecular construct ABCDE of FIGS. 3A and 3B is reported in FIG. 10A side by side with the structure of construct G3A8B12 of related application No. 61/613,617 illustrated in FIG. 10B. Notable differences between the construct of FIG. 10A and the construct of FIG. 10B comprise the fact that in the construct of FIG. 10B the targeting domain (A:B1/B2) has in the inactive state a distance between the 5-3' base pair at opposite ends of the targeting domain approximately of 3 nm while in the construct of FIG. 10A the targeting domain a distance between the 5-3' base pair at opposite ends of the targeting domain approximately 5.75 nm in both an active and inactive state.

Additionally, in the construct of FIG. 10A, protection segments C and D are complementary to a third molecule E in the new construct, while in the construct of FIG. 10B segments C and B are complementary to each other. Furthermore in the construct of FIG. 10B, the toehold is covalently attached to the segment C or D which are covalently attached to the targeting domain, while in the construct of FIG. 10A the toehold is attached to sensory strand E which is detached from the targeting domain. In the construct of FIG. 10B, one of the overhangs (C or D) of the targeting domain binds the activating RNA while in the construct of FIG. 10A, strand E binds the activating RNA or other activating signal molecule. In the construct of FIG. 10B, the overhangs (C or D) of the targeting domain binding the activating RNA has typically extensive chemical modifications, in the construct of FIG. 10A, sensory strand E has typically one or more modifications of the strand.

A further difference between constructs of FIG. 10B and the activatable construct of the present disclosure such as the one of FIG. 10A is that in the tile structure of the construct of this disclosure is that the sensor strand is not covalently linked to the rest of the complex. Such configuration allows a sensor strand to completely dissociate from the targeting domain when the sensor is bound to an activating transcript. The dissociation of the targeting domain from the sensor-signal duplex leads to a substantial increase in RNAi activity.

Another difference is that the in the structure of activatable constructs of the disclosure such as the one of FIG. 10A the sensor and targeting domains are maintained adjacent to each other so that the overall length of the complex is not longer in any dimension than the sensor or targeting domain independently. In the construct of FIG. 10B, the sensor domain can stack linearly with a portion of the targeting domain, leading to a longer complex which is expected to possibly be more immunogenic.

Variations in the targeting domain, the sensor domain, and related molecular complexes shown in the illustration of FIGS. 3A-B are identifiable by a skilled person in view of the present disclosure. For example, the targeting domain RNA duplex can vary in length from 19 to 30 base pairs; the sensor duplex can vary from 12 to 30 bp possibly 14 to 30 or 16 to 30 base pairs in length, and can form an RNA:RNA, DNA:DNA, or DNA:RNA duplex; the toehold segment can vary in length.

In particular, the exemplary targeting domain illustrated in FIGS. 3A-3B is an RNA duplex that is 23 base pairs in length; the guide strand of the duplex comprises a 3' overhang of two base pairs. In some embodiments, the 3' end of the guide strand can be blunt, comprising no overhangs.

In some embodiments, mismatches and bulges in the RNA duplex are permitted as long as the melting temperature Tm of the duplex is predicted to be greater than the operating temperature (e.g., 37° C. in embodiments in which detection of formation of RNA duplex is desired through methods known to one skilled in the art such as Native PAGE followed by visualization or UV-vis spectroscopy). In embodiments herein described, duplex formation can be verified by Native PAGE or UV vis spectroscopy or additional techniques identifiable by a skilled person.

In some embodiments, the targeting domain duplex RNA can have a length from 26 to 27 bp or from 28 to 30 bp. In those embodiments, the assemblies are preferably purified to minimize interference of mis-assemblied complexes. For example, the assemblies can be run on an 8% Native PAGE gel, the band corresponding to the correct assembly can be cut from the gel. The extracted bands can be ground and the assemblies extracted using a DNA gel extraction kit (such as: qiaquick-gel-extraction-kit Qiagen) or an electrodialysis extraction system identifiable by a skilled person.

In some embodiments, the targeting domain duplex RNA can have a length from 28 to 30 bp. In those embodiments, the assemblies are also preferably purified to minimize interference of mis-assemblied complexes. Complexes herein described with a 28 to 30 bp targeting domain are also preferably tested for nonspecific toxicity and the concentrations are preferably optimized to minimize RNAi activity in the OFF inactive conformation and to minimize toxicity while maximizing the ON state RNAi. In some of those embodiments, the targeting domain is attached to a matching length sensor domain and the matching length sensor domain can include fewer modifications with respect to other constructs herein described to obtain thermodynamic stability as will be understood by a skilled person.

In preferred embodiments of the activatable constructs herein described, the targeting domain duplex RNA is from 23 to 25 bp. In those embodiments, the bases of the targeting domain are preferably RNA nucleotides with no modification and in particular the region between the $19^{th}$ and $21^{st}$ base pair of the targeting domain preferably includes no modification of the ribonucleotides. In those embodiments, the sensor domain can be a RNA:DNA, DNA:DNA or RNA:RNA duplex modified or unmodified in various positions as will be understood by a skilled person upon reading of the disclosure. In some of those embodiments the sensor domain and the targeting domain are preferably of a same length which can be predicted with molecular modeling which can also be used to select the length of appropriate linkers.

In embodiments with a targeting domain duplex RNA from 19- to 21 bp the 5' terminus of the guide strand and passenger strand are protected by base modifications described in the present disclosure to minimize occurrence of processing of the construct in an inactive conformation.

In embodiments where the targeting domain duplex RNA is 22 bp higher concentrations of construct are preferably used with respect to constructs having a 23 to 25 base pairing to maximize the ON state RNAi activity of the targeting domain, Even higher concentrations of construct with respect to constructs having 23 to 25 bp are also preferred for embodiments where the targeting domain duplex RNA is 19 to 22 bp.

In embodiments where the targeting domain duplex RNA is 19 to 22 bp the $19^{th}$ and $20^{th}$ base paired base on the guide strand and the $21^{st}$ and $22^{nd}$ bp on the passenger side and those two bases are preferably not be modified are in particular are not modified to include a phosphorothioate linkage. In those embodiments the 2n base-pair is preferably unmodified and in particular the $2^{nd}$ does not include a 2'-O-methyl or other nuclease resistant base. In those embodiments the 5' terminus is modified to minimize loading by non-Dicer processing in an inactive conformation.

In some embodiments, the guide strand, passenger strand, first and second protection segments, at least one displacement segment, toehold segment, and any other portion of the sensor strand of the signal activatable complexes are mainly or entirely composed of RNA and/or RNA derivatives.

The term "derivative" as used herein with reference to a first compound (e.g., RNA or ribonucleotide) indicates a second compound that is structurally related to the first compound and is derivable from the first compound by a modification that introduces a feature that is not present in the first compound while retaining functional properties of the first compound. Accordingly, a derivative of a molecule of RNA, usually differs from the original molecule by modification of the chemical formula that might or might not be associated with an additional function not present in the original molecule. A derivative molecule of RNA retains however one or more functional activities that are herein described in connection with complementary base paring with other nucleotides. Typically, ribonucleotides and deoxyribonucleotides can be modified at the 2', 5', or 3' positions or the phosphate backbone chemistry is replaced. Exemplary chemical modifications of a ribonucleotide according to the current disclosure include 2'-o-methyl RNA, 2'-Fluoro RNA, locked nucleic acid (LNA), peptide nucleic acid (PNA), morpholino, phosphorothioate oligonucleotides, and the like that are identifiable by a skilled person (see e.g. "Modified Nucleosides: in Biochemistry, Biotechnology and Medicine. Piet herdewijn (Editor), Wiley-VCH, 2008, herein incorporated by reference in its entirety). Also applicable are nucleosides which are not normally comprised in DNA and RNA polynucleotides, such as inosine. In some embodiments, a single oligonucleotide can be composed of more than one type of the above derivatives.

Figure 11A:
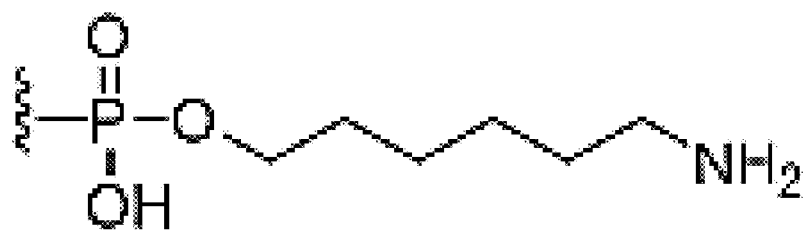
FIGS. 11A-B show the line drawing illustrations of structures of exemplary chemical groups comprised in the exemplary signal activated molecular constructs of the present disclosure.
Figure 11B:
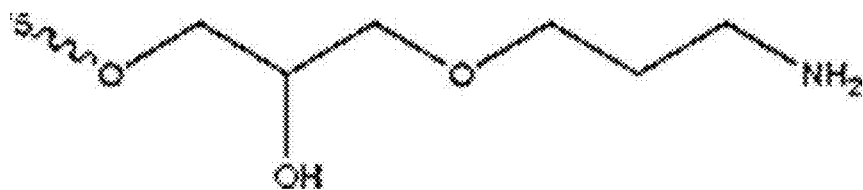

In several embodiments herein described, modified bases can be used throughout the complexes herein described to increase thermodynamic stability, and nuclease resistance, decrease toxicity, and/or increase specificity. FIGS. 11A-B show the line drawing illustrations of structures of exemplary chemical groups comprised in the exemplary signal activated molecular constructs of the present disclosure. FIG. 11A illustrates the chemical structure of the C6 amino chemical group modification from GE Dharmacon. FIG. 11B illustrates the chemical structure of the 3AmMO 3' amino chemical group modification from IDT and Exiqon Inc.

Additional suitable modifications comprise, for example, 2'-O-methyls, introduction of a non-nucleic acid linker and/or an unstructured RNA segment, and terminal modifications. In particular, 2'-O-methyls can be used in particular in displacement segment (ED) and toehold segment (ET) to increase thermodynamic stability and prevent unwinding by RNA binding proteins. In addition, non-nucleic acid linkers can be used confer desirable properties to the construct and/or portions thereof. Exemplary non nucleic acid linkers suitable to be used herein comprise C3 linkers and tri and hexa-ethylene glycol linkers as well as any biocompatible polymeric linker group with no-nonspecific association with DNA. In particular, molecular constructs herein described can comprise a non-nucleic acid polymer linker group with a lower persistence length than nucleic acids (e.g.: C3, polyethylene glycol (PEG)) to increase flexibility at the attachment point. Such a linker group can reduce interference of long overhangs against Dicer binding. Molecular constructs herein described can also comprise a non-nucleic acid linker group to interfere with degradation by exonucleases and endonucleases, including RNAi pathway enzymes. Molecular constructs herein described can further comprise an unstructured RNA segment to have non-canonical interactions with other RNA segments, leading to unpredictable tertiary conformations. Molecular constructs herein described can further comprise a terminal modification can prevent binding of the PAZ domain of Dicer, as well as other terminal modifications useful for preventing Dicer binding, such as Inverted dT Fluorescein and other groups incompatible with the PAZ domain such as cytidine biphosphate, propanediol, puromycin, and additional groups identifiable by a skilled person.

In some embodiments herein described, exemplary targeting domains herein described can comprise exonuclease resistant polynucleotides. The term "exonuclease" as used herein, indicates a type of enzyme that works by cleaving nucleotides one at a time from the end (exo) of a polynucleotide chain. A hydrolyzing reaction that breaks phosphodiester bonds at either the 3' or the 5' end occurs. A 3' and 5' exonuclease can degrade RNA and DNA in cells, and can degrade RNA and DNA in the interstitial space between cells and in plasma, with a high efficiency and a fast kinetic rate. A close relative is the endonuclease, which cleaves phosphodiester bonds in the middle (endo) of a polynucleotide chain. 3' and 5' exonuclease and exonucleolytic complexes can degrade RNA and DNA in cells, and can degrade RNA and DNA in the interstitial space between cells and in plasma. The term "exoribonuclease" as used herein, refers to exonuclease ribonucleases, which are enzymes that degrade RNA by removing terminal nucleotides from either the 5' end or the 3' end of the RNA molecule. Enzymes that remove nucleotides from the 5' end are called 5'-3' exoribonucleases, and enzymes that remove nucleotides from the 3' end are called 3'-5' exoribonucleases.

The term "exonuclease resistant" as used herein with reference to a molecule and in particular a polynucleotide, indicates resistance to exonucleolytic degradation. Exonucleolytic degradation is the processive degradation of an oligonucleotide from the 5' or 3' end by enzymes called exonucleases. Exonucleases are enzymes that work by cleaving nucleotides one at a time from the end (exo) of a polynucleotide chain. A hydrolyzing reaction that breaks phosphodiester bonds occurs. Its close relative is the endonuclease, which cleaves phosphodiester bonds in the middle (endo) of a polynucleotide chain.

In some embodiments herein described, the passenger strand of the targeting domain is an exonuclease resistant polynucleotide comprising a blocker domain providing the polynucleotide with exonuclease resistance.

A "blocker domain" in the sense of the present disclosure indicates a part of the polynucleotide having the function of reducing polynucleotide degradation by exonuclease activity.

In the passenger strand exonuclease resistant polynucleotide herein described, the blocker domain is formed by a non-nucleic acid polymer segment and a phosphorothioate segment.

The term "non-nucleic acid polymer" as used herein refers to molecule composed of repeated subunits, known as monomers which do not comprise nucleotides or modified nucleotides linked by a phosphodiester or phosphorothioate linkages. The physical properties of a polymer, such as flexibility, chain mobility strength and toughness are dependent on the size or length of the polymer chain. A common means of expressing the length of a chain is the degree of polymerization, which quantifies the number of monomers incorporated into the chain. As with other molecules, a polymer's size can also be expressed in terms of molecular weight. The weight of a polymer is often expressed statistically to describe the distribution of chain lengths present in the same. Common examples are the number average molecular weight and weight average molecular weight. The ratio of these two values is the polydispersity index, commonly used to express the "width" of the molecular weight distribution. An additional measurement is contour length, which can be understood as the length of the chain backbone in its fully extended state. Exemplary non-nucleic acid polymers comprise alkanes, polyamides, polyethers, polyesters, polycarbonates, polysaccharides, polypeptides, polypropylenes, aliphatic chains, polymers with heterogeneous residues and residue to residue linkage chemistry and additional polymers identifiable by a skilled person.

The term "linear polymer" as used herein indicates a polymer wherein the residues are connected in a single linear and non-circular chain without branches. The flexibility of an unbranched chain polymer is characterized by its persistence length. The term "persistence length" as used herein refers to the length over which correlation in the direction of the ends of the polymer are lost. The persistence length is a basic mechanical property quantifying the stiffness of a polymer and is measurable with methods identifiable.

In particular, in blocker domain herein described the non-nucleic acid polymer segment comprises a linear polymer having two to six monomer residues linked by residue to residue bonds. The term "residue to residue bond" refers to a covalent bond connecting consecutive residues of the polymer.

In particular, in embodiments herein described, the end to end distance for the non-nucleic acid linear polymer in fully extended conformation can be up to about 1.00 nm, and in particular can be about 0.2 nm, about 0.4 nm, about 0.5 nm, about 0.65, about 0.8 nm, about 0.9 nm and about 1 nm. The end to end distance for the fully extended polymer can be determined by drawing the polymer in a maximally extended configuration with optimal bond length and bond angles expected for the monomer residues and measuring the distance between the first atom and the last atom in the polymer chain.

In embodiments herein described, the non-nucleic acid linear polymer has a persistence length of the polymer up to about 0.5 nm. In particular in embodiments herein described the persistence length can be about 0.38 nm.

In embodiments herein described the non-nucleic acid linear polymer has a stability such that polymer degradation is not faster than an unmodified RNA with the same number of monomers measured by gel shift assay or mass spectroscopy. Polymer degradation is not faster than an unmodified RNA when under comparable degradation conditions the average length of the polymer is equal to or longer than the length of the unmodified RNA. For example, a polymer of N residues can be incubated in cell lysate at 37° C. and compared with a control oligonucleotide with an equal number of nucleotides and the average length of the polymer over time can be measured by mass spectroscopy and compared to the control oligonucleotide. Under these conditions, the half-life of the full length polymer is longer than the half-life of the full length control oligonucleotide when the polymer degradation is not faster than an unmodified RNA.

In embodiments herein described the non-nucleic acid linear polymer has no covalent cross reactivity with the PAZ domain of Dicer which can be determined by radiolabeling experiments comprising providing a PAZ domain in a cell lysate buffer, contacting a candidate polymer labeled with a terminal $P_{32}$ at 25 C. temperature for a time and under condition to allow interaction of the PAZ domain and the labeled non-nucleic acid linear polymer. Following the contacting the method comprises further extracting the protein under denaturing conditions and detecting the radioactivity using suitable techniques such as Western Blot or other techniques identifiable by a skilled person. Additional methodology to measure covalent cross reactivity between the non-nucleic acid linear polymer and PAZ domain are identifiable by a skilled person.

In embodiments herein described, the degradation can occur as fast, or faster than the unmodified RNA as long as the degradation occurs such that a terminal phosphate is exposed or a terminal —OH group that can be phosphorylated by a kinase is exposed. A method to test the kination is to incubate the —OH terminated polymer with the target kinase in the appropriate buffer with P32 labeled Adenosine triphosphate as a source of the phosphate and detect labeling of the polymer with radioactive P32.

In some embodiments, polymers suitable to be comprised in the non-nucleic acid polymer segment as non-nucleic acid linear polymer herein described comprise a substituted or unsubstituted alkyl chain, a polyether, a polypeptide (alkanes, polyamides, polyethers, polyesters, polycarbonates, polysaccharides, polypeptides, polypropylenes, aliphatic chains, polymers with heterogeneous residues and residue to residue linkage chemistry) as well as additional polymers that show the required number of residues, end-to-end distance, persistence length, stability and cross reactivity as will be understood by a skilled person. In particular in some embodiments, non-nucleic acid linear polymers comprising different but chemically compatible monomer units (e.g. an amino acid flanked by an alkyl monomer) can be comprised in the non-nucleic acid polymer segment as long as such the required number of residues, end-to-end distance, persistence length, stability and cross reactivity as will be understood by a skilled person.

In the passenger strand comprising the exonuclease resistant polynucleotide herein described, the phosphorothioate segment of the blocker domain comprises at least one to five nucleotides linked by phosphorothioate linkages to form a phosphorothioate sequence having a 5' and a 3' end, and attaching at the 5' end the first end of the non-nucleic acid polymer segment through a phosphodiester linkage.

The term "phosphorothioate linkage" as used herein, indicates a bond between nucleotides in which one of the nonbridging oxygens is replaced by a sulfur. The term "phosphodiester linkage" as described herein indicates the normal sugar phosphate backbone linkage in DNA and RNA wherein a phosphate bridges the two sugars.

In particular, in a blocker domain herein described the phosphorothioate sequence comprises at least two bases wherein the at least two bases are connected by a phosphorothioate linkage. The bases can be modified or unmodified nucleotides, nucleosides, and related analog forming RNA, DNA, or alternative nucleic acids as would be understood by a person skilled in the art.

The term "modified nucleotides" refers to a nucleic acid monomer that is not the standard DNA or RNA nucleotide or nucleoside. In particular, modified nucleotides comprise nucleotide analogs presenting one or more individual atoms which have been replaced with a different atom or with a different functional group. Exemplary functional groups that can be comprised in an analog include methyl groups and hydroxyl groups and additional groups identifiable by a skilled person.

The term "present" as used herein with reference to a compound or functional group indicates attachment performed to maintain the chemical reactivity of the compound or functional group as attached. Accordingly, a functional group presented on residue, a segment, or a molecule is able to perform under the appropriate conditions the one or more chemical reactions that chemically characterize the functional group.

In particular, a modified nucleotide in the sense of the disclosure can be any nucleotides or nucleosides modified in the 2' position with a group that interferes with hydrogen bonding. In particular, modified nucleotide such has 2' O-methyl, 2'F 2'NH$_4$ and additional groups identifiable by a skilled person can be used in polynucleotides herein described. Exemplary modified nucleotide can also include locked nucleic acids alone or in combination with be 2' O-methyl, and/or 2' Fluoro modified residues.

In some embodiments, the phosphorothioate segment can have two to three residues modified to present a 2' O-methyl. In an exemplary modification schematically illustrated in FIGS. 3A-B, a first phosphorothioate links the first nucleotide, a mG, to a second nucleotide mG, and a second phosphorothioate links the second nucleotide mG to the third nucleotide mU.

In embodiments of the passenger strand comprising the exonuclease resistant polynucleotide herein described, inclusion of a phosphodiester linkage between the phosphorothioate sequence and the linear polymer of the non-nucleic acid polymer segment allows the resulting polynucleotide, when comprised at the 5' end of either strands of a duplex polynucleotide configured to allow processing by Dicer and/or Argonaute to maintain the duplex' processability by Dicer and/or Argonaute.

In some other embodiments herein described, the passenger strand does not comprise an exonuclease resistant polynucleotide as described herein, but can comprise one or more exemplary chemical modifications such as modified polynucleotides and/or phosphorothioate linkages, as well as exemplary non-nucleic acid polymer segments on the passenger strand 5' and 3' ends.

In some embodiments herein described, the guide strand, first and second protection segments, displacement segment, and toehold segment can comprise chemical modifications, modified polynucleotides, non-nucleic acid polymer segments, and/or phosphorothioate linkages.

Exemplary chemical modifications comprise replacement of nucleotides that are needed to be base-paired to form a desired secondary structure with modified nucleotides that are known to increase thermodynamic stability (e.g., 2'-O-methyl modified nucleotides, LNA, PNA and Morpholino). Additional exemplary modifications comprise replacement of nucleotides that are not desired according to a certain thermodynamic stability with modified nucleotides to ensure that the resulting modified structures are likely to retain the desired secondary structure conformations and thermodynamic stability (e.g., replace a ribonucleotide base with a deoxyribonucleic base). A person skilled in the art will be able to identify other suitable modifications upon reading of the current disclosure.

In particular, in some embodiments, the guide strand can comprise one or more exemplary chemical modifications such as modified polynucleotides and/or phosphorothioate linkages, as well as exemplary non-nucleic acid polymer linkers on the guide strand 5' end. For example, in embodiments wherein the targeting duplex length is greater than 19 base pairs, the 5' end of the guide strand can have a terminal phosphorothioate and/or non-oligonucleotide terminal groups (e.g., C3 or PEG linkers) to prevent spurious PAZ domain association. In an exemplary guide strand modification schematically illustrated in FIGS. 3A-B, for example, a first phosphorothioate links the first nucleotide, a 2'-O-methyl modified C (mC), to a PEG linker, and a second phosphorothioate links the first nucleotide mC to the second nucleotide mG. The guide strand can comprise any other modifications known to the art to be compatible with Dicer processing and RNAi functioning, as described, for example, in Collingwood et al. (*Oligonucleotides*. 2008 June; 18(2):187-200), herein incorporated by reference in its entirety.

Figure 12A:
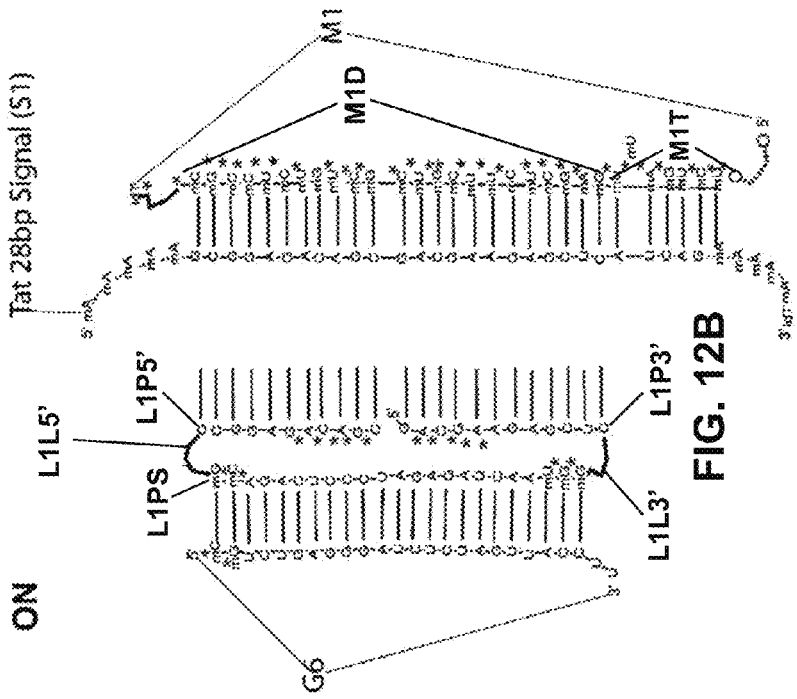
FIGS. 12A-B show a schematic illustration of an exemplary signal-activated molecular construct G6L1M according to embodiments herein described showing the OFF inactive conformation (FIG. 12A) and the ON active conformation (FIG. 12B). The construct G6L1M1 comprises a guide strand G6 (SEQ ID NO. 8), a passenger strand L1Ps (SEQ ID NO. 10) which attaches a first (5') protection segment L1P5" (SEQ ID NO: 11) and a second (3') protection segment L1P3' (SEQ ID NO: 9) through C3 linkers L1L5' and L1L3' (indicated by black lines). The construct G6L1M1 further includes a sensor strand M1 (SEQ ID NO. X12 which includes a displacement segment M1D and a 5' toehold segment M1T. The 5' ends of the guide strand and the toehold further comprise 3×EG linkers, indicated by dashed lines with black unfilled circles on the ends.

In some embodiments of signal activated molecular complexes herein described, each of the first 5' terminal protection segment and second 3' terminal protection segments can comprise phosphorothioate linkages. For example, the 5' terminus of the second 3' terminal protection segment and the 3' terminus of the first 5' terminal protection segment can comprise phosphorothioate bases or nuclease resistant bases to decrease spurious activation of the constructs in the OFF inactive state, as long as the modifications to the first and second protection segments allow strand displacement reactions following binding to a signal molecule to proceed. For example, as shown in FIGS. 3A and 1C, the first 5' terminal protection segment can comprise phosphorothioate linkages between the three nucleotides on the 3' most end (FIG. 3A), or between the six nucleotides on the 3' most end (FIG. 12A). The second 3' terminal protection segment can comprise phosphorothioate linkages between the three nucleotides on the 5' most end (FIG. 3A), or between the six nucleotides on the 5' most end (FIG. 12A). Additional positioning of phosphorothioate modifications is possible, and will be recognizable to one skilled in the art.

In embodiments of exemplary molecular complexes herein described, the first and second protection segments are covalently linked to the passenger strand of the targeting duplex. In particular, in the molecular complex, the sensor domain is bound to the targeting domain through covalent attachment of the 5' end of first 5' terminal protection segment to the 3' end of passenger strand, and through covalent attachment of the 3' end of the second 3' terminal protection segment to the 5' end of passenger strand. In some embodiments, the linkage occurs with unmodified RNA or DNA polynucleotides. Advantageously, the linkage occurs with an exemplary non-nucleic acid polymer linker, such as a C3, C6, tri-ethylene glycol, or hex-ethylene glycol linkers, or with phosphorothioate and 2'-O-methyl modified RNA. In these advantageous embodiments, spurious activation of the molecular complex is reduced.

In particular, in embodiments wherein non-nucleic acid polymer linkers are used to link the first and second protection segments to the passenger strand, the dimensions of the linkers can be determined using techniques identifiable by one skilled in the art. For example, in an exemplary approach the dimensions of the linkers can be determined by constructing two three-dimensional models of the targeting and sensor domains. In constructing such a model, the targeting domain model can be an RNA:RNA duplex with the correct number of base-pairs. The sensor domain model can be a RNA:RNA, RNA:DNA, or DNA:DNA duplex with the correct number of base-pairs. If in the resulting construct there is a gap between the duplex comprising a first 5' terminal protection segment and a first displacement segment and the duplex comprising a second 3' terminal protection segment and a second displacement segment, and the corresponding gap is bridged by RNA bases on the sensor strand, the RNA bases are added to fill in a gap in an A form alpha helical configuration, thus bridging the gap. If the corresponding gap is bridged by an unstructured linker, the fully stretched linker is positioned between the duplex comprising the first 5' terminal protection segment and a displacement segment and the duplex comprising the second 3' terminal protection segment and a displacement segment without rotating the sensor strand. The two resulting duplexes are then positioned next to each other as close as possible without touching (at least 0.1 nm distance between all atoms) and oriented them to minimize the distance between the 3' terminus of the passenger strand and the 5' terminus of the first 5' terminal protection segment and between the 5' terminus of the passenger strand and the 3' terminus of the second 3' terminal protection segment. The distance between each pair of termini can then be measured and ~0.3 nm can be added to provide the minimum length of the linkers. In preferred embodiments, the linkers allow no less than 0.3 nm and no more than 2 nm separation between the sensor and targeting duplexes. The maximum distance between the duplexes can be 5 nm. For a polymeric linker, to determine the minimum linker length, the fully stretched length of the polymer is utilized. For a polymeric linker, to determine linker length (in polymer units) allowed for the maximum separation, the estimated end-to-end distance of the polymer is calculated according to polymer physics methods known to the art. For example, for a well solvated polymer such as PEG, the distance is $\sim n^{(3/5)}*d$ where n=(the fully outstretched length of the polymer)/(2*persistence length of the polymer) and d=(2*persistence length of the polymer). The persistence length of many polymers such as DNA, and PEG are well known and documented in the literature. Using the above model, the gap in the sensor duplex is positioned on the side facing towards the targeting duplex by changing the length of the duplex comprising the first 5' terminal protection segment and a displacement segment and the duplex comprising the second 3' terminal protection segment and a displacement segment until the gap is approximately in the middle.

In some embodiments of signal activated molecular complexes herein described, the sensor strand can comprise one or more exemplary chemical modifications such as modified polynucleotides and/or phosphorothioate linkages, as well as exemplary non-nucleic acid polymer linkers on the sensor strand 5' and 3' ends. In particular, the sensor strand can comprise chemical modifications that increase nuclease resistance, prevent protein binding, and increase thermodynamic stability. Modification of the sensor strand for nuclease resistance and thermodynamic stability greatly reduces spurious RNAi processing of the inactivated state of exemplary molecular constructs.

In some embodiments, the sensor strand can comprise one or more phosphorothioate linkages between adjacent nucleotides; advantageously, the sensor strand can comprise only phosphorothioate linkages to increase nuclease resistance and decrease protein binding. In some embodiments, the sensor strand can comprise LNA modifications and/or 2'-O-methyl bases. In some embodiments, inclusion of LNA modifications in the sensor strand positioned across from the gap between the first and second protection segments can increase the conformational stability of the sensor duplex. In some embodiments, the sensor strand is completely modified with phosphorothioate backbone connections and nuclease resistant bases. If complete modification of the sensor strand causes toxicity, the number of phosphorothioates and nuclease resistant bases can be reduced to optimize the balance between toxicity, leakage, and cost. When reducing phosphorothioates and modified bases, the bases in the toeholds and bases flanking the toeholds are preferably modified to be more protected. Accordingly in embodiments where the number of phosphorothioates and modified bases are reduced in the sensor strand, the bases in the toeholds and bases flanking the toeholds preferably comprise more phosphorothioates and modified bases, than the bases in the interior of the base-paired regions of the sensor strand.

Advantageously, and as illustrated on FIG. 3A, the sensor strand can comprise LNA modifications every four bases, and 2'-O-methyl bases for all non-LNA bases. In some embodiments, the sensor strand can comprise non-nucleic acid polymer linkers such as PEG or C3 or other chemical groups that block protein binding, exonuclease loading, or Dicer binding at the 3' and 5' end sensor strand ends. In some embodiments, the sensor strand can comprise non-nucleic acid polymer linkers positioned across from the gap between the first and second protection segments, and between at least one displacement segment and the toehold. In particular, in some embodiments, the 5' and 3' termini of the sensor strand can have non-nucleic acid polymer groups to prevent binding of Dicer, exonucleases, and other helicases. These groups can be C3, PEG, fluorophore, terminal amine, inverted dT or other groups that do not present a terminal phosphate at the 5' end and a terminal nucleotide at the 3'.

In several embodiments, the toehold segment can comprise a polynucleotide sequence (herein also toehold sequence) that is at least 2 nucleotides in length and is complementary to at least a portion of the signal polynucleotide. This configuration of the toehold segment is expected to allow binding of a signal polynucleotide to bind to the signal activatable construct and initiate the branch migration process. A smaller toehold sequence is expected to result in better sequence specificity for signal discrimination, while a longer toehold sequence is expected to result in an increased ability to bind to the signal polynucleotides to form a desired secondary structure with respect to the ability of a shorter toehold segment. In some embodiments, the toehold segment can be arranged in single-stranded form and free of secondary structure. In particular, in some of those embodiments, the toehold sequence can be 4 to 12 nucleotides in length. In some embodiments, the toehold segment is composed of unmodified ribonucleotide. In particular, in other embodiments, the toehold segment comprises modified nucleotide configured for improved nuclease resistance. Exemplary modifications include but are not limited to 2'-O-methyl modification, 2'-Fluoro modifications, inclusions of LNA and PNA, and the like that are identifiable by a skilled person. In some embodiments, the connection point between the toehold and the rest of sensor strand preferably comprise nuclease resistant and thermodynamically stabilizing chemical modifications to avoid spurious exonuclease induced activation of the molecular construct.

Figure 12B:
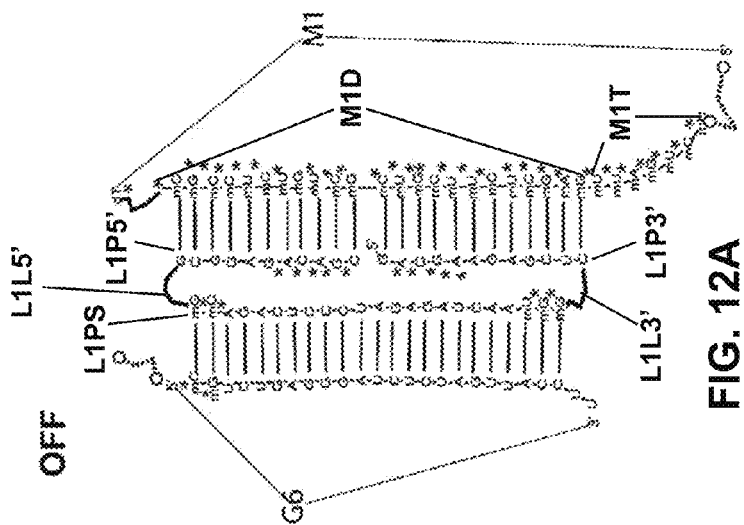

The exemplary construct G6L1M1 illustrated in FIGS. 12A and 12B. The guide strand G6 and the passenger strand L1PS are complementary to each other and bind to each other to form a targeting domain duplex. In the exemplary construct of FIGS. 1C-1D, the passenger strand L1Ps of the targeting domain RNA duplex is covalently attached to a first and second RNA protection segments L1P5' and L1P3', each having a 5' end and a 3' end. In particular, the 5' end of the passenger strand L1Ps is covalently linked to the 3' end of the second protection segment L1P5', and the 3' end of the passenger strand L1Ps is covalently linked to the 5' end of the first 5' terminal protection segment L1P5', with a gap between the 3' end of first the 5' terminal protection segment L1P5' and the 5' end of the second 3' terminal protection segment L1P3'. In the inactive conformation of FIG. 12A, the 5' protection segment L1P5' and the 3' protection segment L1P3' of the passenger strand are complementary to different portions of the displacement segment E1D of the sensor strand and bind to the displacement segment E1D to form a sensor domain duplex. In the inactive conformation of FIG. 12A the targeting domain and the sensor domains form a tile small activating RNA (saRNA). In the illustration of FIGS. 12A-12B, the switching from the inactive conformation of FIG. 12A to the active conformation of FIG. 12B is performed through displacement of the sensor strand E1 from the L1P5' and L1P3' protection segments of the passenger strand following binding of a signal strand S0 labeled RNA signal in FIGS. 12A-12B.

In particular the exemplary illustrations of FIGS. 12A-B, the guide strand (G6) is the guide strand of an RNAi trigger, which in the illustration of FIGS. 3A-B is a siRNA, but can be other RNAai triggers such as a Dicer substrate siRNA, a miRNA, or another Dicer substrates.

In some embodiments, the signal can be a single signal polynucleotide of a length shorter than 30 nucleotides, and the toehold segment and the displacement segment are fully complementary to the signal polynucleotide. In other embodiments, the signal can be formed by multiple homologous signal polynucleotides. In these embodiments, the signal polynucleotides can be tested with a sensor design. Mismatches and wobble pairings or permissive bases such as inosine can be placed at positions in the 3:5 duplex corresponding to the variable sequences. In particular, in several embodiments, the Tm for the duplex formed by the signal polynucleotides with the toehold segment and the displacement segment is typically at least 25° C. and is typically at least equal to the operating temperature under which the construct will be used.

In some embodiments the signal polynucleotide used in the experiment can be selected to approximate the expected state of the signal in the cell. In particular, in embodiments wherein the signal polynucleotide is expected to be a short oligonucleotide or RNA segment, such as a miRNA, a short oligonucleotide of the same sequence as the signal polynucleotide can be used in experiments to simulate the topological constraints imposed by having the toehold segment in a hairpin loop. In embodiments wherein the signal is an mRNA sequence, a polynucleotide having the same sequence as the mRNA signal nucleotide can be used to simulate the topological constraints imposed by having the toehold segment in a hairpin loop. In embodiments wherein the region known to bind to the toehold segment is in a hairpin loop, the signal nucleotide used in the displacement experiment can have the toehold sequence in a hairpin loop to simulate the topological constraints imposed by having the toehold segment in a hairpin loop.

In some embodiments, the toehold segment can be connected to the displacement segment through covalent linkage. In particular, in some embodiments, the toehold segment can be arranged to the 5' terminus of the displacement segment (see exemplary embodiments in FIGS. 3A-B, 12A-27B). In some embodiments, the toehold segment can be arranged as a single strand terminal sequence of the displacement strand; in other embodiments, the toehold segment can be provided as a single strand middle sequence of the displacement strand, which can be arranged within a loop structure of the displacement strand. In particular, in some embodiments, where the toehold domain can be arranged within a loop structure of the displacement strand, the loop can comprise at least 20 nucleotide unmodified nucleotides, which in some cases can be ribonucleotides. In some embodiments, the toehold segment can be at least 3 nucleotides in length. In particular, in some embodiments, the toehold segment can be at least 4 nucleotides in length.

In some embodiments, the signal-activatable constructs herein described can comprise one or more toehold segments. For example, an exemplary sensor strand herein described can comprise a first toehold segment as single strand terminal sequence of one end of the displacement segment, and a second toehold segment as a single terminal sequence of the opposite end of the displacement segment. In some embodiments, an exemplary sensor strand herein described can comprise a first toehold segment as single strand terminal sequence of one end of the displacement segment, and a second toehold segment arranged within a loop structure of the displacement strand as described herein. In other embodiments, an exemplary sensor strand herein described can comprise a first toehold segment as single strand terminal sequence of one end of the displacement segment, a second toehold segment as a single terminal sequence of the opposite end of the displacement segment, and a third toehold segment arranged within a loop structure of the displacement strand as described herein. In some embodiments, the one or more exemplary toehold segments herein described are configured to bind the same signal molecule. In alternate embodiments, the one or more exemplary toehold segments herein described are configured to bind different signal molecules.

According to embodiments herein described, a signal molecule can comprise a signal polynucleotide. A signal molecule can also comprise a protein, peptide fragment, a biological metabolite, or other natural biological product, or a metal ion or other molecules known to bind aptamers.

The term "aptamers" as used here indicates oligonucleic acid or peptide molecules that bind a specific target. In particular, nucleic acid aptamers can comprise, for example, nucleic acid species that have been engineered through repeated rounds of in vitro selection or equivalently, SELEX (systematic evolution of ligands by exponential enrichment) to bind to various molecular targets such as small molecules, proteins, nucleic acids, and even cells, tissues and organisms. Aptamers are useful in biotechnological and therapeutic applications as they offer molecular recognition properties that rival that of the antibodies. Peptide aptamers are peptides that are designed to specifically bind to and interfere with protein-protein interactions inside cells. In particular, peptide aptamers can be derived, for example, according to a selection strategy that is derived from the yeast two-hybrid (Y2H) system. In particular, according to this strategy, a variable peptide aptamer loop attached to a transcription factor binding domain is screened against the target protein attached to a transcription factor activating domain. In vivo binding of the peptide aptamer to its target via this selection strategy is detected as expression of a downstream yeast marker gene.

The term "small molecule" as used herein indicates an organic compound that is of synthetic or biological origin and that, although might include monomers and/or primary metabolites, is not a polymer. In particular, small molecules can comprise molecules that are not protein or nucleic acids, which play a biological role that is endogenous (e.g. inhibition or activation of a target) or exogenous (e.g. cell signaling), which are used as a tool in molecular biology, or which are suitable as drugs in medicine. Small molecules can also have no relationship to natural biological molecules. Typically, small molecules have a molar mass lower than 1 kg·mol-l. Exemplary small molecules include secondary metabolites (such as actinomicyn-D), certain antiviral drugs (such as amantadine and rimantadine), teratogens and carcinogens (such as phorbol 12-myristate 13-acetate), natural products (such as penicillin, morphine and paclitaxel) and additional molecules identifiable by a skilled person upon reading of the present disclosure.

The terms "peptide" and "oligopeptide" usually indicate a polypeptide with less than 50 amino acid monomers, wherein the term "polypeptide" as used herein indicates an organic linear, circular, or branched polymer composed of two or more amino acid monomers and/or analogs thereof. The term "polypeptide" includes amino acid polymers of any length including full length proteins and peptides, as well as analogs and fragments thereof. As used herein the term "amino acid", "amino acidic monomer", or "amino acid residue" refers to any of the twenty naturally occurring amino acids, non-natural amino acids, and artificial amino acids and includes both D an L optical isomers. In particular, non-natural amino acids include D-stereoisomers of naturally occurring amino acids (these including useful ligand building blocks because they are not susceptible to enzymatic degradation). The term "artificial amino acids" indicate molecules that can be readily coupled together using standard amino acid coupling chemistry, but with molecular structures that do not resemble the naturally occurring amino acids. The term "amino acid analog" refers to an amino acid in which one or more individual atoms have been replaced, either with a different atom, isotope, or with a different functional group but is otherwise identical to original amino acid from which the analog is derived.

Exemplary embodiments of possible variations of activatable construct herein described with reference to the exemplary construct of FIGS. 3A-3B and FIGS. 12A-12B are provided in the illustration of FIGS. 13A-17B, and 19-27B, showing exemplary molecular complexes of the disclosure configured in an inactive conformation (FIGS. 13A, 14A, 15A, 16A 17A, 19, 20, 21A, 21B, 22A, 23A, 24 25, 26 and 27A-B) or presented in an active conformation (FIGS. 13B, 14B, 15B, 16B, 17B, and 22B, 23B and 28).

Figure 13A:
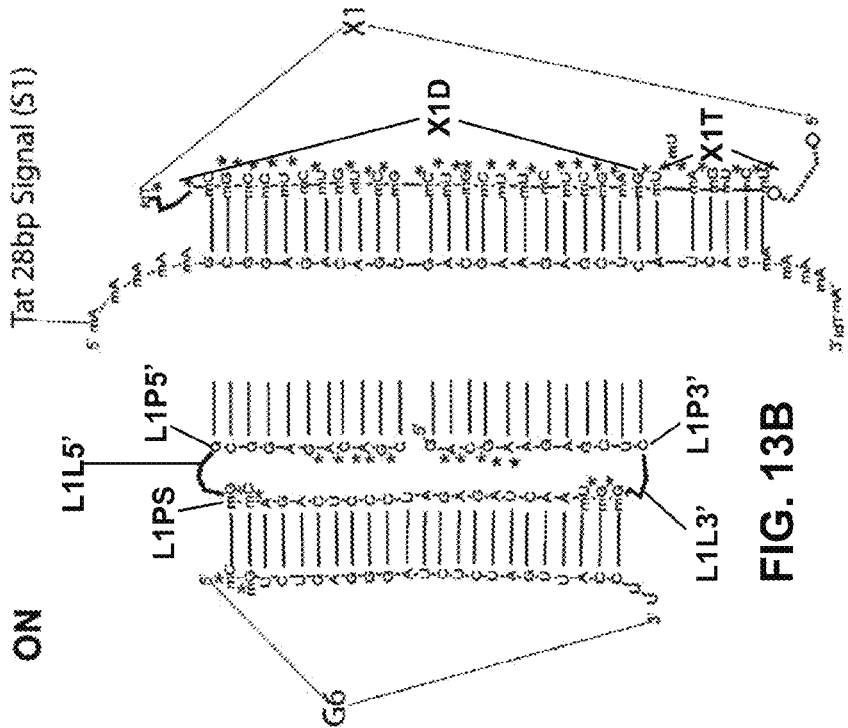
FIGS. 13A-B show a schematic illustration of an exemplary signal-activated molecular construct G6L1X1 according to embodiments herein described in the OFF inactive conformation (FIG. 13A) and in the ON active conformation (FIG. 13B). The exemplary construct G6L1X1 comprises a guide strand G6 (SEQ ID NO.8), passenger strand L1PS (SEQ ID NO. 10) 5' protection segment L1P5" (SEQ ID NO: 11) and a 3' protection segment L1P3" (SEQ ID NO: 9) attached to the passenger strand L1PS (SEQ ID NO: 10) by C3 linkers L1L5' and L1L3' (indicated by black lines) and a sensor strand X1 (SEQ ID NO. 13) comprising a displacement segmentX1D (SEQ ID NO: 15) and a 5' toehold segment X1T (SEQ ID NO: 14). The various strands of the signal-activated constructs comprise unmodified RNA bases, 2'-O-methyl RNA bases (indicated by mN, wherein N is any of the four bases), LNA (indicated by +), phosphorothioate linkages (indicated by an asterisk *), primary amine groups (indicated by NH2), PEG linkers (indicated by black lines with black circles on ends), C3 linkers (indicated by black lines), 3× or 6×EG linkers (indicated by dashed lines with black unfilled circles on ends), and inverted dT exonuclease blockers (indicated by idT). The switching from one conformation to another is performed through displacement of the sensor strand from the 5' and 3' protection segments following binding of a signal strand S1 (SEQ ID NO. 41); labeled Tat 28 bp Signal) to the toehold and displacement segment of signal strand X1.
Figure 13B:
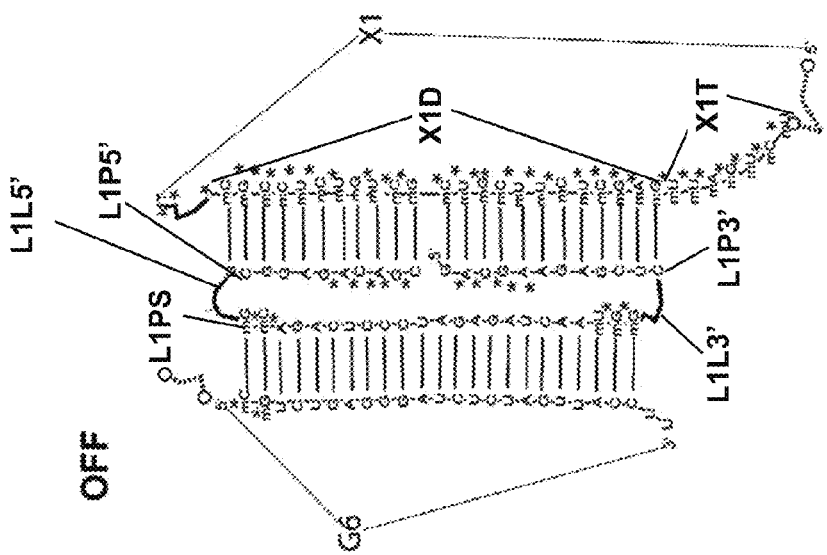

FIGS. 13A-B show a schematic illustration of an exemplary signal-activated molecular construct G6L1X1 according to embodiments herein described in the OFF inactive conformation (FIG. 13A) and in the ON active conformation (FIG. 13B). In the illustration of FIGS. 13A-B show the OFF state of the construct and the ON state when the sensor strand of the construct is fully base-paired with the activating RNA transcript and decoupled from the activated RNAi targeting domain. G6 is the guide strand for the targeting domain. L1Ps is the passenger strand attaching a 5' terminal L1P5' overhang and a 3' terminal L1P3' overhang through C3 linkers. The 5' and 3' overhang of L1Ps form a sensor duplex with sensor strand X1. X1 is a 2'-O-methyl modified RNA strand with phosphorothioate backbone modifications. The 5' of X1 has a toehold for binding of the signal RNA transcript. In the illustration of FIGS. 13A-B, the signal molecule is an activating RNA signal S1 and binds to the sequence mUmCmUmGmA in the toehold. The binding of the signal to the sensor strand leaves an unpaired base, mU, between the toehold and the rest of the base-pairs.

FIGS. 14A-B show a schematic illustration of an exemplary signal-activated molecular complex, G6L2X2, in which the guide strand G6 and the passenger strand L2Ps form the targeting duplex. The overhangs of L2 (L2p5' and L2P3') and the displacement segment E2D of the sensor strand X2 form the sensor duplex. In the illustration of FIGS.

14A-B, the L2 strand differs from the L1 strand of the construct of FIGS. 13A-B in the pattern of chemical modifications at the connection point to the L1P3' over hang. L2 segment has the sequence " . . . C*mG—overhang" instead of " . . . *mC*mG—overhang". The change from the *mC of the L1Ps strand to the C residues in the corresponding position of the L2Ps resulted in improved RNAi activity in the ON state (see Examples section).

FIGS. 15A-B show a schematic illustration of an exemplary signal-activated molecular complex, G6L2X3, in which the guide strand G6 and the passenger strand L2Ps form the targeting duplex and the overhangs of L2P5' and L2P3' form the sensor duplex by complementarily binding displacement segment X3D of sensor strand X3. In the construct of FIGS. 15A-B, the X3 strand differs from X2 strand in construct of FIGS. 14A-B in that X3 contains LNA modifications that increase the thermodynamic stability of the construct. This results in significantly lower OFF state RNAi activity compared with the construct of FIGS. 14A-B (see Examples section).

FIGS. 16A-B show a schematic illustration of an exemplary signal-activated molecular complex, G6L2X5, in which, the guide strand G6 and the passenger strand L2Ps form the targeting duplex and the overhangs of L2P5' and L2P3' form the sensor duplex by complementarily binding the displacement segment X5D of the sensor strand X5 form the sensor duplex. In the construct of FIGS. 16A-B, the X5 strand differs from the X3 strand of the construct of FIGS. 15A-B, in that X5 has a longer toehold sequence that increase the rate of isothermal strand displacement reactions allowing the activation of the construct by the RNA activation sequence. (see Examples section).

Figure 17A:
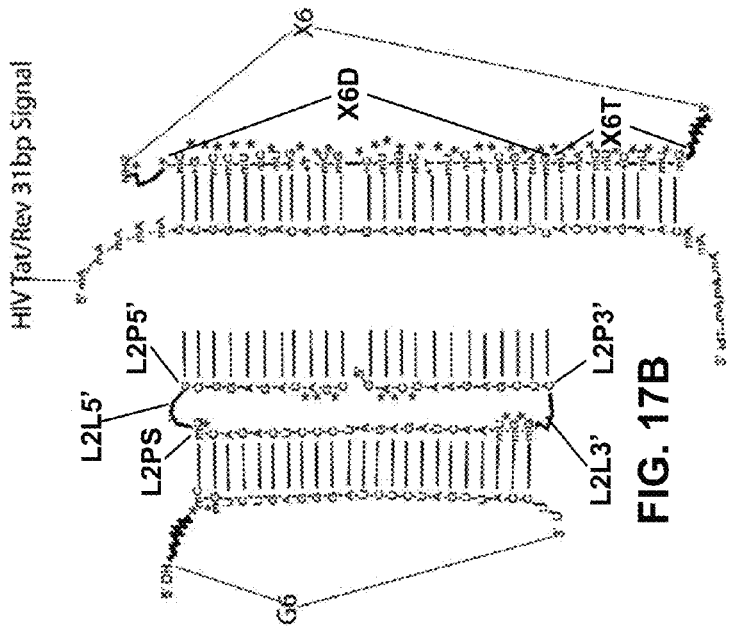
FIGS. 17A-B show a schematic illustration of an exemplary signal-activated molecular complex, G6L2X6, comprising a guide strand G6 (SEQ ID NO. 8), a passenger strand L2PS (SEQ ID NO. 17) which attaches a 5' protection segment L2P5' (SEQ ID NO: 18) and a 3' protection segment L2P3' (SEQ ID NO: 16) modified to include phosphorothioate linkages as indicated in the figure and connected to the passenger strand L1P6 (SEQ ID NO: 17) by C3 linkers L2L5' and L2L3' (indicated by black lines), and a sensor strand X6 (SEQ ID NO. 28) comprising a toehold segment X6T (SEQ ID NO:29) and a displacement segment X6D (SEQ ID NO: 30) also modified to include phosphorothioate linkages as indicated in the figure. In particular.
Figure 17B:
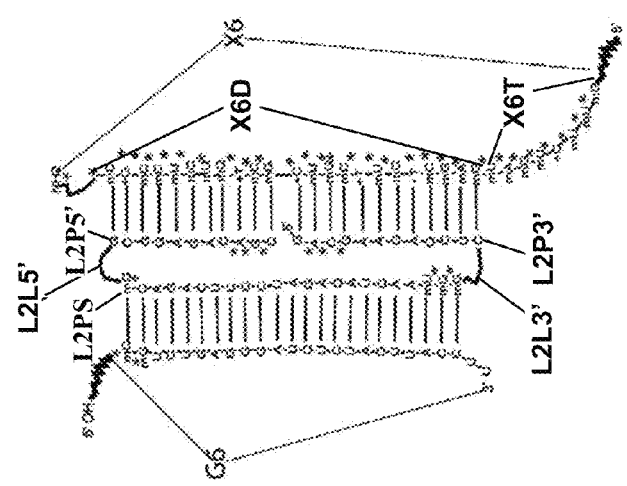

FIGS. 17A-B show a schematic illustration of an exemplary signal-activated molecular complex, G6L2X6, in which the guide strand G6 and the passenger strand L2Ps form the targeting duplex and the overhangs of L2P5' and L2P3' form the sensor duplex by complementarily binding the displacement segment X6D of the sensor strand X6 form the sensor duplex. In the construct of FIGS. 17A-B, the X6 strand differs from X5 strand in the construct of FIGS. 16A-B in that X6 has an LNA modified base in its toehold to increase the toehold stability and thereby the rate of isothermal strand displacement reactions allowing the activation of the construct by the RNA activation sequence (see Examples section).

FIGS. 18A-C illustrate exemplary toeholds according to some embodiments of the present disclosure. In particular, FIG. 18A illustrates the 5' toehold of construct G6L2X3 (FIGS. 15A-B), which comprises six base pairs complementary to a signal strand and a mismatch to said strand at position 7 of the toehold. FIG. 18B illustrates the 5' toehold of construct G6L2X5 (FIGS. 16A-B), which comprises eight base pairs complementary to a signal strand and has no mismatches. FIG. 18C illustrates the 5' toehold of construct G6L2X6 (FIGS. 17A-B), which comprises eight base pairs complementary to a signal strand, has no mismatches, and further comprises an LNA modified base. Different configuration of the toehold affect the activation rate of the construct and the related performance (see e.g. Example 3).

Figure 19:
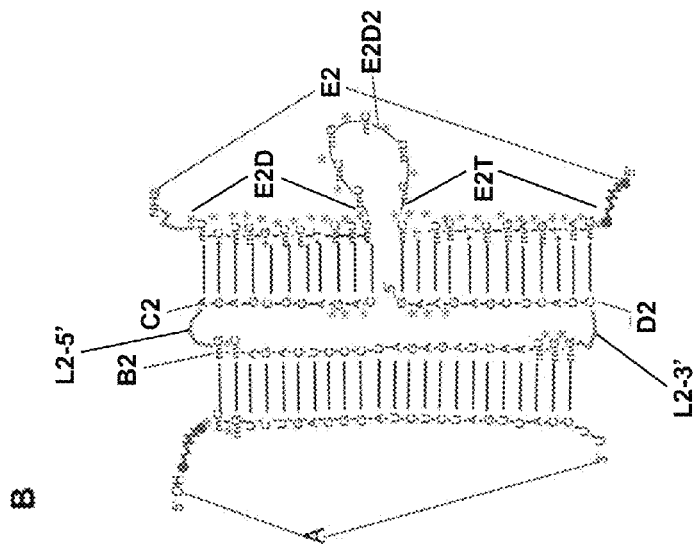
FIG. 19 shows the exemplary molecular construct AB1-C1D1E1 having a guide strand A (SEQ ID NO. 1), a passenger strand B1 (SEQ ID NO.45) attaching at the 5' terminus a second, 5' protection segment C1 (SEQ ID NO: 46) and attaching at the 3' terminus a first, 3' protection segment D1 (SEQ ID NO: 44) connected to the passenger strand B1 (SEQ ID NO:45) by C3 linkers L15' and L13' (indicated by black lines), and a sensor strand E1 (SEQ ID NO. X). Sensor E1 comprises displacement segment E1D (SEQ ID NO: 47) a first toehold segment E1T1 (SEQ ID NO:48) attached at the 5' terminus of the displacement segment E1D (SEQ ID NO: 49) and an additional toehold E1T2.(SEQ ID NO: 50)attached at the 3' terminus of the displacement segment E1D (SEQ ID NO: 49).
Figure 20:
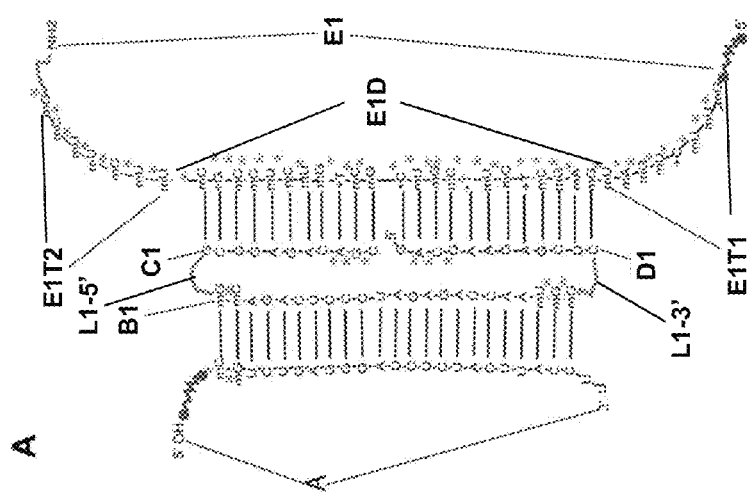
FIG. 20 shows the exemplary molecular construct A-B2C2D2-E2 having a guide strand A (SEQ ID NO. 1), a passenger strand B2 (SEQ ID NO.53) attaching at the 5' terminus a second, 5' protection segment C2 (SEQ ID NO: 54) and at the 3' terminus a first, 3' protection segment D2 (SEQ ID NO: 52) attached to the passenger strand B2 (SEQ ID NO: 53) by C3 linkers L2-5' and L2-3' (indicated by black lines), and a sensor strand E2 (SEQ ID NO. 55). Sensor E2 comprises two displacement segments E2D1 (SEQ ID NO: 57) and E2D2 (SEQ ID NO:58) and an internal toehold segment E2T (SEQ ID NO:56).

FIGS. 19 to 21B illustrate exemplary embodiments including more than one toehold (FIGS. 19, 21A and 21B) and/or toehold in positions alternative or additional to the 5' terminus of the sensor strand (FIGS. 19 to 21B). In particular FIG. 19: Part A illustrates a tile saRNA construct with both a 5' toehold Et1 and a 3' toehold ET2segments. In the illustration of FIG. 19, both toeholds base-pair to different portions of HIV tat/rev mRNA, thereby increasing the likelihood of activation by the matching tat/rev RNA transcripts present in the host cell. In a possible variation a 5' toehold ET1 and a 3' toehold ET2 can specifically bind different signal molecule thus allowing a controlled activation in different environments. FIG. 16B illustrates a tile saRNA construct with an internal toehold E2T. The toehold allows base-pairing to the HIV tat/rev mRNA. Compared with the construct of FIG. 19, the passenger strand overhang are modified and the pattern of LNA modifications on the sensor strand is changed to accommodate the new secondary structure. In particular in the illustration of FIG. 20, the sensor strand E2 comprises two displacement segments E2D1 and ED2 complementary to C2 and D2 overhang protection segments attached to the targeting domain through C3 linkers. In the illustration of FIG. 16B the displacement segments E2D1 and ED2 flan the internal toehold E2T which is directly attached with its 5' terminus to the 3' terminus of E2D1 and with its 3' terminus with the 5' terminus of E2D2

Figure 21A:
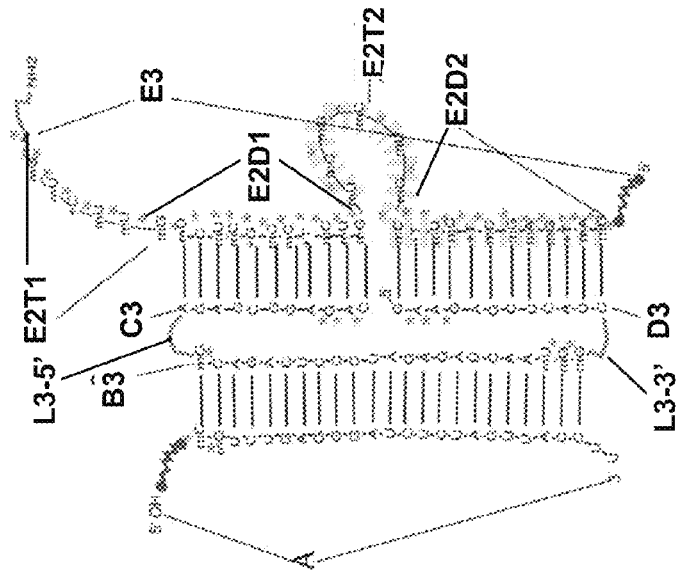
FIGS. 21A and FIG. 21B show the exemplary molecular construct A-B3C3D3-E3 having a guide strand A (SEQ ID NO. 1), a passenger strand B3 (SEQ ID NO.61) attaching at the 5' terminus a second, 5' protection segment C3 (SEQ ID NO: 62) and attaching at the 3' terminus a first, 3' protection segment D3 (SEQ ID NO: 60) connected to the passenger strand B3 (SEQ ID NO: 61) by C3 linkers L3-5' and L3-3' (indicated by black lines), and a sensor strand E3 (SEQ ID NO. 63). Sensor E3 comprises two displacement segments E3D1 (SEQ ID NO: 65) and E3D2 (SEQ ID NO:66), an internal toehold segment E3T1 (SEQ ID NO:64) and a second toehold at the 3; terminus E3T2 (SEQ ID NO: 67).
Figure 21B:
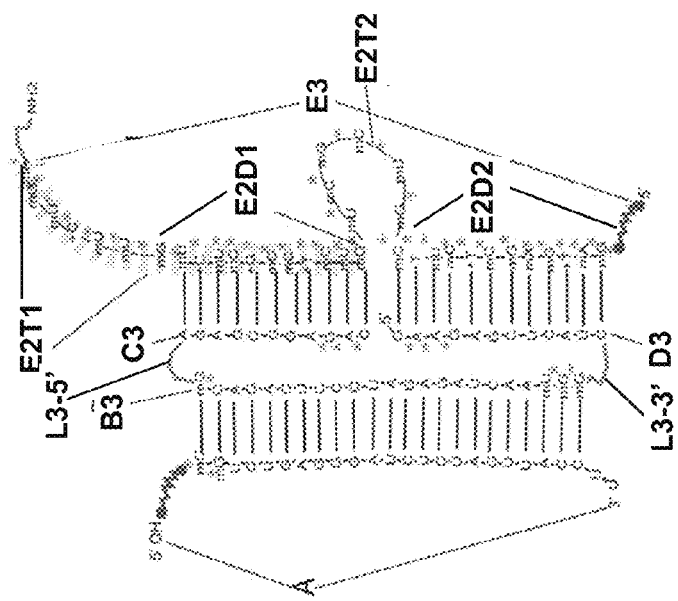

In the exemplary constructs of FIGS. 21A and 21B the tile saRNA has two toeholds and is designed to be activated by two separate transcripts. In the illustration of FIG. 21A the binding position of the first transcript to the toehold E2T1 is highlighted. In the illustration of FIG. 21B, the binding position of the second transcript to the toehold E2T2 is highlighted. The two transcripts can be, for example, miRNAs expressed in the cell. In some embodiments, in constructs such as the one of FIGS. 21A and 21B, the sequences can be configured so that both transcripts and/or other signal molecule need to be present to fully displace the sensor strand E2 and activate the tile saRNA.

Figures 22A, 22B:
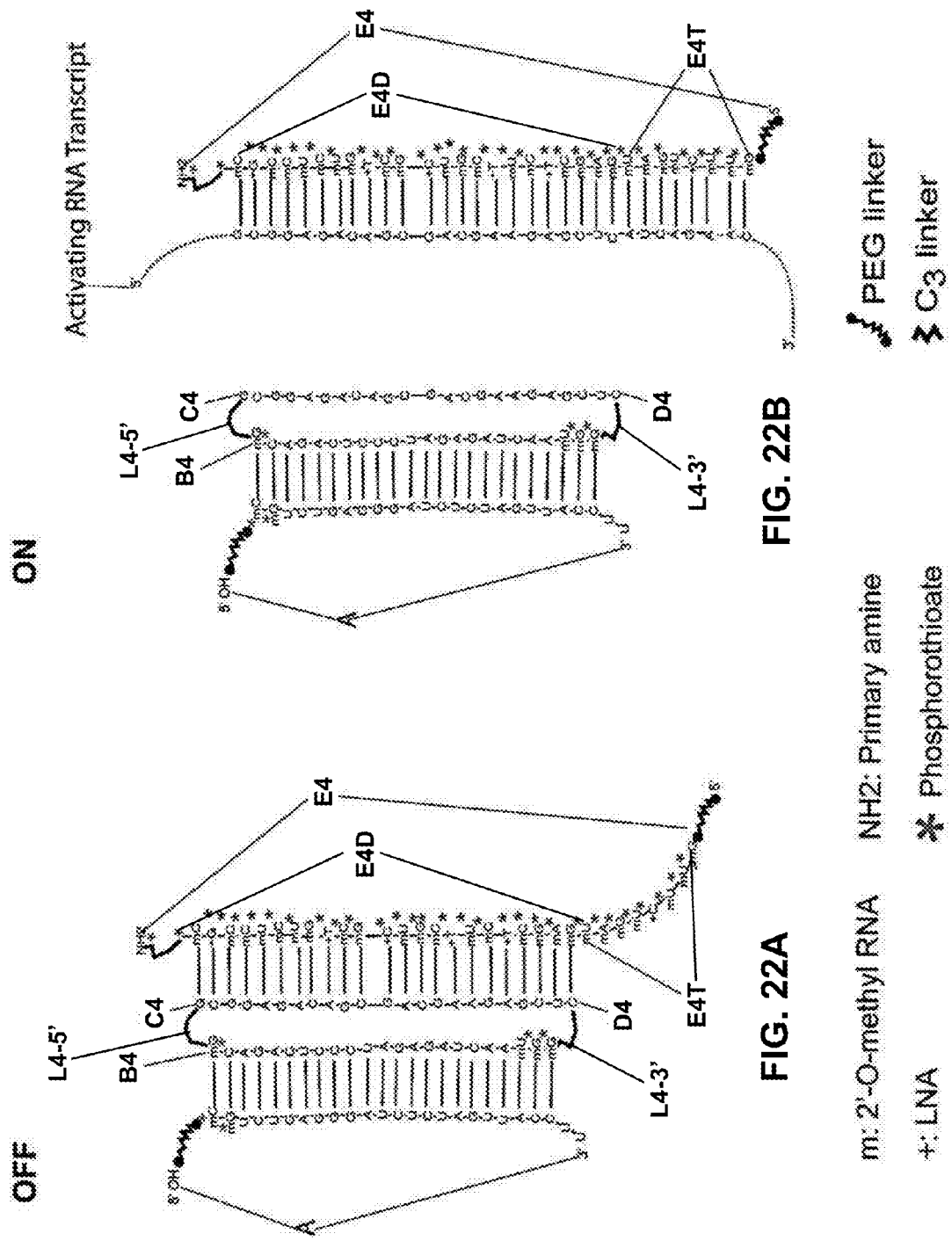
FIG. 22A and FIG. 22B shows the exemplary molecular construct A-B4C4D4-E4 having a guide strand A (SEQ ID NO. 1), a passenger strand B4 (SEQ ID NO.71) attaching at the 5' terminus the 3' terminus of a second, 3' protection segment D4 (SEQ ID NO: 72) through a C3 linker L4-3', B4 (SEQ ID NO: 71) also attaching at the 3' terminus the 5' terminus a first 5' protection segment C4 (SEQ ID NO: 70) through a C3 linker L4-5' to form a circular B4C4D4 segment. The construct A-B4C4D4-E4, also comprise a sensor strand E4 (SEQ ID NO. 73). Sensor E4 comprises a displacement segment E4D (SEQ ID NO: 75) and a 5' terminal toehold E4T (SEQ ID NO: 74).

In the exemplary construct of FIGS. 22A and 22B, the gap between the protection 5' terminal protection segment D4 and 3' terminal protection segment C4 has been filled by unmodified RNA nucleotides and the passenger strand B4 has consequently been circularized (for example, by enzymatic ligation) so that there is no gap between overhang segments C4 and D4. In constructs of FIGS. 22A and 22B the bases positioned in positions where in corresponding constructs the gap is present are preferably unmodified in view of the covalent linkages interfering and protecting from exonuclease degradation. In embodiments where constructs have a configuration such as the one exemplified in FIGS. 22A and 22B, use of a higher concentration of the construct is preferred.

Figures 23A, 23B:
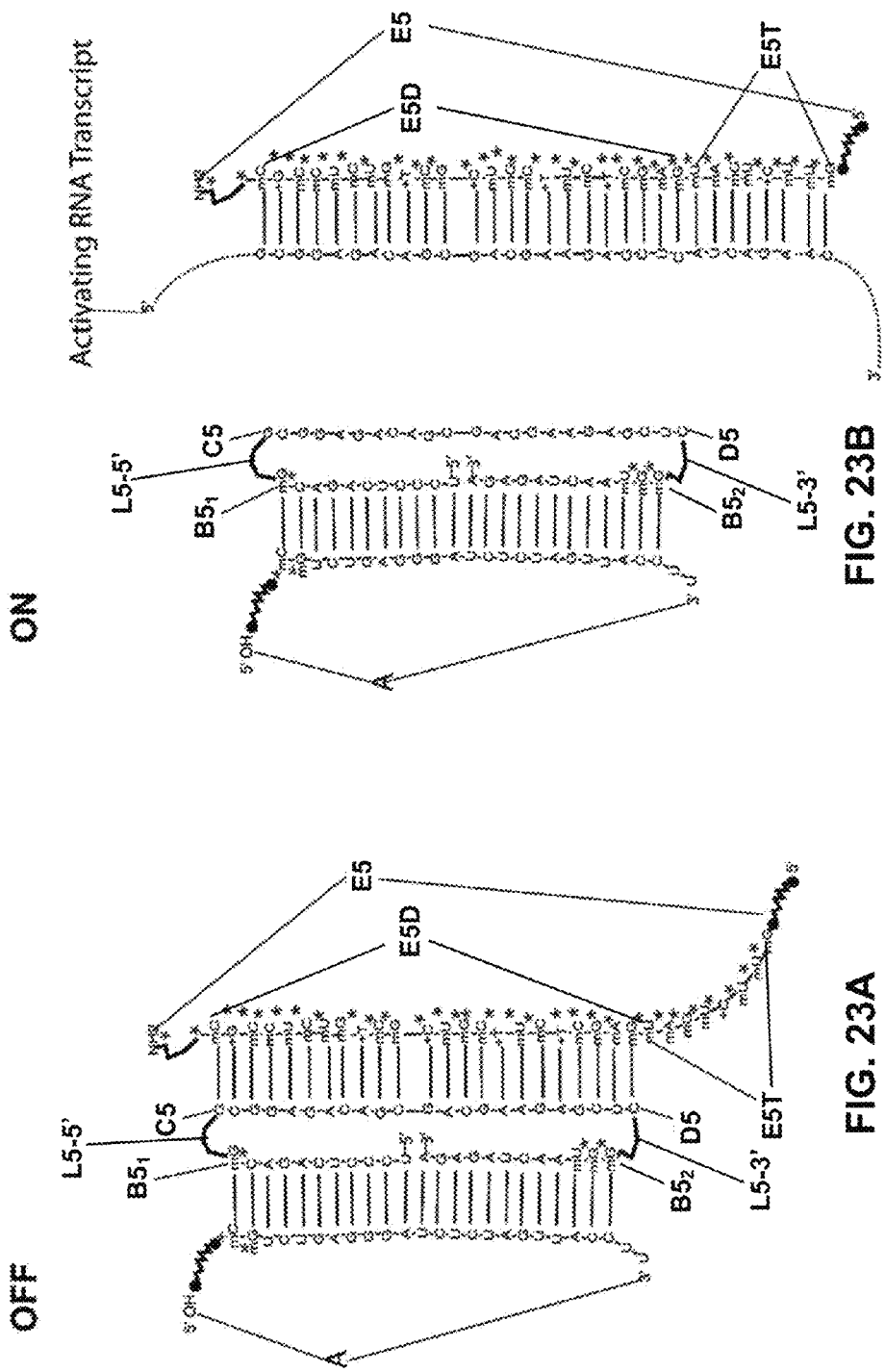
FIG. 23A and FIG. 23B shows the exemplary molecular construct A B5$_1$C5D5 B5$_2$-E5 having a guide strand A (SEQ ID NO. 1), a passenger strand B5 nicked in two segments B5$_1$ (SEQ ID NO: 77) and B5$_2$ (SEQ ID NO: 79) which complementarily binding the guide strand with a gap between the 5' terminus of B5$_1$ and the 3' terminus of the segment B5$_2$ as shown. In the construct A B5$_1$C5D5 B5$_2$-E5 segment B5$_1$ (SEQ ID NO: 77) attaches the 5' terminus of a, 5' protection segment C5 (C5 portion of protection sequence SEQ ID NO: 78) through a C3 linker L5-5'and segment B5$_2$ (SEQ ID NO: 79) attaches the 3' terminus of a 3' protection segment D5 (D5 portion of protection sequence SEQ ID NO: 78) through a C3 linker L5-3' to form a B5$_1$C5D5B5$_2$ segment. The construct A B5$_1$C5D5 B5$_2$-E5 also comprise a sensor strand E5 (SEQ ID NO. 80), comprising a displacement segment E5D (SEQ ID NO: 82) and a 5' terminal toehold E5T (SEQ ID NO: 81).

In the exemplary construct of FIGS. 23A and 23B, the gap between protection segments C and D is moved segment B forming the passenger strand. In those embodiments the targeting domain is maintained in a straight conformation by the rigid and gapless sensor domain, in absence of circularization of the passenger strand of the targeting domain which is nicked.

The term "nicked" as used herein with reference to a polynucleotide strand of a double stranded polynucleotides, indicates a gap in the direct covalent linkage between two nucleotides of the polynucleotide chain forming the strand that are engaged in complementary binding within double stranded polynucleotide. Accordingly, an RNA duplex comprising a nicked passenger strand can be obtained by cleaving the covalent linkage between suitable nucleotides e.g. by using suitable endoribonucleases (such as an RNAase III enzyme) or by synthesis of the a double stranded polynucleotide with selected dideoxyribonucleotides used to introduce the nick as will be understood by a skilled person. Additional approaches will also be identifiable by the skilled person directed to obtain a passenger strand in which two of the nucleotides forming the polynucleotide chain engaged in the complementary binding with the guide strand are not directly covalently linked to each other.

FIGS. 24 and 25 illustrate an exemplary constructs including additional chemical modifications capable of influencing the cellular distribution and localization of tile saRNA complexes to increase or decrease the tile saRNA's sensitivity to the presence of activating RNA transcripts. FIG. 24 shows the exemplary molecular construct G6-L2-X3-Inosine in which the 5' toehold of the sensor strand X3 is modified with a tract of 5 deoxyinosines. These universal bases (see webpages idtdna.com/site/Catalog/Modifications/Product/1061 at the date of filing of the present disclosure) form weak base pairings with single stranded DNA and RNA bases, thereby allowing for example the construct to more efficiently sample cellular RNA transcripts. FIG. 25 shows the exemplary molecular construct G6-L2-X3-Inosine-HMW-PEG where construct is modified with an additional high molecular weight (10000 to 100000 Daltons) PEG to decrease spurious association with cellular proteins and modify the cellular distribution.

Figure 26:
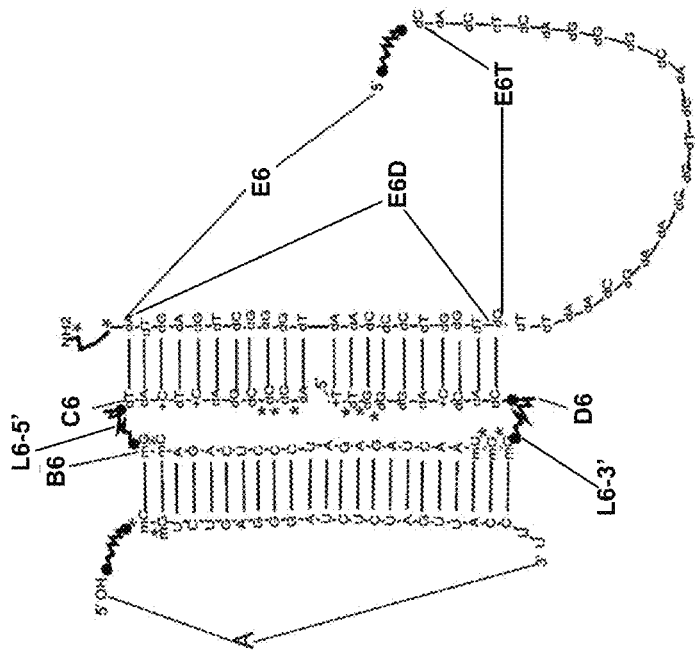
FIG. 26 shows the exemplary molecular construct A-B6C6D6-E6having a guide strand A (SEQ ID NO. 1), and a segment B6C6D6 comprising a passenger strand B6 (SEQ ID NO.91) attaching at a 5' protection segment C6 (SEQ ID NO: 92) and a 3' terminal protection segment D6 (SEQ ID NO: 90) both connected to the passenger strand B6 (SEQ ID NO:91) by C3 linkers L6-5' and L6-3' (indicated by black lines), and a sensor strand E6 (SEQ ID NO. 93). Sensor E6 comprises a displacement segment E6D (SEQ ID NO:95) directly attaching a 5' terminal toehold segment E6T (SEQ ID NO:94) which comprise an aptamer presented for binding.

FIG. 26 shows the exemplary molecular construct AB6-C6D6E6 configured so that the RNA sensor is replaced by a DNA aptamer based sensor for platelet derived growth factor B. In the constructs of FIG. 26, PDGF-B binds to the aptamer toehold and displaces the sensor strand E (the aptamer) from base-pairing to C and D (Douglas, S. M., Bachelet, I. & Church, G. M. A Logic-Gated Nanorobot for Targeted Transport of Molecular Payloads. *Science* 335, 831-834).

In some variation of the construct of FIG. 26 since the aptamer is unlikely to tolerate extensive chemical modifications that differ from the original SELEX generated sequence (Green, L. S., Jellinek, D., Jenison, R., Östman, A., Heldin, C.-H. & Janjic, N. Inhibitory DNA Ligands to Platelet-Derived Growth Factor B-Chain. *Biochemistry* 35, 14413-14424, doi:10.1021/bi961544+ (1996) thermodynamically stabilizing LNA modifications can be placed on the passenger strand overhangs, although this might compromise activation kinetics. In some variations chemical blocking groups can also be added to the 3' (C3+3' amino) and 5' (PEG) termini of the DNA aptamer to help reduce exonuclease degradation.

In some variations of the construct of FIG. 26, the two helices with 1.5 nm long PEG linkers to lower the geometric strain consequent to the inclusion in the duplex of DNA:DNA and RNA:RNA bases, wherein DNA:DNA duplexes are longer than RNA:RNA duplexes of equal base-pair number as will be understood by a skilled person.

Figures 27A, 27B:
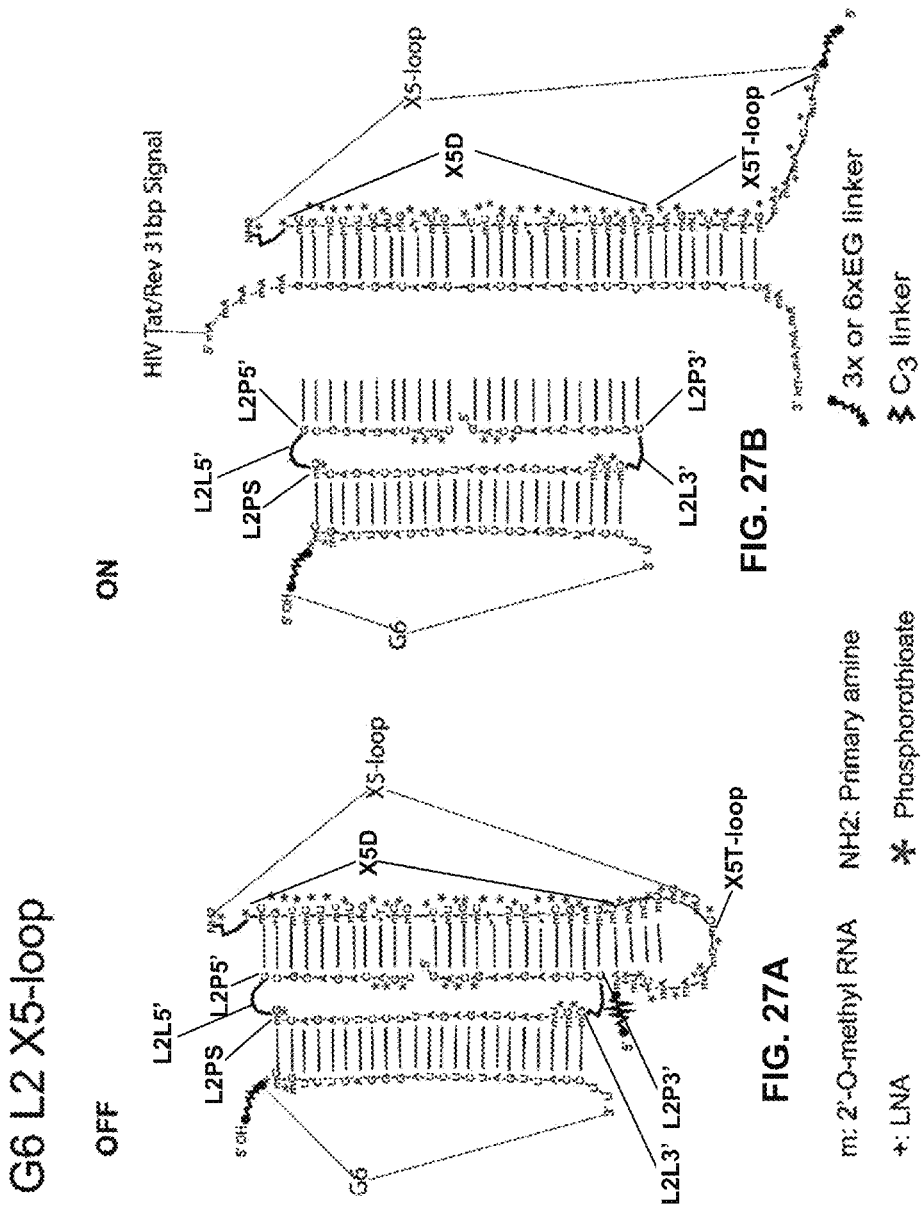
FIGS. 27A and FIG. 27B show the exemplary molecular construct G6 L2 X5-Loop having a guide strand G6 (SEQ ID NO. 8) a segment L2 comprising a passenger strand L2PSs (SEQ ID NO:17) attaching at the 5' terminus a second, 5' protection segment L2P5' (SEQ ID NO: 18) and attaching at the 3' terminus a 3' terminal protection segment L2P3' (SEQ ID NO: 16) both connected to the passenger strand B2 (SEQ ID NO: 17) by C3 linkers L2L5' and L2L3' (indicated by black lines), and a sensor strand X5-loop (SEQ ID NO. 96).

FIG. 27A and FIG. 27B show the exemplary molecular construct G6 L2 X5-Loop which provides a variation of the G6 L2 X5 construct to have a 5' toeholdX5T redesigned as a terminal loop X5T-loop. In the construct of FIGS. 27A and 27B activating RNA transcripts use the *mG* mU* mU *mC* sequence in the loop as the initial toehold. The *mA*mA tract is used to increase the size of the loop to lower steric hindrance for activation. Additional nucleotides or linkers can be used to further open up the loop. The terminal loop is held in place by four base-pair, including an LNA modification. To minimize toxicity, the size of the terminal loop's base-pairs plus the length of the sensor duplex is preferably below 28 total base pairs.

Signal activatable constructs and related components herein described can be designed and manufactured based on techniques described herein and/or identifiable by the skilled person upon reading of the present disclosure. In particular the configuration of the segments of the constructs can be identified and designed based on calculation of the thermodynamic stability of the various conformation of the segments and constructs as a whole. For example, thermodynamic stability of polynucleotide conformation dependents on several factors identifiable by a skilled person, including its i) chemical composition (for example, DNA: RNA duplex is less than RNA: RNA duplex); ii) base composition (for example, G/C base paring is more stable than A/T base paring, which is approximately as stable as G/T, G/U wobble base pairing, and the formation of a stable RNA hairpin requires at least 3 G/C base pairs or at least 5 A/U, G/U base pairs); iii) nearest neighbors such as presence of mismatches, open ends, and junctions near a base-pair can substantially influence its energy contribution according to the second-nearest neighbor model (for example, the stacking of successive base-pairs is primarily responsible for the stability of DNA helices); iv) non-canonical base pairing (for example, RNA and DNA can form triple helix and quadraplex structures via Hoogsteen base-pairing, which is less stable base pairings than canonical base pairing); v) Geometry (e.g. polynucleotide sequences can only adopt secondary structures that are geometrically consistent or similar with the known tertiary structural characteristics of RNA and DNA helices); vi) Environmental factors, such as pH value, counter-ion concentration and temperature and additional factors identifiable by a skilled person.

Accordingly, designing the polynucleotide sequences comprised in the signal activatable complexes can be performed identifying the combination of length, sequence, complementarity and substitutions that is associated with a desired relative thermodynamic stability resulting in the configuration herein described and the environment wherein the enzyme assisted molecular delivery is desired. Specific sequences of desired signal polynucleotides can be identified by a skilled person based on environment (and in particular, specific cells and tissues) where delivery is desired. For applications where molecular delivery in cells is desired, polynucleotide sequences can be designed according to the corresponding physiological conditions, such as approximately, pH 7.3-7.4, about150 millimolar potassium or sodium chloride or equivalent salt, and about 37° C.

For base pairing between unmodified DNA segments or between unmodified RNA segments, the base-pairing energies and the most stable secondary structure conformations can be estimated by computational methods known to and well established in the art. Several packages are available and published in documents also discussing in detail factors affecting the energy and stability of nucleic acid secondary structures. Exemplary publications describing the packages and factors comprise for i) NUPACK web server: J. N. Zadeh, et al., J Comput Chem, 32, 170-173, (2011); ii) NUPACK analysis algorithms: R. M. Dirks et al., SIAM Rev, 49, 65-88 (2007); R. M. Dirks et al., J Comput Chem, 24, 1664-1677 (2003); R. M. Dirks et al., J Comput Chem, 25, 1295-1304 (2004); iii) NUPACK design algorithms: J. N. Zadeh et al., J Comput Chem, 32, 439-452, (2011); iv) mfold web server: M. Zuker, Nucleic Acids Res. 31 (13), 3406-3415, (2003); A. Waugh et al., RNA 8 (6), 707-717, (2002); M. Zuker et al., RNA 4, 669-679, (1998); v) UNAFold & mfold: N. R. Markham et al., Bioinformatics: Volume 2, Chapter 1, pp 3-31, Humana Press Inc., (2008); M. Zuker, et al., 11-43, J. Barciszewski and B. F. C. Clark, eds., NATO ASI Series, Kluwer Academic Publishers, Dordrecht, NL, (1999); M. Zuker, A. M. Griffin and H. G. Griffin eds. Methods in Molecular Biology, Humana Press Inc., 267-294, (1994); J. A. Jaeger et al., Methods in Enzymology 183, 281-306 (1990); M. Zuker, Science 244, 48-52, (1989); vi) Free energies for RNA: D. H. Mathews et al., J. Mol.

Biol. 288, 911-940, (1999); A. E. Walter et al., Proc. Natl. Acad. Sci. USA 91, 9218-9222, (1994); vii) Methods and theory of RNA secondary structure prediction: D. H. Mathews et al., Secondary Structure Prediction. In Current Protocols in Nucleic Acid Chemistry S. Beaucage, D. E. Bergstrom, G. D. Glick, and R. A. Jones eds., John Wiley & Sons, New York, 11.2.1-11.2.10, (2007); D. H. Mathews et al., Predicting RNA Secondary Structure. In The RNA World, R. F. Gesteland, T. R. Cech and J. F. Atkins eds., 3rd edition, Cold Spring Harbor Laboratory Press, Cold Spring Harbor, N.Y., Chapter 22, (2006); D. H. Mathews et al. 3rd edition, John Wiley & Sons, New York, Chapter 7, (2005); D. H. Mathews et al., (2004); M. Zuker, Bull. Mathematical Biology 46, 591-621, (1984); M. Zuker et al., Nucleic Acids Res. 9, 133-148, (1981) D.H Mathews et al Folding and Finding RNA Secondary Structure in Cold Spring Harb Perspect Biol. (2010); viii) Exemplary mfold & UNAFold applications: J.-M. Rouillard et al., Nucleic Acids Res. 31 (12), 3057-3062 (2003); J.-M. Rouillard, et al., Bioinformatics 18 (3), 486-487, (2002). In addition, since some polynucleotide structures typically fluctuate between an ensemble of secondary structure conformations, the composition of the relevant ensemble can be determined using computational methods known in the art (see for example, see Sfold web server for statistical folding and rational design of nucleic acids. Nucleic Acids Res. 32 Web Server issue, W135-W141, (2004), and Ye Ding et al., RNA 11, 1157-1166. 2005, herein incorporated by reference in its entirety).

Accordingly, in several embodiments, design of a polynucleotide sequence of the targeting and sensor domains of the signal activatable construct herein described, can be performed for sequences or portions of sequences consisting of unmodified DNA and/or RNA base pairs, by computational methods and/or software packages to calculate the free energy of the sequence and the secondary structure conformation. In embodiments, wherein polynucleotide sequences comprise derivatives of nucleotides, such as chemically modified bases and analogues, and/or chimeric polynucleotide sequences composed of a mixture of deoxyribonucleotides and ribonucleotides, design can be performed by computationally designing unmodified RNA structures with the desired secondary structure conformations and thermodynamic stability, and then introducing one or more chemical modifications to achieve the desired thermodynamic stability.

In some embodiments addition of chemical moieties can be performed to direct or control location and/or activation in selected environment as will be understood by a skilled person. For example the addition of an inosine tract (2 to 20 inosines) to the end of the toehold domain could help the construct sample RNA transcript inside cells by providing transient base-pairing to arbitrary single stranded RNA domains. Also aptamers or chemical moieties may be added to the 5' terminus of the guide strand or the 3' or 5' termini of the sensor strand to attach to cellular structures or chemical moieties that could direct localization, RNA sampling, or aid delivery Attachment of the saRNA to cellular proteins, RNA structures, or chemical moieties known to localize in certain cellular compartments (nucleus, mitochondria, membranes), in some embodiments can help the saRNA preferentially sample RNA transcripts in those compartments. Attachment of the construct to other RNA binding domains such as polypeptides (see e.g. Tan, R. & Frankel, A. D. in *Proceedings of the National Academy of Sciences* 92, 5282-5286 (1995) proteins (see e.g. Castello, A., in. *Cell* 149, 1393-1406, (2012) and Dreyfuss, G., et al in *Nat Rev Mol Cell Biol* 3, 195-205 (2002)), cationic polymers, or RNA structures such as ribosome (e.g. Yusupov, M. M., et al in. *Science* 292, 883-896, (2001) and Kahan, M., et al in *Physica D: Nonlinear Phenomena* 237, 1165-1172 (2008))., and tRNA (Scherer, L. J., in *Nucleic Acids Research* 35, 2620-2628, (2007)) can also increase targeting of saRNA sample RNA transcripts in the cell.

The signal activatable construct designed according the present disclosure can be synthesized using standard methods for oligonucleotide synthesis well establish in the art, for example, see Piet Herdewijn (2005), herein incorporated by reference in its entirety.

The synthesized oligonucleotide can be allowed to form its secondary structure under a desirable physiological condition, (e.g. 1× phosphate buffered saline at pH 7.5 with 1 mmolar concentration MgCl2 at 37° C.). The formed secondary structure can be tested using standard methods known in the art such as chemical mapping or NMR (see e.g. Kertesz, M., et al in. *Nature* 467, 103-107, (2010), Mathews, D. H., et al in. *Cold Spring Harbor Perspectives in Biology* 2, (2010), and Watts, J. M., et al in. *Nature* 460, 711-716, (2009)). For example, see Stephen Neidle, Neidle, S. *Principles of nucleic acid structure*. (Academic Press, 2010) herein incorporated by reference in its entirety. The designed construct can be further modified, according to the test result, by introducing or removing chemical modifications, mismatches, wobble pairings, as necessary, until the desired structure is obtained. Reference is made in this connection to the exemplary procedure provided in the Examples section.

In some embodiments, the construct is configured to minimize immune responses. In these embodiments, each consecutive 30 base pairs duplex can have at least 5% 2'-O-methyl modifications (Molecular Therapy (2006) 13, 494-505, herein incorporated by reference in its entirety) or one or two mismatches. In other embodiments, the construct is configured to stimulate immune responses. In these embodiments, the construct can comprises at least one consecutive 30 base-pair duplex with no 2'-O-methyl modifications when the construct is in the activated conformation. For example, the total length of the toehold segment and the sensor segment can be at least 30 nucleotides without 2'-O-methyl modifications, and will be perfectly base paired with the signal polynucleotide sequence.

In some embodiments, the guide strand is configured to interfere with a target intracellular process of the cells through RNAi in presence of the signal polynucleotide. Accordingly suitable targeting domain include siRNA, microRNA and additional duplex structure suitable to be used in connection with RNA interfering.

The term "RNA interfering" or "RNAi" as used herein refers to a mechanism or pathway of living cells that controls level of gene expression that has been found in many eukaryotes, including animals. The RNAi pathway has many important roles, including but not limited to defending cells against parasitic genes such as viral and transposon genes, directing development and regulating gene expression in general. The enzyme Dicer, which is an endoribonuclease in the RNAse III family, initiates the RNAi pathway by cleaving double-stranded RNA (dsRNA) molecules into short fragments of dsRNAs about 20-25 nucleotides in length. Dicer contains two RNase III domains and one PAZ domain; the distance between these two regions of the molecule is determined by the length and angle of the connector helix and determines the length of the siRNAs it produces. Dicer cleaves with the highest efficiency dsRNA substrates 21 bp and longer with a two-base overhang at the 3' end.

The small fragments of dsRNAs produced by Dicer are known as small interfering RNA (siRNA). The term "small interfering RNA" or "siRNA", sometimes also known as short interfering RNA or silencing RNA, refers to a class of dsRNA molecules which is typically 20-25 nucleotides in length and plays a variety of roles in biology. The most notable role of siRNA is its involvement in the RNAi pathway. In addition to its role in the RNAi pathway, siRNA also acts in RNAi-related pathways, including but not limited to several antiviral pathways and shaping chromatin structure of a genome.

Each siRNA is unwound into two single-stranded (ss) ssRNAs, namely the passenger strand and the guide strand. The passenger strand is degraded, while the guide strand is incorporated into a multiprotein complex, known as the RNA-induced silencing complex (RICS). RICS uses the incorporated ssRNA as a template for recognizing a target messenger RNA (mRNA) molecule that has complementary sequence to the ssRNA. Upon binding to the target mRNA, the catalytic component of RICS, Argonaute, is activated, which is an endonuclease that degrades the bound mRNA molecule.

Similar to siRNAs, microRNAs (miRNAs) also mediate the RNAi pathway. The term "microRNA" or "miRNA" as used herein indicates a class of short RNA molecules of about 22 nucleotides in length, which are found in most eukaryotic cells. miRNAs are generally known as post-transcriptional regulators that bind to complementary sequences on target mRNA transcripts, usually resulting in translational repression and gene silencing.

miRNAs are encoded by miRNA genes and are initially transcribed into primary miRNAs (pri-miRNA), which can be hundreds or thousands of nucleotides in length and contain from one to six miRNA precursors in hairpin loop structures. These hairpin loop structures are composed of about 70 nucleotides each, and can be further processed to become precursor-miRNAs (pre-miRNA) having a hairpin-loop structure and a two-base overhang at its 3' end.

In the cytoplasm, the pre-miRNA hairpin is cleaved by the RNase III enzyme Dicer. Dicer interacts with the 3' end of the hairpin and cuts away the loop joining the 3' and 5' arms, yielding an imperfect miRNA:miRNA duplex about 22 nucleotides in length. Overall hairpin length and loop size influence the efficiency of Dicer processing, and the imperfect nature of the miRNA:miRNA base pairing also affects cleavage. Although either strand of the duplex can potentially act as a functional miRNA, only one strand is usually incorporated into RICS where the miRNA and its mRNA target interact.

In those embodiments, wherein the guide strand is configured for interfering a target intracellular process through RNAi, the double-stranded duplex typically formed by the guide strand and passenger strands can have a melting temperature (Tm) of at least about 25° C. In particular, the 5' terminal nucleotide of the guide strand can be base paired to one of the passenger strands. In some embodiments, nicked double-stranded duplex formed by the guide strand and passenger strands are stable under conditions of the environment where delivery will be performed. In embodiments where RNAi is performed in mammals the nicked double-stranded duplex typically formed by the guide strand and passenger strand can have a melting temperature (Tm) of at least about 37° C.

In some embodiments, a double-stranded polynucleotide duplex with a 3' overhang of 2 nucleotides in length is most efficiently bound by the PAZ domain of the endonucleases enzyme Dicer (Jin-Biao Ma, et al, 2004). In human cells, RNAse H commonly cleaves the RNA sequence of a DNA:RNA duplex at a position that is 5 nucleotides from the 5' end of the RNA sequence forming the duplex. If the duplex is longer than 7 base pairs, RNAse H can cleave at additional positions to the 3' of the first cleavage site. Accordingly, in embodiments using an RNAse H substrate, the DNA:RNA duplex formed in the activated conformation according to the current disclosure is at least 5 nucleotides, and in particular 7-8 nucleotides.

In those embodiments where the targeting domain is configured to interfere with a target intracellular process of the cells through RNAi, the passenger strand and the guide strand are at least 16 nucleotides in length. In particular, in some embodiments, they are no shorter than 22 nucleotides. In particular, in some embodiments, the guide strand is at least 2 nucleotides longer than the passenger strand. Accordingly, in some embodiment, the double-stranded duplex formed by the guide strand and passenger strand has a 2-base single strand overhang at the 3' terminus of the guide strand.

In particular, in some embodiments, the double-stranded duplex formed by the passenger strand and the guide strand is no longer than 30 consecutive base pairs, if the duplex comprises only unmodified ribonucleotides. In other embodiments, the double-stranded duplex formed by the passenger strand and the guide strand can be longer than 30 base pairs, if the duplex comprises mismatches and/or modified ribonucleotides. The mismatches and/or modifications are likely to prevent activation of innate immune system responses. Exemplary modifications to the passenger strand and the guide strand include but are not limited to 2'-O-methylation, 2'-Fluoro modifications, 2'-amino modifications, and inclusion of LNA or PNA nucleotides. In particular, 2'-O-methyl, 2' Fluoro, 2' amino, LNA and PNA are expected to improve stability of the structure.

Further, in these embodiments, at least one at least one strand of the duplex is configured for interfering with a target intracellular process through RNAi. In some embodiments, the at least one strand is at least partially complementary to a target gene sequence for silencing that gene through RNAi. In other embodiments, the at least one strand is at least partially complementary to a common sequence shared by multiple genes or members of a gene family. In other embodiments, the at least one strand is configured to be incorporated into a protein complex to activate the complex and/or the substrate of the complex or to initiate a cascade of activation of downstream effectors of the complex. In some embodiments, from 2 to 8 bases of the at least one strand incorporated into RISC is complementary with a target gene forming a "seed region" usually considered particularly important for RNAi activity as will be understood by a skilled person.

According to several embodiments, the duplex formed by the guide strand and the passenger strand has a blunt end at the 3' end of the guide strand. The duplex formed by the passenger strand and the guide strand is at least 21 bp long. In particular, the first 21 nucleotide from the 3' terminus of the guide strand are configured for interfering with a target intracellular process through RNAi, and the $21^{st}$ and $22^{nd}$ 5' terminus of the passenger strand and from the 3' terminus of the passenger strand and the guide strand are unmodified RNA nucleotides so as to allow efficient Dicer processing after signal activation of the signal activatable construct.

In particular, in some embodiments, at least one of the passenger strand and the guide strand comprises a sequence homologous to an endogenous microRNA sequence. More particularly, in some embodiments, the passenger strand and the guide strand have the exact same sequence and structure as a known or predicted pre-miRNA. In some embodiments, at least one of the passenger strands and the guide strands has the same sequence as a known or predicted mammalian miRNA. In some embodiments, the double-stranded duplex formed by the passenger and guide strands comprises mismatches and/or bulges configured to mimic a known or predicted mammalian miRNA. In some embodiments at least one of the passenger strands or guide strands is homologous to the sequence of a known or predicted mammalian miRNA. The term "homologous" or "homology" used herein with respect to biomolecule sequences as indicates sequence similarity between at least two sequences. In particular, according to the current disclosure, a homologous sequence of a mammalian miRNA can have the same sequence located at base position 2-7 from the 5' terminus of the guide strand of the miRNA.

In some embodiments, a system for intracellular information processing and controlling of cells is described. The system comprising two or more signal activatable constructs as described for simultaneous combined or sequential use in the cells, in which the targeting domain of at least one construct of the two or more constructs is configured to release a second signal in the presence of the signal polynucleotide, and the second signal is configured to activate one or more construct of the two or more constructs.

In one embodiment, a sensor gated siRNA can be provided with selectively activated RNAi activity in cells expressing a specific RNA sequence. The activating sequence switches ON the siRNA by binding to its sensor domain and triggering internal conformational changes that induce processing by endogenous XRN1 or other enzymes. The result is an active Dicer substrate that can direct targeted RNAi.

As disclosed herein, the signal activated constructs and related components herein described can be provided as a part of systems for molecule delivery, including any of the deliveries described herein. The systems can be provided in the form of kits of parts. In a kit of parts, the signal activated constructs and related components and other reagents to perform delivery can be comprised in the kit independently. The signal activated constructs and related components can be included in one or more compositions, and each construct or component can be in a composition together with a suitable vehicle.

Additional components can include labeled molecules and in particular, labeled polynucleotides, labeled antibodies, labels, microfluidic chip, reference standards, and additional components identifiable by a skilled person upon reading of the present disclosure. The terms "label" and "labeled molecule" as used herein as a component of a complex or molecule referring to a molecule capable of detection, including but not limited to radioactive isotopes, fluorophores, chemiluminescent dyes, chromophores, enzymes, enzymes substrates, enzyme cofactors, enzyme inhibitors, dyes, metal ions, nanoparticles, metal sols, ligands (such as biotin, avidin, streptavidin or haptens) and the like. The term "fluorophore" refers to a substance or a portion thereof which is capable of exhibiting fluorescence in a detectable image. As a consequence, the wording "labeling signal" as used herein indicates the signal emitted from the label that allows detection of the label, including but not limited to radioactivity, fluorescence, chemiluminescence, production of a compound in outcome of an enzymatic reaction and the like.

In some embodiments, detection of molecule delivery can be carried either via fluorescent based readouts, in which the labeled antibody is labeled with fluorophore, which includes, but not exhaustively, small molecular dyes, protein chromophores, quantum dots, and gold nanoparticles. Additional techniques are identifiable by a skilled person upon reading of the present disclosure and will not be further discussed in detail.

In particular, the components of the kit can be provided, with suitable instructions and other necessary reagents, in order to perform the methods here described. The kit will normally contain the compositions in separate containers. Instructions, for example written or audio instructions, on paper or electronic support such as tapes or CD-ROMs, for carrying out the assay, will usually be included in the kit. The kit can also contain, depending on the particular method used, other packaged reagents and materials (i.e. wash buffers and the like).

In some embodiments, one or more signal activated constructs and/or related components, (e.g., sensor domain) herein described are comprised in a composition together with a suitable vehicle. The term "vehicle" as used herein indicates any of various media acting usually as solvents, carriers, binders or diluents for signal activated constructs and related components that are comprised in the composition as an active ingredient. In particular, the composition including the signal activated constructs and related components can be used in one of the methods or systems herein described.

In some embodiments, a composition for signal activated molecular delivery can comprise one or more of the signal activatable construct as described together with a suitable vehicle. In some embodiments, the vehicle is suitable for delivering the signal activatable construct to cells. Exemplary suitable vehicles according to the current disclosure include but are not limited to nanoparticle, such as cyclodextrin, gold nanoparticle and dendrimer; liposome and liposome analogues; conjugated aptamer; conjugated antibody; conjugated cell penetrating peptide or peptide analogue; carbon nanotubes; conjugated fatty acids and quantum dots.

In some embodiments the signal activated constructs herein described can be used in method for controlled release of a targeting domain from an activated complex. The methods comprise contacting the activated molecular complex with a signal molecule capable of binding to the toehold segment for a time and under condition to allow release of the targeting domain from the activated molecular complex. In some embodiments the contacting can be performed with methods identifiable by a skilled person that will depend on specific target taking into account the selective activation allows a contacting in environment other than the one where the target is located (e.g. different cells and tissues). For example in embodiments where a selective contacting in one or more specific cell types is desired one or more constructs of this disclosure can be used comprising moieties allowing a targeted delivery of the construct to one or more specific cells types (e.g. by including RNA aptamers to cell surface proteins that will bind one or more target cell types). In embodiments where a more general contacting is desired (e.g. in vivo) the administration can be performed with or without moiety that maximize delivery in various cell types (e.g. pegylation).

In embodiments herein described, the concentrations of constructs to be provided in the contacting depend on the structure of the construct and the related efficiency and on the concentration of the target and can be determined based on the desired effect as will be understood by a skilled person. For example in an exemplary embodiments where knock out of a target in a blood cell is desired, an initial verification of the concentration of the specific construct to be used can be performed by providing the specific RNA, designing a construct based on the specific RNA and the specific signal and verifying the concentration of the related ON and OFF conformation for the construct and testing it on the target with a series of dilutions (e.g. 10 fold dilutions series of each of ON and OFF construct) and detecting the knock down of the target gene and/or target protein with methods identifiable by a skilled person, such as real time quantitative PCR (qRT PCR) for the target mRNA and/or Western Blotting for the protein with a preferable use of methods allowing quantitative detection. On this basis it is possible to select the concentration range of the specific constructs that provides the desired effect. In some embodiments this method can be performed in vitro. For example the contacting can be performed in immortalized cell lines, and/or primary cells depending on the experimental settings. In other embodiments, contacting can be performed in vivo for example in animals e.g. by using one or more set of concentrations tracking the construct (e.g. with a fluorophore) to be able to verify the delivery in the cells comprising the target. In some embodiments following identification of effective concentrations of the constructs to be used in vivo performed in animal models, the concentration can be used to target a gene or a protein in individuals according to approached identifiable by a skilled person.

In some embodiments, the signal activated constructs and related components herein described are comprised in pharmaceutical compositions together with an excipient or diluent.

The term "excipient" as used herein indicates an inactive substance used as a carrier for the active ingredients of a medication. Suitable excipients for the pharmaceutical compositions herein described include any substance that enhances the ability of the body of an individual to absorb the signal activated constructs and related components herein described or combinations thereof. Suitable excipients also include any substance that can be used to bulk up formulations with the peptides or combinations thereof, to allow for convenient and accurate dosage. In addition to their use in the single-dosage quantity, excipients can be used in the manufacturing process to aid in the handling of the peptides or combinations thereof concerned. Depending on the route of administration, and form of medication, different excipients can be used. Exemplary excipients include, but are not limited to, antiadherents, binders, coatings, disintegrants, fillers, flavors (such as sweeteners) and colors, glidants, lubricants, preservatives, sorbents.

The term "diluent" as used herein indicates a diluting agent which is issued to dilute or carry an active ingredient of a composition. Suitable diluents include any substance that can decrease the viscosity of a medicinal preparation.

In particular, in some embodiments, disclosed are pharmaceutical compositions which contain at least one signal activated constructs and related components as herein described, in combination with one or more compatible and pharmaceutically acceptable vehicles, and in particular with pharmaceutically acceptable diluents or excipients. In those pharmaceutical compositions the signal activated constructs and related components can be administered as an active ingredient for treatment or prevention of a condition in an individual.

The term "treatment" as used herein indicates any activity that is part of a medical care for, or deals with, a condition, medically or surgically.

The term "prevention" as used herein indicates any activity which reduces the burden of mortality or morbidity from a condition in an individual. This takes place at primary, secondary and tertiary prevention levels, wherein: a) primary prevention avoids the development of a disease; b) secondary prevention activities are aimed at early disease treatment, thereby increasing opportunities for interventions to prevent progression of the disease and emergence of symptoms; and c) tertiary prevention reduces the negative impact of an already established disease by restoring function and reducing disease-related complications.

The term "condition" as used herein indicates a physical status of the body of an individual (as a whole or as one or more of its parts), that does not conform to a standard physical status associated with a state of complete physical, mental and social well-being for the individual. Conditions herein described include but are not limited disorders and diseases wherein the term "disorder" indicates a condition of the living individual that is associated to a functional abnormality of the body or of any of its parts, and the term "disease" indicates a condition of the living individual that impairs normal functioning of the body or of any of its parts and is typically manifested by distinguishing signs and symptoms.

The wording "associated to" as used herein with reference to two items indicates a relation between the two items such that the occurrence of a first item is accompanied by the occurrence of the second item, which includes but is not limited to a cause-effect relation and sign/symptoms-disease relation.

The term "individual" as used herein in the context of treatment includes a single biological organism, including but not limited to, animals and in particular higher animals and in particular vertebrates such as mammals and in particular human beings.

In some embodiments, a method for treating a disease in an individual through signal activated molecular delivery in cells, comprises administering to the individual an effective amount of one or more of the signal activatable constructs herein described and in particular one or more of the molecular complexes, activatable molecular complex, activated complexes and/or exonuclease resistant complexes herein described, in effective concentration which can be identified according to approaches identifiable by a skilled person upon reading of the present disclosure (e.g. by determining effective concentrations in immortalized cell lines, primary cell lines and the in animal models followed by clinical trials in individuals). In some embodiments, a multi-stage therapeutic nanoparticles can be provided that utilize enzyme activated release of a cargo in a cell to achieve controlled step-wise disassembly and cargo release in target environment such as solid tumor microenvironments.

A skilled person will be able to identify further application and in particular therapeutic applications as well as cargo molecules to be used as active agents in the treatment and design a corresponding signal activatable construct to be administered according to the features of the construct and the desired effect. In particular, in applications wherein signal activatable construct is desired system administration of the agent can be performed. In embodiments, where an activated construct is instead used, topical administration to the specific target cell and tissue can be performed.

Further advantages and characteristics of the present disclosure will become more apparent hereinafter from the following detailed disclosure by way or illustration only with reference to an experimental section.

EXAMPLES

The signal activatable constructs herein disclosed are further illustrated in the following examples, which are provided by way of illustration and are not intended to be limiting.

The following material and methods were used in the experiments illustrated in the following examples.

Transfections for Luciferase analyses: Briefly, HCT116 cells were transfected with the indicated exemplary constructs, duplexes, or controls at the indicated final concentrations (ranging from 0.04 to 5 nMolar) with pBluescript (pBS) as carrier, using Lipofectamine2000 according to the manufacturer's (Invitrogen) protocol. The cell medium was replaced at 18 hours post-transfection and lysates collected at 24 hours post-transfection for analysis. Specifically, one day before transfection, cells were seeded in growth medium in 48-well cluster plates without antibiotics so that cells would reach 90-95% confluency at the time of transfection (as recommended by Invitrogen protocols). Each well was transfected with a final DNA mix consisting of: 40 nanograms (ng) psiCHECK (Promega) plasmid bearing a Firefly luciferase (Fluc) control reporter and a Renilla luciferase (Fluc) reporter with the target in the 3' UTR (untranslated region); 120 ng pBluescript carrier DNA; and the experimental constructs or duplex diluted in 10 mM Tris/1 mM EDTA pH 6.7 (TE). The final DNA mix therefore consisted of 16 ul of target mix in OptiMEM and 4 ul of experimental DNA at 50× the final desired concentration in TE. To reduce sample to sample variability, the psiCHECK target mix was made in batch in OptiMEM and aliquoted to allow 3 technical replicates (wells) for each condition prior to addition of the experimental DNA. An equal volume of a 1/50 dilution of Lipofectamine2000 in OptiMEM was added (bringing the volume to ⅕th the final) and incubated according to the manufacturer's instructions. The liposome/DNA constructs or duplexes were added, along with fresh complete medium to the cells to give a final volume of 200 ul. Medium was replaced at 18 hours post-transfection. At 24 hours, samples were collected for luciferase analysis using the Promega Dual-Luciferase Reporter Assay System kit according to the manufacturer's protocol. For each replicate, the Renilla luciferase (target) value was normalized to the Firefly luciferase (internal control) value. Triplicates were averaged, and the experimental values as a fraction of carrier alone (no experimental construct), whose value is set at 1. Therefore, the greater the RNAi activity, the lower the relative luciferase units.

Theoretical and experimental prediction tools: the following theoretical and experimental prediction tools can also be used in procedures to make and use activatable construct of the present disclosure: Thermodynamic prediction tools for RNA and DNA (e.g. see webpages nupack.org, mfold.rna.albany.edu/?q=mfold and sfold.wadsworth.org/cgi -bin/index.pl at the date of filing of the present disclosure); Thermodynamic prediction tools and structure design tools for LNA modified oligos (e.g. web page exiqon.com/oligo-tools at the date of filing of the present disclosure); Experiments for determining melting temperature (e.g. Temperature regulated UV-Vis and High precision calorimetry techniques identifiable by a skilled person); Experimental and theoretical measurements for determining end to end distance (e.g. by molecular simulation, FRET measurements techniques, TEM or AFM measurements if nanoparticles or carbon nanotubes are tethered at either end, according to approaches identifiable by a skilled person); Experimental measurements of general structure and base-paired ness (e.g. by Gel migration assay on native structures and nuclease protection mapping to understand secondary structure techniques identifiable by a skilled person) and Experimental measurements of strand displacement (e.g. by incubation of 1 nM pre-annealed OFF state construct with 1 nM activating transcript at 37 C for 1 hour in PBS buffer, followed by running of native PAGE assay and select constructs where at least 10 percent of constructs switch to activated form); and Experimental measurements of activation specificity (e.g. by performing the same procedure indicated in this paragraph to verify strand displacement with strands that are configured not to activate the construct and select the constructs where no activation be detected within a set time limit e.g. an 1 hour).

Example 1

Exemplary Activatable Constructs

Exemplary molecular constructs were provided having the features summarized in Table 1 below. All sequences are listed in the 5' to 3' direction.

TABLE 1

| RNA Complexes and Component Strands | | | |
|---|---|---|---|
| Complexes Abbreviation | Sequences | SEQ ID NOs | FIG. |
| AB-CDE | | | FIGS. 3A, 3B, 9 (panels A-D) and 10A |
| A | PEG*mC*mG UCU GAG GGA UCU CUA GUU ACC UU | SEQ ID NO.: 1 | |
| D/B/C | G*A*C*GAA GAG CUC C3 mG*mG*mU AAC UAG AGA UCC CUC AGA*mC*mG C3 GCG GAG AC*A*G*C | SEQ ID NO. 2; SEQ ID NO. 3; SEQ ID NO. 4 | |
| E | PEG*mG*mU*mU* <u>C+</u> mU*mG*mA*mU*mG*mA*mG* mC* <u>T+</u> *mC* mU*<u>T+</u>*mC* mG*mU*<u>C+</u> *mG*mC*<u>T+</u>* mG*mU*mC* mU*mC*mC* <u>G+</u>*mC* C3 *NH₂ | SEQ ID NO. 5 | |
| ET | PEG*mG*mU*mU* +C*mU*mG*mA*mU* | SEQ ID NO: 6 | |

TABLE 1-continued

RNA Complexes and Component Strands

| Complexes Abbreviation | Sequences | SEQ ID NOs | FIG. |
|---|---|---|---|
| ED | mG*mA*mG* mC* +T *mC* mU*+T*mC* mG*mU*+C *mG*mC*+T* mG*mU*mC* mU*mC*mC* +G*mC* C3 *NH$_2$ | SEQ ID NO; 7 | |
| G6 L1 M1/G6 L1 X1/ | | | FIGS. 12A and 12B/FIGS. 13A and 13B |
| G6 | 9s*mC*mG UCU GAG GGA UCU CUA GUU ACC UU | SEQ ID NO. 8 | |
| L1P3'/L1Ps/ L1P5' | G*A*C*G*A A GAG CUC C3 mG*mG*mU AAC UAG AGA UCC CUC AGA*mC*mG C3 GCG GAG*A*C*A*G*C | SEQ ID NO. 9; SEQ ID NO. 10; SEQ ID NO. 11 | |
| M1 | *PEG*mG*mU*mU* +C mU*mG*mA*mU*mG*mA*mG* mC* +T *mC* mU*+T*mC* mG*mU*+C *mG*mC*+T* mG*mU*mC* mU*mC*mC* +G*mC* C3 *NH$_2$ | SEQ ID NO. 12 | |
| X1 | 9s*mU*mC*mU*mG*mA*mU*mU* *mG*mA*mG* mC*mU*mC* mU*mU*mC* mG*mU*mC *mG*mC*mU* mG*mU*mC* mU*mC*mC* mG*mC* C3 *idT | SEQ ID NO. 13 | |
| X1 T | 9s*mU*mC*mU*mG*mA*mU*mU* | SEQ ID NO. 14 | |
| X1D | *mG*mA*mG* mC*mU*mC* mU*mU*mC* mG*mU*mC *mG*mC*mU* mG*mU*mC* mU*mC*mC* mG*mC* C3 *idT | SEQ ID NO. 15 | |
| G6 L2 X2 | | | FIGS. 14A and 14B |
| G6 | 9s*mC*mG UCU GAG GGA UCU CUA GUU ACC UU | SEQ ID NO. 8 | |
| L2P3'/L2PS/ L2P5' | G*A*C*G AAG AGC UC C3 mG*mG*mU AAC UAG AGA UCC CUC AGA C*mG C3 GCG GAG AC*A*G*C | SEQ ID NO. 16 SEQ ID NO. 17; SEQ ID NO. 18 | |
| X2 | 9s*mU*mC*mU*mG*mA*mU*mU*mG*m A*mG*mC*mU*mC*mU*mU*mC*mG*mU *mC *mG*mC*mU* mG*mU*mC* mU*mC*mC* mG*mC*c3*(3'C6 Amino) | SEQ ID NO. 19 | |
| X2T | 9s*mU*mC*mU*mG*mA*mU*mU | SEQ ID NO. 20 | |
| X2D | *mG*mA*mG*mC*mU*mC*mU*mU*mC* mG*mU*mC *mG*mC*mU* mG*mU*mC* mU*mC*mC* mG*mC*c3*(3'C6 Amino) | SEQ ID NO. 21 | |
| G6 L2 X3 | | | FIGS. 15A and 15B, |
| G6 | 9s*mC*mG UCU GAG GGA UCU CUA GUU ACC UU | SEQ ID NO. 8 | |
| L2P3'/L2Ps/ L2P5' | G*A*C*G AAG AGC UC C3 mG*mG*mU AAC UAG AGA UCC CUC AGA mC*mG C3 GCG GAG AC*A*G*C | SEQ ID NO. 16; SEQ ID NO. 17; SEQ ID NO. 18 | |
| X3 | /5Sp9/mU*mC*mU*mG*mA*mU*mU*mG* mA*mG*mC*+T*mC*mU*+T*mC*mG*m U*+C*mG*mC*+T*mG*mU*mC*mU*mC* mC*+G*mC*/3AmMO/ | SEQ ID NO. 22 | |
| X3T | /5Sp9/mU*mC*mU*mG*mA*mU*mU* | SEQ ID NO: 23 | See also FIGS. 18A |

TABLE 1-continued

RNA Complexes and Component Strands

| Complexes Abbreviation | Sequences | SEQ ID NOs | FIG. |
|---|---|---|---|
| X3D | mG*mA*mG*mC*+T*mC*mU*+T*mC*m G*mU*+C*mG*mC*+T*mG*mU*mC*mU* mC*mC*+G*mC*/3AmMO/ | SEQ ID NO: 24 | |
| G6 L2 X5 | | | FIGS. 16A and 16B |
| G6 | 9s*mC*mG UCU GAG GGA UCU CUA GUU ACC UU | SEQ ID NO. 8 | |
| L2P3'/L2PS/ L2P5' | G*A*C*G AAG AGC UC C3 mG*mG*mU AAC UAG AGA UCC CUC AGA mC*mG C3 GCG GAG AC*A*G*C | SEQ ID NO. 16; SEQ ID NO. 17; SEQ ID NO. 18 | |
| X5 | //5Sp9/ mG*mU*mU*mC*mU*mG*mA*mU*mG* mA*mG*mC*+T*mC*mU*+T*mC*mG*m U*+C*mG*mC*+T*mG*mU*mC*mU*mC* mC*+G*mC*/3AmMO/ | SEQ ID NO. 25 | |
| X5T | //5Sp9/ mG*mU*mU*mC*mU*mG*mA*mU* | SEQ ID NO: 26 | See also FIG. 18B |
| X5D | mG*mA*mG*mC*+T*mC*mU*+T*mC*m G*mU*+C*mG*mC*+T*mG*mU*mC*mU* mC*mC*+G*mC*/3AmMO/ | SEQ ID NO 27 | |
| G6 L2 X6 | | | FIGS. 17A and 17B |
| G6 | 9s*mC*mG UCU GAG GGA UCU CUA GUU ACC UU | SEQ ID NO. 8 | |
| L2P3'/L2Ps/ L2P5' | G*A*C*G AAG AGC UC C3 mG*mG*mU AAC UAG AGA UCC CUC AGA C*mG C3 GCG GAG AC*A*G*C | SEQ ID NO. 16; SEQ ID NO. 17; SEQ ID NO. 18 | |
| X6 | /5Sp9/mG*mU*mU*+C*mU*mG*mA*mU* mG*mA*mG*mC*+T*mC*mU*+T*mC*m G*mU*+C*mG*mC*+T*mG*mU*mC*mU* mC*mC*+G*mC*/3AmMO/ | SEQ ID NO. 28 | |
| X6T | /5Sp9/mG*mU*mU*+C*mU*mG*mA*mU* | SEQ ID NO: 29 | See also FIG. 18C |
| X6D | mG*mA*mG*mC*+T*mC*mU*+T*mC*m G*mU*+C*mG*mC*+T*mG*mU*mC*mU* mC*mC*+G*mC*/3AmMO/ | SEQ ID NO; 30 | |
| G6 L3 X7 | | | |
| G6 | 9s*mC*mG UCU GAG GGA UCU CUA GUU ACC UU | SEQ ID NO. 8 | |
| L3P3'/LP/ LP5 | G*C*G*GAGACAGCG C3 mG*mG*mU AACUAGAGAUCCCUCAGA C*mG C3 GGCAGGAA*G*A*A | SEQ ID NO. 31; SEQ ID NO. 32; SEQ ID NO. 33 | |
| X7 | /5Sp9/mC*mU*mC*mU*mU*mC*mG*mU* mC*mG*mC*+T*mG*mU*mC*+T*mC*mC *mG*+C*mU*+T*mC*mU*mU*+C*mC*m U*mG*+C*mC* /3AmMO/ | SEQ ID NO. 34 | |
| X7T | /5Sp9/mC*mU*mC*mU*mU*mC*mG*mU* | SEQ ID NO. 35 | |
| X7D | mC*mG*mC*+T*mG*mU*mC*+T*mC*mC *mG*+C*mU*+T*mC*mU*mU*+C*mC*m U*mG*+C*mC* /3AmMO/ | SEQ ID NO. 36 | |

TABLE 1-continued

RNA Complexes and Component Strands

| Complexes Abbreviation | Sequences | SEQ ID NOs | FIG. |
|---|---|---|---|
| G6 L3 X8 | | | |
| G6 | 9s*mC*mG UCU GAG GGA UCU CUA GUU ACC UU | SEQ ID NO. 8 | |
| L3P5'/LP/ LP3 | G*C*G*GAGACAGCG C3 mG*mG*mU AACUAGAGAUCCCUCAGA C*mG C3 GGCAGGAA*G*A*A | SEQ ID NO. 31; SEQ ID NO. 32; SEQ ID NO. 33 | |
| X8 | /5Sp9/mC*mU*+C*mU*mU*mC*mG*mU* mC*mG*mC*+T*mG*mU*mC*+T*mC*mC *mG*+C*mU*+T*mC*mU*mU*+C*mC*m U*mG*+C*mC* /3AmMO/ | SEQ ID NO. 37 | |
| X8T | /5Sp9/mC*mU*+C*mU*mU*mC*mG*mU* | SEQ ID NO. 38 | |
| X8D | mC*mG*mC*+T*mG*mU*mC*+T*mC*mC *mG*+C*mU*+T*mC*mU*mU*+C*mC*m U*mG*+C*mC* /3AmMO/ | SEQ ID NO. 39 | |
| tat activator strand unmodified S0 | | | |
| S0 | G C G G A G A C A G C G A C G A A G A G C U C A U C A G | SEQ ID NO. 40 | |
| tat activator strand S1 28 bp | | | |
| S1 | mA mA mA mA mA G C G G A G A C A G C G A C G A A G A G C U C A U C A G mA mA mA mA mA idT | SEQ ID NO. 41 | |
| tat activator strand S2 31 bp | | | |
| S2 | mA mA mA mA mA G C G G A G A C A G C G A C G A A G A G C U C A U C A G A A C mA mA mA mA mA idT | SEQ ID NO. 42 | |
| tat activator strand S4 | | | |
| S4 | mA mA mA mA mA GGC AGG AAG AAG CGG AGA CAG CGA CGA AGA GCU CAU CAG AAC A mA mA mA mA mA idT | SEQ ID NO. 43 | |

In Table 1, PEG refers to a polyethylene glycol (PEG) linker; $NH_2$ refers to a primary amine group; * asterisk refers to phosphothiester linkages; mN refers to 2'-O-methyl bases, with N representing any of the four bases; C3 refers to a three carbon spacer; 9s refers to a tri-ethyleneglycol spacer; +N refers to an LNA base; (3'C6 Amino) refers to a C6 Amino modification; idT refers to an inverted dT exonuclease blocker; /5Sp9/ refers to a 5' triethyleneglycol spacer; and /3AmMO/ refers to a 3' amino modifier.

Additional exemplary constructs are summarized in Table 2 below

TABLE 2

Additional RNA constructs and related strands

| Complexes Abbreviation | Sequences | SEQ ID NOs | FIG. |
|---|---|---|---|
| AB1-C1D1E1 | | | FIG. 19 |
| A | PEG*mC*mG UCU GAG GGA UCU CUA GUU ACC UU | SEQ ID NO. 1 | |
| D1/B1//C1 | G*A*C*G AAG AGC UC C3 mG*mG*mU AAC UAG AGA UCC CUC AGA mC*mG C3 GCG GAG AC*A*G*C C | SEQ ID NO. 44; SEQ ID NO. 45; SEQ ID NO. 46 | |
| E1 | (/5Sp9/mG*mU*mU*+C*mU*mG*mA*mU*mU*mG*mA*mG*mC*+T*mC*mU*+T*mC*mG*mU*+C*mG*mC*+T*mG*mU*mC*mU*mC*mC*+G*mC*mU*mU*mC*mU*mU*mC*mG*/3AmMO/) | SEQ ID NO. 47 | |
| E1T1 | /5Sp9/mG*mU*mU*+C*mU*mG*mA*mU*mU* | SEQ ID NO. 48 | |
| E1D | mG*mA*mG*mC*+T*mC*mU*+T*mC*mG* mU*+C*mG*mC*+T*mG*mU*mC*mU*mC* mC*+G*Mc | SEQ ID NO. 49 | |
| E1T2 | mU*mU*mC*mU*mU*mC*mC*/3AmMO/ | SEQ ID NO. 50 | |
| Activation sequence for AB1-C1D1E1 | GGAGAAGCGGAGACAGCGACGAAGAGC UCAAUCAGA | SEQ ID NO. 51 | N/A |
| AB2-C2D2E2 | | | FIG. 20 |
| A | PEG*mC*mG UCU GAG GGA UCU CUA GUU ACC UU | SEQ ID NO. 1 | |
| D2/B2/C2 | G*A*A*GAGCUCAUC C3 mG*mG*mU AACUAGAGAUCCCUCAGA mC*mG C3 AGAGCGGA*G*A*C | SEQ ID NO. 52 SEQ ID NO. 53 SEQ ID NO. 54 | |
| E2 | (/5Sp9/*mG*mA*+T*mG*mA*mG*mC*+T* mC*mU*+T*mC*mG*mU*mC*mG*mC*mU* mG*mU*mC*+T*mC*mC*+G*mC*mU*+C*mU *C3*/3AmMO/) | SEQ ID NO. 55 | |
| E2T | mC*mG*mU*mC*mG*mC*mU*mG | SEQ ID NO. 56 | |
| E2D1 | /5Sp9/*mG*mA*+T*mG*mA*mG*mC*_T*mC *mU*+T* | SEQ ID NO. 57 | |
| E2D2 | mU*mC*+T*mC*mC*+G*mC*mU*+C*mU* C3*/3AmMO/ | SEQ ID NO. 58 | |
| Activation sequence for AB2-C2D2E2 | AGAGCGGAGACAGCGACGAAGAGCUCA UC | SEQ ID NO. 59 | N/A |
| AB3-C3D3E3 | | | FIGS. 21A and 21B |
| A | PEG*mC*mG UCU GAG GGA UCU CUA GUU ACC UU | SEQ ID NO. 1 | |
| D3/B3/C3 | (G*A*A*GAGCUCAUC C3 mG*mG*mU | SEQ ID | |

TABLE 2-continued

Additional RNA constructs and related strands

| Complexes Abbreviation | Sequences | SEQ ID NOs | FIG. |
|---|---|---|---|
| | AACUAGAGAUCCCUCAGAmC*mG C3 AGAGCGGA*G*A*C) | SEQ ID NO. 60 SEQ ID NO. 61; SEQ ID NO. 62 | |
| E3 | (/5Sp9/*mG*mA*+T*mG*mA*mG*mC* +T*mC*mU*+T*mC*mG*mU*mC*mG*mC* mU*mG*mU*mC*+T*mC*mC*+G*mC*mU*+C *mU*mG*mU*mU*+C*mU*mG*mA*C3*/3AmMO//) | SEQ ID NO. 63 | |
| E3T1 | mG*mU*mU*+C*mU*mG*mA*C3*/3AmMO//) | SEQ ID NO. 64 | |
| E3D1 | mG*mU*mC*+T*mC*mC*+G*mC*mU*+C*mU* | SEQ ID NO. 65 | |
| E3D2 | (/5Sp9/*mG*mA*+T*mG*mA*mG*mC* +T*mC*mU*+T*mC | SEQ ID NO. 66 | |
| E3T2 | mG*mU*mC*mG*mC*mU* | SEQ ID NO. 67 | |
| 1st Activation sequence for AB3-C3D3E3 | UCAGAACAGAGCGGAGAC | SEQ ID NO. 68 | N/A |
| 2nd Activation sequence for AB3-C3D3E3 | AGCGACGAAGAGCUCAUC | SEQ ID NO. 69 | N/A |
| A-B4C4D4-E4 | | | FIGS. 22A and 22B |
| A | PEG*mC*mG UCU GAG GGA UCU CUA GUU ACC UU | SEQ ID NO. 1 | |
| D4/B4/C4 | GACGAAGAGCUC C3 mG*mG*mU AACUAGAGAUCCCUCAGA C*mG C3 GCGGAGACAGC (Circularized) | SEQ ID NO. 70; SEQ ID NO. 71; SEQ ID NO. 72 | |
| E4 | (:/5Sp9/mG*mU*mU*+C*mU*mG*mA*mU *mG*mA*mG*mC*+T*mC*mU*+T*mC*mG* mU*+C*mG*mC*+T*mG*mU*mC*mU*mC* mC*+G*mC*/3AmMO/) | SEQ ID NO. 73 | |
| E4T | /5Sp9/mG*mU*mU*+C*mU*mG*mA*mU | SEQ ID NO. 74 | |
| E4D | mG*mA*mG*mC*+T*mC*mU*+T*mC*mG* mU*+C*mG*mC*+T*mG*mU*mC*mU*mC* mC*+G*mC*/3AmMO/) | SEQ ID NO. 75 | |
| Activation sequence for A-BCD-E4 | G C G G A G A C A G C G A C G A A G A G C U C A U C A G A A C | SEQ ID NO. 76 | FIG. 22B |
| A-B5₁CD5 B5₂-E5 | | | FIGS. 23A and 23B |
| A | PEG*mC*mG UCU GAG GGA UCU CUA GUU ACC UU | SEQ ID NO. 1 | |
| B5₁C5D5 | UCCCUCAGA C*mG C3 GCGGAGACAGC | SEQ ID | |

TABLE 2-continued

Additional RNA constructs and related strands

| Complexes Abbreviation | Sequences | SEQ ID NOs | FIG. |
|---|---|---|---|
| B5₂ | GACGAAGAGCUC C3 mG*mG*mU AACUAGAGA | SEQ ID NO. 77; SEQ ID NO. 78; SEQ ID NO. 79 | |
| E5 | (:/5Sp9/mG*mU*mU*+C*mU*mG*mA*mU *mG*mA*mG*mC*+T*mC*mU*+T*mC*mG* mU*+C*mG*mC*+T*mG*mU*mC*mU*mC* mC*+G*mC*/3AmMO/) | SEQ ID NO. 80 | |
| E5T | /5Sp9/mG*mU*mU*+C*mU*mG*mA*mU | SEQ ID NO 81 | |
| E5D | mG*mA*mG*mC*+T*mC*mU*+T*mC*mG* mU*+C*mG*mC*+T*mG*mU*mC*mU*mC* mC*+G*mC*/3AmMO/) | SEQ ID NO. 82 | |
| Activation sequence for A-B5₁CD5 B5₂-E5 | G C G G A G A C A G C G A C G A A G A G C U C A U C A G A A C | SEQ ID NO.83 | FIG. 23B |
| G6 L2 X3-Inosine | | | FIG. 24 |
| G6 | 9s*mC*mG UCU GAG GGA UCU CUA GUU ACC UU | SEQ ID NO. 8 | |
| L2P3'/L2Ps/ L2P5' | G*A*C*G AAG AGC UC C3 mG*mG*mU AAC UAG AGA UCC CUC AGA C*mG C3 GCG GAG AC*A*G*C | SEQ ID NO. 16; SEQ ID NO. 17; SEQ ID NO. 18 | |
| X3-Inosine | (/5Sp9//ideoxyI/*/ideoxyI/*/ideoxyI/*/ ideoxyI/*/ideoxyI/*mG*mU*mU*+C*mU*mG*mA*mU* mG*mA*mG*mC*+T*mC*mU*+T*mC*mG* mU*+C*mG*mC*+T*mG*mU*mC*mU*mC* mC*+G*mC*/3AmMO/) | SEQ ID NO. 84 | |
| X3T-Inosine | /5Sp9//ideoxyI/*/ideoxyI/*/ideoxyI/* /ideoxyI/*/ideoxyI/*mG*mU*mU*+C*mU*mG*mA*mU* | SEQ ID NO. 85 | |
| X3D | mG*mA*mG*mC*+T*mC*mU*+T*mC*mG* mU*+30C*mG*mC*+T*mG*mU*mC*mU*mC* mC*+G*mC* | SEQ ID NO. 86 | |
| G6 L2 X3-Inosine-HMW-PEG | | | FIG. 25 |
| G6 | 9s*mC*mG UCU GAG GGA UCU CUA GUU ACC UU | SEQ ID NO. 8 | |
| L2P3'/L2Ps/ L2P5' | G*A*C*G AAG AGC UC C3 mG*mG*mU AAC UAG AGA UCC CUC AGA C*mG C3 GCG GAG AC*A*G*C | SEQ ID NO. 16; SEQ ID NO. 17; SEQ ID NO. 18 | |
| X3-Inosine-HMWp-PEG | (/5Sp9//ideoxyI/*/ideoxyI/*/ideoxyI/* /ideoxyI/*/ideoxyI/*mG*mU*mU*+C*mU*mG*mA*mU* mG*mA*mG*mC*+T*mC*mU*+T*mC*mG* mU*+C*mG*mC*+T*mG*mU*mC*mU*mC* mC*+G*mC*HMW-PEG | SEQ ID NO. 87 | |
| X3T-Inosine-HMW-PEG | /5Sp9//ideoxyI/*/ideoxyI/*/ideoxyI/* /ideoxyI/*/ideoxyI/*mG*mU*mU*+C*mU*mG*mA*mU* | SEQ ID NO. 88 | |

TABLE 2-continued

Additional RNA constructs and related strands

| Complexes Abbreviation | Sequences | SEQ ID NOs | FIG. |
|---|---|---|---|
| X3D | mG*mA*mG*mC*+T*mC*mU*+T*mC*mG* mU*+C*mG*mC*+T*mG*mU*mC*mU*mC* mC*+G*mC*-HMW-PEG | SEQ ID NO. 89 | |
| AB6-C6D6E6 | | | FIG. 26 |
| A | PEG*mC*mG UCU GAG GGA UCU CUA GUU ACC UU | SEQ ID NO. 1 | |
| D6/B6/C6 | +T*dT*dG*dG dG dA +C dC dA dC PEG mG* mG* mU AACUAGAGAUCCCUCAGA mC*mG PEG dT dA +C dT +C dA dG dC * dC *dC* dA | SEQ ID NO. 90; SEQ ID NO. 91; SEQ ID NO. 92 | |
| E6 | dC dA dC dT dC dA dG dG dG dC dA dC dT dG dC dA dA dG dC dA dA dT dT dG dT dG dG dT dC dC dC dA dA dT dG dG dG dC dT dG dA dG dT dA ² | SEQ ID NO. 93 | |
| E6T | dC dA dC dT dC dA dG dG dG dC dA dC dT dG dC dA dA dG dC dA dA dT dT | SEQ ID NO. 94 | |
| E6D | dG dT dG dG dT dC dC dC dA dA dT dG dG dG dC dT dG dA dG dT dA ² | SEQ ID NO. 95 | |
| G6 L2 X5-Loop | | | FIG. 27A and 27B |
| G6 | 9s*mC*mG UCU GAG GGA UCU CUA GUU ACC UU | SEQ ID NO. 8 | |
| L2P3'/L2P5/ L2P5' | G*A*C*G AAG AGC UC C3 mG*mG*mU AAC UAG AGA UCC CUC AGA C*mG C3 GCG GAG AC*A*G*C | SEQ ID NO. 16; SEQ ID NO. 17; SEQ ID NO. 18 | |
| X5-Loop | /5Sp9/mA*mU*+C*mA*mA*mA*mG*mU*m U*mC*mU*mG*mA*mU*mG*mA*mG*mC* +T*mC*mU*+T*mC*mG*mU*+C*mG*mC*+T *mG*mU*mC*mU*mC*mC*+G*mC*/3AmMO/ | SEQ ID NO. 96 | |
| X5T-Loop | mG*mU*mU*mC*mU*mG*mA*mU* | SEQ ID NO. 97 | |
| X5D | mG*mA*mG*mC*+T*mC*mU*+T*mC*mG* mU*+C*mG*mC*+T*mG*mU*mC*mU*mC* mC*+G*mC*/3AmMO/ | SEQ ID NO. 98 | |
| Activation sequence for G6 L2 X5-Loop | G C G G A G A C A G C G A C G A A G A G C U C A U C A G A A C | SEQ ID NO. 99 | FIG. 27B |

In particular, Table 1 and Table 2 indicate for each exemplary molecular construct the specific sequences of the strands that are complementarily bound to provide the molecular constructs herein described, as well as the specific sequences of the signal strands utilized to convert the exemplary molecular constructs from the OFF state to the ON state by isothermal strand displacement. The corresponding configurations are illustrated in FIGS. 3A to 27B, wherein each construct is identified by the corresponding abbreviation.

Example 2A

Process of Designing a Signal Activated Construct

Exemplary processes are described below for the designing, synthesis, and testing the activity of a signal activated construct, which comprise a targeting domain configured for interfering a target intracellular process through RNAi.

To determine linker dimensions construct a possible approach a process comprise building two three dimensional models of targeting domain and the sensor domain.

In such an approach the targeting domain model is just an RNA:RNA duplex with the correct number of base-pairs. The sensor domain model is a RNA:RNA, RNA:DNA, or DNA:DNA duplex with the correct number of base-pairs.

If in the final construct there is a gap between the protection segments bound to one or more of the displacement segments in the sensor strand with the gap is bridged by RNA bases in the sensor strand, RNA bases can be added to create an RNA:RNA duplex model with the duplex formed by the protection segments with the corresponding displacement segments bridged by the correct number of base-pairs and then remove the bases opposing the displacement segment at the gap.

If in the final construct the gap is bridged by an unstructured linker, position the fully stretched linker between duplex formed by the protection segments with the corresponding displacement segments without rotating the sensor strand.

Position the two duplexes next to each other as close as possible without touching (at least 0.1 nm distance between all atoms) and orient them to minimize the distance between the 3' terminus of B and the 5' terminus of C and between the 5' terminus of B and the 3' terminus of D Measure the distance between each pair of termini and add ~0.3 nm. This is the minimum length of the linkers.

Preferably, the linkers allow no less than 0.3 nm and no more than 2 nm separation between the duplexes with a maximum distance between the duplexes of approximately 5 nm.

For a polymeric linker, to determine the minimum linker length, use the fully stretched length of the polymer.

For a polymeric linker, to determine linker length (in polymer units) allowed for the maximum separation, calculate the estimated end-to-end distance of the polymer according to polymer physics methods known to the art Using the above model, one can position the nick on the sensor duplex on the side facing towards the targeting duplex. This can be performed by changing the length of the duplexes formed by protection segments and displacement segments in the sensor until the gap is in the middle, preferably with duplexes formed by protection segments and displacement segments independently of a length of 8 base pairs or more. Verification is preferably made that each segment has a Tm>37 C or in any case a Tm associated with thermodynamic stability in the environment where the construct is to be used.

Example 2B

Design of the Constructs Used in the Experiments a Signal Activated Construct

To design a construct, Applicants started with the analysis of a RNA sequence that was to be targeted (interference) by RNAi, such as a target mRNA or a set of target mRNAs. According to the RNA sequence to be targeted, applicants selected the sequences for the targeting domain of the construct that were known in the art.

For example, in the G6L1X1 construct shown in FIGS. 13A-B, Applicants started with the Dicer substrate siRNA with the guide strand sequence 5' UGAGGGAUCUC-UAGUUACC 3' (SEQ ID NO. 100), which targets the sequence 5'-GGUAACUAGAGAUCCCUC-3' (SEQ ID NO. 101), for knockdown. The guide strand G6: L1 was configured as a 23 bp Dicer substrate siRNA. Applicants then selected an HIV viral RNA related sequence: 5'-GCG-GAGACAGCGAAGAGCUCAUCAGA-3' (SEQ ID NO. 102), as the activation signal molecule. Applicants split this sequence into three parts: 5' GCGGAGACAGC (SEQ ID NO. 103), became the 3' extension of the passenger strand L1; 5' GACGAAGAGCUC (SEQ ID NO. 104), became the 5' extension of the passenger strand L1; finally, the remaining sequence, UCAGA (SEQ ID NO:. 105), became the binding partner for the toehold. The sequence of the sensor strand, X1, could immediately be written as the complement of the activation sequence: UCUGA-U-UGAGCUCUU-GUC-GCUGUCUCCGC (SEQ ID NO:. 106-SEQ ID NO:. 107-SEQ ID NO:. 108) (SEQ ID NO:. 109)). An extra base, "U", was optionally added between the toehold and the rest of the sensor strand to reduce the toxicity of the sensor-signal duplex.

To determine the linker to be used in connecting the passenger strand L1 to its overhangs, a 3D model of the sensor and targeting domain duplexes were positioned parallel to one another using molecular modeling software to minimize the distance that the linkers need to bridge. From this measurement, Applicants determined that a C3 linker was sufficiently long to connect the two duplexes without unacceptable strain.

The split between the two non-toehold domains was determined to give approximately equal thermodynamic stability to each separate duplex section, and to position the gap between the 3' and 5' extension of L1 approximately between the two parallel RNA helices.

The Applicants added tri-ethylene glycol linker/spacers to the 5' of G6 and X1 to decrease spurious binding by Dicer and other RNA binding proteins. The 3' of X1 was modified with a C3 linker connected to an inverted dT base for the same purpose.

Applicants then modified the entire X1 strand with phosphorothioate and 2'-O-methyl modifications to increase thermodynamic stability and to minimize spurious exonuclease degradation and helicase unwinding of the L1:X1 duplex.

To increase the stability of L1's overhangs from potential spurious exonuclease degradation, the 5' and 3' bases of L1 were modified with phosphorothioates. However, 2'-O-methyl modifications were not used because they might impede strand displacement switching.

The segments connecting L1 to the C3 linker connecting its 5' overhang was modified with a special pattern of 2'-O-methyl bases and phosphorothioates to ensure that, in the activated state, XRN1 can degrade the 5'-overhang while leaving a terminal phosphate for binding to Dicer's PAZ domain. Although not strictly necessary, the same pattern was used to connect the 3' overhang.

Finally, Applicants added 5' terminal phosphorothioates and 2'-O-methyl bases to G6 to improve the thermodynamic stability and nuclease resistance of the targeting domain while taking care to avoid chemical modification patterns that could compromise its RNAi efficiency. The applicants also took care to keep the targeting domain less stable to nuclease degradation than the sensor domain. This helps avoid spurious activation of the complex via premature degradation of the sensor domain.

Figure 29:
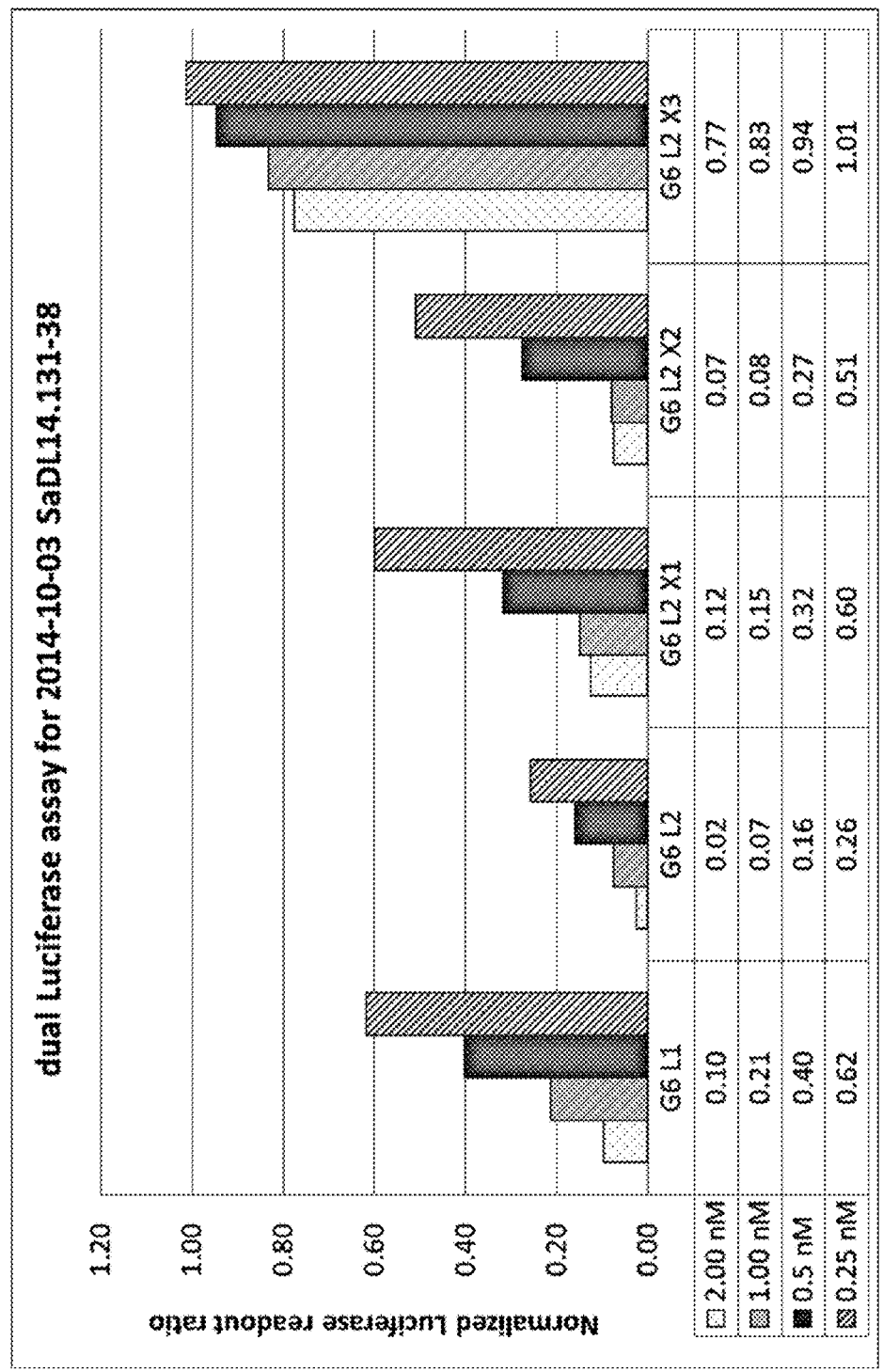
FIG. 29 shows a diagram illustrating the results of a luciferase assay of exemplary constructs herein described where the y-axis represents relative luciferase unit ratio and the x-axis represents the exemplary complexes used in the assay, with the rows below the x axis indicating the relative luciferase ratio for each final nanomolar concentration of each molecular construct used. In particular.

Several optimizations of the base construct were performed to enhance desired activity. A first optimization of the construct G6 L1 X1 concerned the chemical modification pattern near the C3 linker connecting the L1 strand to its 3' overhang. In G6 L1 X1 the chemical modification interfered to some extent with Dicer processing of the activated targeting domain by placing a phosphorothioate backbone modification and a 2'-O-methyl base near the Dicer cleavage site. Thus, in an evolution of the design, the L2 strand eliminated these modifications and achieved a higher RNAi efficiency as shown in FIG. 29.

An additional optimization of the X1 strand concerned the related thermodynamic stability in connection with the ability to turn OFF RNAi activity to a sufficient extent. In particular Applicants added LNA modifications to strands X3, X5 and X6, thereby achieving lower OFF state RNAi activity as desired.

Figure 28:
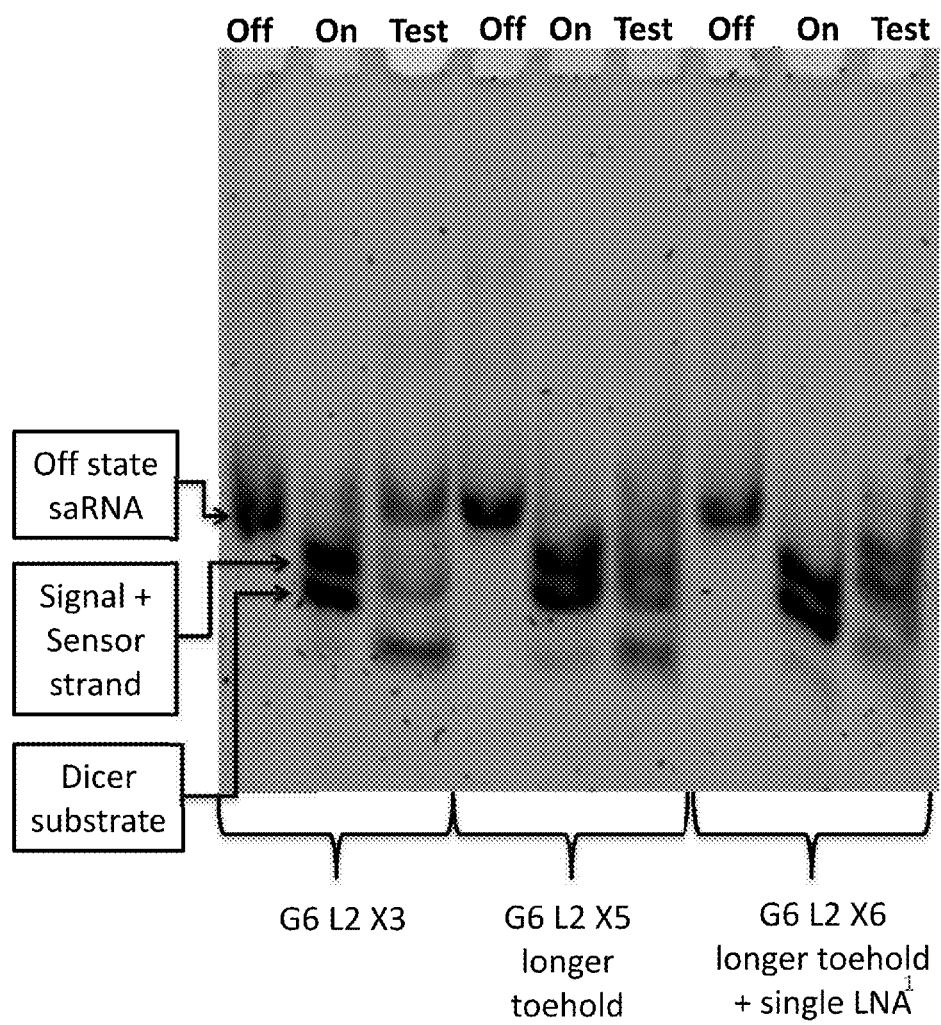
FIG. 28 shows a representation of a PAGE gel performed on exemplary constructs G6L2X3 (FIGS. 15A-B), G6L2X5 (FIGS. 16A-B), and G6L2X6 (FIGS. 17A-B). In particular, in the illustration of FIG. 28, lane 1, contains construct G6L2X3 on the OFF state; lane 2, G6L2X3 in the ON state; lane 3, G6L2X3 incubated with synthetic signal strand to test for conversion of OFF state construct to ON state construct by isothermal strand displacement; lane 4, construct G6L2X5 on the OFF state; lane 5, G6L2X5 in the ON state; lane 6, G6L2X6 incubated with synthetic signal strand to test for conversion of OFF state construct to ON state construct by isothermal strand displacement; lane 7, construct G6L2X6 on the OFF state; lane 8, G6L2X6 in the ON state; lane 9, G6L2X6 incubated with synthetic signal strand to test for conversion of OFF state construct to ON state construct by isothermal strand displacement. Arrows indicate the OFF state assembled construct, the dissociated signal-sensor strand duplex, and the activated Dicer substrate targeting duplex.

Additionally, a further optimization of the X1 strand was performed on the length of the toehold and number of mismatch that did not allow a desired isothermal switching of the construct by the signal strand. Thus, X5 and X6 adopted longer toeholds, thereby achieving efficient isothermal switching, as shown in FIG. 28.

Example 3

Design of the Sensor Strand Toehold

Several variations of the 5' sensor strand toehold were designed to increase the kinetic rate of strand migration following signal strand binding to the sensor strand. In particular, according to Srinivas, N., et al. Nucleic Acids Research 41, 10641-10658, (2013) (herein incorporated by reference), there is an extra barrier to the initiation of branch migration in DNA, and increasing the number of base pairs in a toehold can lead to an improvement in strand displacement kinetics of six orders of magnitude.

In addition, elimination of mismatches between the toehold and the signal strand and the addition of LNA modification in the toehold can allow the signal strand to overcome any extra kinetic barrier present due to the inclusion of LNA modifications in the sensor strand.

Thus, several variations of the toehold were designed, and are illustrated in FIGS. 18A-C. As illustrated in FIG. 18A, the toehold of the G6L2X3 construct contains the sequence, 5' to 3', mU*mC*mU*mG*mA* mU*mU* (SEQ ID NO:. 110) with a mismatch at position 7 (with mN representing 2'-O-methyl bases, and asterisks * representing phosphothiester linkages). FIG. 18B shows the toehold of construct G6L2X5, which contains the sequence mG*mU*mU*mC*mU*mG*mA*mU (SEQ ID NO:. 111) and no mismatches to the signal strand. FIG. 18C shows the toehold of construct G6L2X6, which contains the sequence mG*mU*mU*C+mU*mG*mA*mU, (SEQ ID NO:. 111) no mismatches to the signal strand, and an LNA base (represented by +N).

Example 4

Assembly and Activation of Exemplary Activatable Constructs.

The exemplary activatable constructs listed in Table 1 were assembled by combining all three component strands and annealing by incubation at 100 nM concentrations in 1× PBS buffer with 1 mM EDTA. The individual strands composing G6, L, and X were ordered from one of three commercial companies—IDT, GE Dharmacon, or Exiqon, Inc. A. Assembly took place by thermal annealing of the three strands from 85° C. to 25° C. at 1 degree Celsius per minute cooling rate. The component strands were combined in concentrations of 100 nM G strand, 100 nM L strand, 120 nM X strand.

The quality of assembly is affected by the concentration and stoichiometric ratio of the strands used in the assembly, the duration of the annealing step, the temperature profile, the salt concentration, the pH, and other constituents of the assembly buffer.

When deviating from the described assembly procedure, the quality of assembly can preferably be checked e.g. via native PAGE. The assembled complex is typically presented as a single band with minimal detectable higher molecular weight aggregates or lower molecular weight fragments.

Preferably, a purification process can be used to extract the proper molecular weight band. If a purification process is not possible, it is desirable to use a slight (e.g. approximately 10%) excess of the sensor strand in relation to the guide strand and the passenger strand to ensure that all assembled targeting domains are switched OFF.

Furthermore, it is preferable to have the structures optimally assembled immediately before use. If the structures need to be stored, they are best stored at −80 C. The quality of frozen assemblies is preferably checked periodically to ensure that the structures are not degraded.

Constituent strands and assembled structures are preferably protected from RNA and DNA nucleases, which may degrade the structures, resulting in increased leakage or lower RNAi activity when switched ON.

The assembly buffer can be for example PBS near pH7.0, use of a different buffer may lead to lower assembly efficiency depending on the experimental conditions as will be understood by a skilled person. The ionic strength of the assembly buffer is preferably similar than PBS. A lower ionic strength buffer is expected to possibly increase the leakage rate due to misassembly depending on the reaction conditions.

To test the assembly and activation of exemplary constructs, the three component strands of each of constructs G6L2X3, G6L2X5, and G6L2X6 were combined with 100 mM of activation strand S1 and assembled by thermal annealing by heating the mixture to 85° C. and then cooling to room temperature. This directly formed the ON state of the constructs. Additionally, component strands of constructs G6L2X3, G6L2X5, and G6L2X6 were assembled as above to form the OFF constructs, and 200 nM S1 activation strand was added to each construct (at 100 mM concentration) and incubated in 1× PBS buffer with 1 mM EDTA for one hour at 37° C. to form the "Test" group of constructs to verify conversion of the OFF state to the ON state by isothermal strand displacement (a schematic of which is illustrated in FIG. 9, panels A to D). Samples were then run on 8% TBE polyacrylamide gel electrophoresis (PAGE) gels in 1× TBE for one hour at 150V according to methods known in the art. Samples were post-stained with Sybr Gold to visualize the various bands.

FIG. 28 illustrates the visualization on the TBE PAGE gels from the above experiment. In particular, for each of the three constructs tested, the "Off" lanes illustrate a single band representing the assembled construct, indicating that the strands assemble into the desired complexes with minimal formation of higher order spurious assemblies. The "On" lanes represent two bands—the signal strand-sensor strand duplex and the processed target duplex Dicer substrate—as well as a small amount of remaining unactivated OFF state constructs. The "Test" lanes show a single band representing the assembled OFF construct and the two bands representing the ON state, indicating successful conversion of the OFF state product into the ON state product by isothermal strand displacement. As expected, G6L2X5 and G6L2X6 had more efficient conversion into the ON state due to improved thermodynamic stability of their toeholds.

Example 5

Confirmation of RNAi Processing of the Guide Strand in Exemplary Complexes by Luciferase Analysis To test successful release and processing of the guide strand from a targeting domain in an activated conformation of the exemplary molecular complexes of Example 1, Applicant transformed some of the constructs of Example 1 into cells, and performed dual Luciferase assays, the results of which are illustrated in FIGS. 29-33.

In particular, pre-annealed ON and OFF state constructs assembled as described in Example 4 above were transfected into HCT 116 cells and incubated for 24 hours, after which time readout was performed. The Renilla Luciferase utilized in the assay comprised an HIV sequence targeted by the guide strand of the targeting duplex. In these dual Luciferase assays, the ratio of Renilla Luciferase to Firefly Luciferase luminosity is compared to a negative control. A value of 1.0 signifies undetectable RNAi activity. A value of 0.0 constitutes perfect RNAi activity, meaning there is zero activity from the Renilla luciferase target of RNAi knockdown. As a positive control, assembled targeting domains, which are configured to provide have RNAi activity without any signal activation, are used.

FIG. 29 illustrates a diagram showing the result of the dual luciferase assay carried out with targeting domains G6L1 and G6L2, as well as assembled constructs G6L2X1, G6L2X2, and G6L2X3 in the OFF state. The y-axis represents relative luciferase unit ratio and the x-axis represents the exemplary complexes used; the rows below the x-axis indicate the normalized luciferase readout ratio for each concentration of each construct. Constructs and targeting domains were co-transfected with the dual luciferase construct at concentrations of 0.25, 0.5, 1.0, and 2.0 nM. As illustrated in FIG. 29, targeting domain G6L2 has improved RNAi efficiency compared to G6L1 due to the adjustment to the chemical modification pattern. In particular, the L2 passenger strand (shown in FIGS. 14A-B) differs from the L1 strand (shown in FIGS. 13A-B) in the pattern of chemical modifications at the connection point to the 3' over hang. L2 has the sequence C*mG immediately 5' of the C3 linker, while L1 instead has the sequence *mC*mG. The *mC portion of the L1 strand interferes with RNAi processing of the targeting domain because the modifications are too close to the passenger strand cleavage site for Dicer. The change from *mC to C in the G6L2 targeting duplex improves RNAi activity in the ON state.

Additionally, as also illustrated in FIG. 29, construct G6L2X3 has clearly lower OFF state RNAi activity than constructs G6L2X1 and G6L2X3 due to the incorporation of LNA modifications in the X3 sensor strand.

Figure 30:
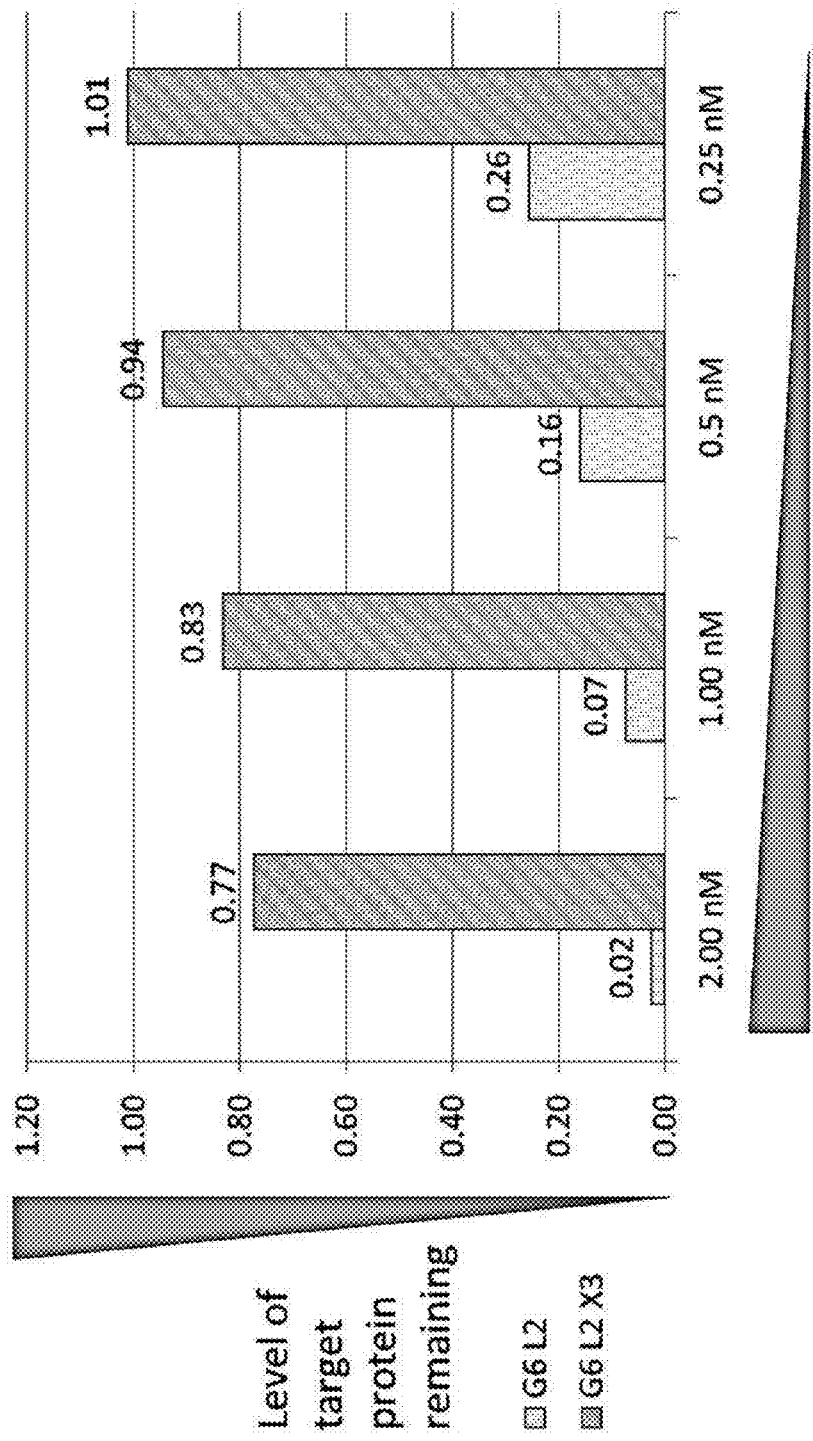
FIG. 30 shows a diagram illustrating the results of the luciferase assay of FIG. 29. In particular.

FIG. 30 illustrates a diagram showing the comparison the RNAi activity of the OFF state G6L2X3 construct versus the targeting domain G6L2 alone observed from the experiment above. The y-axis represents the level of the target protein remaining, and the x-axis represents the final nanomolar concentrations of each of the two exemplary complexes used. There is a high ON/OFF ratio of RNAi activity between the OFF state of the G6L2X3 construct and the constitutively active G6L2 domain at all transfection concentrations. The ON/OFF ratio is highest at 2.0 nM concentration, with a ratio of ~30, and lowest at the 0.25 nM concentration, with a ratio of ~4.

Figure 31:
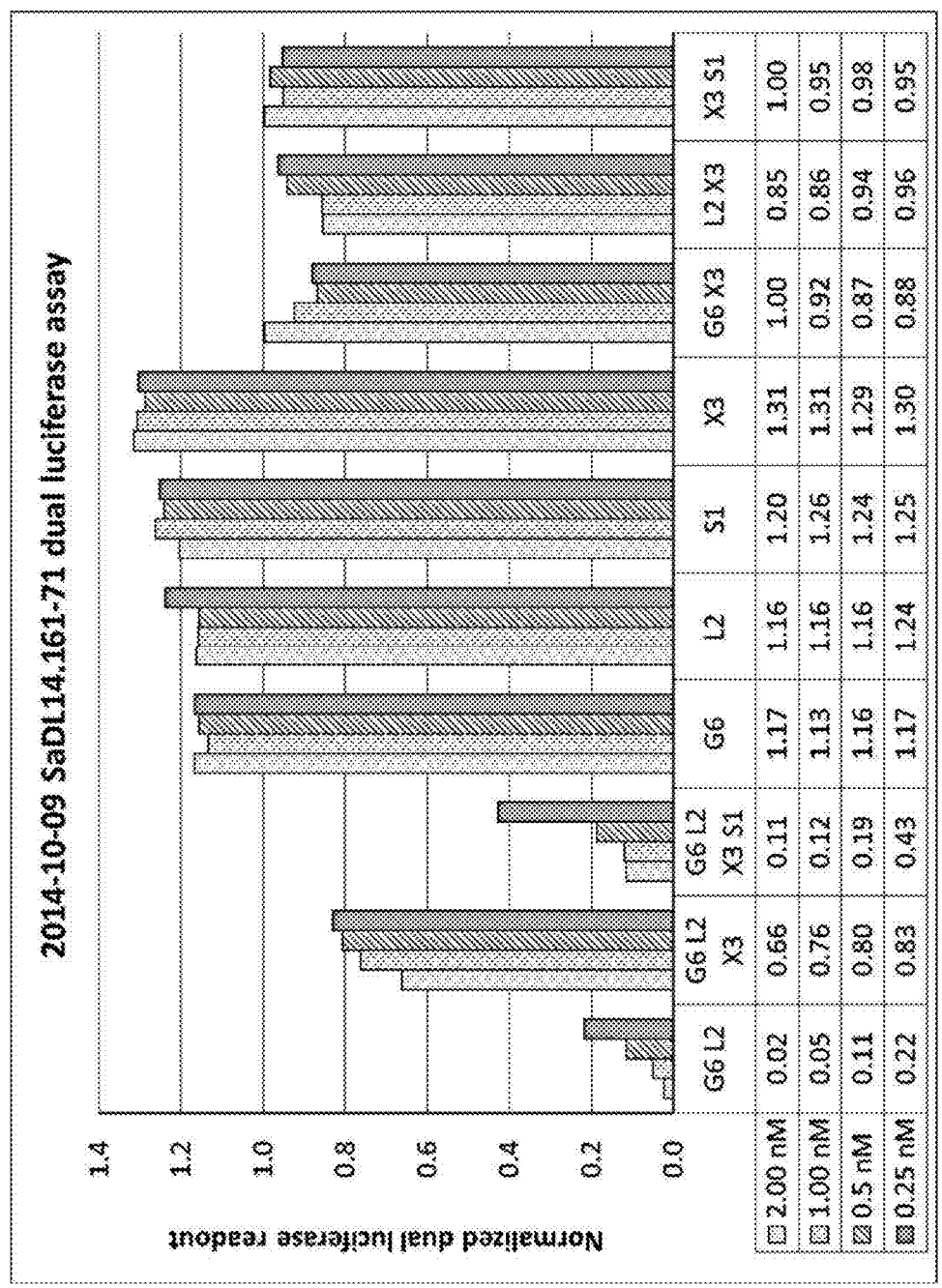
FIG. 31 shows a diagram illustrating the results of a luciferase assay of exemplary constructs herein described where the y-axis represents relative luciferase unit ratio and the x-axis represents the exemplary complexes used in the assay, with the rows below the x axis indicating the relative luciferase ratio for each final nanomolar concentration of each molecular construct used. In particular.

FIG. 31 illustrates a diagram showing the activity of the G6L2X3 construct, shown in FIGS. 15A-B, in the ON and OFF state. The y-axis represents relative luciferase unit ratio and the x-axis represents the exemplary complexes used; the rows below the x-axis indicate the normalized luciferase readout ratio for each concentration of each construct. The construct was co-transfected with the dual luciferase construct at concentrations of 0.25, 0.5, 1.0, and 2.0 nM. In addition, components and subassemblies of G6L2X3, including the G2L6 targeting domain, the G6, L2, X3, and S1 strands alone, and assemblies consisting of G6 and X3, L2 and X3, and X3 and S1 were transfected at the same concentrations as the assembled construct. As illustrated in FIG. 31, individual component strands of the G6L2X3 construct did not have any detectable RNAi activity, while the targeting domain G2L6 alone and the activated ON construct G6L2X3S1 had significant RNAi activity. Additionally, there was a high ON/OFF ratio of RNAi activity when comparing G6L2X3S1 (ON) with G6L2X3 (OFF).

Figure 32:
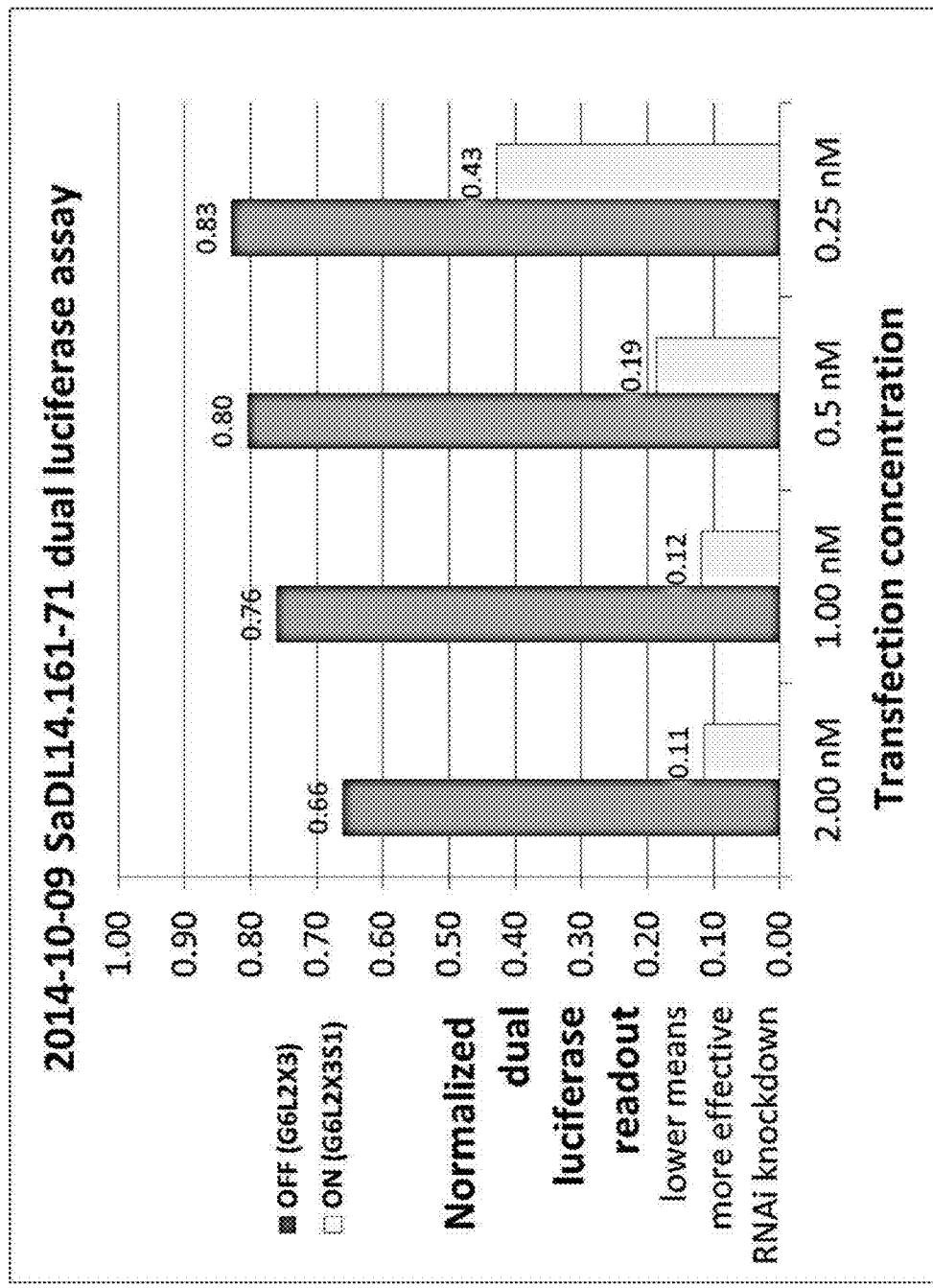
FIG. 32 shows a diagram illustrating the results of the luciferase assay of FIG. 31. In particular.

FIG. 32 illustrates a diagram showing the comparison in the RNAi activity of the OFF state G6L2X3 construct versus the ON state G6L2X3S1 construct from the experiment above. The y-axis represents the normalized dual luciferase value, and the x-axis represents the final nanomolar concentrations of each of the two exemplary complexes used. There is a high ON/OFF ratio of RNAi activity between the OFF state of the G6L2X3 construct and the ON state G6L2X3S1 construct at all transfection concentrations. The ON/OFF ratio is highest at 2.0 nM concentration, with a ratio of ~6, and lowest at the 0.25 nM concentration, with a ratio of ~2.

Figure 33:
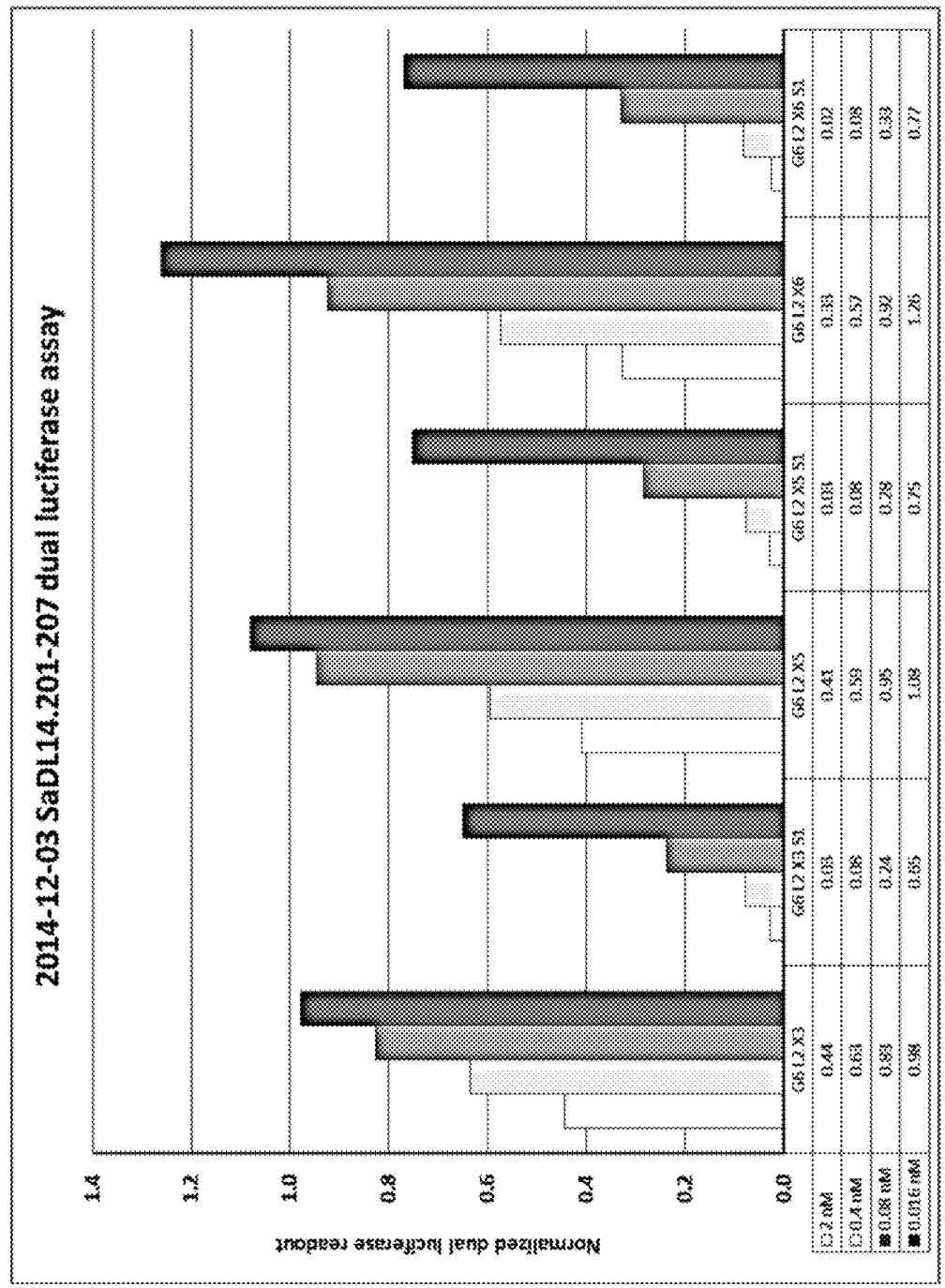
FIG. 33 shows a diagram illustrating the results of a luciferase assay of exemplary constructs herein described where the y-axis represents relative luciferase unit ratio and the x-axis represents the exemplary complexes used in the assay, with the rows below the x axis indicating the relative luciferase ratio for each final nanomolar concentration of each molecular construct used. In particular.

FIG. 33 illustrates a diagram showing the results of the dual luciferase assay carried out with constructs G6L2X3, G6L2X5, and G6L2X6 in the OFF state and the same constructs in the ON state (G6L2X3S1, G6L2X5S1, and G6L2X6S1). The y-axis represents relative luciferase unit ratio and the x-axis represents the exemplary complexes used; the rows below the x-axis indicate the normalized luciferase readout ratio for each concentration of each construct. The constructs were co-transfected with the dual luciferase construct at concentrations of 0.016, 0.08, 0.4, and 2.0 nM. As illustrated in FIG. 33, all three constructs have similar OFF state RNAi activity and ON/OFF ratios, and all three constructs shown significant RNAi activity in the ON state. Additionally, all three constructs achieved low OFF state RNAi activity and large ON/OFF RNAi activity ratios. The maximum ON/OFF activity ratio observed was ~10× at 2.0 nM concentration, and the minimum ration was observed at 0.016 nM and was ~1.4. At the highest concentration, there was some spurious RNAi activity observed in the OFF state.

FIG. 29 in particular demonstrates that the energetic stability of the sensor domain is a key feature to prevent OFF state leakage. G6L2X3 is significantly more stable thermodynamically than G6 L2 X1 and G6 L2 X2 due to extensive incorporation of LNA modifications. Non-LNA modifications that are observed to significantly increase the duplex stability of the sensor domain (tested via, for example, melting curves obtained by monitoring the UV absorbance as temperature is increased), are expected to have the same effect. The adjustment of a phosphorothioate near the $21^{st}$ base pair in L2 vs L1 lead to significant increase in RNAi activity. Thus, the ability of Dicer to efficiently process the RNAi targeting domain at the cleavage positions next to the $19^{th}$ and $21^{st}$ base pairs is important to the ON state activity. Thus, a 23 bp to 27 bp targeting domains is expected to have significantly better ON state RNAi activity compared to targeting domain outside the range.

The examples set forth above are provided to give those of ordinary skill in the art a complete disclosure and description of how to make and use the embodiments of the materials, compositions, systems and methods of the disclosure, and are not intended to limit the scope of what the inventors regard as their disclosure.

All patents and publications mentioned in the specification are indicative of the levels of skill of those skilled in the art to which the disclosure pertains.

The entire disclosure of each document cited (including patents, patent applications, journal articles, abstracts, laboratory manuals, books, or other disclosures) in the Background, Summary, Detailed Description, and Examples is hereby incorporated herein by reference. All references cited in this disclosure are incorporated by reference to the same extent as if each reference had been incorporated by reference in its entirety individually. However, if any inconsistency arises between a cited reference and the present disclosure, the present disclosure takes precedence. Further, the computer readable form of the sequence listing, submitted on May 20, 2015 as an ASCII text file named P1632-US_ST25, is incorporated herein by reference in its entirety.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure claimed. Thus, it should be understood that although the disclosure has been specifically disclosed by embodiments, exemplary embodiments and optional features, modification and variation of the concepts herein disclosed can be resorted to by those skilled in the art, and that such modifications and variations are considered to be within the scope of this disclosure as defined by the appended claims.

It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

When a Markush group or other grouping is used herein, all individual members of the group and all combinations and possible subcombinations of the group are intended to be individually included in the disclosure. Every combination of components or materials described or exemplified herein can be used to practice the disclosure, unless otherwise stated. One of ordinary skill in the art will appreciate that methods, device elements, and materials other than those specifically exemplified may be employed in the practice of the disclosure without resort to undue experimentation. All art-known functional equivalents, of any such methods, device elements, and materials are intended to be included in this disclosure. Whenever a range is given in the specification, for example, a temperature range, a frequency range, a time range, or a composition range, all intermediate ranges and all subranges, as well as, all individual values included in the ranges given are intended to be included in the disclosure. Any one or more individual members of a range or group disclosed herein may be excluded from a claim of this disclosure. The disclosure illustratively described herein suitably may be practiced in the absence of any element or elements, limitation or limitations which is not specifically disclosed herein.

A number of embodiments of the disclosure have been described. The specific embodiments provided herein are examples of useful embodiments of the invention and it will be apparent to one skilled in the art that the disclosure can be carried out using a large number of variations of the devices, device components, methods steps set forth in the present description. As will be obvious to one of skill in the art, methods and devices useful for the present methods may include a large number of optional composition and processing elements and steps.

In particular, it will be understood that various modifications may be made without departing from the spirit and scope of the present disclosure. Accordingly, other embodiments are within the scope of the following claims.

The invention claimed is:

1. A signal activatable construct for signal-activated molecular delivery, the construct comprising
a 17 to 30 bp targeting domain duplex RNA having a guide strand complementarily bound to a passenger strand, the targeting domain duplex RNA having opposite ends each presenting a 5'-3' terminal base pair and being in a configuration in which a distance between centers of the 5'-3' terminal base pairs at the opposite ends is equal to the length of the targeting domain ±25%,
wherein in a first inactive conformation of the activatable construct
a 5' end of the passenger strand is covalently attached to a 3' end of at least one protection strand and a 3' end of the passenger strand is covalently attached to a 5' end of the at least one protection strand, the covalent attachment independently performed by a linker segment of the at least one protection strand having a relaxed average end-to-end distance of up to approximately 12 nm,
a protection segment of the at least one protection strand is complementarily bound to at least one displacement segment of a sensor strand to form a 14 to 30 bp sensor domain duplex polynucleotide in which the sensor strand further comprises at least one toehold segment presented for binding to a signal molecule, and
the targeting domain is in a configuration minimizing processing by Dicer and/or an Argonaute enzyme of the targeting domain;

and wherein in a second activated conformation of the activatable construct:
   the sensor strand is bound to the signal molecule and is detached from the at least one protection strand and from the targeting domain; and
   the targeting domain is in a configuration allowing processing by Dicer and/or an Argonaute enzyme in which a 5' end of the passenger strand is covalently attached to a 3' end of at least one protection strand and a 3' end of the passenger strand is covalently attached to a 5' end of the at least one protection strand.

2. The signal activatable construct of claim 1 wherein the at least one protection strand is formed by a 5' terminal protection strand and a 3' terminal protection strand, each of the 5' terminal and 3' terminal protection strand having a 5' end and a 3' end, the 5' end of the 5' terminal protection strand being covalently attached to the 3' end of the passenger strand, the 3' end of the 3' terminal protection strand being covalently attached to the 5' end of the passenger strand, wherein
   in the first inactive conformation, a protection segment of each of the 5' terminal protection strand and the 3' terminal protection strand is complementarily bound to the at least one displacement segment of the sensor domain, thus forming a 5' terminal protection segment and a 3' terminal protection segment of the sensor domain duplex polynucleotide, with a gap between the 3' end of the 5' terminal protection segment and the 5' end of the 3' terminal protection segment, and
   in the second activated conformation the 5' terminal protection strand is presented as an overhang of the 3' end of the passenger strand and the 3' terminal protection strand is presented as an overhang of the 5' end of the passenger strand.

3. The signal activatable construct of claim 2, wherein
   the 5' terminal protection strand comprises a modified polynucleotide portion, and/or a phosphorothioate portion to form a blocker domain providing the 5' terminal protection strand with exonuclease resistance, and
   the 3' terminal protection strand comprises a modified polynucleotide portion, and/or a phosphorothioate portion to form a blocker domain providing the 3' terminal protection strand with exonuclease resistance.

4. The signal activatable construct of claim 1, wherein the sensor strand comprises a modified polynucleotide portion, a non-nucleic acid portion, and/or a phosphorothioate portion to form a blocker domain providing the sensor strand with exonuclease resistance.

5. The signal activatable construct of claim 1, wherein the passenger strand comprises a modified polynucleotide portion, and/or a phosphorothioate portion to form a blocker domain of 1 to 5 nucleotides from the 5'terminus of the passenger strand providing the passenger strand with exonuclease resistance.

6. The signal activatable construct of claim 1 wherein the at least one toehold segment comprises a terminal toehold segment presented at a 5' end or at a 3' end of the sensor strand.

7. The signal activatable construct of claim 1 wherein the at least one toehold segment comprises a 5' toehold segment presented a 5' end the sensor strand, and/or a 3' toehold segment presented a 3' end the sensor strand, the 5' toehold segment and the 3' toehold segment capable of binding a same or different signal molecule.

8. The signal activatable construct of claim 7, wherein, the 5' toehold segment and/or the 3' toehold segment comprise a modified polynucleotide portion, a non-nucleic acid portion, and/or a phosphorothioate portion to form a blocker domain providing the 5' toehold segment and/or the 5' toehold segment with exonuclease resistance.

9. The signal activatable construct of claim 1 wherein the at least one displacement segment comprises a 5' terminal displacement segment and a 5' terminal displacement segment, a 5' end of the 5' terminal displacement segment covalently attached to a 5' end of a central toehold segment, a 5' end of the 5' terminal displacement segment covalently attached to a 5' and of the central toehold segment.

10. The signal activatable construct of claim 1, wherein the distance between centers of the 5'-3' terminal base pairs at the opposite ends is equal to the length of the targeting domain ±5%.

11. The signal activatable construct of claim 1, wherein the distance between centers of the 5'-3' terminal base pairs at the opposite ends is equal to the length of the targeting domain ±1%.

12. The signal activatable construct of claim 1, wherein the linker segment of the at least one protection strand having a relaxed average end-to-end distance of approximately less than 5 nm.

13. The signal activatable construct of claim 1, wherein the linker segment of the at least one protection strand having a relaxed average end-to-end distance of between approximately 0.3 nm and approximately 2 nm.

14. The signal activatable construct of claim 1, wherein the targeting domain and the sensor domain duplex polynucleotide have approximately a same length.

15. The signal activatable construct of claim 1, wherein the targeting domain has a length of approximately 23 to 25 bp.

16. The signal activatable construct of claim 1, wherein the targeting domain is configured to interfere with a target intracellular process of the cells through RNAi in the presence of the signal polynucleotide.

17. The signal activatable construct of claim 16, wherein the targeting domain comprises an siRNA, microRNA, and/or additional duplex structure suitable to be used in connection with RNA interfering.

18. A method for signal-activated molecular delivery in vitro, the method comprising:
   contacting the signal activatable construct of claim 1 with the signal molecule for a time and under conditions to allow release of the targeting domain from the molecular complex in vitro.

19. A system for signal-activated molecular delivery, the system comprising:
   at least two of one or more signal activatable constructs of claim 1 and a signal polynucleotide complementary to the at least one toehold segment of the signal activatable construct, for simultaneous, combined, or sequential use to control release of the targeting domain from the one or more of the signal activatable constructs of claim 1.

20. A composition comprising one or more of the signal activatable constructs of claim 1 together with a suitable vehicle.

21. A method for targeting a disease-associated gene through enzyme-assisted signal activated molecular delivery in cells in vitro, the method comprising:
   administering to the cells in vitro an effective amount of one or more of the signal activatable construct of claim 1,
   wherein the passenger strand of the target domain is configured to target the disease-associated gene.

* * * * *